(12) United States Patent
Burke et al.

(10) Patent No.: US 9,388,131 B2
(45) Date of Patent: Jul. 12, 2016

(54) AUTOMATED SYNTHESIS OF SMALL MOLECULES USING CHIRAL, NON-RACEMIC BORONATES

(71) Applicant: The Board of Trustees of the University of Illinois, Urbana, IL (US)

(72) Inventors: Martin D. Burke, Champaign, IL (US); Junqi Li, Champaign, IL (US); Eric P. Gillis, Wallingford, CT (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 0 days.

(21) Appl. No.: 14/692,088

(22) Filed: Apr. 21, 2015

(65) Prior Publication Data

US 2015/0329567 A1 Nov. 19, 2015

Related U.S. Application Data

(62) Division of application No. 14/112,985, filed as application No. PCT/US2012/035247 on Apr. 26, 2012, now Pat. No. 9,012,658.

(60) Provisional application No. 61/590,225, filed on Jan. 24, 2012, provisional application No. 61/479,596, filed on Apr. 27, 2011.

(51) Int. Cl.
| | |
|---|---|
| *C07F 5/02* | (2006.01) |
| *C07D 207/44* | (2006.01) |
| *C07C 227/32* | (2006.01) |
| *C07C 229/24* | (2006.01) |

(52) U.S. Cl.
CPC ............ *C07D 207/44* (2013.01); *C07C 227/32* (2013.01); *C07C 229/24* (2013.01); *C07F 5/025* (2013.01); *C07C 2101/08* (2013.01); *C07C 2101/14* (2013.01); *C07C 2102/42* (2013.01)

(58) Field of Classification Search
None
See application file for complete search history.

(56) References Cited

U.S. PATENT DOCUMENTS

| | | |
|---|---|---|
| 2009/0030238 A1 | 1/2009 | Burke et al. |
| 2010/0121062 A1 | 5/2010 | Burke et al. |
| 2011/0201806 A1 | 8/2011 | Burke et al. |
| 2012/0059184 A1 | 3/2012 | Burke et al. |
| 2013/0243670 A1 | 9/2013 | Burke et al. |

FOREIGN PATENT DOCUMENTS

WO   WO-2012/012756 A1   1/2012

OTHER PUBLICATIONS

Gillis, E. P. et al., "A Simple and Modular Strategy for Small Molecule Synthesis: Iterative Suzuki-Miyaura Coupling of B-Protected Haloboronic Acid Building Blocks", *J. Am. Chem. Soc.*, 129:6716-6717 (USA, 2007).
Li, J. et al., "Pinene-Derived Iminodiacetic Acid (PIDA): A Powerful Ligand for Stereoselective Synthesis and Iterative Cross-Coupling of C(sp$^3$) Boronate Building Blocks", *J. Am. Chem. Soc.*, 133:13774-13777 (USA, Aug. 8, 2011).
International Search Report and Written Opinion from parent PCT application PCT/US2012/035247 dated Nov. 23, 2012.

*Primary Examiner* — Samantha Shterengarts
(74) *Attorney, Agent, or Firm* — Dana M. Gordon; Foley Hoag LLP

(57) ABSTRACT

Provided are methods for making and using chiral, non-racemic protected organoboronic acids, including pinene-derived iminodiacetic acid (PIDA) boronates, to direct and enable stereoselective synthesis of organic molecules. Also provided are methods for purifying PIDA boronates from solution. Also provided are methods for deprotection of boronic acids from their PIDA ligands. The purification and deprotection methods may be used in conjunction with methods for coupling or otherwise reacting boronic acids. Iterative cycles of deprotection, coupling, and purification can be performed to synthesize chiral, non-racemic compounds. The methods are suitable for use in an automated chemical synthesis process. Also provided is an automated small molecule synthesizer apparatus for performing automated stereoselective synthesis of chiral, non-racemic small molecules using iterative cycles of deprotection, coupling, and purification.

20 Claims, 14 Drawing Sheets

FIG. 8A
FIG. 8B
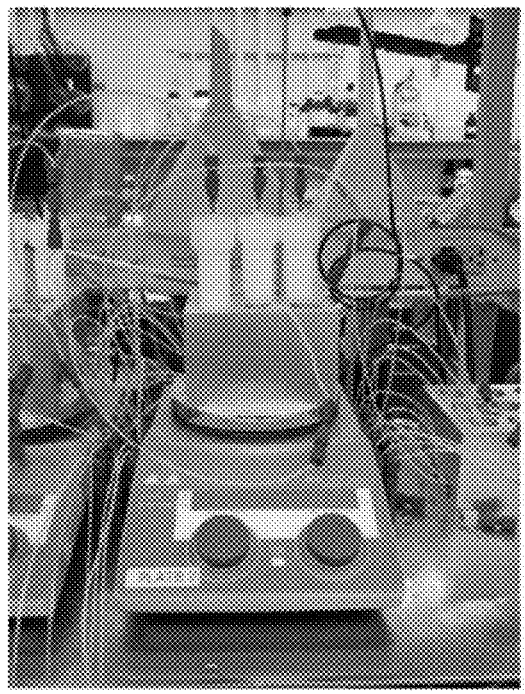
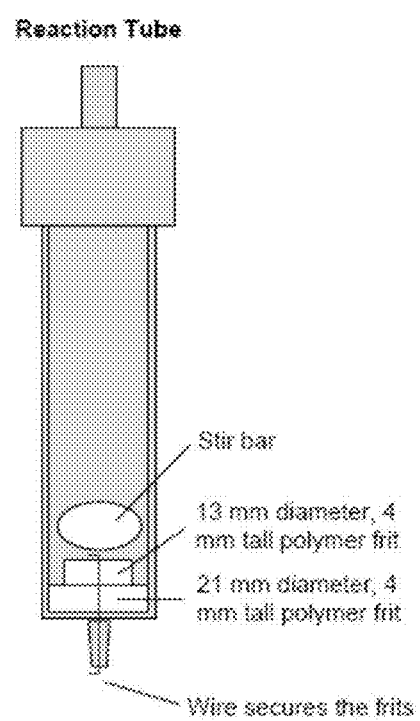
FIG. 8C
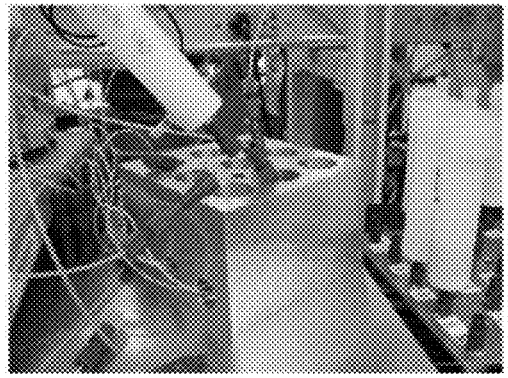

AUTOMATED SYNTHESIS OF SMALL MOLECULES USING CHIRAL, NON-RACEMIC BORONATES

RELATED APPLICATIONS

This application is a divisional of U.S. patent application Ser. No. 14/112,985, filed Dec. 12, 2013, which is the U.S. national phase of International Patent Application No. PCT/US2012/035247, filed Apr. 26, 2012, which claims the benefit of priority to U.S. Provisional Patent Application Ser. No. 61/479,596, filed Apr. 27, 2011; and U.S. Provisional Patent Application Ser. No. 61/590,225, filed Jan. 24, 2012.

STATEMENT OF GOVERNMENT SUPPORT

This invention was made with government support under CAREER Award No. 0747778 awarded by the National Science Foundation. The government has certain rights in the invention.

BACKGROUND OF THE INVENTION

Similar to peptides, oligonucleotides, and oligosaccharides, most small molecule natural products are modular in their constitution. Like the aforementioned oligomers, the majority of naturally occurring small molecules are biosynthesized via the sequential coupling of bifunctional building blocks. Specifically, polyketides are derived from multiple malonyl-CoA and/or methylmalonyl-CoA units, non-ribosomal peptides are built from amino acids, polyterpenes are stitched together from isopentenyl pyrophosphate and/or dimethylallyl pyrophosphate building blocks, and fatty acids are prepared from fragments of malonyl-CoA. Other classes of modular natural products result from the oxidative coupling of common building blocks, such as shikimic acid, amino acids, and/or their respective derivatives.

With peptides and oligonucleotides, and increasingly with oligosaccharides, the inherent modularity is now routinely harnessed to enable fully automated syntheses from suitably protected bifunctional building blocks (R. B. Merrifield, *Science* 1965, 150, 178-185; M. H. Caruthers, *Science* 1985, 24, 799; and O. J. Plante, M. R. Palmacci, P. H. Seeberger, *Science* 2001, 291, 1523). As a direct result of these advances, research in these areas is primarily focused on discovering and understanding new molecular function. In stark contrast, despite tremendous advances over the course of nearly two centuries, the laboratory synthesis of small molecules remains a relatively complex, inflexible, and non-systematized process practiced almost exclusively by highly-trained specialists. (For pioneering developments in the automated synthesis of small molecules via polymer-assistance and/or flow chemistry, see: a) C. H. Hornung, M. R. Mackley, I. R. Baxendale, and S. V. Ley, *Org. Proc. Res. Dev.* 2007, 11, 399-405; b) Nikzad Nikbin, Mark Ladlow, and Steven V. Ley, *Org. Process Res. Dev.* 2007, 11, 458-462; and c) S. France, D. Bernstein, A. Weatherwax, and T. Lectka, *Org. Lett.* 2005, 7, 3009-3012.) Thus, research in this area is still heavily weighted towards synthesis. Given the special properties of many small molecules that make them uniquely suited for a wide range of applications in science, engineering, and medicine, increased access to these compounds via a highly general and automated synthesis platform that is accessible to the non-expert would be highly enabling. Ultimately, such a process could help shift the primary focus from the synthesis of small molecules to the discovery and understanding of important small molecule functions.

Organoboron compounds have had a profound impact on organic synthesis. Their unique reactivity has made them among the most versatile organometallic intermediates (boronate building blocks) for the construction of complex organic molecules.

The Suzuki-Miyaura reaction is a palladium- or nickel-catalyzed cross-coupling between a boronic acid or a boronic ester and an organohalide or an organo-pseudohalide. Miyaura et al. (1995) *Chem Rev* 95:2457-83. This cross coupling transformation is a powerful method for C—C bond formation in complex molecule synthesis. The reaction is tolerant of functional groups and has become increasingly general and widespread in its use for coupling of organic compounds. Barder et al. (2005) *J Am Chem Soc* 127:4685-96; Billingsley et al. (2007) *J Am Chem Soc* 129:3358-66; Littke et al. (2000) *J Am Chem Soc* 122:4020-8; Nicolaou et al. (2005) *Angew Chem Int Ed* 44:4442-89.

Boronic acids, on the other hand, are notoriously sensitive to many common reagents. Hall D G, *Boronic Acids*, Wiley-VCH, Germany, 2005, pp 3-14; Tyrell et al. (2003) *Synthesis* 4:469-83. It is therefore typical to introduce the boronic acid functional group during the last step of a building block synthesis. However, many of the methods for doing so (hydroboration, trapping organometallic reagents with trimethylborate, etc.) are intolerant to a variety of common functional groups, such as alcohols, aldehydes, ketones, alkynes and olefins. This makes the synthesis of structurally complex boronic acid building blocks quite challenging.

Conventional boronic acids are characterized by $sp^2$-hybridized boron covalently linked to a carbon atom of an organic moiety of interest. Incompatibility of most oxidants with these boronic acids represent a significant limitation because it severely restricts the ability to modify the organic moiety while retaining the carbon-boron bond.

Recently there has been keen interest in the development of protecting groups for the boronic acid functional group. A compound that includes a protected boronic acid and another functional group can undergo chemical transformations of the other functional group without chemically transforming the boron. Removal of the protecting group (deprotection) then provides the free boronic acid, which can undergo a Suzuki-Miyaura reaction to cross-couple the compound with an organohalide or an organo-pseudohalide.

Toward this end, Molander and Ribagorda described potassium organotrifluoroborates useful in Suzuki-Miyaura cross-coupling reactions and epoxidation reactions. Molander et al. (2003) *J Am Chem Soc* 125:11148-9.

More recently, N-methyliminodiacetic acid (MIDA) "rigid cage" boronates have been described as a highly versatile platform for synthesizing boronate building blocks. US 2009/0030238 (incorporated herein by reference). These MIDA boronates are characterized by the presence of boron having $sp^3$ hybridization covalently linked to a carbon atom of an organic moiety of interest, wherein the boron is remarkably stable in the face of harsh chemical conditions capable of transforming the functional group, yet deprotection is effectively achieved using mild aqueous basic conditions (e.g., treatment with 1 M aqueous sodium hydroxide in tetrahydrofuran for 10 minutes). Dozens of MIDA boronates are now commercially available from Aldrich.

Many biologically active compounds and pharmaceuticals are synthesized as racemic mixtures, while most, if not all, of the desired biological activity is typically associated with only one enantiomer of such compounds. It is, therefore, not surprising that there is tremendous interest in being able to synthesize organic molecules with directed stereochemistry, including, for example, for high throughput screening for biologically relevant activity.

A building-block approach to small molecule synthesis is an attractive strategy for constructing specific complex molecules as well as for generating libraries of compounds. In an idealized form of the building-block approach to small molecule synthesis, off-the-shelf subunits having all the required functional groups pre-installed in the correct oxidation states and with the desired stereochemical relationships are brought together using a single reaction iteratively.

SUMMARY OF THE INVENTION

One aspect of the invention pertains to stereoisomerically enriched or substantially pure chiral protected organoboronic acids and their synthesis, characteristics, and use in directing and enabling stereoselective synthesis of organic molecules, including, in certain embodiments, their use in directing and enabling stereoselective synthesis of organic molecules in an automated manner. A stereoisomerically enriched or substantially pure chiral protected organoboronic acid includes a boron atom having $sp^3$ hybridization, a conformationally rigid protecting group bonded to the boron atom, a chiral group bonded to or forming part of the protecting group, and an organic group bonded to the boron atom through a covalent boron-carbon (B—C) bond. The protecting group may be a trivalent group. The chiral group, bonded to or forming part of the protecting group, is arranged to be in such proximity to the organic group that it can influence the stereoselectivity of a chemical transformation of the organic group while it remains bonded to the boron through the boron-carbon bond. Typically, the organic group can undergo a chemical transformation without chemically transforming the boron atom. In one embodiment the organic group is or includes a prochiral group.

In one embodiment the protecting group is derived from an iminodiacetic acid (IDA) in which the chiral group is a chiral moiety appended to the nitrogen of the IDA group through a covalent bond.

In one embodiment the protecting group is derived from an IDA in which the chiral group is part of the IDA.

In one embodiment the protecting group is derived from an IDA in which the IDA itself comprises a chiral group, and a second chiral moiety is covalently bonded to the nitrogen of the IDA group.

In contrast to the stereoisomerically enriched or substantially pure chiral protected organoboronic acids of the invention, conventional protected organoboronic acids include either a boron having $sp^2$ hybridization, a boron present in an anionic compound, or a boron bonded to a protecting group that is not conformationally rigid, for example, the potassium organotrifluoroborates described by Molander and Ribagorda. Molander et al. (2003) *J Am Chem Soc* 125:11148-9.

Certain aspects of the invention relate to a process that iteratively utilizes a carbon-carbon bond-forming reaction to assemble a wide range of small molecules from pre-fabricated building blocks. In one embodiment, the process is an automated process. In certain embodiments, analogous to the automated preparation of peptides from suitably protected amino acids, the automated process involves the controlled, iterative assembly of bifunctional haloboronic acid building blocks protected as the corresponding chiral, non-racemic N-pinene-derived iminodiacetic acid (PIDA) boronates. In certain embodiments, obviating the need for any covalent attachment to a solid support, purification of intermediates is achieved by harnessing two remarkably general physical properties of PIDA boronates: the capacity for catch-and-release chromatography with silica gel; and their insolubility in hexanes.

In one embodiment, the process is carried out using an apparatus specifically suited to perform the steps of the process in an automated fashion.

An aspect of the invention is a method of purifying a chiral, non-racemic pinene-derived iminodiacetic acid (PIDA) boronate from a solution. The method includes the steps of diluting the solution with hexane, thereby selectively precipitating the chiral, non-racemic PIDA boronate; and isolating the precipitated chiral, non-racemic PIDA boronate.

An aspect of the invention is a method of purifying a chiral, non-racemic pinene-derived iminodiacetic acid (PIDA) boronate from a solution. The method includes the steps of passing the solution through a silica plug; passing a first liquid through the silica plug; and passing a second liquid through the silica plug, thereby eluting the chiral, non-racemic PIDA boronate in the second liquid; wherein the first liquid contains diethyl ether or the polarity of the first liquid is less than or equal to about the polarity of a mixture of 98.5:1.5 (v/v) $Et_2O$:MeOH; and the polarity of the second liquid is greater than or equal to about the polarity of tetrahydrofuran (THF).

An aspect of the invention is a method of purifying a chiral, non-racemic pinene-derived iminodiacetic acid (PIDA) boronate from a solution. The method includes the steps of diluting the solution with hexane, thereby selectively precipitating the chiral, non-racemic PIDA boronate; passing the diluted solution through a silica plug, thereby depositing the precipitated chiral, non-racemic PIDA boronate on the silica plug; passing a first liquid through the silica plug; and passing a second liquid through the silica plug, thereby eluting the chiral, non-racemic PIDA boronate in the second liquid; wherein the first liquid contains diethyl ether or the polarity of the first liquid is less than or equal to about the polarity of a mixture of 98.5:1.5 (v/v) $Et_2O$:MeOH; and the polarity of the second liquid is greater than or equal to about the polarity of tetrahydrofuran (THF).

An aspect of the invention is a method of deprotecting a chiral, non-racemic pinene-derived iminodiacetic acid (PIDA) boronate. The method includes the step of contacting a solution, comprising the chiral, non-racemic PIDA boronate and a solvent, with a solid-supported ammonium hydroxide reagent, thereby deprotecting the chiral, non-racemic PIDA boronate and forming a boronic acid and a PIDA.

An aspect of the invention is a method of deprotecting a chiral, non-racemic pinene-derived iminodiacetic acid (PIDA) boronate. The method includes the step of contacting a solution comprising the chiral, non-racemic PIDA boronate and a solvent with an aqueous solution of NaOH, thereby deprotecting the chiral, non-racemic PIDA boronate and forming a boronic acid and a PIDA ligand.

In certain embodiments, the chiral, non-racemic PIDA boronate is represented by

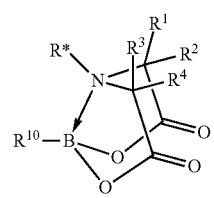

(I)

wherein:
B is a boron atom having sp³ hybridization;
R* is a chiral group

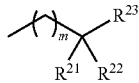

of at least 90% enantiomeric excess;
R²¹ and R²² are independently selected from the group consisting of hydrogen, alkyl, cycloalkyl, heterocyclyl, aryl, heteroaryl, aralkyl, and heteroaralkyl; or R²¹ and R²², taken together, form a 5-10-membered cycloalkyl or aromatic ring, or form a 5-10-membered heterocyclic or heteroaromatic ring comprising 1-3 heteroatoms independently selected from the group consisting of N, O, and S;
R²³ is selected from the group consisting of hydrogen, alkyl, cycloalkyl, heterocyclyl, aryl, heteroaryl, aralkyl, and heteroaralkyl;
R¹⁰ is selected from the group consisting of

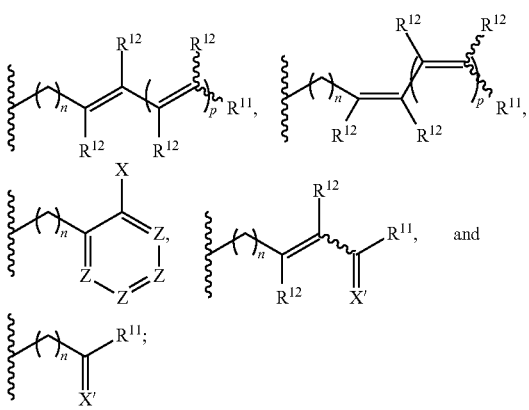

R¹¹ and each instance of R¹² are independently selected from the group consisting of hydrogen, halogen, hydroxyl, (C1-C10)alkyl, cycloalkyl, aryl, aralkyl, heteroaralkyl, alkoxyl, acyl, acyloxy, aryloxy, amino, and trialkylsilyloxy; or R¹¹ and any one instance of R¹², or any two instances of R¹², taken together, form a 3-10-membered ring;
X is halogen;
each instance of Z is independently selected from the group consisting of CH and N, provided that no more than two instances of Z are N;
X' is selected from the group consisting of CR⁵R⁶, O, S, and NR⁷;
R¹ and R² are both hydrogen or identically selected (C1-C3)alkyl;
R³ and R⁴ are both hydrogen or identically selected (C1-C3)alkyl;
R⁵ and R⁶ are independently selected from the group consisting of hydrogen, halogen, hydroxyl, (C1-C10)alkyl, cycloalkyl, aryl, aralkyl, heteroaralkyl, alkoxyl, acyl, acyloxy, aryloxy, amino, and trialkylsilyloxy;
R⁷ is selected from the group consisting of hydrogen and (C1-C3)alkyl;
m is 0, 1, or 2;
n is 0, 1, or 2; and
p is 0, 1, or 2.

Additional aspects, embodiments, and advantages of the invention are discussed below in detail.

BRIEF DESCRIPTION OF THE FIGURES

FIG. 8A is a photograph depicting an example of three reaction tubes.

FIG. 8B depicts a schematic of a reaction tube.

FIG. 8C is a photograph depicting an example of a reaction tube.

DETAILED DESCRIPTION OF THE INVENTION

Figure 1:
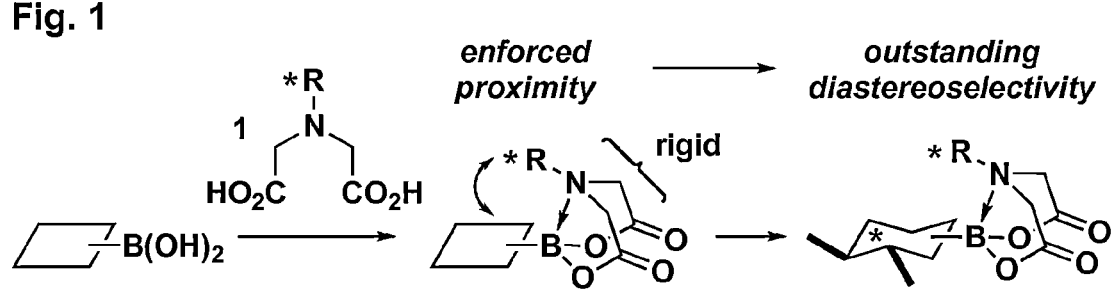
FIG. 1 represents, generically, the chemical structure and reactions of compounds of formula (I) of the invention.

The invention is based at least in part on the discovery of a pinene-derived iminodiacetic acid (PIDA) ligand that enables the *facile* synthesis of a wide range of versatile Csp³ chiral boronate building blocks in a highly stereocontrolled fashion. Together, the conformational rigidity of the iminodiacetic acid framework protecting the boron atom having sp³ hybridization and the chirality of the group appended to the nitrogen atom, result in effective transfer of stereochemical information during functionalizations of the boronate due to enforced proximity. See FIG. 1.

Beginning with their discovery of the PIDA ligand, the inventors have developed and characterized a class of chiral IDA-based ligands and corresponding stereoisomerically enriched or substantially pure chiral organoboronic acids useful in the preparation and use of boronate building blocks for organic synthesis.

Certain aspects of the present invention are directed to methods and apparatuses suitable for the automated stereoselective synthesis of small molecules comprising at least one chiral center. In certain embodiments, the small molecules are prepared by using a single reaction iteratively to unite a collection of bifunctional building blocks having all of the required functionality, oxidation states, and stereochemistry pre-installed.

DEFINITIONS

The following definitions are included to provide a clear and consistent understanding of the specification and claims.

The articles "a" and "an" are used herein to refer to one or to more than one (i.e., to at least one) of the grammatical object of the article. By way of example, "an element" means one element or more than one element.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

For the purposes of this invention, the chemical elements are identified in accordance with the Periodic Table of the Elements, CAS version, Handbook of Chemistry and Physics, 67$^{th}$ Ed., 1986-1987, inside cover.

The term "acyl" or "acyl group" means any group or radical of the form —C(=O)R, where R is an organic group. An example of the acyl group is the acetyl group (—C(=O) CH$_3$).

The term "acyloxy" or "acyloxy group" as used herein refers to means an acyl group, as defined herein, appended to the parent molecular moiety through an oxygen atom.

The term "alkenyl" or "alkenyl group" means a group formed by removing a hydrogen from a carbon of an alkene, where an alkene is an acyclic or cyclic compound consisting entirely of hydrogen atoms and carbon atoms, and including at least one carbon-carbon double bond. An alkenyl group may include one or more substituent groups.

The term "alkoxy" or "alkoxy group" as used herein means an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy. The terms "alkyenyloxy", "alkynyloxy", "carbocyclyloxy", and "heterocyclyloxy" are likewise defined.

The term "alkyl" or "alkyl group" means a group formed by removing a hydrogen from a carbon of an alkane, where an alkane is an acyclic or cyclic compound consisting entirely of hydrogen atoms and saturated carbon atoms. In various embodiments an alkyl contains 1 to 20, 1 to 15, or 1 to 10 carbon atoms. In one embodiment an alkyl contains 1 to 3 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 2-methylcyclopentyl, 1-(1-ethylcyclopropyl) ethyl and 1-cyclohexylethyl. An alkyl group may include one or more substituent groups.

The term "alkynyl group" means a group formed by removing a hydrogen from a carbon of an alkyne, where an alkyne is an acyclic or cyclic compound consisting entirely of hydrogen atoms and carbon atoms, and including at least one carbon-carbon triple bond. An alkynyl group may include one or more substituent groups.

The term "amino", "amino group", or "amine" as used herein refers to $-NH_2$ and substituted derivatives thereof wherein one or both of the hydrogens are independently replaced with substituents selected from the group consisting of alkyl, haloalkyl, fluoroalkyl, alkenyl, alkynyl, carbocyclyl, heterocyclyl, aryl, aralkyl, heteroaryl, heteroaralkyl, alkylcarbonyl, haloalkylcarbonyl, fluoroalkylcarbonyl, alkenylcarbonyl, alkynylcarbonyl, carbocyclylcarbonyl, heterocyclylcarbonyl, arylcarbonyl, aralkylcarbonyl, heteroarylcarbonyl, heteroaralkylcarbonyl, sufonyl, and sulfinyl groups; or when both hydrogens together are replaced with an alkylene group (to form a ring which contains the nitrogen). Representative examples include, but are not limited to methylamino, acetylamino, and dimethylamino.

The term "amido" as used herein means an amino group, as defined herein, appended to the parent molecular moiety through a carbonyl.

The term "arylalkyl" or "aralkyl" as used herein means an aryl group, as defined herein, appended to the parent molecular moiety through an alkyl group, as defined herein. Representative examples of aralkyl include, but are not limited to, benzyl, 2-phenylethyl, 3-phenylpropyl, and 2-naphth-2-ylethyl.

The term "aromatic" or "aromatic group" refers to a planar or polycyclic structure characterized by a cyclically conjugated molecular moiety containing 4n+2 electrons, wherein n is the absolute value of an integer. Aromatic molecules containing fused, or joined, rings also are referred to as bicyclic aromatic rings. For example, bicyclic aromatic rings containing heteroatoms in a hydrocarbon ring structure are referred to as bicyclic heteroaryl rings.

The term "aryl" or "aryl group" means a group formed by removing a hydrogen from a ring carbon atom of an aromatic hydrocarbon. An aryl group may by monocyclic or polycyclic and may include one or more substituent groups.

The term "aryloxy" or "aryloxy group" as used herein means an aryl group, as defined herein, appended to the parent molecular moiety through an oxygen atom. The term "heteroaryloxy" or "heteroaryloxy group" as used herein means a heteroaryl group, as defined herein, appended to the parent molecular moiety through an oxygen atom. An aryloxy group may include one or more substituent groups.

The term "azido" as used herein means a $-N_3$ group.

The term "carbonyl" as used herein refers to a $-C(=O)-$ group.

The term "chemical transform" of a substance means a product of a chemical transformation of the substance, where the product has a chemical structure different from that of the substance.

The term "chemical transformation" means the conversion of a substance into a product, irrespective of reagents or mechanisms involved.

The term "cyano" as used herein means a $-C\equiv N$ group.

The term "cyclic" pertains to compounds and/or groups which have one or more rings (e.g., spiro, fused, bridged).

The term "cycloalkyl" or "cycloalkyl group" is a subset of alkyl which refers to a cyclic hydrocarbon radical containing from 3 to 15, 3 to 10, or 3 to 7 carbon atoms. Representative examples of cycloalkyl include, but are not limited to, cyclopropyl, cyclobutyl, cyclopentyl, and cyclohexyl. A cycloalkyl group may include one or more substituent groups.

The term "enantiomeric excess" (ee) means the absolute difference between the mole fraction of each enantiomer.

The term "functional group" means an atom or collection of atoms in a molecule that are responsible for characteristic chemical reactions of the molecule. Nonlimiting examples of functional groups include halogen, alcohol (—OH), aldehyde (—CH=O), ketone (—C(=O)—), carboxylic acid (—C(=O)OH), thiol (—SH), sulfone, sulfoxide, amine, phosphine, phosphite, phosphate, and combinations thereof. Of particular interest as functional groups in connection with the invention are alkenyl (olefinic) groups. Additional examples of organic groups including functional groups that may be present in a protected organoboronic acid are illustrated or described throughout the present application.

The term "group" means a linked collection of atoms or a single atom within a molecular entity, where a molecular entity is any constitutionally or isotopically distinct atom, molecule, ion, ion pair, radical, radical ion, complex, conformer, etc., identifiable as a separately distinguishable entity. The description of a group as being "formed by" a particular chemical transformation does not imply that this chemical transformation is involved in making the molecular entity that includes the group.

The term "halogen" means —F, —Cl, —Br or —I.

The term "heteroalkenyl" or "heteroalkenyl group" means a group formed by removing a hydrogen from a carbon of a heteroalkene, where a heteroalkene is an acyclic or cyclic compound consisting entirely of hydrogen atoms, carbon atoms, and one or more heteroatoms, and including at least one carbon-carbon double bond. A heteroalkenyl group may include one or more substituent groups.

The term "heteroalkyl group" means a group formed by removing a hydrogen from a carbon of a heteroalkane, where a heteroalkane is an acyclic or cyclic compound consisting entirely of hydrogen atoms, saturated carbon atoms, and one or more heteroatoms. A heteroalkyl group may include one or more substituent groups.

The term "heteroalkynyl" or "heteralkynyl group" means a group formed by removing a hydrogen from a carbon of a heteroalkyne, where a heteroalkyne is an acyclic or cyclic compound consisting entirely of hydrogen atoms, carbon atoms and one or more heteroatoms, and including at least one carbon-carbon triple bond. A heteroalkynyl group may include one or more substituent groups.

The term "heteroaralkyl", "heteroaralkyl group", "heteroarylalkyl", or "heteroarylalkyl group" as used herein means a heteroaryl, as defined herein, appended to the parent molecular moiety through an alkyl group, as defined herein. Representative examples of heteroarylalkyl include, but are not limited to, pyridin-3-ylmethyl and 2-(thien-2-yl)ethyl. A heteroaralkyl group may include one or more substituent groups.

The term "heteroaromatic" or "heteroaromatic group" as used herein means an aromatic group as defined herein, in which at least one carbon atom is replaced by a heteroatom. Representative examples of heteroaromatic groups include, without limitation, pyrrolyl, furanyl, thiophenyl, imidazolyl, oxazolyl, thiazolyl, pyrazolyl, pyridinyl, pyrimidinyl, purinyl, quinolinyl, isoquinolinyl, and carbazolyl. A heteroaromatic group may include one or more substituent groups.

The term "heteroaryl" or "heteroaryl group" as used herein means a radical of aromatic ring systems, including, but not limited to, monocyclic, bicyclic and tricyclic rings, which have 3 to 12 atoms including at least one heteroatom, such as nitrogen, oxygen, or sulfur. Representative examples of heteroaryl groups include, without limitation, aminobenzimidazolyl, benzimidazolyl, azaindolyl, benzo(b)thienyl, benzimidazolyl, benzofuranyl, benzoxazolyl, benzothiazolyl, benzothiadiazolyl, benzotriazolyl, benzoxadiazolyl, furanyl, imidazolyl, imidazopyridinyl, indolyl, indolinyl, indazolyl, isoindolinyl, isoxazolyl, isothiazolyl, isoquinolinyl, oxadiazolyl, oxazolyl, purinyl, pyranyl, pyrazinyl, pyrazolyl, pyridinyl, pyrimidinyl, pyrrolyl, pyrrolo[2,3-d]pyrimidinyl, pyrazolo[3,4-d]pyrimidinyl, quinolinyl, quinazolinyl, triazolyl, thiazolyl, thiophenyl, tetrahydroindolyl, tetrazolyl, thiadiazolyl, thienyl, thiomorpholinyl, triazolyl or tropanyl. The heteroaryl groups of the invention may include one or more substituent groups.

The term "heteroatom" means any atom that is not carbon or hydrogen. In certain embodiments a heteroatom is an atom selected from any of nitrogen, oxygen, sulfur, and phosphorus.

The term "heterocyclyl", "heterocyclic", or "heterocyclic group" as used herein refers to a radical of a non-aromatic ring system, including, but not limited to, monocyclic, bicyclic and tricyclic rings, which can be completely saturated or which can contain one or more units of unsaturation, and has 3 to 12 atoms including at least one heteroatom, such as nitrogen, oxygen, or sulfur. For the avoidance of doubt, the degree of unsaturation does not result in an aromatic ring system. For purposes of exemplification, which should not be construed as limiting the scope of this invention, the following are examples of heterocyclic rings: aziridinyl, azirinyl, oxiranyl, thiiranyl, thiirenyl, dioxiranyl, diazirinyl, azetyl, oxetanyl, oxetyl, thietanyl, thietyl, diazetidinyl, dioxetanyl, dioxetenyl, dithietanyl, dithietyl, furyl, dioxalanyl, pyrrolyl, oxazolyl, thiazolyl, imidazolyl, oxadiazolyl, thiadiazolyl, triazolyl, triazinyl, isothiazolyl, isoxazolyl, thiophenyl, pyrazolyl, tetrazolyl, pyridyl, pyridazinyl, pyrimidinyl, pyrazinyl, triazinyl, tetrazinyl, quinolinyl, isoquinolinyl, quinoxalinyl, quinazolinyl, pyridopyrazinyl, benzoxazolyl, benzothiophenyl, benzimidazolyl, benzothiazolyl, benzoxadiazolyl, benzthiadiazolyl, indolyl, benztriazolyl, naphthyridinyl, azepines, azetidinyl, morpholinyl, oxopiperidinyl, oxopyrrolidinyl, piperazinyl, piperidinyl, pyrrolidinyl, quinicludinyl, thiomorpholinyl, tetrahydropyranyl and tetrahydrofuranyl. The heterocyclyl groups of the invention may include one or more substituent groups.

The term "heteroaryl group" means a group formed by replacing one or more methine (—C=) and/or vinylene (—CH=CH—) groups in an aryl group with a trivalent or divalent heteroatom, respectively. A heteroaryl group may by monocyclic or polycyclic and may include one or more substituent groups.

The term "hydroxyl" or "hydroxyl group" as used herein means an —OH group.

The term "organic group" means a group containing at least one carbon atom.

The term "organoboronic acid" means a compound represented by R—B(OH)$_2$, where R is an organic group that is bonded to the boron through a boron-carbon bond.

The term "phosphinyl" as used herein includes —PH$_3$ and substituted derivatives thereof wherein one, two or three of the hydrogens are independently replaced with substituents selected from the group consisting of alkyl, haloalkyl, fluoroalkyl, alkenyl, alkynyl, carbocyclyl, heterocyclyl, aryl, aralkyl, heteroaryl, heteroaralkyl, alkoxy, haloalkoxy, fluoroalkyloxy, alkenyloxy, alkynyloxy, carbocyclyloxy, heterocyclyloxy, aryloxy, aralkyloxy, heteroaryloxy, heteroaralkyloxy, and amino.

The term "phosphoryl" as used herein refers to —P(=O)OH$_2$ and substituted derivatives thereof wherein one or both of the hydroxyls are independently replaced with substituents selected from the group consisting of alkyl, haloalkyl, fluoroalkyl, alkenyl, alkynyl, carbocyclyl, heterocyclyl, aryl, aralkyl, heteroaryl, heteroaralkyl, alkoxy, haloalkoxy, fluoroalkyloxy, alkenyloxy, alkynyloxy, carbocyclyloxy, heterocyclyloxy, aryloxy, aralkyloxy, heteroaryloxy, heteroaralkyloxy, and amino.

The term "protected organoboronic acid" means a chemical transform of an organoboronic acid, in which the boron has a lower chemical reactivity relative to the original organoboronic acid.

The term "silyl" as used herein includes H$_3$Si— and substituted derivatives thereof wherein one, two or three of the hydrogens are independently replaced with substituents selected from alkyl, haloalkyl, fluoroalkyl, alkenyl, alkynyl, carbocyclyl, heterocyclyl, aryl, aralkyl, heteroaryl, and heteroaralkyl. Representative examples include trimethylsilyl (TMS), tert-butyldiphenylsilyl (TBDPS), tert-butyldimethylsilyl (TBS/TBDMS), triisopropylsilyl (TIPS), and [2-(trimethylsilyl)ethoxy]methyl (SEM).

The term "sp$^3$ hybridization" means that an atom is bonded and/or coordinated in a configuration having a tetrahedral character of at least 50%. For tetracoordinate boron atoms, the tetrahedral character of the boron atom is calculated by the method of Hopfl, H. (1999) *J Organomet Chem* 581:129-49. In this method, the tetrahedral character (THC) is defined as:

$$THC_{DA}(\%) = 100 \times (1 - (\Sigma_{n=1-6} |109.5 - \theta_n|°/90°))$$

where $\theta_n$ is one of the six bond angles of the boron atom.

The term "substituent" or "substituent group" means a group that replaces one or more hydrogen atoms in a molecular entity. Except as may be specified otherwise, substituent groups can include, without limitation, alkyl, alkenyl, alkynyl, halo, haloalkyl, fluoroalkyl, hydroxy, alkoxy, alkyenyloxy, alkynyloxy, carbocyclyloxy, heterocyclyloxy, haloalkoxy, fluoroalkyloxy, sulfhydryl, alkylthio, haloalkylthio, fluoroalkylthio, alkyenylthio, alkynylthio, sulfonic acid, alkylsulfonyl, haloalkylsulfonyl, fluoroalkylsulfonyl, alkenylsulfonyl, alkynylsulfonyl, alkoxysulfonyl, haloalkoxysulfonyl, fluoroalkoxysulfonyl, alkenyloxysulfonyl, alkynyloxysulfony, aminosulfonyl, sulfinic acid, alkylsulfinyl, haloalkylsulfinyl, fluoroalkylsulfinyl, alkenylsulfinyl, alkynylsulfinyl, alkoxysulfinyl, haloalkoxysulfinyl, fluoroalkoxysulfinyl, alkenyloxysulfinyl, alkynyloxysulfiny, aminosulfinyl, formyl, alkylcarbonyl, haloalkylcarbonyl, fluoroalkylcarbonyl, alkenylcarbonyl, alkynylcarbonyl, carboxyl, alkoxycarbonyl, haloalkoxycarbonyl, fluoroalkoxycarbonyl, alkenyloxycarbonyl, alkynyloxycarbonyl, alkylcarbonyloxy, haloalkylcarbonyloxy, fluoroalkylcarbonyloxy, alkenylcarbonyloxy, alkynylcarbonyloxy, alkylsulfonyloxy, haloalkylsulfonyloxy, fluoroalkylsulfonyloxy, alkenylsulfonyloxy, alkynylsulfonyloxy, haloalkoxysulfonyloxy, fluoroalkoxysulfonyloxy, alkenyloxysulfonyloxy, alkynyloxysulfonyloxy, alkylsulfinyloxy, haloalkylsulfinyloxy, fluoroalkylsulfinyloxy, alkenylsulfinyloxy, alkynylsulfinyloxy, alkoxysulfinyloxy, haloalkoxysulfinyloxy, fluoroalkoxysulfinyloxy, alkenyloxysulfinyloxy, alkynyloxysulfinyloxy, aminosulfinyloxy, amino, amido, aminosulfonyl, aminosulfinyl, cyano, nitro, azido, phosphinyl, phosphoryl, silyl, and silyloxy.

The term "sulfinyl" as used herein refers to a —S(=O)— group.

The term "sulfonyl" as used herein refers to a —S(=O)$_2$— group.

The term "trialkylsilyloxy" or "trialkylsilyloxy group" as used herein refers to a trialkylysilyl group, as defined herein, appended to the parent molecular moiety through an oxygen atom.

Exemplary Chiral IDA Compounds

An aspect of the invention is novel iminodiacetic acid (IDA) molecules. The novel IDA molecules of the invention include at least one chiral carbon atom or have appended to them through the nitrogen atom a substituent characterized by having at least one chiral carbon atom. In one embodiment the novel IDA molecules of the invention include at least one chiral carbon atom and have appended to them through the nitrogen atom a substituent characterized by having at least one chiral carbon atom.

In one embodiment the IDA molecules of the invention have appended to them through the nitrogen atom a chiral group R*. In one embodiment the IDA molecules of the invention have appended to them through the nitrogen atom a chiral group R* of at least 90% enantiomeric excess.

In one embodiment an IDA molecule of the invention is a compound of formula (III)

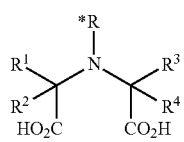

(III)

wherein:

R* is a chiral group

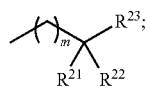

$R^{21}$ and $R^{22}$ are independently selected from the group consisting of hydrogen, alkyl, cycloalkyl, heterocyclyl, aryl, heteroaryl, aralkyl, and heteroaralkyl; or $R^{21}$ and $R^{22}$, taken together, form a 5-10-membered cycloalkyl or aromatic ring, or form a 5-10-membered heterocyclic or heteroaromatic ring comprising 1-3 heteroatoms independently selected from the group consisting of N, O, and S;

$R^{23}$ is selected from the group consisting of hydrogen, alkyl, cycloalkyl, heterocyclyl, aryl, heteroaryl, aralkyl, and heteroaralkyl;

$R^1$ and $R^2$ are both hydrogen or identically selected (C1-C3)alkyl;

$R^3$ and $R^4$ are both hydrogen or identically selected (C1-C3)alkyl; and m is an integer 0, 1, or 2.

In one embodiment the IDA molecule in accordance with formula (III) is not

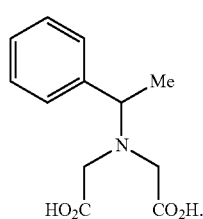 [SMILES: CC(c1ccccc1)N(CC(=O)O)CC(=O)O]

In one embodiment, R* is

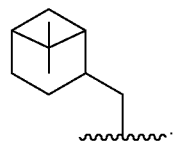 [SMILES: *CC1CCC2CC1C2(C)C]

In one embodiment, R* is

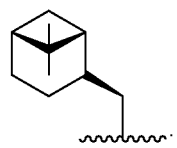

In one embodiment, R* is

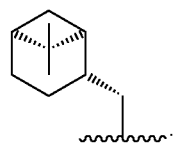

In one embodiment, R* is

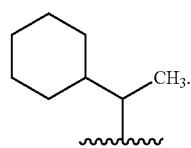

In one embodiment, R* is

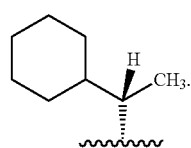

In one embodiment, R* is

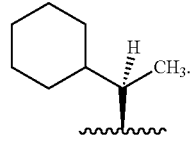

In one embodiment, $R^{21}$ and $R^{22}$, taken together, form a 5-10-membered cycloalkyl or aromatic ring, or form a 5-10-membered heterocyclic or heteroaromatic ring comprising 1-3 heteroatoms independently selected from the group consisting of N, O, and S.

In one embodiment, R* is

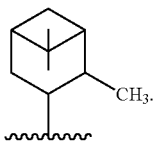 [SMILES: *C1CC2CC(C1C)C2(C)C]

In one embodiment, R* is

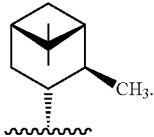

In one embodiment, R* is

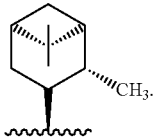

In one embodiment, R* is

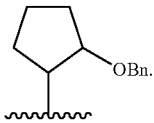 [SMILES: *C1CCCC1OCc1ccccc1]

In one embodiment, R* is

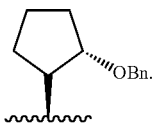

In one embodiment, R* is

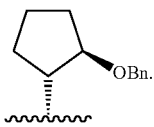

In one embodiment, m in any one of the foregoing embodiments is 0.

In one embodiment, R* in any one of the foregoing embodiments is a chiral group of at least 90% enantiomeric excess. In one embodiment, R* in any one of the foregoing embodiments is a chiral group of at least 95% enantiomeric excess. In one embodiment, R* in any one of the foregoing embodiments is a chiral group of at least 98% enantiomeric excess. In one embodiment, R* in any one of the foregoing embodiments is a chiral group of at least 99% enantiomeric excess.

In an alternative embodiment, all else being the same, $R^1$ and $R^2$, and/or $R^3$ and $R^4$, are independently selected from the group consisting of hydrogen and (C1-C3)alkyl.

In one embodiment, an IDA molecule of the invention is selected from the group consisting of

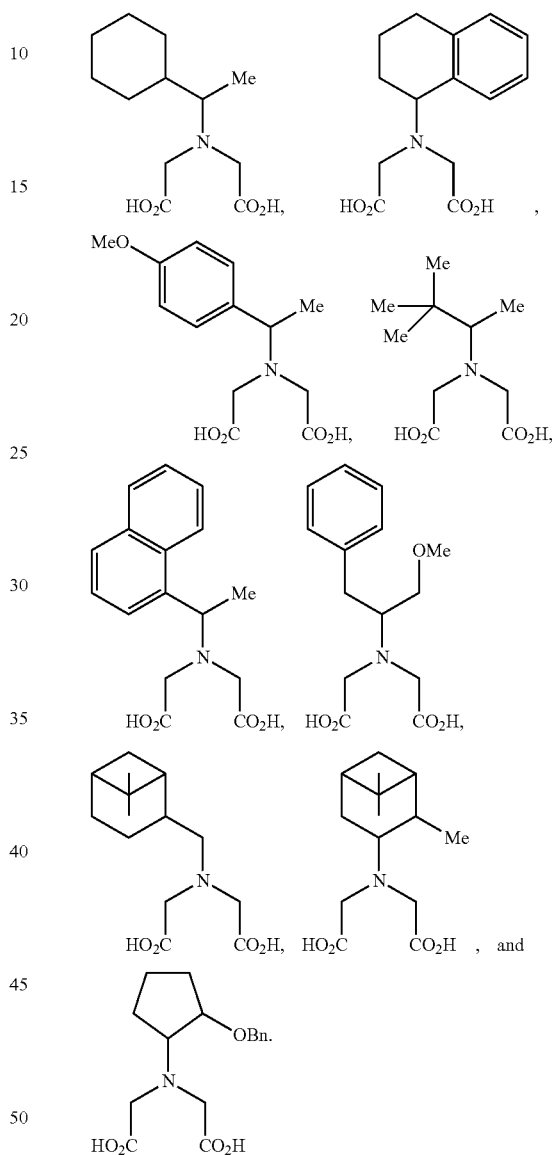

In one embodiment, an IDA molecule of the invention is selected from the grout) consisting of

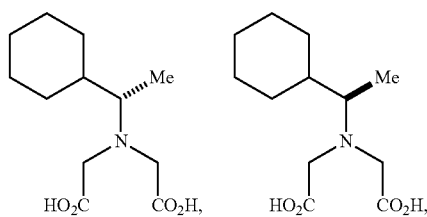

-continued
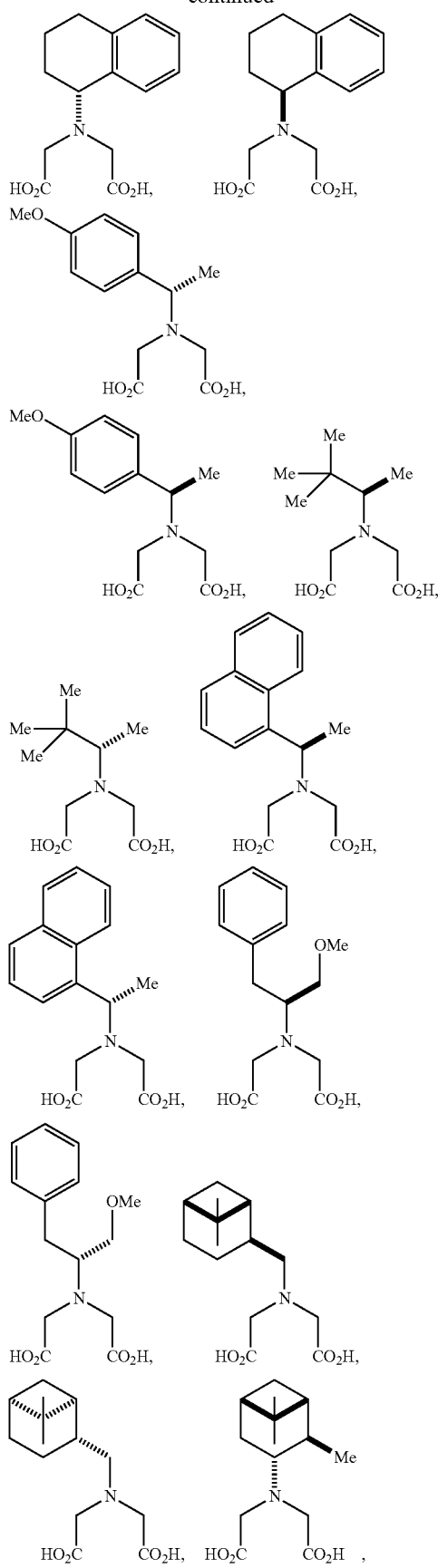
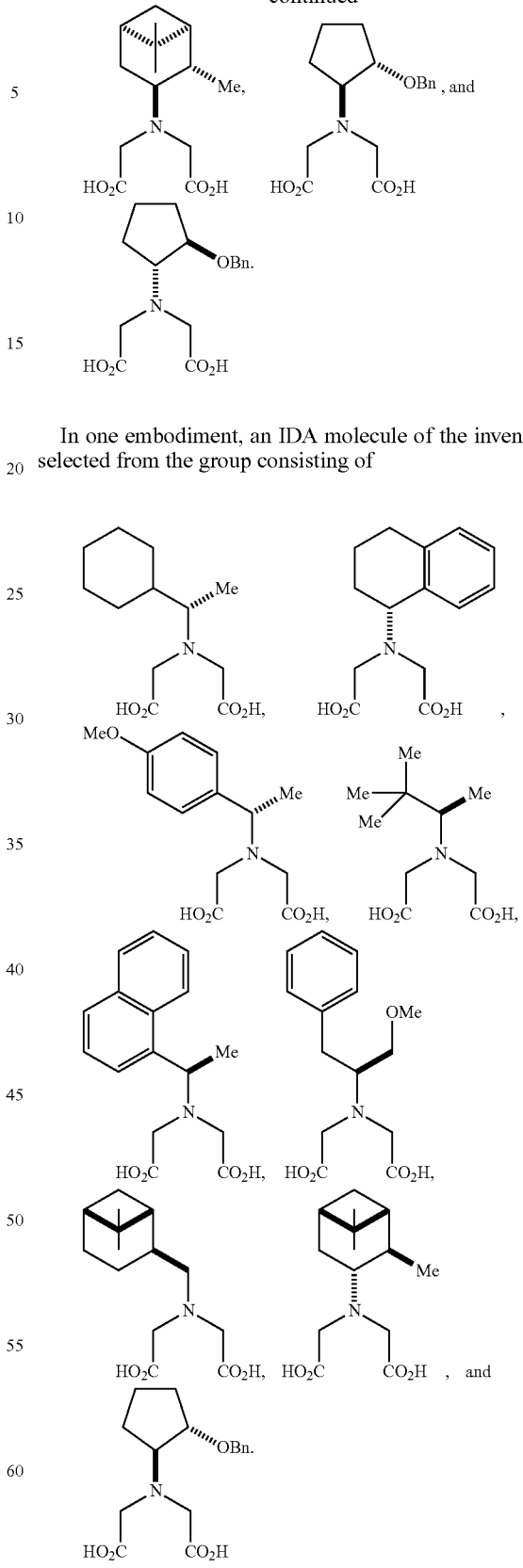
In one embodiment, an IDA molecule of the invention is selected from the group consisting of
In one embodiment the IDA molecules of the invention include at least one chiral carbon atom. In one embodiment the IDA molecules of the invention include at least one chiral carbon atom, wherein the chiral carbon atom is a chiral carbon atom of at least 90% enantiomeric excess.

In one embodiment an IDA molecule of the invention is a compound of formula (IV)

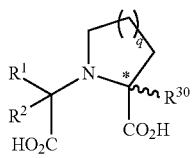

wherein:
$R^1$ and $R^2$ are both hydrogen or identically selected (C1-C3)alkyl;
$R^{30}$ is selected from the group consisting of hydrogen and (C1-C3)alkyl; and
q is 1 or 2.

In one embodiment, the IDA molecule in accordance with formula (IV) is not

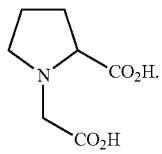 [SMILES: O=C(O)CN1CCCC1C(=O)O]

In one embodiment, q is 1 in any one of the foregoing embodiments.

In one embodiment the carbon atom marked "*" in formula (IV) is a chiral carbon atom of at least 90% enantiomeric excess. In one embodiment, the carbon atom marked "*" in formula (IV) in any one of the foregoing embodiments is a chiral carbon of at least 95% enantiomeric excess. In one embodiment, the carbon atom marked "*" in formula (IV) in any one of the foregoing embodiments is a carbon atom of at least 98% enantiomeric excess. In one embodiment, the carbon atom marked "*" in formula (IV) in any one of the foregoing embodiments is a carbon atom of at least 99% enantiomeric excess.

In an alternative embodiment, all else being the same, $R^1$ and $R^2$ are independently selected from the group consisting of hydrogen and (C1-C3)alkyl.

As is described in greater detail below, the foregoing IDA molecules and certain IDA molecules similar to the foregoing may be referred to as ligands and are useful for forming or preparing stereoisomerically enriched or substantially pure chiral organoboronic acid molecules of the invention.

An aspect of the invention concerns certain novel stereoselective protected organoboronic acid compounds. These stereoselective protected organoboronic acid compounds of the present invention share certain features and advantages of MIDA boronate compounds disclosed in US 2009/0030238, but they include the additional feature of having a chiral carbon, present in substantial enantiomeric excess, that is part of or appended to an IDA-derived ligand in such a manner as to be able to transfer stereochemical information to the organic group due to enforced proximity between the chiral center and the organic group.

In particular, an aspect of the invention is a compound of formula (I):

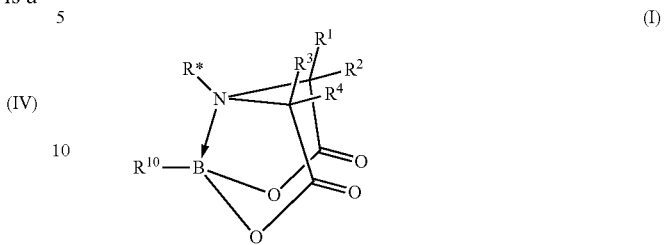

wherein:
B is a boron atom having sp³ hybridization;
R* is a chiral group

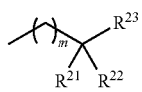

of at least 90% enantiomeric excess;
$R^{21}$ and $R^{22}$ are independently selected from the group consisting of hydrogen, alkyl, cycloalkyl, heterocyclyl, aryl, heteroaryl, aralkyl, and heteroaralkyl; or $R^{21}$ and $R^{22}$, taken together, form a 5-10-membered cycloalkyl or aromatic ring, or form a 5-10-membered heterocyclic or heteroaromatic ring comprising 1-3 heteroatoms independently selected from the group consisting of N, O, and S;
$R^{23}$ is selected from the group consisting of hydrogen, alkyl, cycloalkyl, heterocyclyl, aryl, heteroaryl, aralkyl, and heteroaralkyl;
$R^{10}$ is selected from the group consisting of

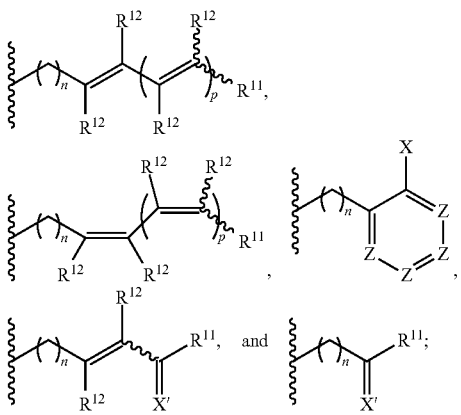

$R^{11}$ and each instance of $R^{12}$ are independently selected from the group consisting of hydrogen, halogen, hydroxyl, (C1-C10)alkyl, cycloalkyl, aryl, aralkyl, heteroaralkyl, alkoxyl, acyl, acyloxy, aryloxy, amino, and trialkylsilyloxy; or $R^{11}$ and any one instance of $R^{12}$, or any two instances of $R^{12}$, taken together, form a 3-10-membered ring;
X is halogen;
each instance of Z is independently selected from the group consisting of CH and N, provided that no more than two instances of Z are N;

X' is selected from the group consisting of $CR^5R^6$, O, S, and $NR^7$;

$R^1$ and $R^2$ are both hydrogen or identically selected (C1-C3)alkyl;

$R^3$ and $R^4$ are both hydrogen or identically selected (C1-C3)alkyl;

$R^5$ and $R^6$ are independently selected from the group consisting of hydrogen, halogen, hydroxyl, (C1-C10)alkyl, cycloalkyl, aryl, aralkyl, heteroaralkyl, alkoxyl, acyl, acyloxy, aryloxy, amino, and trialkylsilyloxy;

$R^7$ is selected from the group consisting of hydrogen and (C1-C3)alkyl;

m is 0, 1, or 2;

n is 0, 1, or 2; and p is 0, 1, or 2.

In an alternative embodiment, all else being the same, $R^1$ and $R^2$, and/or $R^3$ and $R^4$, are independently selected from the group consisting of hydrogen and (C1-C3)alkyl.

In one embodiment, R* is

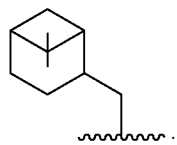 [SMILES: *CC1CCC2CC1C2(C)C]

In one embodiment, R* is

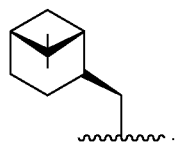

In one embodiment, R* is

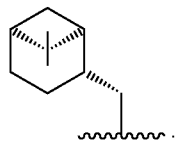

In one embodiment, R* is selected from the group consisting of

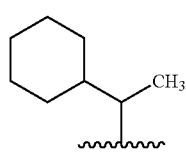 and 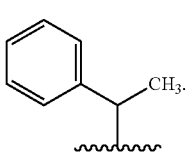

In one embodiment, R* is selected from the group consisting of

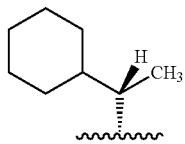 and 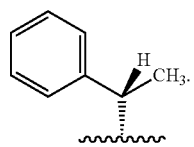

In one embodiment, R* is selected from the group consisting of

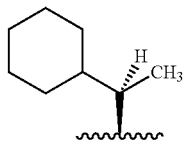 and 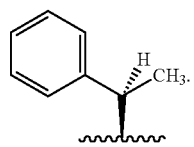

In one embodiment, $R^{21}$ and $R^{22}$, taken together, form a 5-10-membered cycloalkyl or aromatic ring, or form a 5-10-membered heterocyclic or heteroaromatic ring comprising 1-3 heteroatoms independently selected from the group consisting of N, O, and S.

In one embodiment, R* is

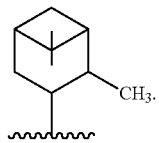 [SMILES: *C1CC2CC(C1C)C2(C)C]

In one embodiment, R* is

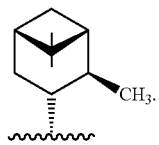

In one embodiment, R* is

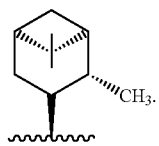

In one embodiment, R* is

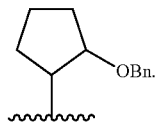 [SMILES: *C1CCCC1OCc1ccccc1]

In one embodiment, R* is

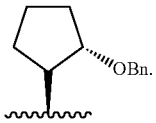

In one embodiment, R* is

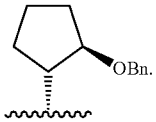

In accordance with any one of the foregoing embodiments, in one embodiment, $R^5$ and $R^6$ are independently selected from the group consisting of hydrogen and (C1-C3)alkyl.

In accordance with any one of the foregoing embodiments, in one embodiment, m is 0. Alternatively, in accordance with any one of the foregoing embodiments, in one embodiment, m is 1. Alternatively, in accordance with any one of the foregoing embodiments, in one embodiment, m is 2.

In accordance with any one of the foregoing embodiments, in one embodiment, n is 0. Alternatively, in accordance with any one of the foregoing embodiments, in one embodiment, n is 1. Alternatively, in accordance with any one of the foregoing embodiments, in one embodiment, n is 2.

In accordance with any one of the foregoing embodiments, in one embodiment, p is 0. Alternatively, in accordance with any one of the foregoing embodiments, in one embodiment, p is 1. Alternatively, in accordance with any one of the foregoing embodiments, in one embodiment, p is 2.

In accordance with any one of the foregoing embodiments not otherwise excluded, in one embodiment, $R^{10}$ is

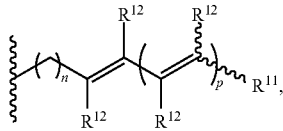

n is 0, p is 0, each instance of $R^{12}$ is hydrogen, and $R^{11}$ is selected from the group consisting of aryl and methyl.

Alternatively, in accordance with any one of the foregoing embodiments not otherwise excluded, in one embodiment, $R^{10}$ is

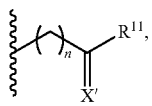

n is 0, X' is $CH_2$, and $R^{11}$ is methyl.

Alternatively, in accordance with any one of the foregoing embodiments not otherwise excluded, in one embodiment, $R^{10}$ is

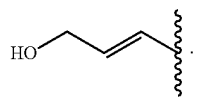

Alternatively, in accordance with any one of the foregoing embodiments not otherwise excluded, in one embodiment, $R^{10}$ is

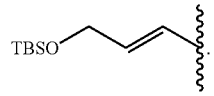

In accordance with any one of the foregoing embodiments, in one embodiment, R* is a chiral group

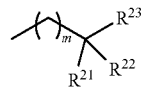

of at least 95% enantiomeric excess. In accordance with any one of the foregoing embodiments, in one embodiment, R* is a chiral group

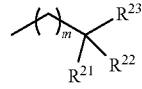

of at least 98% enantiomeric excess. In accordance with any one of the foregoing embodiments, in one embodiment, R* is a chiral group

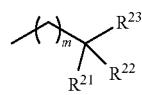

of at least 99% enantiomeric excess.

It will be appreciated that $R^{10}$ represents an organic group bonded to the boron atom through a B—C bond. Alternatively or in addition to embodiments of $R^{10}$ recited above, $R^{10}$ can, in accordance with this and other aspects of the invention, represent any suitable radical derived from a prochiral compound, including, for example, prochiral compounds disclosed in U.S. Pat. Nos. 4,713,380, 4,772,752, 5,068,432, and 5,159,116 (all four of which are incorporated by reference) to H. C. Brown, and including, but not limited to, cis-alkenes, trans-alkenes, cycloalkenes, phenyl-substituted alkenes, heterocyclic olefins, 2,3-dihydrofuran, 2,3-dihydrothiophene, 3,4-dihydro-2H-pyran, 3,4-dihydro-2H-thiophan, prochiral ketones, acetylenic ketones, aralkyl ketones, heteroaralkyl ketones, 3,3-dimethyl-2-butanone, acetophenone, 3-methyl-2-butanone, 2'-acetonapthone, 3-acetylpyridine, 2-acetylthiophene, butyrophenone, isobutyrophenone, pivalophenone, 1-indanone, 2-butanone, ethyl 2,2-dimethylcyclopentanone, 2,2-dimethylcyclohexanone, spiro[4,4]nonan-1-one, methyl 1-methyl-2-oxo-cyclopentane carboxylate, 1-methyl-2-norbornanone, haloarylalkylketone, acetylcyclohexane, 2,2-dimethylcyclopentanone, 2-chloroacetophenone, methyl benzoylformate, trans-4-phenyl-3-buten-2-one, 2-cyclohexen-1-one, 4-phenyl-3-butyn-2-one, and methylcyclohexanone.

Further in connection with stereoisomerically enriched or substantially pure chiral organoboronic acid compounds of the invention, an aspect of the invention is a compound of formula (II):

(II)

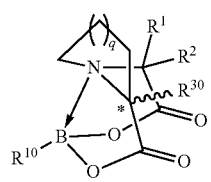

wherein:

B is a boron atom having sp³ hybridization;

the carbon atom marked "*" is a chiral carbon atom of at least 90% enantiomeric excess;

R¹⁰ is selected from the group consisting of

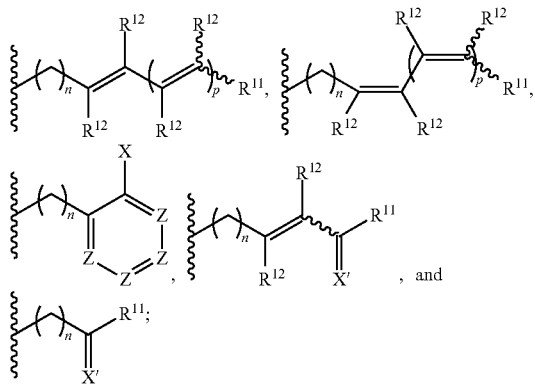

R¹¹ and each instance of R¹² are independently selected from the group consisting of hydrogen, halogen, hydroxyl, (C1-C10)alkyl, cycloalkyl, aryl, aralkyl, heteroaralkyl, alkoxyl, acyl, acyloxy, aryloxy, amino, and trialkylsilyloxy; or R¹¹ and any one instance of R¹², or any two instances of R¹², taken together, form a 3-10-membered ring;

X is halogen;

each instance of Z is independently selected from the group consisting of CH and N, provided that no more than two instances of Z are N;

X' is selected from the group consisting of CR⁵R⁶, O, S, and NR⁷;

R¹ and R² are both hydrogen or identically selected (C1-C3)alkyl;

R⁵ and R⁶ are independently selected from the group consisting of hydrogen, halogen, hydroxyl, (C1-C10)alkyl, cycloalkyl, aryl, aralkyl, heteroaralkyl, alkoxyl, acyl, acyloxy, aryloxy, amino, and trialkylsilyloxy;

R⁷ and R³⁰ are independently selected from the group consisting of hydrogen and (C1-C3)alkyl;

n is 0, 1, or 2;

p is 0, 1, or 2; and q is 1 or 2.

In an alternative embodiment, all else being the same, R¹ and R² are independently selected from the group consisting of hydrogen and (C1-C3)alkyl.

In one embodiment, the compound of formula (II) is

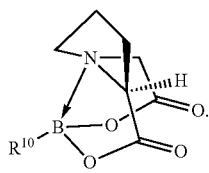

In accordance with any one of the foregoing embodiments, in one embodiment, n is 0. Alternatively, in accordance with any one of the foregoing embodiments, in one embodiment, n is 1. Alternatively, in accordance with any one of the foregoing embodiments, in one embodiment, n is 2.

In accordance with any one of the foregoing embodiments, in one embodiment, p is 0. Alternatively, in accordance with any one of the foregoing embodiments, in one embodiment, p is 1. Alternatively, in accordance with any one of the foregoing embodiments, in one embodiment, p is 2.

In accordance with any one of the foregoing embodiments, in one embodiment, q is 1. Alternatively, in accordance with any one of the foregoing embodiments, in one embodiment, q is 2.

In accordance with any one of the foregoing embodiments not otherwise excluded, in one embodiment, R¹⁰ is

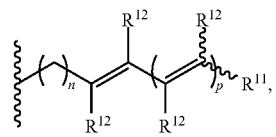

n is 0, p is 0, each instance of R¹² is hydrogen, and R¹¹ is selected from the group consisting of aryl and methyl.

Alternatively, in accordance with any one of the foregoing embodiments not otherwise excluded, in one embodiment, R¹⁰ is

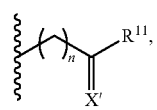

n is 0, X' is CH₂, and R¹¹ is methyl.

Alternatively, in accordance with any one of the foregoing embodiments not otherwise excluded, in one embodiment, R¹⁰ is

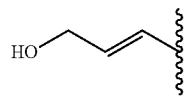

Alternatively, in accordance with any one of the foregoing embodiments not otherwise excluded, in one embodiment, R¹⁰ is

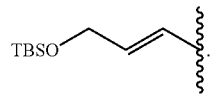

In accordance with any one of the foregoing embodiments, in one embodiment the carbon atom marked "*" is a chiral carbon atom of at least 95% enantiomeric excess. In accordance with any one of the foregoing embodiments, in one embodiment the carbon atom marked "*" is a chiral carbon atom of at least 98% enantiomeric excess. In accordance with any one of the foregoing embodiments, in one embodiment the carbon atom marked "*" is a chiral carbon atom of at least 99% enantiomeric excess.

Exemplary Methods Relating to Chiral IDA Compounds

Protected organoboronic acids according to formula (I) may be prepared by reaction of an appropriate N-substituted imino-di-carboxylic acid, such as appropriate ligands described above (e.g., in accordance with formula (III)), with the corresponding unprotected boronic acid of formula (V), as illustrated in the following reaction scheme:

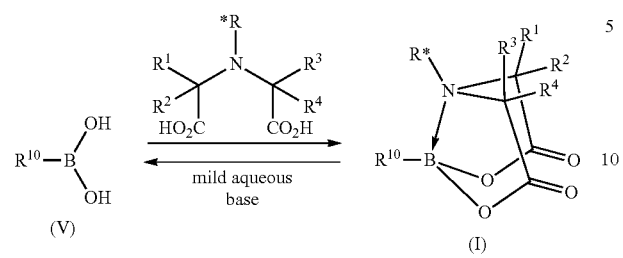

In a specific example, protected organoboronic acids according to formula (I) may be prepared by reaction of N-pinene-iminodiacetic acid (PIDA) with the corresponding unprotected boronic acid (V), as illustrated in the following reaction scheme:

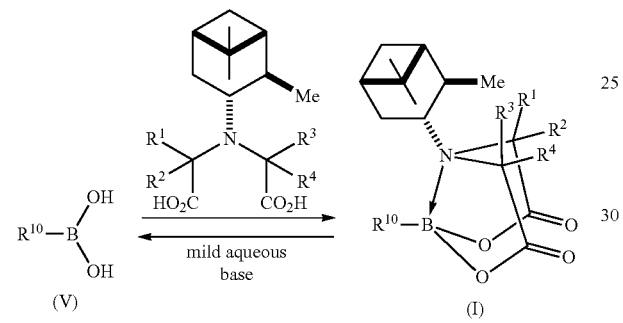

In each case, the protected organoboronic acid may be deprotected by contact with a mild aqueous base, to provide the free boronic acid (V).

Protected organoboronic acids according to formula (I) also may be prepared without using an isolated boronic acid as a reactant. The boronic acid may be formed in situ, just prior to its conversion to a protected organoboronic acid. Protected organoboronic acids also may be formed without ever forming the free boronic acid.

In one example, the boronic acid may be produced in situ, such as by hydrolysis of a boronate ester (i.e., $R^{10}$—B—(OR')(OR"), where R' and R" are organic groups). The boronate ester may be formed, for example, by addition of HB(OR')(OR") across the C—C multiple bond of an alkene or an alkyne. Brown (1972) *J Am Chem Soc* 94:4370-1. The boronate ester also may be formed, for example, by a Miyaura borylation (Miyaura et al. (1997) *Tet Lett* 38:3447-50; Miyaura et al. (1995) *J Org Chem* 60:7508-10); by reaction of an organohalide with an organolithium reagent, followed by reaction with boronate triester (i.e., B(OR)$_3$); or by reaction of a boronate triester with an organometal reagent (i.e., R—Li, R—Mg, R—Zn; Brown et al. (1983) *Organometallics* 2:1316-9. In another example, the boronic acid may be produced in situ, such as by treatment of a tri-substituted borane (i.e., $R^{10}$—BR'R") with acetaldehyde (R' and R" are organic groups). The tri-substituted borane may be formed, for example, by hydroborylation of an alkene or an alkyne with HBR'R", to add the HBR'R" across the C—C multiple bond.

In another example, a boronic halide (VI) may be reacted with a diacid or its corresponding salt to provide protected organoboronic acid (I), as illustrated in the following reaction scheme:

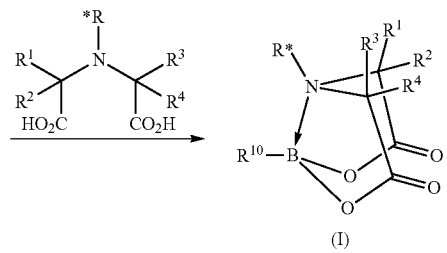

The boronic halide may be formed by hydroborylation of an alkene or an alkyne with HBX$_2$ (Brown (1984) *Organometallics* 3:1392-5; Brown (1982) *J Org Chem* 47:3808-10) or with BX$_3$. Soundararajan et al. (1990) *J Org Chem* 55:2274-5. The boronic halide also may be formed by treatment of a silane such as $R^1$—SiR$_3$ with BBr$_3$. Qin (2002) *J Am Chem Soc* 124:12672-3; Qin (2004) *Macromolecules* 37:7123-31.

An aspect of the invention concerns a method of forming a compound of formula (I)

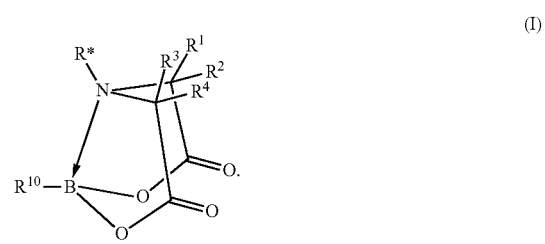

The method includes the step of reacting a compound represented by formula (III)

with a compound of formula (V)

wherein:
B in formula (I) is boron having sp$^3$ hybridization;
R* is a chiral group

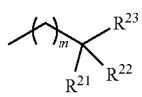

of at least 90% enantiomeric excess;
$R^{21}$ and $R^{22}$ are independently selected from the group consisting of hydrogen, alkyl, cycloalkyl, heterocyclyl, aryl, heteroaryl, aralkyl, and heteroaralkyl; or $R^{21}$ and $R^{22}$, taken together, form a 5-10-membered cycloalkyl or aromatic ring, or form a 5-10-membered heterocyclic or heteroaromatic ring comprising 1-3 heteroatoms independently selected from the group consisting of N, O, and S;

$R^{23}$ is selected from the group consisting of hydrogen, alkyl, cycloalkyl, heterocyclyl, aryl, heteroaryl, aralkyl, and heteroaralkyl;

$R^{10}$ is selected from the group consisting of

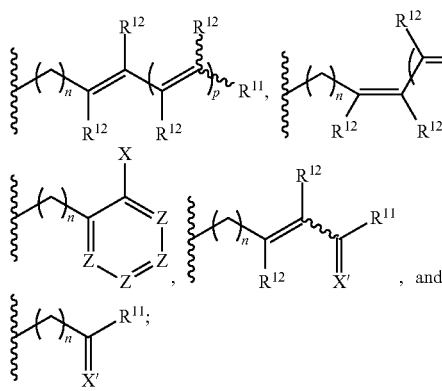

$R^{11}$ and each instance of $R^{12}$ are independently selected from the group consisting of hydrogen, halogen, hydroxyl, (C1-C10)alkyl, cycloalkyl, aryl, aralkyl, heteroaralkyl, alkoxyl, acyl, acyloxy, aryloxy, amino, and trialkylsilyloxy; or $R^{11}$ and any one instance of $R^{12}$, or any two instances of $R^{12}$, taken together, form a 3-10-membered ring;

X is halogen;

each instance of Z is independently selected from the group consisting of CH and N, provided that no more than two instances of Z are N;

X' is selected from the group consisting of $CR^5R^6$, O, S, and $NR^7$;

$R^1$ and $R^2$ are both hydrogen or identically selected (C1-C3)alkyl;

$R^3$ and $R^4$ are both hydrogen or identically selected (C1-C3)alkyl;

$R^5$ and $R^6$ are independently selected from the group consisting of hydrogen, halogen, hydroxyl, (C1-C10)alkyl, cycloalkyl, aryl, aralkyl, heteroaralkyl, alkoxyl, acyl, acyloxy, aryloxy, amino, and trialkylsilyloxy;

$R^7$ is selected from the group consisting of hydrogen and (C1-C3)alkyl;

m is 0, 1, or 2;

n is 0, 1, or 2; and p is 0, 1, or 2.

In one embodiment, R* is

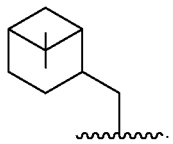 [SMILES: *CC1CCC2CC1C2(C)C]

In one embodiment, R* is

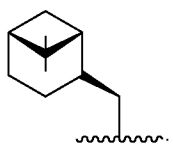

In one embodiment, R* is

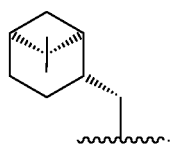

In one embodiment, R* is selected from the group consisting of

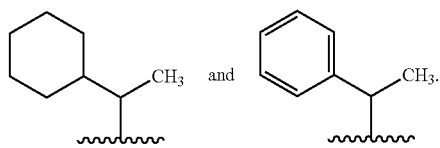

In one embodiment, R* is selected from the group consisting of

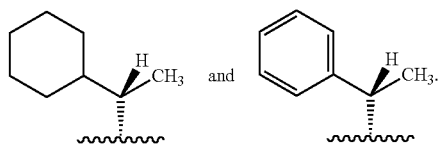

In one embodiment, R* is selected from the group consisting of

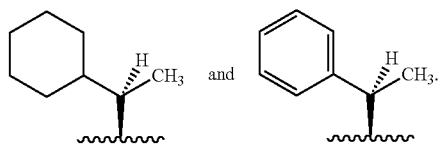

In one embodiment, $R^{21}$ and $R^{22}$, taken together, form a 5-10-membered cycloalkyl or aromatic ring, or form a 5-10-membered heterocyclic or heteroaromatic ring comprising 1-3 heteroatoms independently selected from the group consisting of N, O, and S.

In one embodiment, R* is

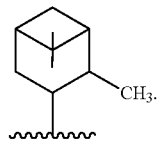 [SMILES: *C1CC2CC(C1C)C2(C)C]

In one embodiment, R* is

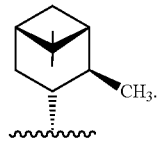

In one embodiment, R* is

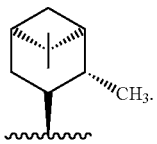

In one embodiment, R* is

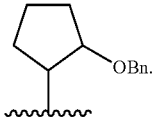 [SMILES: *C1CCCC1OCc1ccccc1]

In one embodiment, R* is

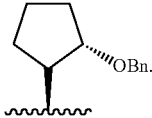

In one embodiment, R* is

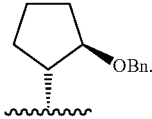

In accordance with any one of the foregoing embodiments, in one embodiment, $R^5$ and $R^6$ are independently selected from the group consisting of hydrogen and (C1-C3)alkyl.

In accordance with any one of the foregoing embodiments, in one embodiment, m is 0. Alternatively, in accordance with any one of the foregoing embodiments, in one embodiment, m is 1. Alternatively, in accordance with any one of the foregoing embodiments, in one embodiment, m is 2.

In accordance with any one of the foregoing embodiments, in one embodiment, n is 0. Alternatively, in accordance with any one of the foregoing embodiments, in one embodiment, n is 1. Alternatively, in accordance with any one of the foregoing embodiments, in one embodiment, n is 2.

In accordance with any one of the foregoing embodiments, in one embodiment, p is 0. Alternatively, in accordance with any one of the foregoing embodiments, in one embodiment, p is 1. Alternatively, in accordance with any one of the foregoing embodiments, in one embodiment, p is 2.

In accordance with any one of the foregoing embodiments not otherwise excluded, in one embodiment, $R^{10}$ is

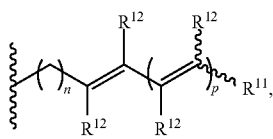

n is 0, p is 0, each instance of $R^{12}$ is hydrogen, and $R^{11}$ is selected from the group consisting of aryl and methyl.

Alternatively, in accordance with any one of the foregoing embodiments not otherwise excluded, in one embodiment, $R^{10}$ is

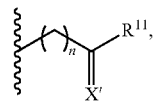

n is 0, X' is $CH_2$, and $R^{11}$ is methyl.

Alternatively, in accordance with any one of the foregoing embodiments not otherwise excluded, in one embodiment, $R^{10}$ is

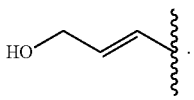

Alternatively, in accordance with any one of the foregoing embodiments not otherwise excluded, in one embodiment, $R^{10}$ is

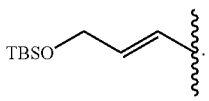

In accordance with any one of the foregoing embodiments, in one embodiment, R* is a chiral group

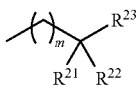

of at least 95% enantiomeric excess. In accordance with any one of the foregoing embodiments, in one embodiment, R* is a chiral group

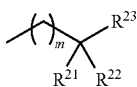

of at least 98% enantiomeric excess. In accordance with any one of the foregoing embodiments, in one embodiment, R* is a chiral group

of at least 99% enantiomeric excess.

An aspect of the invention concerns a method of forming a compound of formula (II)

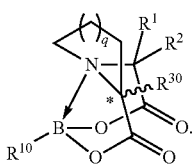
(II)

The method includes the step of reacting a compound represented by formula (IV)

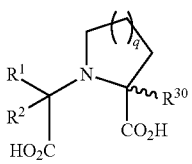
(IV)

with a compound of formula (V)

$R^{10}$—$B(OH)_2$ (V), wherein:
B in formula (II) is a boron atom having $sp^3$ hybridization;
the carbon atom marked "*" is a chiral carbon atom of at least 90% enantiomeric excess;
$R^{10}$ is selected from the group consisting of

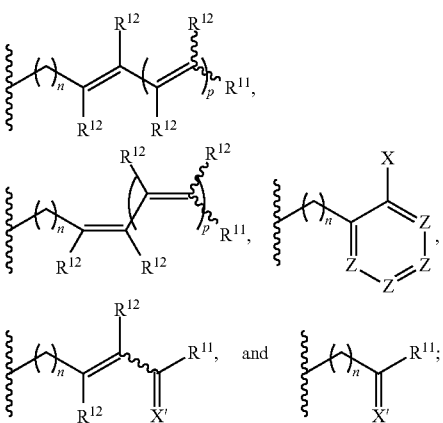

$R^{11}$ and each instance of $R^{12}$ are independently selected from the group consisting of hydrogen, halogen, hydroxyl, (C1-C10)alkyl, cycloalkyl, aryl, aralkyl, heteroaralkyl, alkoxyl, acyl, acyloxy, aryloxy, amino, and trialkylsilyloxy; or $R^{11}$ and any one instance of $R^{12}$, or any two instances of $R^{12}$, taken together, form a 3-10-membered ring;
X is halogen;
each instance of Z is independently selected from the group consisting of CH and N, provided that no more than two instances of Z are N;
X' is selected from the group consisting of $CR^5R^6$, O, S, and $NR^7$;
$R^1$ and $R^2$ are both hydrogen or identically selected (C1-C3)alkyl;
$R^5$ and $R^6$ are independently selected from the group consisting of hydrogen, halogen, hydroxyl, (C1-C10)alkyl, cycloalkyl, aryl, aralkyl, heteroaralkyl, alkoxyl, acyl, acyloxy, aryloxy, amino, and trialkylsilyloxy;
$R^7$ and $R^{30}$ are independently selected from the group consisting of hydrogen and (C1-C3)alkyl;
n is 0, 1, or 2;
p is 0, 1, or 2; and
q is 1 or 2.
In one embodiment, the compound of formula (II) is

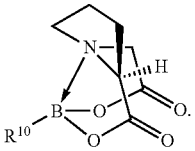

In accordance with any one of the foregoing embodiments, in one embodiment, $R^5$ and $R^6$ are independently selected from the group consisting of hydrogen and (C1-C3)alkyl.

In accordance with any one of the foregoing embodiments, in one embodiment, n is 0. Alternatively, in accordance with any one of the foregoing embodiments, in one embodiment, n is 1. Alternatively, in accordance with any one of the foregoing embodiments, in one embodiment, n is 2.

In accordance with any one of the foregoing embodiments, in one embodiment, p is 0. Alternatively, in accordance with any one of the foregoing embodiments, in one embodiment, p is 1. Alternatively, in accordance with any one of the foregoing embodiments, in one embodiment, p is 2.

In accordance with any one of the foregoing embodiments, in one embodiment, q is 1. Alternatively, in accordance with any one of the foregoing embodiments, in one embodiment, q is 2.

In accordance with any one of the foregoing embodiments not otherwise excluded, in one embodiment, $R^{10}$ is

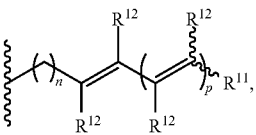

n is 0, p is 0, each instance of $R^{12}$ is hydrogen, and $R^{11}$ is selected from the group consisting of aryl and methyl.

Alternatively, in accordance with any one of the foregoing embodiments not otherwise excluded, in one embodiment, $R^{10}$ is

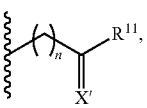

n is 0, X' is $CH_2$, and $R^{11}$ is methyl.

Alternatively, in accordance with any one of the foregoing embodiments not otherwise excluded, in one embodiment, $R^{10}$ is

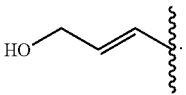 [SMILES: */C=C/CO]

Alternatively, in accordance with any one of the foregoing embodiments not otherwise excluded, in one embodiment, $R^{10}$ is

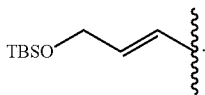

In accordance with any one of the foregoing embodiments, in one embodiment the carbon atom marked "*" is a chiral carbon atom of at least 95% enantiomeric excess. In accordance with any one of the foregoing embodiments, in one embodiment the carbon atom marked "*" is a chiral carbon atom of at least 98% enantiomeric excess. In accordance with any one of the foregoing embodiments, in one embodiment the carbon atom marked "*" is a chiral carbon atom of at least 99% enantiomeric excess.

The stereoisomerically enriched or substantially pure chiral organoboronic acids of the invention are useful in performing stereoselective chemical reactions. In addition to the use of the stereoisomerically enriched or substantially pure chiral organoboronic acids of the invention, the stereoselective reactions can further include the use of one or more chiral reagents, thereby achieving at least an additive effect in terms of the overall stereoselectivity of the reaction.

An aspect of the invention is a method of performing a stereoselective chemical reaction. The method includes the step of contacting a compound of formula (I) with a reagent

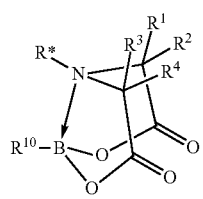

(I)

wherein:
$R^{10}$ is chemically transformed in a stereoselective manner;
B is a boron atom having sp$^3$ hybridization;
R* is a chiral group

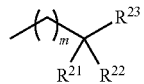

of at least 90% enantiomeric excess;
$R^{21}$ and $R^{22}$ are independently selected from the group consisting of hydrogen, alkyl, cycloalkyl, heterocyclyl, aryl, heteroaryl, aralkyl, and heteroaralkyl; or $R^{21}$ and $R^{22}$, taken together, form a 5-10-membered cycloalkyl or aromatic ring, or form a 5-10-membered heterocyclic or heteroaromatic ring comprising 1-3 heteroatoms independently selected from the group consisting of N, O, and S;
$R^{23}$ is selected from the group consisting of hydrogen, alkyl, cycloalkyl, heterocyclyl, aryl, heteroaryl, aralkyl, and heteroaralkyl;

$R^{10}$ is selected from the group consisting of

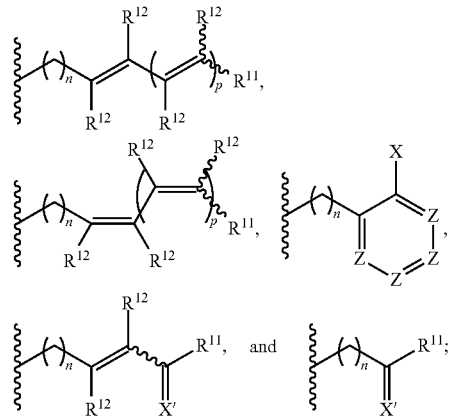

$R^{11}$ and each instance of $R^{12}$ are independently selected from the group consisting of hydrogen, halogen, hydroxyl, (C1-C10)alkyl, cycloalkyl, aryl, aralkyl, heteroaralkyl, alkoxyl, acyl, acyloxy, aryloxy, amino, and trialkylsilyloxy; or $R^{11}$ and any one instance of $R^{12}$, or any two instances of $R^{12}$, taken together, form a 3-10-membered ring;
X is halogen;
each instance of Z is independently selected from the group consisting of CH and N, provided that no more than two instances of Z are N;
X' is selected from the group consisting of $CR^5R^6$, O, S, and $NR^7$;
$R^1$ and $R^2$ are both hydrogen or identically selected (C1-C3)alkyl;
$R^3$ and $R^4$ are both hydrogen or identically selected (C1-C3)alkyl;
$R^5$ and $R^6$ are independently selected from the group consisting of hydrogen, halogen, hydroxyl, (C1-C10)alkyl, cycloalkyl, aryl, aralkyl, heteroaralkyl, alkoxyl, acyl, acyloxy, aryloxy, amino, and trialkylsilyloxy;
$R^7$ is selected from the group consisting of hydrogen and (C1-C3)alkyl;
m is 0, 1, or 2;
n is 0, 1, or 2; and
p is 0, 1, or 2.

In an alternative embodiment, all else being the same, $R^1$ and $R^2$, and/or $R^3$ and $R^4$, are independently selected from the group consisting of hydrogen and (C1-C3)alkyl.

In one embodiment, R* is

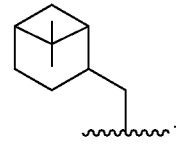

In one embodiment, R* is

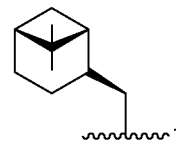

In one embodiment, R* is

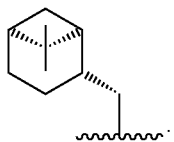

In one embodiment, R* is selected from the group consisting of

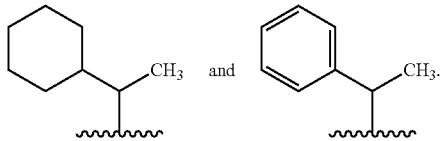

In one embodiment, R* is selected from the group consisting of

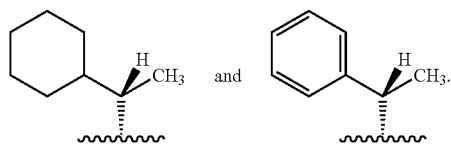

In one embodiment, R* is selected from the group consisting of

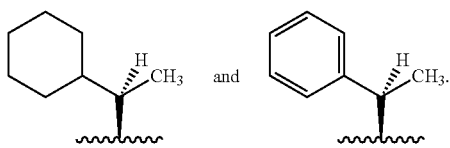

In one embodiment, $R^{21}$ and $R^{22}$, taken together, form a 5-10-membered cycloalkyl or aromatic ring, or form a 5-10-membered heterocyclic or heteroaromatic ring comprising 1-3 heteroatoms independently selected from the group consisting of N, O, and S.

In one embodiment, R* is

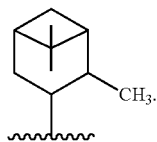 [SMILES: *C1CC2CC(C1C)C2(C)C]

In one embodiment, R* is

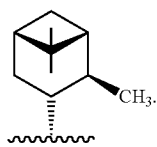

In one embodiment, R* is

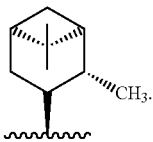

In one embodiment, R* is

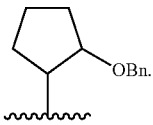 [SMILES: *C1CCCC1OCc1ccccc1]

In one embodiment, R* is

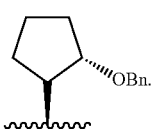

In one embodiment, R* is

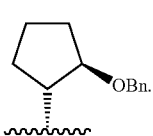

In accordance with any one of the foregoing embodiments, in one embodiment, $R^5$ and $R^6$ are independently selected from the group consisting of hydrogen and (C1-C3)alkyl.

In accordance with any one of the foregoing embodiments, in one embodiment, m is 0. Alternatively, in accordance with any one of the foregoing embodiments, in one embodiment, m is 1. Alternatively, in accordance with any one of the foregoing embodiments, in one embodiment, m is 2.

In accordance with any one of the foregoing embodiments, in one embodiment, n is 0. Alternatively, in accordance with any one of the foregoing embodiments, in one embodiment, n is 1. Alternatively, in accordance with any one of the foregoing embodiments, in one embodiment, n is 2.

In accordance with any one of the foregoing embodiments, in one embodiment, p is 0. Alternatively, in accordance with any one of the foregoing embodiments, in one embodiment, p is 1. Alternatively, in accordance with any one of the foregoing embodiments, in one embodiment, p is 2.

In accordance with any one of the foregoing embodiments not otherwise excluded,
in one embodiment, $R^{10}$ is

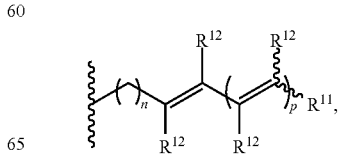

n is 0, p is 0, each instance of $R^{12}$ is hydrogen, and $R^{11}$ is selected from the group consisting of aryl and methyl.

Alternatively, in accordance with any one of the foregoing embodiments not otherwise excluded, in one embodiment, $R^{10}$ is

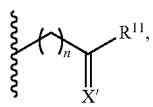

n is 0, X' is $CH_2$, and $R^{11}$ is methyl.

Alternatively, in accordance with any one of the foregoing embodiments not otherwise excluded, in one embodiment, $R^{10}$ is

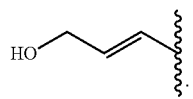

Alternatively, in accordance with any one of the foregoing embodiments not otherwise excluded, in one embodiment, $R^{10}$ is

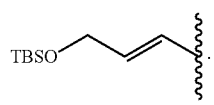 [SMILES: */C=C/CO[Si](C)(C)C(C)(C)C]

In accordance with any one of the foregoing embodiments, in one embodiment, R* is a chiral group

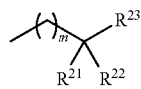

of at least 95% enantiomeric excess. In accordance with any one of the foregoing embodiments, in one embodiment, R* is a chiral group

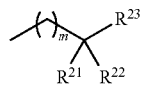

of at least 98% enantiomeric excess. In accordance with any one of the foregoing embodiments, in one embodiment, R* is a chiral group

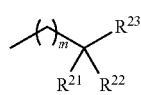

of at least 99% enantiomeric excess.

In accordance with any one of the foregoing embodiments, in one embodiment, the reagent is selected from the group consisting of oxidants, nucleophiles, bases, and electrophiles.

In accordance with any one of the foregoing embodiments, in one embodiment, reagent is meta-chloroperbenzoic acid (mCPBA).

In accordance with any one of the foregoing embodiments, in one embodiment, the chemical reaction is selected from epoxidation, nucleophilic substitution, electrophilic substitution, oxidation, dihydroxylation, carbonylation, alkenation, cyclopropanation, cycloaddition, conjugate addition, Michael addition, Diels-Alder reaction, and transition metal-catalyzed cross-coupling reaction.

In accordance with any one of the foregoing embodiments, in one embodiment, the transition metal-catalyzed cross-coupling reaction is a Suzuki-Miyaura reaction.

In accordance with any one of the foregoing embodiments, in one embodiment, the chemical reaction is epoxidation.

In accordance with any one of the foregoing embodiments, in one embodiment, the epoxidation is selected from the group consisting of Sharpless epoxidation and Jacobsen epoxidation.

In accordance with any one of the foregoing embodiments, in one embodiment, the reagent is a chiral reagent.

In accordance with any one of the foregoing embodiments, in one embodiment, the reagent is an achiral reagent.

An aspect of the invention is a method of performing a stereoselective chemical reaction. The method includes the step of contacting a compound of formula (II) with a

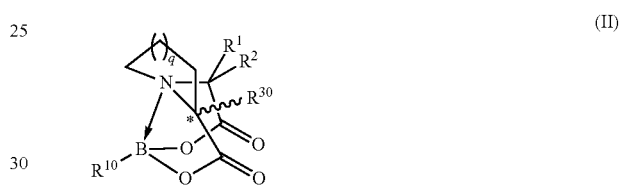

(II)

wherein:
$R^{10}$ is chemically transformed in a stereoselective manner;
the carbon atom marked "*" is a chiral carbon atom of at least 90% enantiomeric excess;
B is a boron atom having $sp^3$ hybridization;
$R^{10}$ is selected from the group consisting of

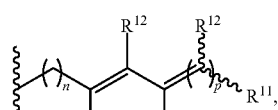

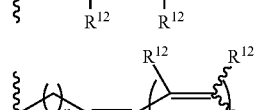

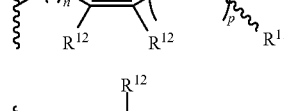

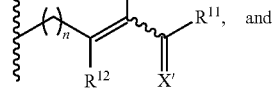

$R^{11}$ and each instance of $R^{12}$ are independently selected from the group consisting of hydrogen, halogen, hydroxyl, (C1-C10)alkyl, cycloalkyl, aryl, aralkyl, heteroaralkyl, alkoxyl, acyl, acyloxy, aryloxy, amino, and trialkylsilyloxy; or $R^{11}$ and any one instance of $R^{12}$, or any two instances of $R^{12}$, taken together, form a 3-10-membered ring;
X is halogen;
each instance of Z is independently selected from the group consisting of CH and N, provided that no more than two instances of Z are N;

X' is selected from the group consisting of $CR^5R^6$, O, S, and $NR^7$;

$R^1$ and $R^2$ are both hydrogen or identically selected (C1-C3)alkyl;

$R^5$ and $R^6$ are independently selected from the group consisting of hydrogen, halogen, hydroxyl, (C1-C10)alkyl, cycloalkyl, aryl, aralkyl, heteroaralkyl, alkoxyl, acyl, acyloxy, aryloxy, amino, and trialkylsilyloxy;

$R^7$ and $R^{30}$ are independently selected from the group consisting of hydrogen and (C1-C3)alkyl;

n is 0, 1, or 2;

p is 0, 1, or 2; and q is 1 or 2.

In an alternative embodiment, all else being the same, $R^1$ and $R^2$ are independently selected from the group consisting of hydrogen and (C1-C3)alkyl.

In one embodiment, the compound of formula (II) is

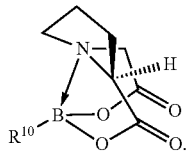

In accordance with any one of the foregoing embodiments, in one embodiment, $R^5$ and $R^6$ are independently selected from the group consisting of hydrogen and (C1-C3)alkyl.

In accordance with any one of the foregoing embodiments, in one embodiment, n is 0. Alternatively, in accordance with any one of the foregoing embodiments, in one embodiment, n is 1. Alternatively, in accordance with any one of the foregoing embodiments, in one embodiment, n is 2.

In accordance with any one of the foregoing embodiments, in one embodiment, p is 0. Alternatively, in accordance with any one of the foregoing embodiments, in one embodiment, p is 1. Alternatively, in accordance with any one of the foregoing embodiments, in one embodiment, p is 2.

In accordance with any one of the foregoing embodiments, in one embodiment, q is 1. Alternatively, in accordance with any one of the foregoing embodiments, in one embodiment, q is 2.

In accordance with any one of the foregoing embodiments not otherwise excluded, in one embodiment, $R^{10}$ is

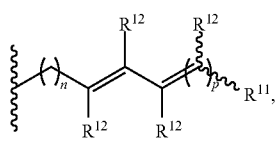

n is 0, p is 0, each instance of $R^{12}$ is hydrogen, and $R^{11}$ is selected from the group consisting of aryl and methyl.

Alternatively, in accordance with any one of the foregoing embodiments not otherwise excluded, in one embodiment, $R^{10}$ is

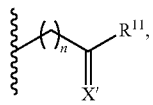

n is 0, X' is $CH_2$, and $R^{11}$ is methyl.

Alternatively, in accordance with any one of the foregoing embodiments not otherwise excluded, in one embodiment, $R^{10}$ is

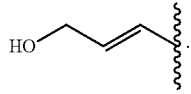

Alternatively, in accordance with any one of the foregoing embodiments not otherwise excluded, in one embodiment, $R^{10}$ is

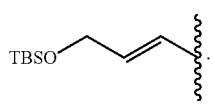 [SMILES: */C=C/CO[Si](C)(C)C(C)(C)C]

In accordance with any one of the foregoing embodiments, in one embodiment the carbon atom marked "*" is a chiral carbon atom of at least 95% enantiomeric excess. In accordance with any one of the foregoing embodiments, in one embodiment the carbon atom marked "*" is a chiral carbon atom of at least 98% enantiomeric excess. In accordance with any one of the foregoing embodiments, in one embodiment the carbon atom marked "*" is a chiral carbon atom of at least 99% enantiomeric excess.

In accordance with any one of the foregoing embodiments, in one embodiment, the reagent is selected from the group consisting of oxidants, nucleophiles, bases, and electrophiles.

In accordance with any one of the foregoing embodiments, in one embodiment, reagent is meta-chloroperbenzoic acid (mCPBA).

In accordance with any one of the foregoing embodiments, in one embodiment, the chemical reaction is selected from epoxidation, nucleophilic substitution, electrophilic substitution, oxidation, dihydroxylation, carbonylation, alkenation, cyclopropanation, cycloaddition, conjugate addition, Michael addition, Diels-Alder reaction, and transition metal-catalyzed cross-coupling reaction.

In accordance with any one of the foregoing embodiments, in one embodiment, the transition metal-catalyzed cross-coupling reaction is a Suzuki-Miyaura reaction.

In accordance with any one of the foregoing embodiments, in one embodiment, the chemical reaction is epoxidation.

In accordance with any one of the foregoing embodiments, in one embodiment, the epoxidation is selected from the group consisting of Sharpless epoxidation and Jacobsen epoxidation.

In accordance with any one of the foregoing embodiments, in one embodiment, the reagent is a chiral reagent.

In accordance with any one of the foregoing embodiments, in one embodiment, the reagent is an achiral reagent.

Similar to protected organoboronic acids including a MIDA boronate ester protecting group, stereoisomerically enriched or substantially pure chiral organoboronic acids of the present invention are readily purified by column chromatography. This is unusual for boronic acids, which are typically unstable to chromatographic techniques. These compounds also may be highly crystalline, which facilitates purification, utilization, and storage. These compounds are extremely stable to long term storage, including storage on the bench top under air. This is also unusual, as many boronic acids are unstable to long term storage.

Stereoisomerically enriched or substantially pure chiral organoboronic acids of the present invention are characterized in part by conformational rigidity of an organic protecting group. Conformational rigidity of an organic protecting group bonded to a boron atom is determined by the following "conformational rigidity test". A 10 milligram (mg) sample of a compound including a boron atom and an organic protecting group bonded to the boron is dissolved in dry $d_6$-DMSO and transferred to an NMR tube. The sample is then analyzed by $^1$H NMR at temperatures ranging from 23° C. to at least 100° C., e.g., to 150° C. At each temperature, the sample shim is optimized and a $^1$H NMR spectrum is obtained. If the protecting group is not conformationally rigid, then split peaks for a set of diastereotopic protons in the $^1$H NMR spectrum obtained at 23° C. will coalesce into a single peak in the $^1$H NMR spectrum obtained at 100° C. If the protecting group is conformationally rigid, then split peaks for a set of diastereotopic protons in the $^1$H NMR spectrum obtained at 23° C. will remain split and will not coalesce into a single peak in the $^1$H NMR spectrum obtained at 100° C.

Similar to the MIDA boronate compounds disclosed in US 2009/0030238, stereoisomerically enriched or substantially pure chiral organoboronic acids of the present invention have a number of advantageous properties. The IDA group is typically effective in decreasing the reactivity of the boronic acid to which it is esterified. One possible explanation for this decrease in reactivity is that a vacant, Lewis acidic boron p-orbital is not available to react with other substances. For example, the protected boron no longer has a vacant, Lewis acidic p-orbital to complex with the palladium catalyst involved in the Suzuki-Miyaura transformation. Thus, this protection strategy should decrease the reactivity of any boronic acid, including its reactivity toward the Suzuki-Miyaura transformation. In addition, the IDA boronate ester group seems to be stable to a wide variety of reaction conditions, besides cross-coupling. This stability may facilitate their utilization in the synthesis of complex synthetic building blocks that contain boronic acid functional groups.

Although these sp$^3$-hybridized boronate esters having a conformationally rigid protecting group bonded to the boron are protected from anhydrous Suzuki-Miyaura coupling even at 80° C. for 28 hours, deprotection can be readily achieved at 23° C. using extremely mild aqueous basic conditions. One example of deprotection conditions is treatment with 1 molar (M) aqueous sodium hydroxide (NaOH) in tetrahydrofuan (THF) for 10 minutes. Another example of deprotection conditions is treatment with saturated aqueous sodium bicarbonate (NaHCO$_3$) in methanol (MeOH) for 6 hours. These mild conditions are in contrast to typical protecting groups based on boronate esters, which can require harsh cleavage conditions.

Stereoisomerically enriched or substantially pure chiral organoboronic acids including a boron atom having sp$^3$ hybridization, a conformationally rigid protecting group bonded to the boron atom, and an organic group may be useful as synthetic building blocks. Examples of building blocks include protected haloorganoboronic acids. Further examples of building blocks include bis-boronates having a first boron atom having sp$^3$ hybridization and a conformationally rigid protecting group bonded to the first boron atom, and a second boron atom that may be present as a boronic acid or as a different type of protected boron. The protecting group in each of these building blocks is represented as the IDA boronate ester. Protected organoboronic acid building blocks may also include compounds having one or more substituent groups on the protecting group, and/or having a different group bonded to the nitrogen of the protecting group. For example, the protecting groups in these building blocks may be a protecting group as described for formula (I) or for formula (II).

These reactions demonstrate some of the possible applications of protected organoboronic acids that include a boron having sp$^3$ hybridization and having a conformationally rigid protecting group bonded to the boron. These compounds may be used for simple, highly modular syntheses of molecules through iterative Suzuki-Miyaura cross-coupling transformations. These transformations may involve bifunctional building blocks, such as protected organoboronic acids that include a halogen or a pseudohalogen group. For a given synthesis, all the building blocks may be prepared having the required functional groups preinstalled in the correct oxidation state and with the desired stereochemical relationships. These building blocks may then be brought together by the recursive application of one mild reaction, such as the Suzuki-Miyaura reaction. In addition to being very simple, efficient, and potentially amenable to automation, this strategy is inherently modular and thus well-suited for making collections of structural derivatives.

The synthesis of polyenes is made challenging by the sensitivity of conjugated double bond frameworks to many common synthetic reagents. Controlling the geometry of each double bond is also a critical issue. Many valuable methods have been developed, but synthetic strategies based on palladium-mediated cross-coupling are particularly attractive due to the mild and stereospecific nature of these reactions. In this vein, a variety of methods based on bis-metallated (Lhermitte et al. (1996) *Synlett* 377-9; Lipshutz et al. (1997) *J Am Chem Soc* 119:4555-6; Pihko et al. (1999) *Synlett* 12:1966-8; Babudri et al. (1998) *Tetrahedron* 54:1085-94; Murakami et al. (2004) *Synthesis* 9:1522-6; Denmark (2005) *J Am Chem Soc* 127:8004-5; Lipshutz et al. (2005) *Org Chem Lett* 7:4561-4; Coleman et al. (2005) *Org Lett* 7:2289-91; Coleman et al. (2007) *J Am Chem Soc* 129:3826-7) or bis-halogenated (Organ et al. (2000) *J Org Chem* 65:7959-70; Antunes et al. (2003) *Tetrahedron Lett* 44:6805-8; Organ et al. (2004) *Tetrahedron* 60:9453-61) lynchpin reagents have been reported. In these approaches, three fragments are brought together using two cross-coupling reactions to engage the orthogonally-reactive termini of the lynchpin.

An important advantage of the iterative cross-coupling strategy using protected organoboronic acids including a boron atom having sp$^3$ hybridization and having a conformationally rigid protecting group bonded to the boron atom is the inherent potential for limitless iteration. That is, all of the required building blocks can in theory be brought together via the recursive application of a single, mild reaction. This may dramatically simplify the synthesis process, and may readily enable analog preparation. The use of only one reaction also can help to minimize the potential for incompatibilities between the functional groups appended to the building blocks and the reaction conditions used to couple them. In addition, the use of bifunctional haloorganoboronic acids can avoid toxic metals such as organostannes, which are frequently employed in bis-metallated lynchpin-type reagents. Finally, the protected haloorganoboronic acids tend to be free-flowing crystalline solids that can be readily purified by silica gel chromatography and/or recrystallization and stored indefinitely on the benchtop under air.

Bifunctional PIDA-Protected Haloboronic Acids

A key to the development of apparatuses and methods for the automated synthesis of small molecules was the use of the Suzuki-Miyaura reaction to achieve the iterative cross-coupling (ICC) of bifunctional "haloboronic acids". However, in order to have an efficient automatable procedure, the development of a mild and selective method for reversibly attenuating one end of each haloboronic acid was required to avoid random oligomerization. In this vein, the apparatuses and methods described herein take advantage of the finding that the trivalent ligand N-pinene-derived iminodiacetic acid (PIDA), similar to N-methyliminodiacetic acid (MIDA), can act as a switch to turn the reactivity of a boronic acid "off" and "on" under very mild conditions (E. P. Gillis, M. D. Burke *J. Am. Chem. Soc.* 2007, 129, 6716-6717; and U.S. Patent Application Publication No. 2009/0030238, which is incorporated herein by reference in its entirety). This property of MIDA boronates has made it possible to prepare a variety of natural products via repeated cycles involving MIDA boronate deprotection, selective cross-coupling, and purification (S. J. Lee, K. C. Gray, J. S. Paek, M. D. Burke *J. Am. Chem. Soc.* 2008, 130, 466-468; E. P. Gillis, M. D. Burke, *J. Am. Chem. Soc.* 2008, 130, 14084-14085; and E. M. Woerly, A. H. Cherney, E. K. Davis, M. D. Burke, *J. Am. Chem. Soc.* 2010, 132, 6941-6943). Further enabling their general utility as building blocks, PIDA boronates are uniformly air-stable, highly crystalline, monomeric, free-flowing solids that are fully compatible with a wide range of common synthetic reagents and silica gel chromatography.

Purification of PIDA-Protected Organoboronic Acids

Transforming an ICC approach into a fully automated process requires a general strategy for purifying the synthetic intermediates. In the case of peptides, oligonucleotides, and oligosaccharides this problem has been solved by linking the growing oligomer to a solid support. At the end of each coupling reaction, the desired product is separated from residual solvents, reagents, and byproducts via a simple filtration. Albeit highly effective in these contexts, there are two major limitations of this purification approach as a foundation for ICC-based small molecule synthesis.

First, this strategy requires a ubiquitous chemical handle that enables covalent linking of the growing oligomer to the solid phase. In the case of peptides, oligonucleotides, and oligosaccharides, the respective monomers all conveniently contain a common heteroatom linking element as an inherent component of the targeted structure. In contrast, although some excellent solid-phase linking systems have been developed, small molecules are quite structurally diverse, and many lack a common functional group available for attachment to a solid phase.

Second, selectively coupling boronic acids in the presence of PIDA boronates requires that relatively anhydrous conditions be utilized because PIDA boronates are stable and unreactive under anhydrous basic conditions, but are readily hydrolyzed to yield reactive boronic acids when treated with aqueous base. In preliminary studies, it was found that translating the chemistry of anhydrous Suzuki-Miyaura cross-couplings to the solid-phase can be problematic.

Surprisingly, the inventors have discovered two remarkable physical properties of PIDA boronates, allowing the circumvention of both of the aforementioned challenges. Collectively, the two properties have enabled a highly effective alternative purification strategy and, thus, allowed the complete automation of ICC with solution-phase chemistry. The two purification strategies—"precipitation" and "catch-and-release"—are discussed in detail below. The two purification strategies can be used alone or in combination, in which case they may be performed sequentially in either order.

Purification by Precipitation. One aspect of the invention relates to the discovery that virtually all molecules containing a PIDA-protected organoboronic acid functional group are insoluble in hexanes:THF (3:1 v/v), while almost all boronic acids, other boronic esters, or related surrogates are soluble in this solvent system. This general physical property of PIDA boronates enables a highly efficient precipitation-based purification. (For background on precipitation-based purification see: H. Perrier, M. Labelle, *J. Org. Chem.* 1999, 64, 2110-2113; T. Bosanac, C. S. Wilcox, *Org. Lett.* 2004, 6, 2321-2324; and J. C. Poupon, A. A. Boezio, A. B. Charette, *Angew. Chem. Int. Ed.* 2006, 45, 1415-1420). Further, because most catalyst species and organic halides are soluble in hexanes:THF (3:1), PIDA boronates can be directly purified from cross-coupling reactions, such as anhydrous Suzuki cross-coupling reactions. Merely transferring a crude product mixture in THF (e.g., from a cross-coupling reaction) to a stirred vessel containing an amount of hexanes which is approximately three times the total volume of THF to be added results in rapid and quantitative precipitation of the chiral, non-racemic PIDA boronate product while the residual unreacted boronic acid, as well as most byproducts and other reaction components, such as palladium and phosphine ligands, all remain soluble in the hexane:THF (3:1 v/v) mixture. Simple filtration of this mixture, followed by dissolution of the precipitated chiral, non-racemic PIDA boronate with THF, yields a solution of semi-purified PIDA boronate.

One aspect of the invention relates to a method of purifying a chiral, non-racemic PIDA boronate from a solution, comprising the steps of diluting with hexane the solution comprising the PIDA boronate, thereby selectively precipitating the PIDA boronate; and isolating the precipitated PIDA boronate. The hexane can be any isomer of hexane or a mixture of hexanes. Exemplary isomers of hexane useful in the invention include unbranched hexane (n-hexane), branched hexanes (e.g., isohexane), and cyclohexane.

In certain embodiments, the present invention relates to any one of the aforementioned methods, wherein the precipitated chiral, non-racemic PIDA boronate is isolated by filtration.

In certain embodiments, the present invention relates to any one of the aforementioned methods, further comprising the step of dissolving the precipitated chiral, non-racemic PIDA boronate in a polar solvent. In certain embodiments, the present invention relates to any one of the aforementioned methods, further comprising the step of dissolving the precipitated chiral, non-racemic PIDA boronate in THF.

In certain embodiments, the present invention relates to any one of the aforementioned methods, wherein the solution comprising the chiral, non-racemic PIDA boronate is a THF solution.

In certain embodiments, the present invention relates to any one of the aforementioned methods, wherein the solution comprising the chiral, non-racemic PIDA boronate is added dropwise to the hexane.

In certain embodiments, the present invention relates to any one of the aforementioned methods, wherein the volume of hexane is between about two and about four times the volume of the solution comprising the PIDA boronate.

In certain embodiments, the present invention relates to any one of the aforementioned methods, wherein the volume of hexane is about three times the volume of the solution comprising the PIDA boronate.

In certain embodiments, the present invention relates to any one of the aforementioned methods, wherein the solution comprising the chiral, non-racemic PIDA boronate is a crude product mixture from a chemical reaction.

In certain embodiments, the present invention relates to any one of the aforementioned methods, wherein the chemical reaction is selected from the group consisting of a Suzuki-Miyaura coupling, an oxidation, a Swern oxidation, a "Jones reagents" oxidation, a reduction, an Evans' aldol reaction, an HWE olefination, a Takai olefination, an alcohol silylation, a desilylation, a p-methoxybenzylation, an iodination, a Negishi cross-coupling, a Heck coupling, a Miyaura borylation, a Stille coupling, and a Sonogashira coupling.

In certain embodiments, the present invention relates to any one of the aforementioned methods, wherein the chemical reaction is selected from epoxidation, nucleophilic substitution, electrophilic substitution, oxidation, dihydroxylation, carbonylation, alkenation, cyclopropanation, cycloaddition, conjugate addition, Michael addition, Diels-Alder reaction, and transition metal-catalyzed cross-coupling reaction.

In accordance with any one of the foregoing embodiments, in one embodiment, the transition metal-catalyzed cross-coupling reaction is a Suzuki-Miyaura reaction.

In accordance with any one of the foregoing embodiments, in one embodiment, the chemical reaction is epoxidation.

In accordance with any one of the foregoing embodiments, in one embodiment, the epoxidation is selected from the group consisting of Sharpless epoxidation and Jacobsen epoxidation.

In certain embodiments, the present invention relates to any one of the aforementioned methods, wherein the chemical reaction comprises the step of contacting a chiral, non-racemic PIDA boronate with a reagent, wherein the chiral, non-racemic PIDA boronate comprises a boron having an $sp^3$ hybridization, a PIDA protecting group bonded to the boron, and an organic group bonded to the boron through a boron-carbon bond; the organic group is chemically transformed, and the boron is not chemically transformed.

In certain embodiments, the present invention relates to any one of the aforementioned methods, wherein the chiral, non-racemic PIDA boronate is represented by

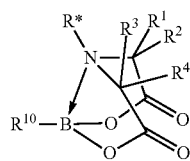

(I)

wherein:
B is a boron atom having $sp^3$ hybridization;
R* is a chiral group

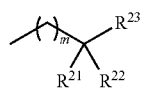

of at least 90% enantiomeric excess;
$R^{21}$ and $R^{22}$ are independently selected from the group consisting of hydrogen, alkyl, cycloalkyl, heterocyclyl, aryl, heteroaryl, aralkyl, and heteroaralkyl; or $R^{21}$ and $R^{22}$, taken together, form a 5-10-membered cycloalkyl or aromatic ring, or form a 5-10-membered heterocyclic or heteroaromatic ring comprising 1-3 heteroatoms independently selected from the group consisting of N, O, and S;
$R^{23}$ is selected from the group consisting of hydrogen, alkyl, cycloalkyl, heterocyclyl, aryl, heteroaryl, aralkyl, and heteroaralkyl;

$R^{10}$ is selected from the group consisting of

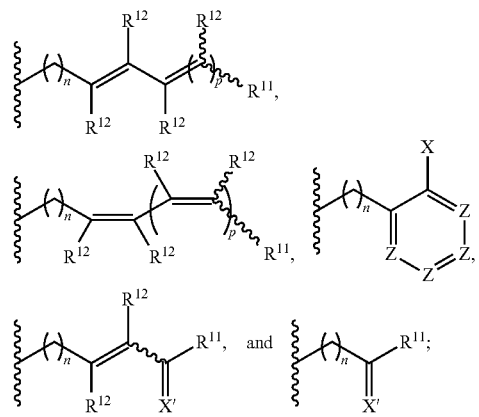

$R^{11}$ and each instance of $R^{12}$ are independently selected from the group consisting of hydrogen, halogen, hydroxyl, (C1-C10)alkyl, cycloalkyl, aryl, aralkyl, heteroaralkyl, alkoxyl, acyl, acyloxy, aryloxy, amino, and trialkylsilyloxy; or $R^{11}$ and any one instance of $R^{12}$, or any two instances of $R^{12}$, taken together, form a 3-10-membered ring;
X is halogen;
each instance of Z is independently selected from the group consisting of CH and N, provided that no more than two instances of Z are N;
X' is selected from the group consisting of $CR^5R^6$, O, S, and $NR^7$;
$R^1$ and $R^2$ are both hydrogen or identically selected (C1-C3)alkyl;
$R^3$ and $R^4$ are both hydrogen or identically selected (C1-C3)alkyl;
$R^5$ and $R^6$ are independently selected from the group consisting of hydrogen, halogen, hydroxyl, (C1-C10)alkyl, cycloalkyl, aryl, aralkyl, heteroaralkyl, alkoxyl, acyl, acyloxy, aryloxy, amino, and trialkylsilyloxy;
$R^7$ is selected from the group consisting of hydrogen and (C1-C3)alkyl;
m is 0, 1, or 2;
n is 0, 1, or 2; and
p is 0, 1, or 2.

In an alternative embodiment, all else being the same, $R^1$ and $R^2$, and/or $R^3$ and $R^4$, are independently selected from the group consisting of hydrogen and (C1-C3)alkyl.

In one embodiment, R* is

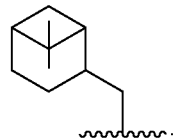 [SMILES: *CC1CCC2CC1C2(C)C]

In one embodiment, R* is

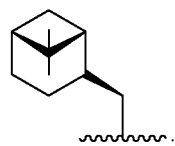

In one embodiment, R* is

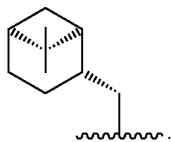

In one embodiment, R* is selected from the group consisting of

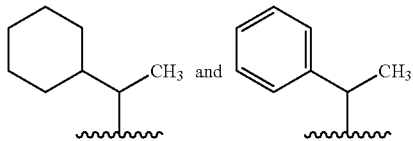

In one embodiment, R* is selected from the group consisting of

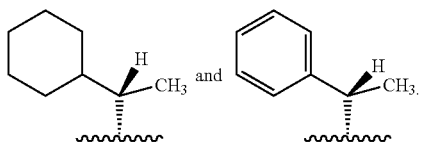

In one embodiment, R* is selected from the group consisting of

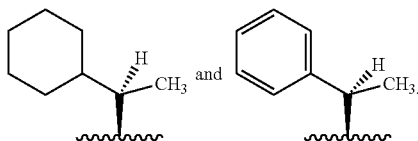

In one embodiment, $R^{21}$ and $R^{22}$, taken together, form a 5-10-membered cycloalkyl or aromatic ring, or form a 5-10-membered heterocyclic or heteroaromatic ring comprising 1-3 heteroatoms independently selected from the group consisting of N, O, and S.

In one embodiment, R* is

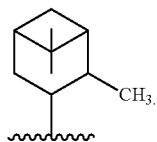 [SMILES: *C1CC2CC(C1C)C2(C)C]

In one embodiment, R* is

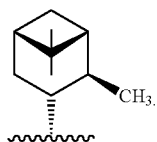

In one embodiment, R* is

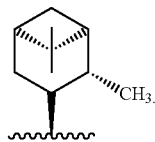

In one embodiment, R* is

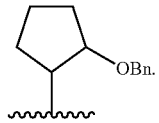

In one embodiment, R* is

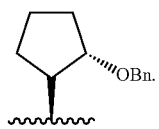

In one embodiment, R* is

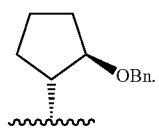

In accordance with any one of the foregoing embodiments, in one embodiment, $R^5$ and $R^6$ are independently selected from the group consisting of hydrogen and (C1-C3)alkyl.

In accordance with any one of the foregoing embodiments, in one embodiment, m is 0. Alternatively, in accordance with any one of the foregoing embodiments, in one embodiment, m is 1. Alternatively, in accordance with any one of the foregoing embodiments, in one embodiment, m is 2.

In accordance with any one of the foregoing embodiments, in one embodiment, n is 0. Alternatively, in accordance with any one of the foregoing embodiments, in one embodiment, n is 1. Alternatively, in accordance with any one of the foregoing embodiments, in one embodiment, n is 2.

In accordance with any one of the foregoing embodiments, in one embodiment, p is 0. Alternatively, in accordance with any one of the foregoing embodiments, in one embodiment, p is 1. Alternatively, in accordance with any one of the foregoing embodiments, in one embodiment, p is 2.

In accordance with any one of the foregoing embodiments not otherwise excluded, in one embodiment, $R^{10}$ is

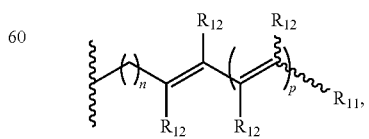

n is 0, p is 0, each instance of $R^{12}$ is hydrogen, and $R^{11}$ is selected from the group consisting of aryl and methyl.

Alternatively, in accordance with any one of the foregoing embodiments not otherwise excluded, in one embodiment, $R^{10}$ is

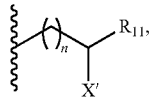

n is 0, X' is $CH_2$, and $R^{11}$ is methyl.

Alternatively, in accordance with any one of the foregoing embodiments not otherwise excluded, in one embodiment, $R^{10}$ is

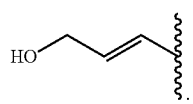

Alternatively, in accordance with any one of the foregoing embodiments not otherwise excluded, in one embodiment, $R^{10}$ is

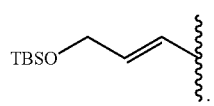 [SMILES: */C=C/CO[Si](C)(C)C(C)(C)C]

In accordance with any one of the foregoing embodiments, in one embodiment, R* is a chiral group

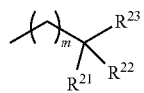

of at least 95% enantiomeric excess. In accordance with any one of the foregoing embodiments, in one embodiment, R* is a chiral group

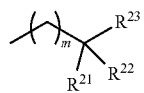

of at least 98% enantiomeric excess. In accordance with any one of the foregoing embodiments, in one embodiment, R* is a chiral group

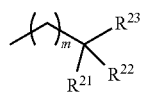

of at least 99% enantiomeric excess.

In certain embodiments, the present invention relates to any one of the aforementioned methods, wherein the chiral, non-racemic PIDA boronate is represented by

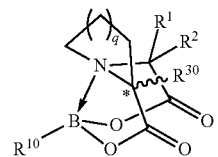

wherein:

B is a boron atom having $sp^3$ hybridization;

the carbon atom marked "*" is a chiral carbon atom of at least 90% enantiomeric excess;

$R^{10}$ is selected from the group consisting of

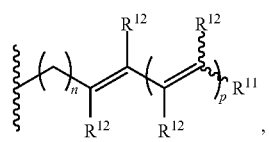

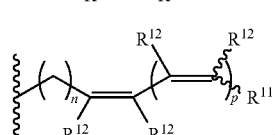

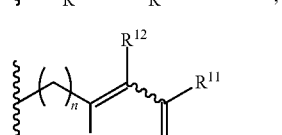

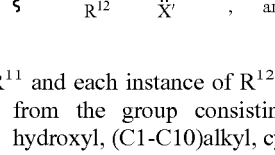

$R^{11}$ and each instance of $R^{12}$ are independently selected from the group consisting of hydrogen, halogen, hydroxyl, (C1-C10)alkyl, cycloalkyl, aryl, aralkyl, heteroaralkyl, alkoxyl, acyl, acyloxy, aryloxy, amino, and trialkylsilyloxy; or $R^{11}$ and any one instance of $R^{12}$, or any two instances of $R^{12}$, taken together, form a 3-10-membered ring;

X is halogen;

each instance of Z is independently selected from the group consisting of CH and N, provided that no more than two instances of Z are N;

X' is selected from the group consisting of $CR^5R^6$, O, S, and $NR^7$;

$R^1$ and $R^2$ are both hydrogen or identically selected (C1-C3)alkyl;

$R^5$ and $R^6$ are independently selected from the group consisting of hydrogen, halogen, hydroxyl, (C1-C10)alkyl, cycloalkyl, aryl, aralkyl, heteroaralkyl, alkoxyl, acyl, acyloxy, aryloxy, amino, and trialkylsilyloxy;

$R^7$ and $R^{30}$ are independently selected from the group consisting of hydrogen and (C1-C3)alkyl;

n is 0, 1, or 2;

p is 0, 1, or 2; and q is 1 or 2.

In an alternative embodiment, all else being the same, $R^1$ and $R^2$ are independently selected from the group consisting of hydrogen and (C1-C3)alkyl.

In one embodiment, the compound of formula (II) is

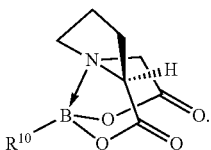

In accordance with any one of the foregoing embodiments, in one embodiment, n is 0. Alternatively, in accordance with any one of the foregoing embodiments, in one embodiment, n is 1. Alternatively, in accordance with any one of the foregoing embodiments, in one embodiment, n is 2.

In accordance with any one of the foregoing embodiments, in one embodiment, p is 0. Alternatively, in accordance with any one of the foregoing embodiments, in one embodiment, p is 1. Alternatively, in accordance with any one of the foregoing embodiments, in one embodiment, p is 2.

In accordance with any one of the foregoing embodiments, in one embodiment, q is 1. Alternatively, in accordance with any one of the foregoing embodiments, in one embodiment, q is 2.

In accordance with any one of the foregoing embodiments not otherwise excluded, in one embodiment, $R^{10}$ is

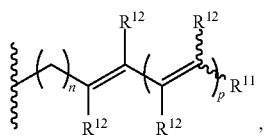

n is 0, p is 0, each instance of $R^{12}$ is hydrogen, and $R^{11}$ is selected from the group consisting of aryl and methyl.

Alternatively, in accordance with any one of the foregoing embodiments not otherwise excluded, in one embodiment, $R^{10}$ is

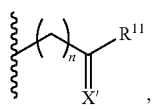

n is 0, X' is $CH_2$, and $R^{11}$ is methyl.

Alternatively, in accordance with any one of the foregoing embodiments not otherwise excluded, in one embodiment, $R^{10}$ is

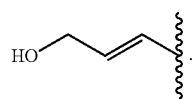

Alternatively, in accordance with any one of the foregoing embodiments not otherwise excluded, in one embodiment, $R^{10}$ is

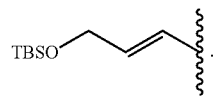

In accordance with any one of the foregoing embodiments, in one embodiment the carbon atom marked "*" is a chiral carbon atom of at least 95% enantiomeric excess. In accordance with any one of the foregoing embodiments, in one embodiment the carbon atom marked "*" is a chiral carbon atom of at least 98% enantiomeric excess. In accordance with any one of the foregoing embodiments, in one embodiment the carbon atom marked "*" is a chiral carbon atom of at least 99% enantiomeric excess.

Catch-and-Release Purification. It has further been found that all molecules which contain a chiral, non-racemic PIDA boronate functional group have exceptionally high affinity for silica gel. For example, it has been discovered that PIDA boronates, regardless of the nature of the organic group appended to boron, have an $R_f$ of essentially zero in hexanes: THF (3:1 v/v), $Et_2O$, and $Et_2O$:MeOH (98.5:1.5 v/v). Therefore, PIDA boronates can be used as a universal tag for catch-and-release purification on silica gel. (For an excellent review on tagging strategies for separations in organic synthesis, see: J. Yoshida, K. Itami, Chem. Rev. 2002, 102, 3693-3716. For an excellent review on modern separation techniques in organic synthesis, see: C. C. Tzschucke, C. Markert, W. Bannwarth, S. Roller, A. Hebel, R. Haag, Angew. Chem. Int. Ed. 2002, 41, 3964-4000. See, also, D. P. Curran, Angew. Chem. Int. Ed. 1998, 37, 1174-1196; P. H. Toy, K. D. Janda, Acc. Chem. Res. 2000, 33, 546-554; S. V. Ley, A. Massi, F. Rodriguez, D. C. Horwell, R. A. Lewthwaite, M. C. Pritchard, A. M. Reid, Angew. Chem. Int. Ed. 2001, 40, 1053-1055; A. R. Brown, S. L. Irving, R. Ramage, G. Raphy Tetrahedron 1995, 51, 11815-11830; L. A. Thompson, Curr. Opin. Chem. Bio. 2000, 4, 324-337; and M. G. Siegel, P. J. Hahn, B. A. Dressman, J. E. Fritz, J. R. Grunwell, S. W. Kaldor, Tetrahedron Lett. 1997, 38, 3357-3360. For the use of catch-and-release type methods to purify proteins, see: J. Porath, J. Carlsson, I. Olsson, G. Belfrage, Nature 1975, 278, 598.) In other words, the chiral, non-racemic PIDA boronate functional group, which is conveniently present in all intermediates utilized in certain ICC sequences, enables the reversible non-covalent attachment of any chiral, non-racemic PIDA boronate to silica gel, a solid support.

The use of hexanes:THF (e.g., 3:1 v/v) as a solvent system is important since it provides a means (via diluting with hexanes) to purify directly THF reaction solutions containing PIDA boronates. With regards to automated synthesis, as discussed below, this feature is important because advanced manipulations, such as solvent evaporation, are not required to prepare the reaction solution for purification. The use of $Et_2O$ is important because in certain coupling reactions almost every other compound present in the reaction solution elutes in $Et_2O$. Interestingly, the addition of 1.5% MeOH (v/v) to the $Et_2O$ ensures that even polar boronic acids are eluted off of the column with a reasonable amount of solvent. The compatibility of MeOH with PIDA boronates in the purification method was unexpected since MeOH can be used to deprotect PIDA boronates to the corresponding boronic acid at room temperature. All of the above-mentioned properties have been tested with many PIDA boronates and have been shown to be general. Once the unreacted boronic acids, as well as reaction regents, have been eluted, pure PIDA boronates generally elute well in THF. Also, PIDA boronates generally elute well with MeCN and acetone.

One aspect of the invention relates to a method of purifying a chiral, non-racemic PIDA boronate from a solution, comprising the steps of passing the solution through a silica plug; passing a first liquid through the silica plug; and passing a second liquid through the silica plug, thereby eluting the chiral, non-racemic PIDA boronate in the second liquid; wherein the first liquid contains diethyl ether or the polarity of the first liquid is less than or equal to about the polarity of a mixture of 98.5:1.5 (v/v) $Et_2O$:MeOH; and the polarity of the second liquid is greater than or equal to about the polarity of THF.

PIDA boronates, like most organic compounds, generally elute more rapidly off of SiO$_2$ (i.e., have a higher R$_f$) when the polarity of the solvent is higher. However, the purification method described above takes advantage of special properties of PIDA boronates in certain solvents. Specifically, there are certain solvent systems in which the R$_f$ of a chiral, non-racemic PIDA boronate is not related to the polarity of the solvent. In fact, in certain solvent systems the R$_f$ can approach or be zero. For example, even though chloroform is more polar than THF, the R$_f$ of dodecyl chiral, non-racemic PIDA boronate in chloroform is 0.00 and in THF is 0.80. While not intending to be bound by any particular theory, this very surprising phenomenon likely involves a unique interaction among all three factors: the solvent, silica gel, and PIDA boronate. Thus, it is possible to isolate a chiral, non-racemic PIDA boronate on a silica column if one picks a solvent that is an exception to the elution rules (such as chloroform or Et$_2$O). To remove a chiral, non-racemic PIDA boronate from the column thus loaded, one switches to a polar solvent that obeys the normal elution rules (such as THF, MeCN, or acetone).

It has also been found that a functionalized silica gel, such as 3-aminopropyl-functionalized silica gel, can be substituted for SiO$_2$ without affecting the properties of the PIDA boronate/SiO$_2$ interaction. The functionalized silica gel can be used to scavenge, for example, metal catalysts from the solution. Therefore, in certain embodiments, the present invention relates to any one of the aforementioned methods, wherein the silica is 3-aminopropyl-functionalized silica.

In certain embodiments, the present invention relates to any one of the aforementioned methods, wherein the first liquid comprises diethyl ether.

In certain embodiments, the present invention relates to any one of the aforementioned methods, wherein the first liquid is diethyl ether.

In certain embodiments, the present invention relates to any one of the aforementioned methods, wherein the first liquid is a mixture of diethyl ether and methanol.

In certain embodiments, the present invention relates to any one of the aforementioned methods, wherein first liquid is a mixture of diethyl ether and methanol; and the ratio of diethyl ether to methanol is 98.5:1.5 (v/v).

In certain embodiments, the present invention relates to any one of the aforementioned methods, wherein the second liquid is THF, MeCN, ethyl acetate or acetone, or a solvent of similar polarity.

In certain embodiments, the present invention relates to any one of the aforementioned methods, wherein the second liquid is THF, MeCN, ethyl acetate or acetone.

In certain embodiments, the present invention relates to any one of the aforementioned methods, wherein the second liquid is THF.

In certain embodiments, the present invention relates to any one of the aforementioned methods, wherein the solution is a crude product mixture from a chemical reaction.

In certain embodiments, the present invention relates to any one of the aforementioned methods, wherein the chemical reaction is selected from the group consisting of a Suzuki-Miyaura coupling, an oxidation, a Swern oxidation, a "Jones reagents" oxidation, a reduction, an Evans' aldol reaction, an HWE olefination, a Takai olefination, an alcohol silylation, a desilylation, a p-methoxybenzylation, an iodination, a Negishi cross-coupling, a Heck coupling, a Miyaura borylation, a Stille coupling, and a Sonogashira coupling.

In certain embodiments, the present invention relates to any one of the aforementioned methods, wherein the chemical reaction is selected from epoxidation, nucleophilic substitution, electrophilic substitution, oxidation, dihydroxylation, carbonylation, alkenation, cyclopropanation, cycloaddition, conjugate addition, Michael addition, Diels-Alder reaction, and transition metal-catalyzed cross-coupling reaction.

In accordance with any one of the foregoing embodiments, in one embodiment, the transition metal-catalyzed cross-coupling reaction is a Suzuki-Miyaura reaction.

In accordance with any one of the foregoing embodiments, in one embodiment, the chemical reaction is epoxidation.

In accordance with any one of the foregoing embodiments, in one embodiment, the epoxidation is selected from the group consisting of Sharpless epoxidation and Jacobsen epoxidation.

In certain embodiments, the present invention relates to any one of the aforementioned methods, wherein the chemical reaction comprises the steps of contacting a chiral, non-racemic PIDA boronate with a reagent, wherein the chiral, non-racemic PIDA boronate comprises a boron having an sp$^3$ hybridization, a PIDA protecting group bonded to the boron, and an organic group bonded to the boron through a boron-carbon bond; the organic group is chemically transformed, and the boron is not chemically transformed.

In certain embodiments, the present invention relates to any one of the aforementioned methods, wherein the chiral, non-racemic PIDA boronate is represented by

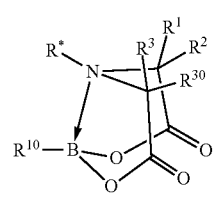

(I)

wherein:
B is a boron atom having sp$^3$ hybridization;
R* is a chiral group

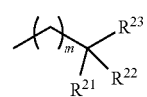

of at least 90% enantiomeric excess;

R$^{21}$ and R$^{22}$ are independently selected from the group consisting of hydrogen, alkyl, cycloalkyl, heterocyclyl, aryl, heteroaryl, aralkyl, and heteroaralkyl; or R$^{21}$ and R$^{22}$, taken together, form a 5-10-membered cycloalkyl or aromatic ring, or form a 5-10-membered heterocyclic or heteroaromatic ring comprising 1-3 heteroatoms independently selected from the group consisting of N, O, and S;

R$^{23}$ is selected from the group consisting of hydrogen, alkyl, cycloalkyl, heterocyclyl, aryl, heteroaryl, aralkyl, and heteroaralkyl;

R$^{10}$ is selected from the group consisting of

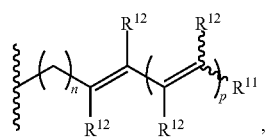

,

-continued

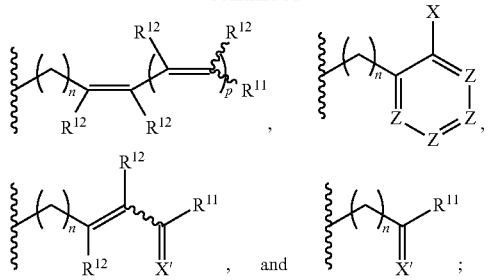

R$^{11}$ and each instance of R$^{12}$ are independently selected from the group consisting of hydrogen, halogen, hydroxyl, (C1-C10)alkyl, cycloalkyl, aryl, aralkyl, heteroaralkyl, alkoxyl, acyl, acyloxy, aryloxy, amino, and trialkylsilyloxy; or R$^{11}$ and any one instance of R$^{12}$, or any two instances of R$^{12}$, taken together, form a 3-10-membered ring;

X is halogen;

each instance of Z is independently selected from the group consisting of CH and N, provided that no more than two instances of Z are N;

X' is selected from the group consisting of CR$^5$R$^6$, O, S, and NR$^7$;

R$^1$ and R$^2$ are both hydrogen or identically selected (C1-C3)alkyl;

R$^3$ and R$^4$ are both hydrogen or identically selected (C1-C3)alkyl;

R$^5$ and R$^6$ are independently selected from the group consisting of hydrogen, halogen, hydroxyl, (C1-C10)alkyl, cycloalkyl, aryl, aralkyl, heteroaralkyl, alkoxyl, acyl, acyloxy, aryloxy, amino, and trialkylsilyloxy;

R$^7$ is selected from the group consisting of hydrogen and (C1-C3)alkyl;

m is 0, 1, or 2;

n is 0, 1, or 2; and p is 0, 1, or 2.

In an alternative embodiment, all else being the same, R$^1$ and R$^2$, and/or R$^3$ and R$^4$, are independently selected from the group consisting of hydrogen and (C1-C3)alkyl.

In one embodiment, R* is

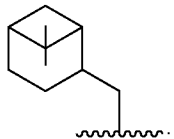

In one embodiment, R* is

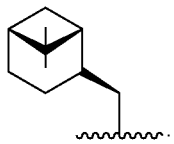

In one embodiment, R* is

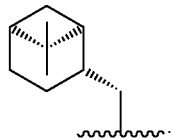

In one embodiment, R* is selected from the group consisting of

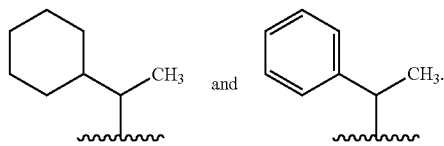

In one embodiment, R* is selected from the group consisting of

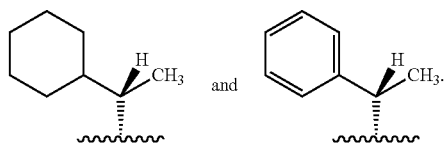

In one embodiment, R* is selected from the group consisting of

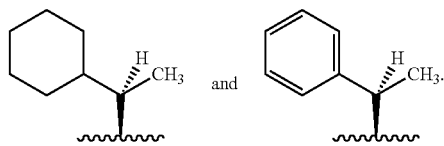

In one embodiment, R$^{21}$ and R$^{22}$, taken together, form a 5-10-membered cycloalkyl or aromatic ring, or form a 5-10-membered heterocyclic or heteroaromatic ring comprising 1-3 heteroatoms independently selected from the group consisting of N, O, and S.

In one embodiment, R* is

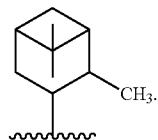 [SMILES: *C1CC2CC(C1C)C2(C)C]

In one embodiment, R* is

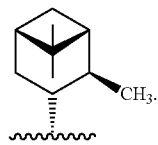

In one embodiment, R* is

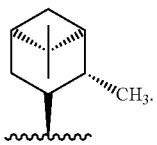

In one embodiment, R* is

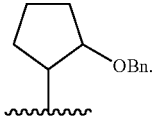 [SMILES: *C1CCCC1OCc1ccccc1]

In one embodiment, R* is

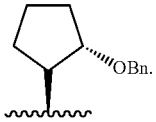

In one embodiment, R* is

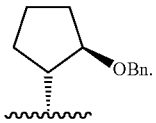

In accordance with any one of the foregoing embodiments, in one embodiment, $R^5$ and $R^6$ are independently selected from the group consisting of hydrogen and (C1-C3)alkyl.

In accordance with any one of the foregoing embodiments, in one embodiment, m is 0. Alternatively, in accordance with any one of the foregoing embodiments, in one embodiment, m is 1. Alternatively, in accordance with any one of the foregoing embodiments, in one embodiment, m is 2.

In accordance with any one of the foregoing embodiments, in one embodiment, n is 0. Alternatively, in accordance with any one of the foregoing embodiments, in one embodiment, n is 1. Alternatively, in accordance with any one of the foregoing embodiments, in one embodiment, n is 2.

In accordance with any one of the foregoing embodiments, in one embodiment, p is 0. Alternatively, in accordance with any one of the foregoing embodiments, in one embodiment, p is 1. Alternatively, in accordance with any one of the foregoing embodiments, in one embodiment, p is 2.

In accordance with any one of the foregoing embodiments not otherwise excluded, in one embodiment, $R^{10}$ is

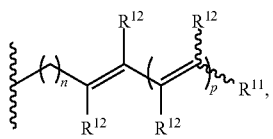

n is 0, p is 0, each instance of $R^{12}$ is hydrogen, and $R^{11}$ is selected from the group consisting of aryl and methyl.

Alternatively, in accordance with any one of the foregoing embodiments not otherwise excluded, in one embodiment, $R^{10}$ is

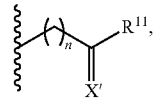

n is 0, X' is $CH_2$, and $R^{11}$ is methyl.

Alternatively, in accordance with any one of the foregoing embodiments not otherwise excluded, in one embodiment, $R^{10}$ is

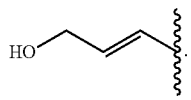

Alternatively, in accordance with any one of the foregoing embodiments not otherwise excluded, in one embodiment, $R^{10}$ is

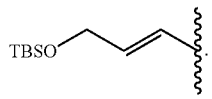

In accordance with any one of the foregoing embodiments, in one embodiment, R* is a chiral group

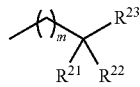

of at least 95% enantiomeric excess. In accordance with any one of the foregoing embodiments, in one embodiment, R* is a chiral group

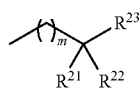

of at least 98% enantiomeric excess. In accordance with any one of the foregoing embodiments, in one embodiment, R* is a chiral group

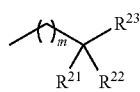

of at least 99% enantiomeric excess.

In certain embodiments, the present invention relates to any one of the aforementioned methods, wherein the chiral, non-racemic PIDA boronate is represented by

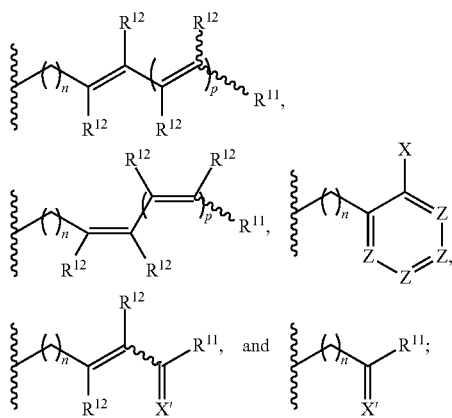

(II)

wherein:

B is a boron atom having sp³ hybridization;

the carbon atom marked "*" is a chiral carbon atom of at least 90% enantiomeric excess;

$R^{10}$ is selected from the group consisting of

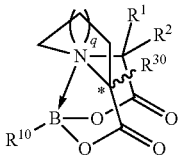

$R^{11}$ and each instance of $R^{12}$ are independently selected from the group consisting of hydrogen, halogen, hydroxyl, (C1-C10)alkyl, cycloalkyl, aryl, aralkyl, heteroaralkyl, alkoxyl, acyl, acyloxy, aryloxy, amino, and trialkylsilyloxy; or $R^{11}$ and any one instance of $R^{12}$, or any two instances of $R^{12}$, taken together, form a 3-10-membered ring;

X is halogen;

each instance of Z is independently selected from the group consisting of CH and N, provided that no more than two instances of Z are N;

X' is selected from the group consisting of $CR^5R^6$, O, S, and $NR^7$;

$R^1$ and $R^2$ are both hydrogen or identically selected (C1-C3)alkyl;

$R^5$ and $R^6$ are independently selected from the group consisting of hydrogen, halogen, hydroxyl, (C1-C10)alkyl, cycloalkyl, aryl, aralkyl, heteroaralkyl, alkoxyl, acyl, acyloxy, aryloxy, amino, and trialkylsilyloxy;

$R^7$ and $R^{30}$ are independently selected from the group consisting of hydrogen and (C1-C3)alkyl;

n is 0, 1, or 2;

p is 0, 1, or 2; and q is 1 or 2.

In an alternative embodiment, all else being the same, $R^1$ and $R^2$ are independently selected from the group consisting of hydrogen and (C1-C3)alkyl.

In one embodiment, the compound of formula (II) is

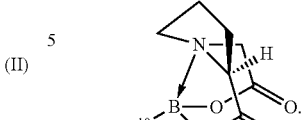

In accordance with any one of the foregoing embodiments, in one embodiment, n is 0. Alternatively, in accordance with any one of the foregoing embodiments, in one embodiment, n is 1. Alternatively, in accordance with any one of the foregoing embodiments, in one embodiment, n is 2.

In accordance with any one of the foregoing embodiments, in one embodiment, p is 0. Alternatively, in accordance with any one of the foregoing embodiments, in one embodiment, p is 1. Alternatively, in accordance with any one of the foregoing embodiments, in one embodiment, p is 2.

In accordance with any one of the foregoing embodiments, in one embodiment, q is 1. Alternatively, in accordance with any one of the foregoing embodiments, in one embodiment, q is 2.

In accordance with any one of the foregoing embodiments not otherwise excluded, in one embodiment, $R^{10}$ is

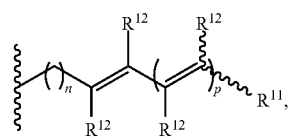

n is 0, p is 0, each instance of $R^{12}$ is hydrogen, and $R^{11}$ is selected from the group consisting of aryl and methyl.

Alternatively, in accordance with any one of the foregoing embodiments not otherwise excluded, in one embodiment, $R^{10}$ is

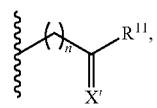

n is 0, X' is $CH_2$, and $R^{11}$ is methyl.

Alternatively, in accordance with any one of the foregoing embodiments not otherwise excluded, in one embodiment, $R^{10}$ is

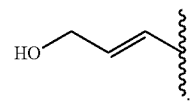 [SMILES: */C=C/CO]

Alternatively, in accordance with any one of the foregoing embodiments not otherwise excluded, in one embodiment, $R^{10}$ is

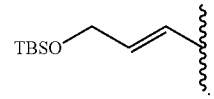 [SMILES: */C=C/CO[Si](C)(C)C(C)(C)C]

In accordance with any one of the foregoing embodiments, in one embodiment the carbon atom marked "*" is a chiral carbon atom of at least 95% enantiomeric excess. In accordance with any one of the foregoing embodiments, in one embodiment the carbon atom marked "*" is a chiral carbon atom of at least 98% enantiomeric excess. In accordance with any one of the foregoing embodiments, in one embodiment the carbon atom marked "*" is a chiral carbon atom of at least 99% enantiomeric excess.

Combination Precipitation & Catch-and-Release Purification. The two purification strategies discussed above can be combined into one robust and general process. Specifically, the solution which is subjected to the catch-and-release purification described above can be a solution which is derived from the selective precipitation of a PIDA boronate.

One aspect of the invention relates to a method of purifying a chiral, non-racemic PIDA boronate from a solution, comprising the steps of diluting the solution with hexane, thereby selectively precipitating the PIDA boronate; passing the diluted solution through a silica plug, thereby depositing the precipitated PIDA-protected organoboronic acid on the silica plug; passing a first liquid through the silica plug; and passing a second liquid through the silica plug, thereby eluting the chiral, non-racemic PIDA boronate in the second liquid; wherein the first liquid contains diethyl ether or the polarity of the first liquid is less than or equal to about the polarity of a mixture of 98.5:1.5 (v/v) Et$_2$O:MeOH; and the polarity of the second liquid is greater than or equal to about the polarity of THF.

In certain embodiments, the present invention relates to any one of the aforementioned methods, wherein the first liquid comprises diethyl ether.

In certain embodiments, the present invention relates to any one of the aforementioned methods, wherein the first liquid is diethyl ether.

In certain embodiments, the present invention relates to any one of the aforementioned methods, wherein the first liquid is a mixture of diethyl ether and methanol.

In certain embodiments, the present invention relates to any one of the aforementioned methods, wherein first liquid is a mixture of diethyl ether and methanol; and the ratio of diethyl ether to methanol is 98.5:1.5 (v/v).

In certain embodiments, the present invention relates to any one of the aforementioned methods, wherein the second liquid is THF, MeCN, ethyl acetate or acetone, or a solvent of similar or greater polarity.

In certain embodiments, the present invention relates to any one of the aforementioned methods, wherein the second liquid is THF, MeCN, ethyl acetate or acetone.

In certain embodiments, the present invention relates to any one of the aforementioned methods, wherein the second liquid is THF.

In certain embodiments, the present invention relates to any one of the aforementioned methods, wherein the solution is a crude product mixture from a chemical reaction.

In certain embodiments, the present invention relates to any one of the aforementioned methods, wherein the chemical reaction is selected from the group consisting of a Suzuki-Miyaura coupling, an oxidation, a Swern oxidation, a "Jones reagents" oxidation, a reduction, an Evans' aldol reaction, an HWE olefination, a Takai olefination, an alcohol silylation, a desilylation, a p-methoxybenzylation, an iodination, a Negishi cross-coupling, a Heck coupling, a Miyaura borylation, a Stille coupling, and a Sonogashira coupling.

In certain embodiments, the present invention relates to any one of the aforementioned methods, wherein the chemical reaction is selected from epoxidation, nucleophilic substitution, electrophilic substitution, oxidation, dihydroxylation, carbonylation, alkenation, cyclopropanation, cycloaddition, conjugate addition, Michael addition, Diels-Alder reaction, and transition metal-catalyzed cross-coupling reaction.

In accordance with any one of the foregoing embodiments, in one embodiment, the transition metal-catalyzed cross-coupling reaction is a Suzuki-Miyaura reaction.

In accordance with any one of the foregoing embodiments, in one embodiment, the chemical reaction is epoxidation.

In accordance with any one of the foregoing embodiments, in one embodiment, the epoxidation is selected from the group consisting of Sharpless epoxidation and Jacobsen epoxidation.

In certain embodiments, the present invention relates to any one of the aforementioned methods, wherein the chemical reaction comprises the steps of contacting a chiral, non-racemic PIDA boronate with a reagent, wherein the chiral, non-racemic PIDA boronate comprises a boron having an sp$^3$ hybridization, a PIDA protecting group bonded to the boron, and an organic group bonded to the boron through a boron-carbon bond; the organic group is chemically transformed, and the boron is not chemically transformed.

In certain embodiments, the present invention relates to any one of the aforementioned methods, wherein the chiral, non-racemic PIDA boronate is represented by

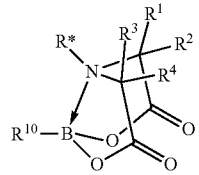

(I)

wherein:
B is a boron atom having sp$^3$ hybridization;
R* is a chiral group

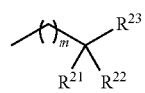

of at least 90% enantiomeric excess;
R$^{21}$ and R$^{22}$ are independently selected from the group consisting of hydrogen, alkyl, cycloalkyl, heterocyclyl, aryl, heteroaryl, aralkyl, and heteroaralkyl; or R$^{21}$ and R$^{22}$, taken together, form a 5-10-membered cycloalkyl or aromatic ring, or form a 5-10-membered heterocyclic or heteroaromatic ring comprising 1-3 heteroatoms independently selected from the group consisting of N, O, and S;
R$^{23}$ is selected from the group consisting of hydrogen, alkyl, cycloalkyl, heterocyclyl, aryl, heteroaryl, aralkyl, and heteroaralkyl;
R$^{10}$ is selected from the group consisting of

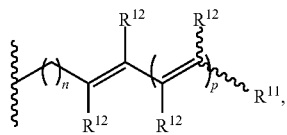

-continued

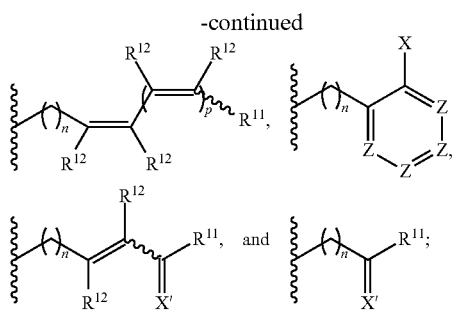

R¹¹ and each instance of R¹² are independently selected from the group consisting of hydrogen, halogen, hydroxyl, (C1-C10)alkyl, cycloalkyl, aryl, aralkyl, heteroaralkyl, alkoxyl, acyl, acyloxy, aryloxy, amino, and trialkylsilyloxy; or R¹¹ and any one instance of R¹², or any two instances of R¹², taken together, form a 3-10-membered ring;

X is halogen;

each instance of Z is independently selected from the group consisting of CH and N, provided that no more than two instances of Z are N;

X' is selected from the group consisting of CR⁵R⁶, O, S, and NR⁷;

R¹ and R² are both hydrogen or identically selected (C1-C3)alkyl;

R³ and R⁴ are both hydrogen or identically selected (C1-C3)alkyl;

R⁵ and R⁶ are independently selected from the group consisting of hydrogen, halogen, hydroxyl, (C1-C10)alkyl, cycloalkyl, aryl, aralkyl, heteroaralkyl, alkoxyl, acyl, acyloxy, aryloxy, amino, and trialkylsilyloxy;

R⁷ is selected from the group consisting of hydrogen and (C1-C3)alkyl;

m is 0, 1, or 2;

n is 0, 1, or 2; and p is 0, 1, or 2.

In an alternative embodiment, all else being the same, R¹ and R², and/or R³ and R⁴, are independently selected from the group consisting of hydrogen and (C1-C3)alkyl.

In one embodiment, R* is

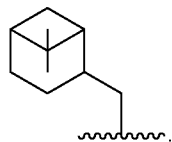

In one embodiment, R* is

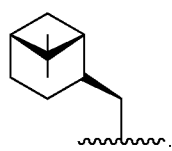

In one embodiment, R* is

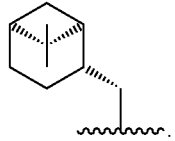

In one embodiment, R* is selected from the group consisting of

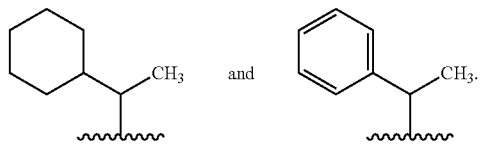

In one embodiment, R* is selected from the group consisting of

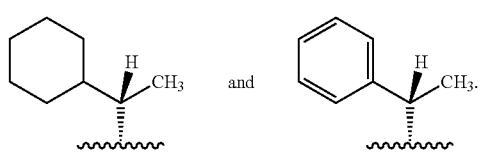

In one embodiment, R* is selected from the group consisting of

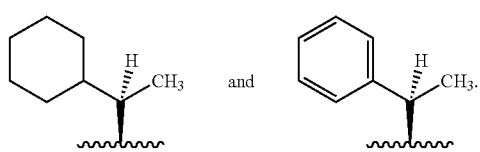

In one embodiment, R²¹ and R²², taken together, form a 5-10-membered cycloalkyl or aromatic ring, or form a 5-10-membered heterocyclic or heteroaromatic ring comprising 1-3 heteroatoms independently selected from the group consisting of N, O, and S.

In one embodiment, R* is

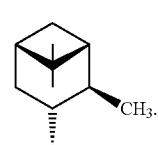

In one embodiment, R* is

In one embodiment, R* is

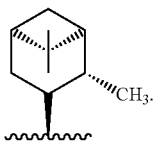

In one embodiment, R* is

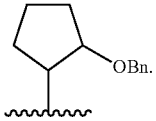

In one embodiment, R* is

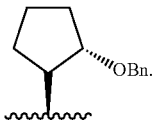

In one embodiment, R* is

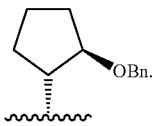

In accordance with any one of the foregoing embodiments, in one embodiment, $R^5$ and $R^6$ are independently selected from the group consisting of hydrogen and (C1-C3)alkyl.

In accordance with any one of the foregoing embodiments, in one embodiment, m is 0. Alternatively, in accordance with any one of the foregoing embodiments, in one embodiment, m is 1. Alternatively, in accordance with any one of the foregoing embodiments, in one embodiment, m is 2.

In accordance with any one of the foregoing embodiments, in one embodiment, n is 0. Alternatively, in accordance with any one of the foregoing embodiments, in one embodiment, n is 1. Alternatively, in accordance with any one of the foregoing embodiments, in one embodiment, n is 2.

In accordance with any one of the foregoing embodiments, in one embodiment, p is 0. Alternatively, in accordance with any one of the foregoing embodiments, in one embodiment, p is 1. Alternatively, in accordance with any one of the foregoing embodiments, in one embodiment, p is 2.

In accordance with any one of the foregoing embodiments not otherwise excluded, in one embodiment, $R^{10}$ is

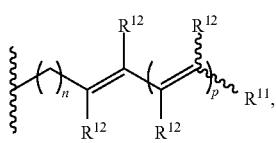

n is 0, p is 0, each instance of $R^{12}$ is hydrogen, and $R^{11}$ is selected from the group consisting of aryl and methyl.

Alternatively, in accordance with any one of the foregoing embodiments not otherwise excluded, in one embodiment, $R^{10}$ is

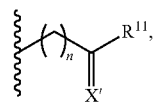

n is 0, X' is $CH_2$, and $R^{11}$ is methyl.

Alternatively, in accordance with any one of the foregoing embodiments not otherwise excluded, in one embodiment, $R^{10}$ is

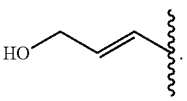

Alternatively, in accordance with any one of the foregoing embodiments not otherwise excluded, in one embodiment, $R^{10}$ is

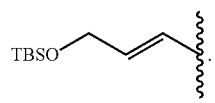

In accordance with any one of the foregoing embodiments, in one embodiment, R* is a chiral group

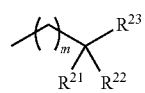

of at least 95% enantiomeric excess. In accordance with any one of the foregoing embodiments, in one embodiment, R* is a chiral group

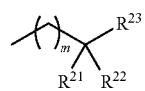

of at least 98% enantiomeric excess. In accordance with any one of the foregoing embodiments, in one embodiment, R* is a chiral group

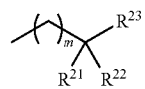

of at least 99% enantiomeric excess.

In certain embodiments, the present invention relates to any one of the aforementioned methods, wherein the chiral, non-racemic PIDA boronate is represented by

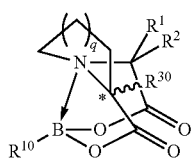

(II)

wherein:

B is a boron atom having sp³ hybridization;

the carbon atom marked "*" is a chiral carbon atom of at least 90% enantiomeric excess;

$R^{10}$ is selected from the group consisting of

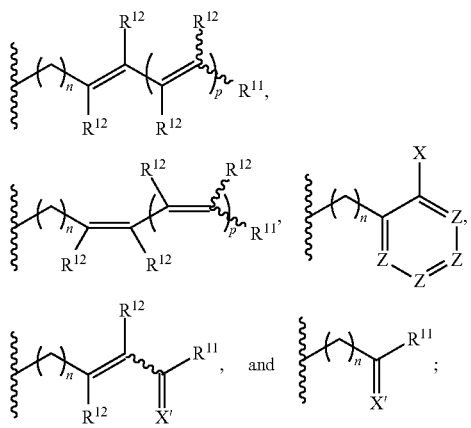

$R^{11}$ and each instance of $R^{12}$ are independently selected from the group consisting of hydrogen, halogen, hydroxyl, (C1-C10)alkyl, cycloalkyl, aryl, aralkyl, heteroaralkyl, alkoxyl, acyl, acyloxy, aryloxy, amino, and trialkylsilyloxy; or $R^{11}$ and any one instance of $R^{12}$, or any two instances of $R^{12}$, taken together, form a 3-10-membered ring;

X is halogen;

each instance of Z is independently selected from the group consisting of CH and N, provided that no more than two instances of Z are N;

X' is selected from the group consisting of $CR^5R^6$, O, S, and $NR^7$;

$R^1$ and $R^2$ are both hydrogen or identically selected (C1-C3)alkyl;

$R^5$ and $R^6$ are independently selected from the group consisting of hydrogen, halogen, hydroxyl, (C1-C10)alkyl, cycloalkyl, aryl, aralkyl, heteroaralkyl, alkoxyl, acyl, acyloxy, aryloxy, amino, and trialkylsilyloxy;

$R^7$ and $R^{30}$ are independently selected from the group consisting of hydrogen and (C1-C3)alkyl;

n is 0, 1, or 2;

p is 0, 1, or 2; and q is 1 or 2.

In an alternative embodiment, all else being the same, $R^1$ and $R^2$ are independently selected from the group consisting of hydrogen and (C1-C3)alkyl.

In one embodiment, the compound of formula (II) is

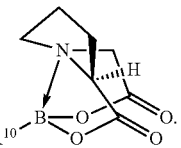

In accordance with any one of the foregoing embodiments, in one embodiment, n is 0. Alternatively, in accordance with any one of the foregoing embodiments, in one embodiment, n is 1. Alternatively, in accordance with any one of the foregoing embodiments, in one embodiment, n is 2.

In accordance with any one of the foregoing embodiments, in one embodiment, p is 0. Alternatively, in accordance with any one of the foregoing embodiments, in one embodiment, p is 1. Alternatively, in accordance with any one of the foregoing embodiments, in one embodiment, p is 2.

In accordance with any one of the foregoing embodiments, in one embodiment, q is 1. Alternatively, in accordance with any one of the foregoing embodiments, in one embodiment, q is 2.

In accordance with any one of the foregoing embodiments not otherwise excluded, in one embodiment, $R^{10}$ is

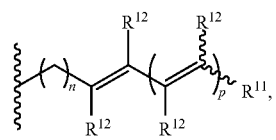

n is 0, p is 0, each instance of $R^{12}$ is hydrogen, and $R^{11}$ is selected from the group consisting of aryl and methyl.

Alternatively, in accordance with any one of the foregoing embodiments not otherwise excluded, in one embodiment, $R^{10}$ is

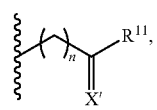

n is 0, X' is $CH_2$, and $R^{11}$ is methyl.

Alternatively, in accordance with any one of the foregoing embodiments not otherwise excluded, in one embodiment, $R^{10}$ is

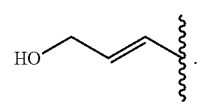

Alternatively, in accordance with any one of the foregoing embodiments not otherwise excluded, in one embodiment, $R^{10}$ is

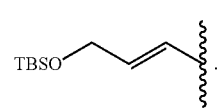 [SMILES: */C=C/CO[Si](C)(C)C(C)(C)C]

In accordance with any one of the foregoing embodiments, in one embodiment the carbon atom marked "*" is a chiral carbon atom of at least 95% enantiomeric excess. In accordance with any one of the foregoing embodiments, in one embodiment the carbon atom marked "*" is a chiral carbon atom of at least 98% enantiomeric excess. In accordance with any one of the foregoing embodiments, in one embodiment the carbon atom marked "*" is a chiral carbon atom of at least 99% enantiomeric excess.

Customized Hybrid Purification Vessels. In certain embodiments, the present invention relates to any one of the aforementioned methods, wherein a customized hybrid purification vessel which contains both a "precipitation chamber" and a "catch-and-release chamber" arranged in series is used. In this system, a crude cross-coupling reaction is transferred to a first (e.g., upper) chamber filled with hexanes, resulting in rapid and quantitative precipitation of the PIDA boronate-containing product while the residual boronic acid (and most byproducts), palladium, and phosphine ligand all remain soluble. As previously noted, simple filtration of this suspension, followed by washing with $Et_2O$:MeOH, places the resulting semi-purified, solid chiral, non-racemic PIDA boronate on top of a silica gel plug that resides in a second (e.g., lower) chamber. This lower chamber is then subjected to washing with copious volumes of, for example, $Et_2O$:MeOH 98.5:1.5 (v/v) followed by a defined small volume of THF to effect the catch-and-release silica gel purification. The resulting THF solution of purified chiral, non-racemic PIDA boronate is conveniently ready for utilization in subsequent cycles of deprotection and coupling.

Purification/Deprotection of PIDA-Protected Organoboronic Acids

The challenges associated with purifying boronic acids include the fact that "the polar and often amphiphilic character tends to make their isolation and purification difficult" (Hall, D. G. Boronic Acids; Wiley-VCH: Weinheim, Germany, 2005; pp 57-58). Further, "[t]he widely known and used boronic acids show variable stability (vinyl-, alkyl-, and alkynylboronic acid are not very stable), and their purification is not straightforward. Moreover, isolated boronic acids generally contain large quantities of anhydrides or boroxines, which result in problems for determining their stoichiometry" (Darses, S.; Genet, J-P. Chem. Rev. 2008, 108, 288-325).

A number of approaches for purifying boronic acids have been developed, but all are limited in their generality. The most basic approach is to recrystallize the boronic acid, typically from an aqueous solution. However, this approach is only efficient if the sample is already relatively pure and when the temperature-dependent solubility of the boronic acid in water is favorable. When non-polar recrystallization solvents are employed, significant dehydration of the boronic acid to afford the boroxine can occur. (Santucci, L.; Gilman, H. J. Am. Chem. Soc. 1958, 80, 193-196). Another approach is "phase switching" liquid/liquid partitioning (Mothana, S.; Grassot, J-M.; Hall, D. G. Angew. Chem. Int. Ed. 2010, 49, 2883-2887). In this approach the boronic acid is converted into the anionic borate species in strong base (pH 10), non-anionic organics are washed away, and then the solution is acidified (pH 1-5) to regenerate the boronic acid. This method is not compatible with boronic acids containing acidic functional groups, basic functional groups, or any functionality that is acid- or base-sensitive, including the boronic acid functionality. A solid supported scavenger for boronic acids based on diethanolamine, abbreviated DEAM-PS, has also been reported (Hall, D. G.; Tailor, J.; Gravel, M. Angew. Chem. Int. Ed. 1999, 38, 3064-3067). However, this method is expensive and does not represent a practical or scalable solution.

Boronic acids can be purified in a two-step process with the intermediacy of a boronic acid surrogate. For example, boronic acids can be converted to the corresponding trifluoroborate salt which can be crystallized (Darses, S.; Genet, J-P. Chem. Rev. 2008, 108, 288-325). However, limitations of this approach include the fact that the crystallization conditions are substrate-specific, large amounts of fluoride are used, some impurities co-crystallize with the product, and regenerating the boronic acid from the trifluoroborate is not efficient (Molander, G. A.; Cavalcanti, L. N.; Canturk, B.; Pan, P-S.; Kennedy, L. E. J. Org. Chem. 2009, 74, 7364-7369). Alternatively, boronic acids can be dehydrated in the presence of a diol (most often pinacol) to form the corresponding boronic ester. Some aryl boronic esters have more favorable chromatography, extraction, and crystallization properties than the corresponding boronic acids. However other classes of boronic esters (heteroaryl, alkenyl, alkyl, alkynyl, etc.) tend to have highly variable features. Further, as the boronic ester becomes stable enough to improve its purification properties, the conditions required to regenerate the boronic acid become harsher. For example, converting a pinacol boronic ester to the corresponding boronic acid typically requires aqueous acid and an oxidant (often $NaIO_4$), which limits the generality of this approach (Murphy, J. M.; Tzschuck, C. C.; Hartwig, J. F. Org. Lett. 2007, 9, 757-760).

Finally, unstable boronic acids present a particularly challenging problem. None of the above-mentioned approaches can be used to purify unstable boronic acids, such as vinyl boronic acids. Remarkably, vinyl boronic acid can be generated from vinyl chiral, non-racemic PIDA boronate in greater than 95% purity (Knapp, D. M.; Gillis, E. P.; Burke, M. D. J. Am. Chem. Soc. 2009, 131, 6961-6963).

To address some of the problems noted above, disclosed herein is a "catch and selective release" type method developed for chiral, non-racemic PIDA boronate hydrolysis. Specifically, a THF solution of a chiral, non-racemic PIDA boronate (reactivity=OFF) is mixed with solid-supported ammonium hydroxide reagent (such as Amberlyst A26(OH); see T. M. Morwick, J. Comb. Chem. 2006, 8, 649-651) to promote the PIDA hydrolysis. At this point, both the cleaved PIDA ligand (likely in the form of $PIDA^{2-}Na^+_2$) and the boronic acid (likely in the form of the corresponding anionic boron-'ate' complex; see D. G. Hall, J. Tailor, M. Gravel, Angew. Chem. Int. Ed. 1999, 38, 3064-3067) remain trapped in the resin (the "catch"). It was determined that subsequent treatment with a THF solution of AcOH (see M. G. Siegel, P. J. Hahn, B. A. Dressman, J. E. Fritz, J. R. Grunwell, S. W. Kaldor, Tetrahedron Lett. 1997, 38, 3357-3360) results in "selective release" of only the boronic acid (reactivity=ON), while the cleaved PIDA ligand conveniently remains trapped in the resin under these mildly acidic conditions. Transferring this THF/AcOH/boronic acid solution to a new vial containing $K_2CO_3$, 4 Å molecular sieves, and Celite®, followed by bubbling argon through the mixture and filtration yields a neutralized, mostly anhydrous, and deoxygenated solution of freshly-prepared boronic acid in THF, ready for the next cross-coupling reaction.

One aspect of the invention relates to the deprotection of a PIDA boronate, comprising the step of contacting a solution comprising the chiral, non-racemic PIDA boronate and a solvent with a solid-supported ammonium hydroxide reagent, thereby deprotecting the chiral, non-racemic PIDA boronate and forming a boronic acid and a free PIDA ligand.

In certain embodiments, the present invention relates to any one of the aforementioned methods, wherein the solvent comprises THF.

In certain embodiments, the present invention relates to any one of the aforementioned methods, wherein the solid-supported ammonium hydroxide reagent binds the PIDA.

In certain embodiments, the present invention relates to any one of the aforementioned methods, further comprising the steps of removing the solvent by filtration, thereby leaving the boronic acid and PIDA ligand trapped inside the solid-supported ammonium hydroxide reagent; and adding additional solvent.

In certain embodiments, the present invention relates to any one of the aforementioned methods, wherein the additional solvent is THF.

In certain embodiments, the present invention relates to any one of the aforementioned methods, wherein the solid-supported ammonium hydroxide reagent is washed with an organic solution comprising an organic solvent and a mild or strong acid in a quantity greater than that needed to neutralize the solid-supported ammonium hydroxide reagent, thereby eluting the boronic acid.

In certain embodiments, the present invention relates to any one of the aforementioned methods, wherein the solid-supported ammonium hydroxide reagent is washed with a THF solution comprising a mild or strong acid, thereby eluting the boronic acid.

In certain embodiments, the present invention relates to any one of the aforementioned methods, wherein the solid-supported ammonium hydroxide reagent is washed with a THF solution comprising acetic acid, thereby eluting the boronic acid.

In certain embodiments, the present invention relates to any one of the aforementioned methods, wherein the eluted boronic acid is treated with base to neutralize the acid (e.g., acetic acid).

In certain embodiments, the present invention relates to any one of the aforementioned methods, wherein the base is potassium carbonate.

In certain embodiments, the present invention relates to any one of the aforementioned methods, wherein the solid-supported ammonium hydroxide reagent is washed with a 1,4-dioxane solution comprising hydrochloric acid, thereby eluting the boronic acid.

In certain embodiments, the present invention relates to any one of the aforementioned methods, wherein the solid-supported ammonium hydroxide reagent is a strong base anion exchange resin, e.g., Amberlite IRA-400 (OH$^-$ form), Amberlite IRA 420 (OH$^-$ form), Amberlite IRA 410 (OH$^-$ form), Amberlite IRN-150, Amberlite IRA 900 (OH$^-$ form), Amberlite IRA 904 (OH$^-$ form), Amberlite IRA 910 (OH$^-$ form), Amberlite A5836, Amberlyst A26 (OH$^-$ form), Ambersep 900, Dowex-1 (OH$^-$ form), Dowex-3 (OW form), Dowex 1-X4 (OH$^-$ form), Dowex 1-I 9880, Dowex 1-I0131, Dowex 550 A (OW form), or Amberjet 4400.

In certain embodiments, the present invention relates to any one of the aforementioned methods, wherein the solid-supported ammonium hydroxide reagent is a strong base, type 1, anionic, macroreticular polymeric resin based on crosslinked styrene divinylbenzene copolymer containing quaternary ammonium groups, e.g., Amberlyst A26 (OH$^-$ form) (Rohm and Haas, Philadelphia, Pa.).

An aspect of the invention relates to a method of deprotecting a PIDA boronate, comprising the step of contacting a solution comprising the chiral, non-racemic PIDA boronate and a solvent with an aqueous solution of NaOH, thereby deprotecting the chiral, non-racemic PIDA boronate and forming a boronic acid and free PIDA ligand. This method is particularly useful in connection with acid-sensitive substrates (boronic acids) because it does not include exposure to acid for elution from a solid support.

Because water will be removed in subsequent steps, it is generally desirable to limit the volume of the aqueous component (solution of NaOH) introduced into the system to a relatively small amount, e.g., about 25-33 percent of the volume of the solution comprising the chiral, non-racemic PIDA boronate and its solvent.

In certain embodiments, the present invention relates to the aforementioned method, wherein the solvent comprises THF.

In certain embodiments, the present invention relates to the aforementioned method, wherein the solvent is THF. In one embodiment, the THF is dry and deoxygenated.

In certain embodiments, the present invention relates to the aforementioned method, further comprising the steps of adding diethyl ether, thereby generating a biphasic mixture comprising an organic phase comprising the boronic acid and free PIDA ligand, and an aqueous phase; and separating the organic phase comprising the boronic acid and free PIDA ligand from the aqueous phase. The step of adding diethyl ether can optionally include adding a reagent effective for quenching the reaction. In one embodiment, the reagent effective for quenching the reaction is a phosphate buffer. Again, because water will be removed in subsequent steps, it is generally desirable to limit the total amount of water introduced into the system to a relatively small amount, e.g., about 25-33 percent of the volume of the combined solution comprising the PIDA boronate, its organic solvent, and the aqueous solution of NaOH. In one embodiment, the phosphate buffer is added in an amount approximately equal to the volume of the aqueous solution of NaOH.

In certain embodiments, the present invention relates to any one of the aforementioned methods, further comprising the step of contacting the organic phase with one or more drying agents selected from the group consisting of magnesium sulfate, diatomaceous earth, and molecular sieves, thereby drying the organic phase comprising the boronic acid and free PIDA ligand. A diatomaceous earth can be, for example, Celite® (Fluka/Sigma-Aldrich, St. Louis, Mo.; Celite Corp., Lompoc, Calif.).

In certain embodiments, the present invention relates to any one of the aforementioned methods, further comprising the step of deoxygenating the dried organic phase comprising the boronic acid and free PIDA ligand. In one embodiment, the deoxygenation is accomplished by bubbling dry oxygen-free gas through the organic phase comprising the boronic acid and free PIDA ligand. In one embodiment, the oxygen-free gas is argon.

Automated Small Molecule Synthesizers

Figure 4:
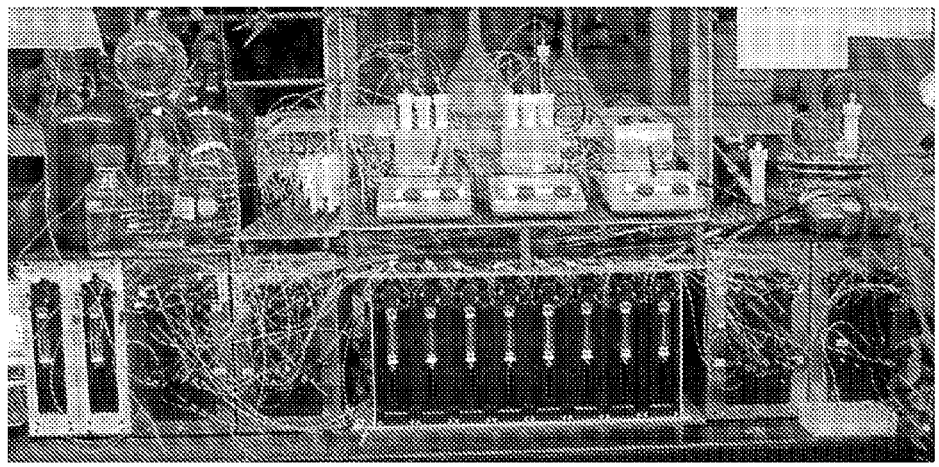
FIG. 4 is a photograph of one embodiment of a fully automated small molecule synthesizer comprising modules for (i) deprotection, (ii) cross-coupling, and (iii) purification, all of which are under the control of a computer equipped with custom-designed software.

With robust and general methods for the purification and deprotection of PIDA boronates in hand, an apparatus with the capacity for fully-automated synthesis of small molecules via ICC (FIG. 4) was designed and built. In certain embodiments, this apparatus is comprised of three modules, each designed to promote a deprotection (D), cross-coupling (CC), or purification (P) step required to execute the ICC scheme described herein. In certain embodiments, all materials are transferred between modules as solutions manipulated by a series of main syringe pumps (e.g., eight) coordinated with a suite of switchable valves (J-KEM Scientific). In certain embodiments, all of the syringe pumps are driven by a computer running a custom-made software program. One embodiment of the machine is depicted in FIG. 4; additional details regarding this machine are provided in the Exemplification below.

Reaction System Design. In certain embodiments, the cross-coupling reactions are run in polypropylene tubes purchased from Luknova, item #FC003012. The dimensions of the tube are 21 mm×120 mm (ID×length). The bottom of the tube is fitted with a 21 mm diameter×4 mm tall frit. On top of this frit is secured via metal wire a 13 mm diameter×4 mm tall frit. On top of the frit is placed a large stir bar containing a rare-earth magnet (Big Science Inc., SBM-1508-REH). The bottom of the tube is accessed through a male Luer tip, while the top of the tube is sealed with an air-tight, threaded cap containing a female Luer port. The tube holds a solvent volume of up to 25 mL. The tubes are placed in an aluminum heating block that was custom fabricated. The heating block holds up to nine reaction tubes. The tubes are held 3 cm above the surface of the stir plate, where the bottom 4 cm of the tube is jacketed by the heating block. The tubing to access the bottom of the reaction tube goes through a hole in the side of the block near the bottom.

The use of a polypropylene tube appears to be important in simplifying the engineering of the reaction tube. Specifically, the material is a good insulator such that only the portion that is jacketed by the heating block becomes hot. When the heating block is heated to 60° C., the reaction solution reaches 60° C. within several minutes. However, the portion of the tube that is not jacketed remains at room temperature, acting as a condenser, and thus the vapor above the solvent remains at room temperature. When other materials such as glass were used, the portion of the tube above the heating block became hot and the solution quickly evaporated. Thus, if glass were to be used instead of polypropylene, there would need to be an additional cooling element in order to keep the solution from escaping.

In certain embodiments of the system the tubes in the reaction block are stirred constantly, regardless of whether there is solution inside the tube. This keeps the system simple since the stir plate does not need to be turned on or off, and further, the start and stop times of the reactions within the block do not need to be coordinated. However, during prolonged stirring the stir bar in the tube acts as a mortar and the frit as a pestle, such that the base becomes finely ground into the pores of the frit. Further, the stir bar may be damaging the top of the frit even in the absence of base. In these situations it becomes nearly impossible to withdraw solutions through the frit since the top surface of the frit is clogged and/or damaged. To overcome this limitation a reaction tube was designed to contain two frits of different sizes (FIG. 8B). This way the stir bar only contacts the smaller top frit, and even if the top surface of this frit is damaged or clogged, the solution can be withdrawn through the sides of the small frit or through the spaces open only to the larger frit. The wire is necessary to secure the top frit so that it does not rotate sideways during the reaction to become perpendicular to the larger frit. In certain embodiments, a single frit could be fabricated to have a shape similar to the combined frits.

Purification System Design. The chromatographic properties of PIDA boronates that enable the simple purification approach are discussed above. Below is described how the engineering of the system supports the catch-and-release chromatography and precipitation-based purification.

Figure 9:
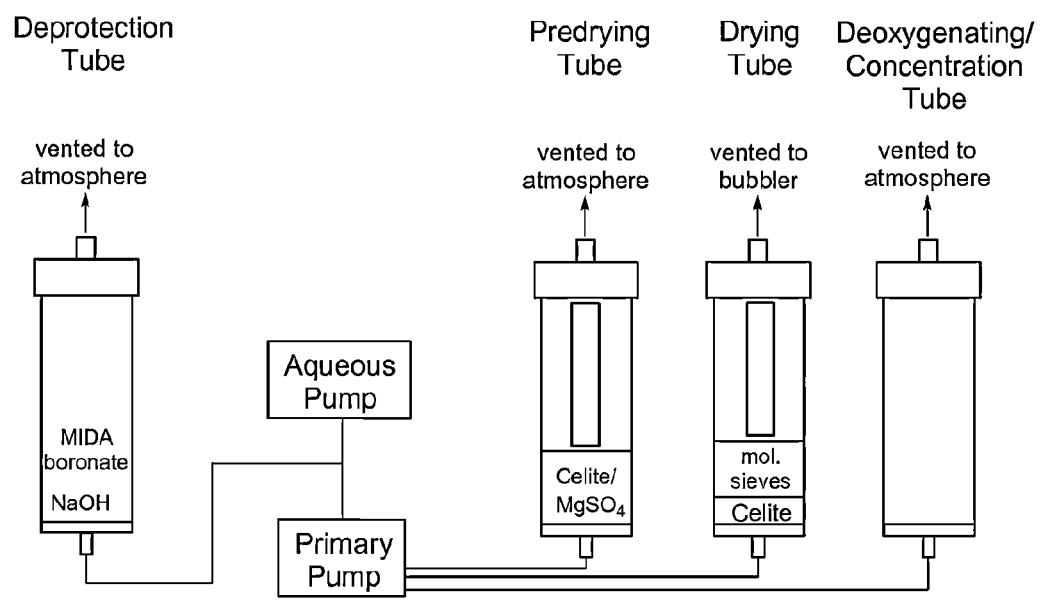
FIG. 9 is a schematic of an example of an aqueous deprotection module.
Figure 10A:
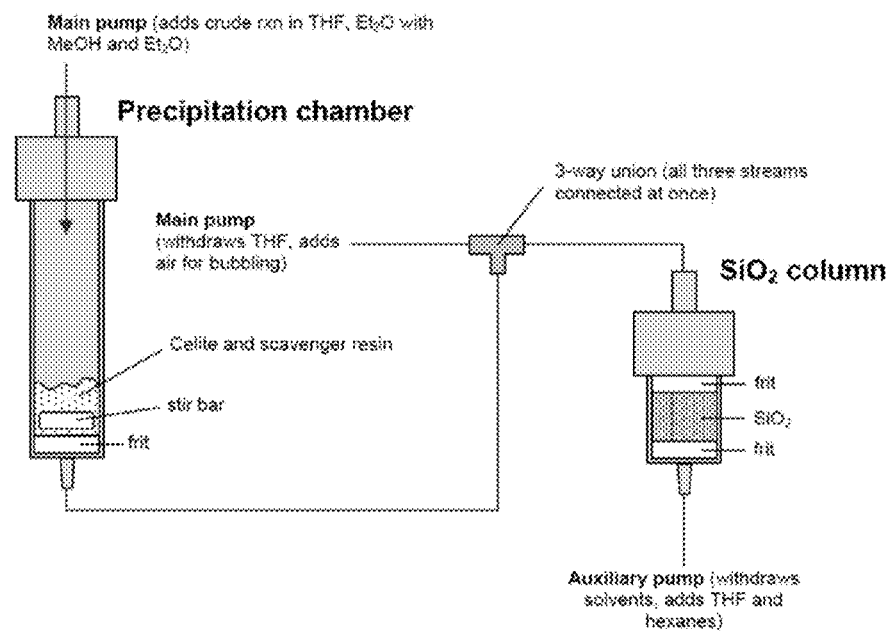
FIG. 10A is a schematic of a precipitation chamber and silica column.
Figure 10B:
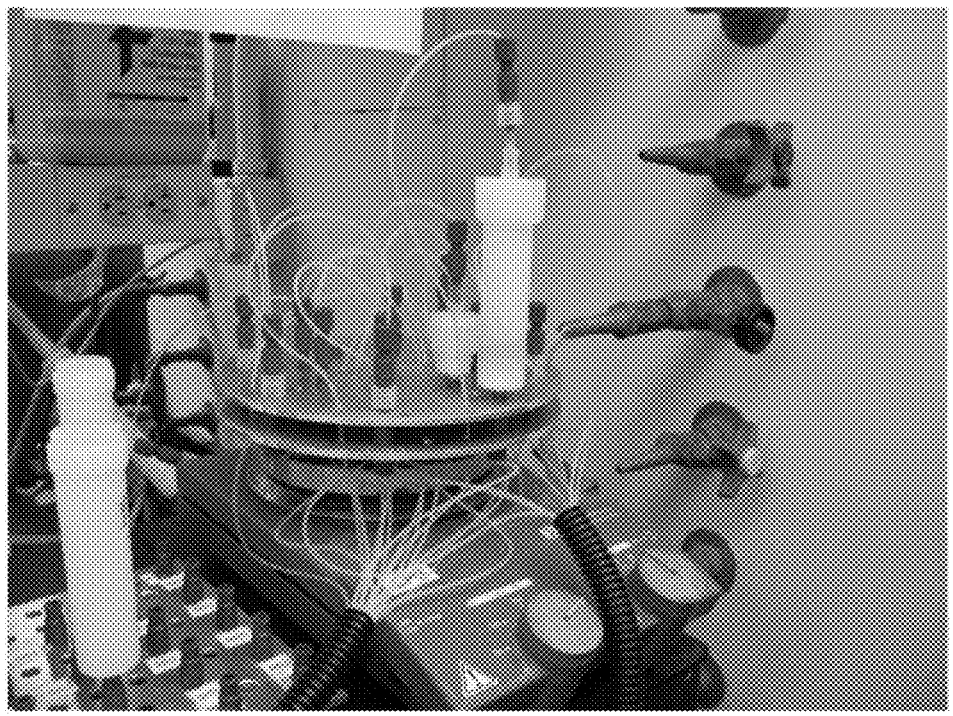
FIG. 10B is a photograph depicting an example of a precipitation chamber and silica column.
Figure 11:
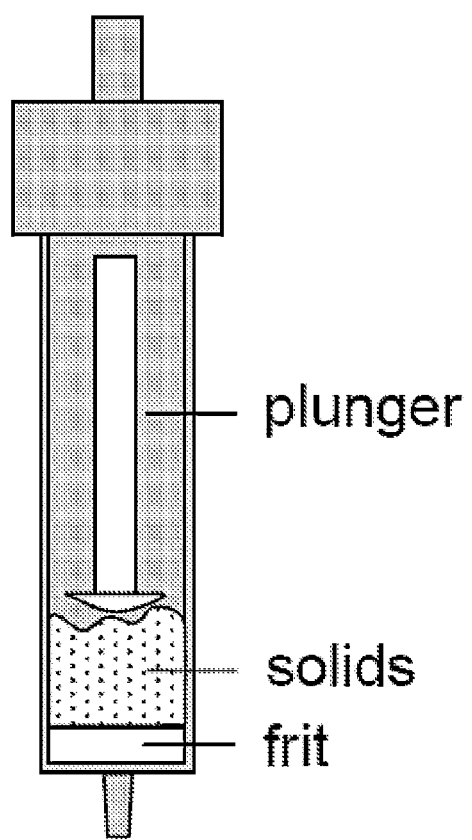
FIG. 11 depicts an example of a drying and degassing tube.

Because diluting the crude THF reaction solution with hexanes will cause immediate precipitation of the chiral, non-racemic PIDA boronate product, the mixing of THF and hexanes must occur in a container of sufficient volume to hold the precipitated product. The solvents must also be thoroughly mixed so that the solution is homogeneous. Finally, the addition of hexanes to the THF solution also causes reaction byproducts to become insoluble. In some cases these byproducts are sticky or form a very fine precipitate that can clog a frit. In certain embodiments, a custom designed precipitation chamber in which to mix the crude THF solution and hexanes can be used (FIG. 9). In certain embodiments, the precipitation chamber contains Celite® which scavenges the sticky impurities that precipitate and keeps this material distributed throughout the Celite® so it does not clog the frit. In certain embodiments, a stir bar in the chamber ensures proper mixing. However, it was observed that if the stir bar stirs continuously for several hours, the Celite® in the tube becomes so finely ground that it can pass through the frit and clog downstream processes. To solve this problem, after the precipitation chamber is filled with solvent and mixed, the solvent is withdrawn so that the stir bar becomes imbedded in the dry Celite® and does not stir. In other words, the stir bar can be made to stir only when it is needed—i.e., when there is solvent in the precipitation chamber—and, therefore, this process does not require turning the stir plate on/off or coordinating the stirring of other processes that use the same stir plate. In certain embodiments, 3-aminopropyl-functionalized silica gel is placed in the precipitation chamber to scavenge palladium from a crude reaction solution.

In certain embodiments of the system the tubes in the reaction block are stirred constantly, regardless of whether there is solution inside the tube. This keeps the system simple since the stir plate does not need to be turned on or off, and further, the start and stop times of the reactions within the block do not need to be coordinated. However, during prolonged stirring the stir bar in the tube acts as a mortar and the frit as a pestle, such that the base becomes finely ground into the pores of the frit. Further, the stir bar may be damaging the top of the frit even in the absence of base. In these situations it becomes nearly impossible to withdraw solutions through the frit since the top surface of the frit is clogged and/or damaged. To overcome this limitation a reaction tube was designed to contain two frits of different sizes (FIG. 8B). This way the stir bar only contacts the smaller top frit, and even if the top surface of this frit is damaged or clogged, the solution can be withdrawn through the sides of the small frit or through the spaces open only to the larger frit. The wire is necessary to secure the top frit so that it does not rotate sideways during the reaction to become perpendicular to the larger frit. In certain embodiments, a single frit could be fabricated to have a shape similar to the combined frits.

Some important features of this setup are: the precipitation event occurs in a mixing chamber; the mixing chamber contains scavengers (Celite® and functionalized silica gel); the stirring can be controlled in a simple way; the precipitation chamber and $SiO_2$ column are spatially separated; and the configuration of pumps allows solvents to be added and withdrawn at various junctions throughout the process.

Software. The software that controls the machine can be described as having three levels of complexity: the basic level, the functional level, and the developed level. The basic level represents essentially the combination of 1's and 0's that can be sent to the equipment to move the syringe pumps and valves. The functional level represents the simplest commands to move the equipment that could be understood by a person looking at the computer code. The developed level represents software specifically tailored to the automated synthesis machine that can be used by non-experts to modify how the synthesis is performed. The basic level is inherent to the equipment manufactured by Kloehn. The functional level came from source code provided by J-KEM when the equipment was purchased. The functional level is source code written in VB.NET that packages the commands of the basic level into easily executed subroutines. The developed level was custom designed and written in VB.NET based on the source code provided in the functional level.

More specifically, the machine is composed of a number of syringe pumps and valves that are OEM parts from Kloehn. The syringe pumps and valves were repackaged and sold by J-KEM as a custom piece of hardware. The equipment is controlled via a RS-485 serial port that sends and receives simple text string commands written in machine language specific to the Kloehn parts. Thus, on the simplest level the machine can be controlled by sending simple text strings such as "/xR", but these commands are unintelligible to anyone using the equipment. The equipment shipped from J-KEM came with source code written in VB.NET that provides subroutines to move the syringe pump to specific positions, change valves to specific positions, control the rate at which the syringe moves, and open/close solenoid valves. The code that was developed uses the subroutines from the code provided by J-KEM. The source code from J-KEM could be removed and the software could communicate with the equipment directly without losing functionality. However, the source code from J-KEM would not be by itself enough to run an automated synthesis. Thus, it was necessary to create software to enable the development of the automated synthesis machine. Details regarding certain embodiments of the software can be found in the Exemplification.

Automated Synthesizers. One aspect of the invention relates to an automated small molecule synthesizer comprising: (a) a deprotection module, in fluid communication with (b) a drying and degassing module, in fluid communication with (c) a reaction module, in fluid communication with (d) a purification module; at least one pump which can move liquid from one module to another; and a computer equipped with software; wherein all of the modules are under the control of the computer.

In one embodiment, the deprotection module comprises immobilized or solid-supported base, e.g., NaOH, as described herein. In one embodiment, the deprotection module is constructed and arranged so as to perform deprotection with aqueous base, e.g., aqueous NaOH, as described herein.

In one embodiment, the purification module comprises a combined (or "hybrid") precipitation and catch-and-release module.

In certain embodiments, the present invention relates to any one of the aforementioned automated small molecule synthesizers, wherein the deprotection module comprises a deprotection chamber which comprises a first opening at the top of the chamber, a second opening at the bottom of the chamber, a first frit covering the second opening, and a solid-supported ammonium hydroxide reagent.

In certain embodiments, the present invention relates to any one of the aforementioned automated small molecule synthesizers, wherein the deprotection chamber comprises a cylindrical tube.

In certain embodiments, the present invention relates to any one of the aforementioned automated small molecule synthesizers, wherein the cylindrical tube of the deprotection chamber is a polypropylene cylindrical tube.

In certain embodiments, the present invention relates to any one of the aforementioned automated small molecule synthesizers, wherein the cylindrical tube of the deprotection chamber has a length of between about 100 mm and 140 mm.

In certain embodiments, the present invention relates to any one of the aforementioned automated small molecule synthesizers, wherein the cylindrical tube of the deprotection chamber has a length of about 120 mm.

In certain embodiments, the present invention relates to any one of the aforementioned automated small molecule synthesizers, wherein the cylindrical tube of the deprotection chamber has an interior diameter of between about 18 mm and about 24 mm.

In certain embodiments, the present invention relates to any one of the aforementioned automated small molecule synthesizers, wherein the cylindrical tube of the deprotection chamber has an interior diameter of about 21 mm.

In certain embodiments, the present invention relates to any one of the aforementioned automated small molecule synthesizers, wherein the cylindrical tube of the deprotection chamber has a volume of about 25 mL.

In certain embodiments, the present invention relates to any one of the aforementioned automated small molecule synthesizers, wherein the solid-supported ammonium hydroxide reagent is a strong base anion exchange resin, e.g., Amberlite IRA-400 (OH$^-$ form), Amberlite IRA 420 (OH$^-$ form), Amberlite IRA 410 (OH$^-$ form), Amberlite IRN-150, Amberlite IRA 900 (OH$^-$ form), Amberlite IRA 904 (OH$^-$ form), Amberlite IRA 910 (OH$^-$ form), Amberlite A5836, Amberlyst A26 (OH$^-$ form), Ambersep 900, Dowex-1 (OH$^-$ form), Dowex-3 (OH$^-$ form), Dowex 1-X4 (OH$^-$ form), Dowex 1-I 9880, Dowex 1-I0131, Dowex 550 A (OH$^-$ form), or Amberjet 4400.

In certain embodiments, the present invention relates to any one of the aforementioned automated small molecule synthesizers, wherein the solid-supported ammonium hydroxide reagent is a strong base, type 1, anionic, macroreticular polymeric resin based on crosslinked styrene divinylbenzene copolymer containing quaternary ammonium groups, e.g., Amberlyst A26 (OH$^-$ form).

In certain embodiments, the present invention relates to any one of the aforementioned automated small molecule synthesizers, wherein the deprotection module further comprises a source of gas; wherein the source of gas can be placed in fluid communication with the deprotecting chamber.

In certain embodiments, the present invention relates to any one of the aforementioned automated small molecule synthesizers, wherein the drying and degassing module comprises a combined drying and degassing chamber which comprises a first opening at the top of the combined drying and degassing chamber, a second opening at the bottom of the combined drying and degassing chamber, a first frit covering the second opening, and a plunger; and the drying and degassing module is in fluid communication with the deprotection module.

In certain embodiments, the present invention relates to any one of the aforementioned automated small molecule synthesizers, wherein the combined drying and degassing chamber further comprises a diatomaceous earth, e.g., Celite®.

In certain embodiments, the present invention relates to any one of the aforementioned automated small molecule synthesizers, wherein the combined drying and degassing chamber further comprises activated molecular sieves.

In certain embodiments, the present invention relates to any one of the aforementioned automated small molecule synthesizers, wherein the molecular sieves are 4 angstrom, 8-12 mesh.

In certain embodiments, the present invention relates to any one of the aforementioned automated small molecule synthesizers, wherein the combined drying and degassing chamber further comprises potassium carbonate.

In certain embodiments, the present invention relates to any one of the aforementioned automated small molecule synthesizers, wherein the fluid communication is a result of the connection of the second opening of the deprotection chamber to the second opening of the combined drying and degassing chamber.

In certain embodiments, the present invention relates to any one of the aforementioned automated small molecule synthesizers, wherein the combined drying and degassing chamber comprises a cylindrical tube.

In certain embodiments, the present invention relates to any one of the aforementioned automated small molecule synthesizers, wherein the cylindrical tube of the combined drying and degassing chamber is a polypropylene cylindrical tube.

In certain embodiments, the present invention relates to any one of the aforementioned automated small molecule synthesizers, wherein the cylindrical tube of the combined drying and degassing chamber has a length of between about 100 mm and 140 mm.

In certain embodiments, the present invention relates to any one of the aforementioned automated small molecule synthesizers, wherein the cylindrical tube of the combined drying and degassing chamber has a length of about 120 mm.

In certain embodiments, the present invention relates to any one of the aforementioned automated small molecule synthesizers, wherein the cylindrical tube of the combined drying and degassing chamber has an interior diameter of between about 18 mm and about 24 mm.

In certain embodiments, the present invention relates to any one of the aforementioned automated small molecule synthesizers, wherein the cylindrical tube of the combined drying and degassing chamber has an interior diameter of about 21 mm.

In certain embodiments, the present invention relates to any one of the aforementioned automated small molecule synthesizers, wherein the cylindrical tube of the combined drying and degassing chamber has a volume of about 25 mL.

In certain embodiments, the present invention relates to any one of the aforementioned automated small molecule synthesizers, further comprising a source of argon.

In certain embodiments, the present invention relates to any one of the aforementioned automated small molecule synthesizers, wherein the argon can be placed in fluid communication with the combined drying and degassing chamber to sparge the contents of the combined drying and degassing chamber; and the plunger prevents solids from lifting during sparging.

In certain embodiments, the present invention relates to any one of the aforementioned automated small molecule synthesizers, wherein the first opening of the combined drying and degassing chamber is vented to an inert gas atmosphere which is maintained near atmospheric pressure via venting through an oil-filled bubbler.

In certain embodiments, the present invention relates to any one of the aforementioned automated small molecule synthesizers, wherein the argon can be placed in fluid communication with the combined drying and degassing chamber through the second opening of the tube of the combined drying and degassing chamber while the first opening of the tube of the combined drying and degassing chamber is vented to an inert gas atmosphere.

In certain embodiments, the present invention relates to any one of the aforementioned automated small molecule synthesizers, wherein the drying and degassing module comprises a drying chamber and a degassing chamber; the drying chamber comprises a first opening at the top of the drying chamber, a second opening at the bottom of the drying chamber, a first frit covering the second opening, and a plunger; the degassing chamber comprises a first opening at the top of the degassing chamber and a second opening at the bottom of the degassing chamber; the drying chamber is in fluid communication with the degassing chamber; and the degassing chamber is in fluid communication with the deprotection module.

In certain embodiments, the present invention relates to any one of the aforementioned automated small molecule synthesizers, wherein the drying chamber further comprises a diatomaceous earth, such as Celite®.

In certain embodiments, the present invention relates to any one of the aforementioned automated small molecule synthesizers, wherein the drying chamber further comprises activated molecular sieves.

In certain embodiments, the present invention relates to any one of the aforementioned automated small molecule synthesizers, wherein the molecular sieves are 4 angstrom, 8-12 mesh.

In certain embodiments, the present invention relates to any one of the aforementioned automated small molecule synthesizers, wherein the drying chamber further comprises potassium carbonate.

In certain embodiments, the present invention relates to any one of the aforementioned automated small molecule synthesizers, wherein the fluid communication between the drying chamber and the degassing chamber is a result of the connection of the second opening of the drying chamber to the second opening of the degassing chamber.

In certain embodiments, the present invention relates to any one of the aforementioned automated small molecule synthesizers, wherein the fluid communication between the drying and degassing module and the degassing chamber is a result of the connection of the second opening of the degassing chamber to the deprotection module.

In certain embodiments, the present invention relates to any one of the aforementioned automated small molecule synthesizers, wherein the drying chamber comprises a cylindrical tube.

In certain embodiments, the present invention relates to any one of the aforementioned automated small molecule synthesizers, wherein the cylindrical tube of the drying chamber is a polypropylene cylindrical tube.

In certain embodiments, the present invention relates to any one of the aforementioned automated small molecule synthesizers, wherein the cylindrical tube of the drying chamber has a length of between about 100 mm and 140 mm.

In certain embodiments, the present invention relates to any one of the aforementioned automated small molecule synthesizers, wherein the cylindrical tube of the drying chamber has a length of about 120 mm.

In certain embodiments, the present invention relates to any one of the aforementioned automated small molecule synthesizers, wherein the cylindrical tube of the drying chamber has an interior diameter of between about 18 mm and about 24 mm.

In certain embodiments, the present invention relates to any one of the aforementioned automated small molecule synthesizers, wherein the cylindrical tube of the drying chamber has an interior diameter of about 21 mm.

In certain embodiments, the present invention relates to any one of the aforementioned automated small molecule synthesizers, wherein the cylindrical tube of the drying chamber has a volume of about 25 mL.

In certain embodiments, the present invention relates to any one of the aforementioned automated small molecule synthesizers, wherein the degassing chamber comprises a cylindrical tube.

In certain embodiments, the present invention relates to any one of the aforementioned automated small molecule synthesizers, wherein the cylindrical tube of the degassing chamber is a polypropylene cylindrical tube.

In certain embodiments, the present invention relates to any one of the aforementioned automated small molecule synthesizers, wherein the cylindrical tube of the degassing chamber has a length of between about 100 mm and 140 mm.

In certain embodiments, the present invention relates to any one of the aforementioned automated small molecule synthesizers, wherein the cylindrical tube of the degassing chamber has a length of about 120 mm.

In certain embodiments, the present invention relates to any one of the aforementioned automated small molecule synthesizers, wherein the cylindrical tube of the degassing chamber has an interior diameter of between about 18 mm and about 24 mm.

In certain embodiments, the present invention relates to any one of the aforementioned automated small molecule synthesizers, wherein the cylindrical tube of the degassing chamber has an interior diameter of about 21 mm.

In certain embodiments, the present invention relates to any one of the aforementioned automated small molecule synthesizers, wherein the cylindrical tube of the degassing chamber has a volume of about 25 mL.

In certain embodiments, the present invention relates to any one of the aforementioned automated small molecule synthesizers, further comprising a source of argon.

In certain embodiments, the present invention relates to any one of the aforementioned automated small molecule synthesizers, wherein the argon can be placed in fluid communication with the degassing chamber to sparge the contents of the degassing chamber.

In certain embodiments, the present invention relates to any one of the aforementioned automated small molecule synthesizers, wherein the first opening of the degassing chamber is vented to an inert gas atmosphere which is maintained near atmospheric pressure via venting through an oil-filled bubbler.

In certain embodiments, the present invention relates to any one of the aforementioned automated small molecule synthesizers, wherein the argon can be placed in fluid communication with the degassing chamber through the second opening of the tube of the degassing chamber while the first opening of the tube of the degassing chamber is vented to an inert gas atmosphere.

In certain embodiments, the present invention relates to any one of the aforementioned automated small molecule synthesizers, wherein the reaction module comprises a reaction chamber which comprises a first opening at the top of the reaction chamber, a second opening at the bottom of the reaction chamber, a first frit covering the second opening, and a stir bar; wherein the reaction module is in fluid communication with the drying and degassing module.

In certain embodiments, the present invention relates to any one of the aforementioned automated small molecule synthesizers, wherein the reaction module comprises a third opening at the top of the reaction chamber through which a liquid can be added to the reaction chamber without contacting the sidewalls or the bottom of the reaction chamber.

In certain embodiments, the present invention relates to any one of the aforementioned automated small molecule synthesizers, wherein the first opening of reaction chamber is vented to an inert atmosphere.

In certain embodiments, the present invention relates to any one of the aforementioned automated small molecule synthesizers, wherein the first opening of the reaction chamber is fitted with a fritted tube to prevent fine solids from escaping from the reaction chamber.

In certain embodiments, the present invention relates to any one of the aforementioned automated small molecule synthesizers, wherein the first opening of the reaction chamber is vented to an inert atmosphere maintained near atmospheric pressure via venting through an oil-filled bubbler.

In certain embodiments, the present invention relates to any one of the aforementioned automated small molecule synthesizers, wherein both the second opening and third opening of the reaction chamber are in fluid communication with the second opening of the drying and degassing chamber at the same time.

In certain embodiments, the present invention relates to any one of the aforementioned automated small molecule synthesizers, wherein the reaction chamber comprises a cylindrical tube.

In certain embodiments, the present invention relates to any one of the aforementioned automated small molecule synthesizers, wherein the cylindrical tube of the reaction chamber is a polypropylene cylindrical tube.

In certain embodiments, the present invention relates to any one of the aforementioned automated small molecule synthesizers, wherein the cylindrical tube of the reaction chamber has a length of between about 100 mm and 140 mm.

In certain embodiments, the present invention relates to any one of the aforementioned automated small molecule synthesizers, wherein the cylindrical tube of the reaction chamber has a length of about 120 mm.

In certain embodiments, the present invention relates to any one of the aforementioned automated small molecule synthesizers, wherein the cylindrical tube of the reaction chamber has an interior diameter of between about 18 mm and about 24 mm.

In certain embodiments, the present invention relates to any one of the aforementioned automated small molecule synthesizers, wherein the cylindrical tube of the reaction chamber has an interior diameter of about 21 mm.

In certain embodiments, the present invention relates to any one of the aforementioned automated small molecule synthesizers, wherein the cylindrical tube of the reaction chamber has a volume of about 25 mL.

In certain embodiments, the present invention relates to any one of the aforementioned automated small molecule synthesizers, wherein the reaction chamber further comprises a second frit between the stir bar and the first frit; wherein the second frit is smaller than the first frit.

In certain embodiments, the present invention relates to any one of the aforementioned automated small molecule synthesizers, wherein the second frit and the first frit are held together with a wire, to prevent the second frit from turning perpendicular to the first frit.

In certain embodiments, the present invention relates to any one of the aforementioned automated small molecule synthesizers, wherein the first frit is disc-shaped; the first frit has a diameter of between about 18 mm and about 24 mm; and the first frit has a height between about 2 mm and about 6 mm.

In certain embodiments, the present invention relates to any one of the aforementioned automated small molecule synthesizers, wherein the first frit is disc-shaped; the first frit has a diameter of about 21 mm; and the first frit has a height of about 4 mm.

In certain embodiments, the present invention relates to any one of the aforementioned automated small molecule synthesizers, wherein the second frit is disc-shaped; the second frit has a diameter between about 16 mm and about 10 mm; and the second frit has a height between about 2 mm and about 6 mm.

In certain embodiments, the present invention relates to any one of the aforementioned automated small molecule synthesizers, wherein the second frit is disc-shaped; the second frit has a diameter of about 13 mm; and the second frit has a height of about 4 mm.

In certain embodiments, the present invention relates to any one of the aforementioned automated small molecule synthesizers, wherein the shape of the first frit is that of a first disc on top of a second disc; wherein the diameter of the first disc is smaller than the diameter of the second disc.

In certain embodiments, the present invention relates to any one of the aforementioned automated small molecule synthesizers, wherein the shape of the first frit prevents solids from passing through the second opening of the reaction chamber.

In certain embodiments, the present invention relates to any one of the aforementioned automated small molecule synthesizers, wherein the reaction module further comprises a stir plate which turns the stir bar.

In certain embodiments, the present invention relates to any one of the aforementioned automated small molecule synthesizers, wherein the reaction module further comprises a heating block which can heat the contents of the reaction chamber.

In certain embodiments, the present invention relates to any one of the aforementioned automated small molecule synthesizers, wherein at least a portion of the reaction chamber is jacketed by the heating block.

In certain embodiments, the present invention relates to any one of the aforementioned automated small molecule synthesizers, wherein the reaction chamber further comprises a transition metal salt.

In certain embodiments, the present invention relates to any one of the aforementioned automated small molecule synthesizers, wherein the transition metal salt is adsorbed onto a solid.

In certain embodiments, the present invention relates to any one of the aforementioned automated small molecule synthesizers, wherein the transition metal salt is palladium acetate.

In certain embodiments, the present invention relates to any one of the aforementioned automated small molecule synthesizers, wherein the solid onto which the transition metal salt is adsorbed is cesium carbonate.

In certain embodiments, the present invention relates to any one of the aforementioned automated small molecule synthesizers, wherein the reaction chamber further comprises a phosphine ligand.

In certain embodiments, the present invention relates to any one of the aforementioned automated small molecule synthesizers, wherein the phosphine ligand is adsorbed onto a solid.

In certain embodiments, the present invention relates to any one of the aforementioned automated small molecule synthesizers, wherein the phosphine ligand is S-Phos (2-dicyclohexylphosphino-2',6'-dimethoxybiphenyl).

In certain embodiments, the present invention relates to any one of the aforementioned automated small molecule synthesizers, wherein the catalyst is derived from an air-stable palladium precatalyst.

In certain embodiments, the present invention relates to any one of the aforementioned automated small molecule synthesizers, wherein the solid onto which the phosphine ligand is adsorbed is cesium carbonate.

In certain embodiments, the present invention relates to any one of the aforementioned automated small molecule synthesizers, wherein the reaction chamber further comprises a base.

In certain embodiments, the present invention relates to any one of the aforementioned automated small molecule synthesizers, wherein the base in the reaction chamber is potassium hydroxide.

In certain embodiments, the present invention relates to any one of the aforementioned automated small molecule synthesizers, wherein the reaction run in the reaction chamber is a cross-coupling reaction.

In certain embodiments, the present invention relates to any one of the aforementioned automated small molecule synthesizers, wherein the reaction run in the reaction chamber is selected from the group consisting of a Suzuki-Miyaura coupling, an oxidation, a Swern oxidation, a "Jones reagents" oxidation, a reduction, an Evans' aldol reaction, an HWE olefination, a Takai olefination, an alcohol silylation, a desilylation, a p-methoxybenzylation, an iodination, a Negishi cross-coupling, a Heck coupling, a Miyaura borylation, a Stille coupling, and a Sonogashira coupling.

In certain embodiments, the present invention relates to any one of the aforementioned methods, wherein the chemical reaction is selected from epoxidation, nucleophilic substitution, electrophilic substitution, oxidation, dihydroxylation, carbonylation, alkenation, cyclopropanation, cycloaddition, conjugate addition, Michael addition, Diels-Alder reaction, and transition metal-catalyzed cross-coupling reaction.

In accordance with any one of the foregoing embodiments, in one embodiment, the transition metal-catalyzed cross-coupling reaction is a Suzuki-Miyaura reaction.

In accordance with any one of the foregoing embodiments, in one embodiment, the chemical reaction is epoxidation.

In accordance with any one of the foregoing embodiments, in one embodiment, the epoxidation is selected from the group consisting of Sharpless epoxidation and Jacobsen epoxidation.

In certain embodiments, the present invention relates to any one of the aforementioned automated small molecule synthesizers, wherein the reaction run in the reaction chamber is a Suzuki-Miyaura coupling.

In certain embodiments, the present invention relates to any one of the aforementioned automated small molecule synthesizers, wherein the chemical reaction run in the reaction chamber comprises the step of contacting a chiral, non-racemic PIDA boronate with a reagent, wherein the chiral, non-racemic PIDA boronate comprises a boron having an sp$^3$ hybridization, a PIDA protecting group bonded to the boron, and an organic group bonded to the boron through a boron-carbon bond; the organic group is chemically transformed, and the boron is not chemically transformed.

In certain embodiments, the present invention relates to any one of the aforementioned automated small molecule synthesizers, wherein the chiral, non-racemic PIDA boronate is represented by

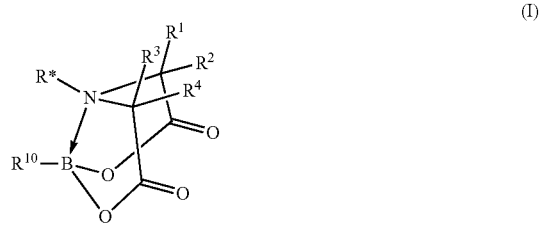

(I)

wherein:

B is a boron atom having sp³ hybridization;

R* is a chiral group

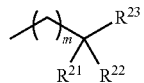

of at least 90% enantiomeric excess;

$R^{21}$ and $R^{22}$ are independently selected from the group consisting of hydrogen, alkyl, cycloalkyl, heterocyclyl, aryl, heteroaryl, aralkyl, and heteroaralkyl; or $R^{21}$ and $R^{22}$, taken together, form a 5-10-membered cycloalkyl or aromatic ring, or form a 5-10-membered heterocyclic or heteroaromatic ring comprising 1-3 heteroatoms independently selected from the group consisting of N, O, and S;

$R^{23}$ is selected from the group consisting of hydrogen, alkyl, cycloalkyl, heterocyclyl, aryl, heteroaryl, aralkyl, and heteroaralkyl;

$R^{10}$ is selected from the group consisting of

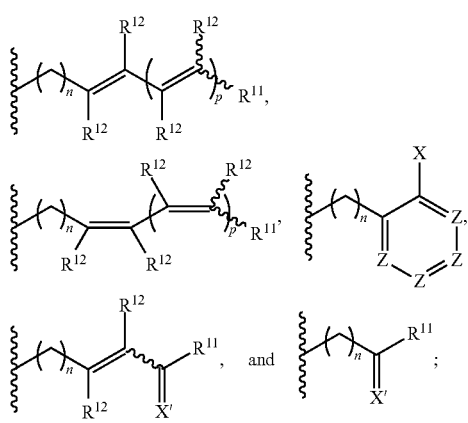

$R^{11}$ and each instance of $R^{12}$ are independently selected from the group consisting of hydrogen, halogen, hydroxyl, (C1-C10)alkyl, cycloalkyl, aryl, aralkyl, heteroaralkyl, alkoxyl, acyl, acyloxy, aryloxy, amino, and trialkylsilyloxy; or $R^{11}$ and any one instance of $R^{12}$, or any two instances of $R^{12}$, taken together, form a 3-10-membered ring;

X is halogen;

each instance of Z is independently selected from the group consisting of CH and N, provided that no more than two instances of Z are N;

X' is selected from the group consisting of $CR^5R^6$, O, S, and $NR^7$;

$R^1$ and $R^2$ are both hydrogen or identically selected (C1-C3)alkyl;

$R^3$ and $R^4$ are both hydrogen or identically selected (C1-C3)alkyl;

$R^5$ and $R^6$ are independently selected from the group consisting of hydrogen, halogen, hydroxyl, (C1-C10)alkyl, cycloalkyl, aryl, aralkyl, heteroaralkyl, alkoxyl, acyl, acyloxy, aryloxy, amino, and trialkylsilyloxy;

$R^7$ is selected from the group consisting of hydrogen and (C1-C3)alkyl;

m is 0, 1, or 2;

n is 0, 1, or 2; and p is 0, 1, or 2.

In an alternative embodiment, all else being the same, $R^1$ and $R^2$, and/or $R^3$ and $R^4$, are independently selected from the group consisting of hydrogen and (C1-C3)alkyl.

In one embodiment, R* is

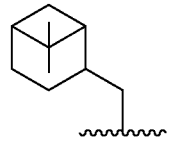

In one embodiment, R* is

In one embodiment, R* is

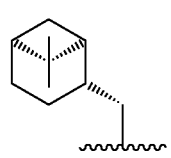

In one embodiment, R* is selected from the group consisting of

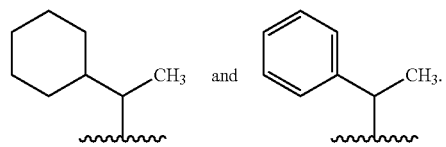

In one embodiment, R* is selected from the group consisting of

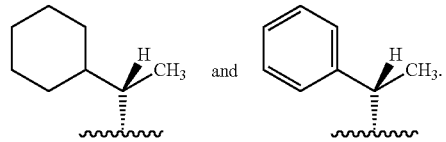

In one embodiment, R* is selected from the group consisting of

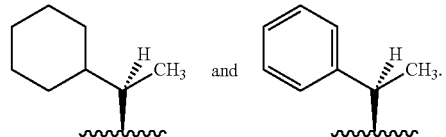

In one embodiment, $R^{21}$ and $R^{22}$, taken together, form a 5-10-membered cycloalkyl or aromatic ring, or form a 5-10- membered heterocyclic or heteroaromatic ring comprising 1-3 heteroatoms independently selected from the group consisting of N, O, and S.

In one embodiment, R* is

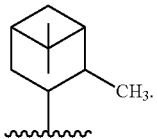

In one embodiment, R* is

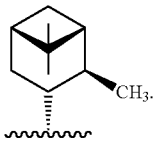

In one embodiment, R* is

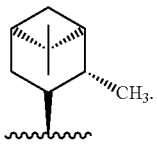

In one embodiment, R* is

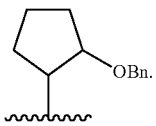 [SMILES: *C1CCCC1OCc1ccccc1]

In one embodiment, R* is

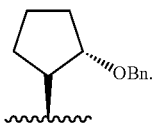

In one embodiment, R* is

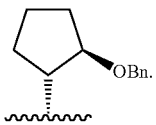

In accordance with any one of the foregoing embodiments, in one embodiment, $R^5$ and $R^6$ are independently selected from the group consisting of hydrogen and (C1-C3)alkyl.

In accordance with any one of the foregoing embodiments, in one embodiment, m is 0. Alternatively, in accordance with any one of the foregoing embodiments, in one embodiment, m is 1. Alternatively, in accordance with any one of the foregoing embodiments, in one embodiment, m is 2.

In accordance with any one of the foregoing embodiments, in one embodiment, n is 0. Alternatively, in accordance with any one of the foregoing embodiments, in one embodiment, n is 1. Alternatively, in accordance with any one of the foregoing embodiments, in one embodiment, n is 2.

In accordance with any one of the foregoing embodiments, in one embodiment, p is 0. Alternatively, in accordance with any one of the foregoing embodiments, in one embodiment, p is 1. Alternatively, in accordance with any one of the foregoing embodiments, in one embodiment, p is 2.

In accordance with any one of the foregoing embodiments not otherwise excluded, in one embodiment, $R^{10}$ is

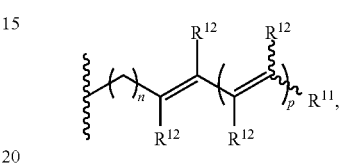

n is 0, p is 0, each instance of $R^{12}$ is hydrogen, and $R^{11}$ is selected from the group consisting of aryl and methyl.

Alternatively, in accordance with any one of the foregoing embodiments not otherwise excluded, in one embodiment, $R^{10}$ is

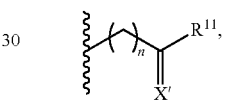

n is 0, X' is $CH_2$, and $R^{11}$ is methyl.

Alternatively, in accordance with any one of the foregoing embodiments not otherwise excluded, in one embodiment, $R^{10}$ is

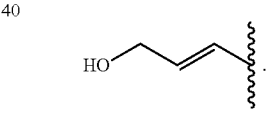

Alternatively, in accordance with any one of the foregoing embodiments not otherwise excluded, in one embodiment, $R^{10}$ is

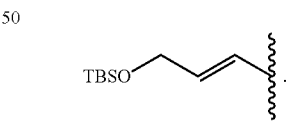

In accordance with any one of the foregoing embodiments, in one embodiment, R* is a chiral group

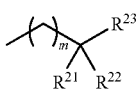

of at least 95% enantiomeric excess. In accordance with any one of the foregoing embodiments, in one embodiment, R* is a chiral group

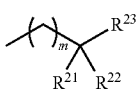

of at least 98% enantiomeric excess. In accordance with any one of the foregoing embodiments, in one embodiment, R* is a chiral group

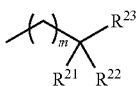

of at least 99% enantiomeric excess.

In certain embodiments, the present invention relates to any one of the aforementioned methods, wherein the chiral, non-racemic PIDA boronate is represented by

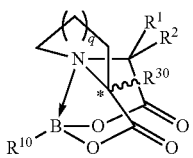

(II)

wherein:

B is a boron atom having $sp^3$ hybridization;

the carbon atom marked "*" is a chiral carbon atom of at least 90% enantiomeric excess;

$R^{10}$ is selected from the group consisting of

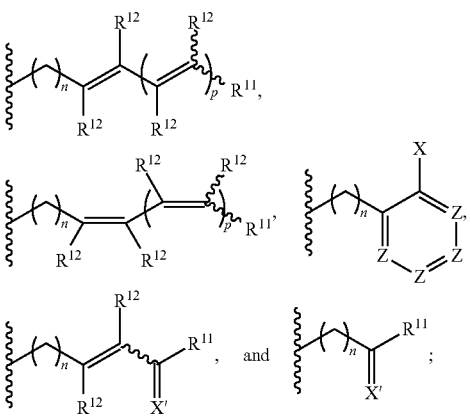

$R^{11}$ and each instance of R' are independently selected from the group consisting of hydrogen, halogen, hydroxyl, (C1-C10)alkyl, cycloalkyl, aryl, aralkyl, heteroaralkyl, alkoxyl, acyl, acyloxy, aryloxy, amino, and trialkylsilyloxy; or $R^{11}$ and any one instance of $R^{12}$, or any two instances of $R^{12}$, taken together, form a 3-10-membered ring;

X is halogen;

each instance of Z is independently selected from the group consisting of CH and N, provided that no more than two instances of Z are N;

X' is selected from the group consisting of $CR^5R^6$, O, S, and $NR^7$;

$R^1$ and $R^2$ are both hydrogen or identically selected (C1-C3)alkyl;

$R^5$ and $R^6$ are independently selected from the group consisting of hydrogen, halogen, hydroxyl, (C1-C10)alkyl, cycloalkyl, aryl, aralkyl, heteroaralkyl, alkoxyl, acyl, acyloxy, aryloxy, amino, and trialkylsilyloxy;

$R^7$ and $R^{30}$ are independently selected from the group consisting of hydrogen and (C1-C3)alkyl;

n is 0, 1, or 2;

p is 0, 1, or 2; and q is 1 or 2.

In an alternative embodiment, all else being the same, $R^1$ and $R^2$ are independently selected from the group consisting of hydrogen and (C1-C3)alkyl.

In one embodiment, the compound of formula (II) is

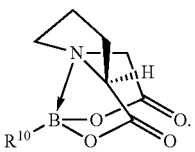

In accordance with any one of the foregoing embodiments, in one embodiment, n is 0. Alternatively, in accordance with any one of the foregoing embodiments, in one embodiment, n is 1. Alternatively, in accordance with any one of the foregoing embodiments, in one embodiment, n is 2.

In accordance with any one of the foregoing embodiments, in one embodiment, p is 0. Alternatively, in accordance with any one of the foregoing embodiments, in one embodiment, p is 1. Alternatively, in accordance with any one of the foregoing embodiments, in one embodiment, p is 2.

In accordance with any one of the foregoing embodiments, in one embodiment, q is 1. Alternatively, in accordance with any one of the foregoing embodiments, in one embodiment, q is 2.

In accordance with any one of the foregoing embodiments not otherwise excluded, in one embodiment, $R^{10}$ is n is 0, p is 0, each instance of $R^{12}$ is hydrogen, and $R^{11}$ is selected from the group consisting of aryl and methyl.

Alternatively, in accordance with any one of the foregoing embodiments not otherwise excluded, in one embodiment, $R^{10}$ is n is 0, X' is $CH_2$, and $R^{11}$ is methyl.

Alternatively, in accordance with any one of the foregoing embodiments not otherwise excluded, in one embodiment, $R^{10}$ is Alternatively, in accordance with any one of the foregoing embodiments not otherwise excluded, in one embodiment, $R^{10}$ is

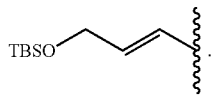 [SMILES: */C=C/CO[Si](C)(C)C(C)(C)C]

In accordance with any one of the foregoing embodiments, in one embodiment the carbon atom marked "*" is a chiral carbon atom of at least 95% enantiomeric excess. In accordance with any one of the foregoing embodiments, in one embodiment the carbon atom marked "*" is a chiral carbon atom of at least 98% enantiomeric excess. In accordance with any one of the foregoing embodiments, in one embodiment the carbon atom marked "*" is a chiral carbon atom of at least 99% enantiomeric excess.

In certain embodiments, the present invention relates to any one of the aforementioned automated small molecule synthesizers, wherein the purification module comprises a precipitation chamber and a silica column; the precipitation chamber comprises a first opening at the top of the precipitation chamber, a second opening at the bottom of the precipitation chamber, a first frit covering the second opening, a stir bar, and a diatomaceous earth (such as Celite®); and the silica column comprises a first opening at the top of the column, a second opening at the bottom of the column, a second frit covering the top opening of the column, a third frit covering the bottom opening of the column, and silica; wherein the purification module is in fluid communication with the reaction module.

In certain embodiments, the present invention relates to any one of the aforementioned automated small molecule synthesizers, wherein the precipitation chamber comprises a cylindrical tube.

In certain embodiments, the present invention relates to any one of the aforementioned automated small molecule synthesizers, wherein the cylindrical tube of the precipitation chamber is a polypropylene cylindrical tube.

In certain embodiments, the present invention relates to any one of the aforementioned automated small molecule synthesizers, wherein the cylindrical tube of the precipitation chamber has a length of between about 100 mm and 140 mm.

In certain embodiments, the present invention relates to any one of the aforementioned automated small molecule synthesizers, wherein the cylindrical tube of the precipitation chamber has a length of about 120 mm.

In certain embodiments, the present invention relates to any one of the aforementioned automated small molecule synthesizers, wherein the cylindrical tube of the precipitation chamber has an interior diameter of between about 18 mm and about 24 mm.

In certain embodiments, the present invention relates to any one of the aforementioned automated small molecule synthesizers, wherein the cylindrical tube of the precipitation chamber has an interior diameter of about 21 mm.

In certain embodiments, the present invention relates to any one of the aforementioned automated small molecule synthesizers, wherein the cylindrical tube of the precipitation chamber has a volume of about 25 mL.

In certain embodiments, the present invention relates to any one of the aforementioned automated small molecule synthesizers, wherein the precipitation chamber further comprises a resin which scavenges metals.

In certain embodiments, the present invention relates to any one of the aforementioned automated small molecule synthesizers, wherein the precipitation chamber further comprises activated charcoal.

In certain embodiments, the present invention relates to any one of the aforementioned automated small molecule synthesizers, wherein the purification module further comprises a stir plate which turns the stir bar.

In certain embodiments, the present invention relates to any one of the aforementioned automated small molecule synthesizers, wherein the diatomaceous earth (e.g., Celite®) in the precipitation chamber prevents the stir bar from turning if there is no solvent in the precipitation chamber.

In certain embodiments, the present invention relates to any one of the aforementioned automated small molecule synthesizers, wherein the first frit of the precipitation chamber keeps the diatomaceous earth in the precipitation chamber.

In certain embodiments, the present invention relates to any one of the aforementioned automated small molecule synthesizers, wherein the silica column is a cylindrical tube.

In certain embodiments, the present invention relates to any one of the aforementioned automated small molecule synthesizers, wherein the cylindrical tube of the silica column is a polypropylene cylindrical tube.

In certain embodiments, the present invention relates to any one of the aforementioned automated small molecule synthesizers, wherein the cylindrical tube of the silica column has a length of between about 100 mm and 140 mm.

In certain embodiments, the present invention relates to any one of the aforementioned automated small molecule synthesizers, wherein the cylindrical tube of the silica column has a length of about 120 mm.

In certain embodiments, the present invention relates to any one of the aforementioned automated small molecule synthesizers, wherein the cylindrical tube of the silica column has an interior diameter of between about 18 mm and about 24 mm.

In certain embodiments, the present invention relates to any one of the aforementioned automated small molecule synthesizers, wherein the cylindrical tube of the silica column has an interior diameter of about 21 mm.

In certain embodiments, the present invention relates to any one of the aforementioned automated small molecule synthesizers, wherein the cylindrical tube of the silica column has a volume of about 25 mL.

In certain embodiments, the present invention relates to any one of the aforementioned automated small molecule synthesizers, wherein the second frit of the silica column and third frit of the silica column keep the silica in the silica column.

In certain embodiments, the present invention relates to any one of the aforementioned automated small molecule synthesizers, wherein the silica is functionalized with amino groups.

In certain embodiments, the present invention relates to any one of the aforementioned automated small molecule synthesizers, wherein the purification module further comprises an auxiliary pump.

In certain embodiments, the present invention relates to any one of the aforementioned automated small molecule synthesizers, further comprising a solvent reservoir containing hexane.

In certain embodiments, the present invention relates to any one of the aforementioned automated small molecule synthesizers, wherein the purification module is in fluid communication with the reservoir of hexane; and the auxiliary pump provides hexane from the reservoir to the precipitation chamber by passing the hexane into the silica column through the second opening of the silica column, out of the silica column through the first opening of the silica column, and into the precipitation chamber through the second opening of the precipitation chamber.

In certain embodiments, the present invention relates to any one of the aforementioned automated small molecule synthesizers, wherein the auxiliary pump can remove the hexane by passing the hexane into the second opening of the precipitation chamber, through the first opening of the silica column and out the second opening of the silica column.

In certain embodiments, the present invention relates to any one of the aforementioned automated small molecule synthesizers, further comprising a solvent reservoir containing diethyl ether.

In certain embodiments, the present invention relates to any one of the aforementioned automated small molecule synthesizers, wherein the purification module is in fluid communication with the reservoir of diethyl ether; and the auxiliary pump provides diethyl ether from the reservoir to the precipitation chamber by passing the diethyl ether into the silica column through the second opening of the silica column, out of the silica column through the first opening of the silica column, and into the precipitation chamber through the second opening of the precipitation chamber.

In certain embodiments, the present invention relates to any one of the aforementioned automated small molecule synthesizers, wherein the auxiliary pump can remove the diethyl ether by passing the diethyl ether into the second opening of the precipitation chamber, through the first opening of the silica column and out the second opening of the silica column.

In certain embodiments, the present invention relates to any one of the aforementioned automated small molecule synthesizers, further comprising a solvent reservoir containing diethyl ether containing 1.5% methanol by volume.

In certain embodiments, the present invention relates to any one of the aforementioned automated small molecule synthesizers, wherein the purification module is in fluid communication with the reservoir of diethyl ether containing 1.5% methanol by volume; and the auxiliary pump provides diethyl ether containing 1.5% methanol by volume from the reservoir to the precipitation chamber by passing the diethyl ether into the silica column through the second opening of the silica column, out of the silica column through the first opening of the silica column, and into the precipitation chamber through the second opening of the precipitation chamber.

In certain embodiments, the present invention relates to any one of the aforementioned automated small molecule synthesizers, wherein the auxiliary pump can remove the diethyl ether containing 1.5% methanol by volume by passing the diethyl ether containing 1.5% methanol by volume into the second opening of the precipitation chamber, through the first opening of the silica column and out the second opening of the silica column.

In certain embodiments, the present invention relates to any one of the aforementioned automated small molecule synthesizers, further comprising a waste container; wherein the second opening of the silica column is in fluid communication with the waste container.

In certain embodiments, the present invention relates to any one of the aforementioned automated small molecule synthesizers, further comprising a solvent reservoir containing THF.

In certain embodiments, the present invention relates to any one of the aforementioned automated small molecule synthesizers, wherein the purification module is in fluid communication with the reservoir of THF; and the auxiliary pump provides THF from the reservoir to the precipitation chamber by passing the THF into the silica column through the second opening of the silica column, out of the silica column through the first opening of the silica column, and into the precipitation chamber through the second opening of the precipitation chamber.

In certain embodiments, the present invention relates to any one of the aforementioned automated small molecule synthesizers, wherein the second opening of the precipitation chamber can be placed in fluid communication with the first opening of the silica column via a three-way valve; wherein a first port on the valve is connected to the second opening of the precipitation chamber, a second port on the valve is connected to the first opening of the silica column, and a third port on the valve can be used to withdraw a solution from the precipitation chamber without passing the solution through the silica column.

Another aspect of the invention relates to any one of the aforementioned automated small molecule synthesizers, comprising: one or more deprotection modules; one or more drying and degassing modules; one or more reaction modules; one or more purification modules; at least one pump which can move liquid from one module to another; and a computer equipped with software; wherein all of the modules are under the control of the computer.

Another aspect of the invention relates to any one of the aforementioned automated small molecule synthesizers comprising: a plurality of deprotection modules; a plurality of drying and degassing modules; a plurality of reaction modules; a plurality of purification modules; at least one pump which can move liquid from one module to another; and a computer equipped with software; wherein all of the modules are under the control of the computer.

Alternative Embodiment Using Aqueous Deprotection Module. The aqueous deprotection module consists of equipment necessary to complete a solution-phase aqueous base-mediated chiral, non-racemic PIDA boronate deprotection, a separation of the resulting biphasic mixture, a predrying and drying of the organic layer (e.g., ethereal solution of the boronic acid), and a deoxygenation/concentration of the dried organic layer in preparation for a cross-coupling.

Specifically, two syringe pumps and an argon solenoid are utilized in the new deprotection module (FIG. 9). The primary syringe pump, which is used for the majority of liquid handling during an entire sequence, handles organic solvents and solutions. A dedicated aqueous syringe pump is utilized to handle all aqueous reagents (water, 0.5 M, pH=6, potassium phosphate buffer, and 50% saturated sodium chloride). This isolation of aqueous solutions to a dedicated syringe pump minimizes water contamination throughout the rest of the machine. The argon solenoid is used to deliver a flow of dry argon for agitating the deprotection and for concentrating and deoxygenating the final solution of boronic acid.

For example, deprotection at the beginning of a multistep sequence begins with solid chiral, non-racemic PIDA boronate (1 mmol, 1 equiv) and solid sodium hydroxide (3 mmol, 3 equivs) in a 12-g Luknova cartridge. The primary pump delivers dry deoxygenated THF (10 mL, 0.1 M) to dissolve the PIDA boronate. The aqueous pump then delivers deionized water (3 mL, 0.33 M), creating a biphasic mixture, to dissolve the sodium hydroxide. A flow of dry argon is then delivered (in short 0.5-2 second pulses) from the bottom of the tube, bubbling through and agitating the biphasic mixture for 10 minutes at which time the deprotection is complete. Then, simultaneously the aqueous pump delivers phosphate buffer (3 mL) to quench the reaction, and the primary pump delivers diethyl ether (5 mL) to prepare for the separation. The aqueous pump then agitates the quenched reaction with several injections of atmospheric air. The aqueous pump then aspirates the biphasic reaction mixture, pauses to allow full separation, and returns the remaining organic layer to the deprotection tube. The aqueous layer is injected to waste and the aqueous pump delivers 50% saturated sodium chloride (3 mL) to the deprotection tube and agitates the mixture with several injections of air. Again, the aqueous pump aspirates the biphasic mixtures, pauses to allow full separation, and returns the organic layer to the deprotection tube. The aqueous layer is injected to waste.

This separation has been shown to be reproducible in the production of aqueous layer volumes. On a 1 mmol scale the first aqueous layer is 6.0 mL (±0.1 mL). On a 0.66 mmol scale the first aqueous layer is 6.2 mL (±0.1 mL). On a 0.33 mmol scale the first aqueous layer is 6.4 mL (±0.1 mL). The aqueous salt volume has been shown to be 3.8 mL (±0.1 mL) regardless of reaction scale.

Subsequent deprotections begin with the purified chiral, non-racemic PIDA boronate as a solution in THF (from the automated purification) being injected into a new deprotection tube containing sodium hydroxide. The remainder of the deprotection proceeds as described above. For these downstream deprotections the only difference in experimental setup is the amount of sodium hydroxide used (the stoichiometry is always 3 equivalents with respect to the PIDA boronate). The solvent and reagent volumes remain the same and are as outlined above. The separation volumes have shown a scale dependency and are as outlined above. The remaining manipulations (predrying, drying, and deoxygenating and concentration) proceed as described below. The relative volumes and quantities of solvents and reagents are independent of reaction scale.

Predrying of the still-wet organic layer (ethereal solution of boronic acid) removes the bulk of the remaining water. In one embodiment, the predrying tube is a 12-g Luknova cartridge containing a mixture of Celite® (800 mg) and anhydrous magnesium sulfate (2.1 g). A 5-mL polypropylene syringe plunger is placed on top of the solid mixture. The two solids are mixed intimately to prevent clumping of the magnesium sulfate clathrate. Additionally, the syringe plunger prevents movement of the solids up the tube as liquids are injected. To begin the predrying step, the primary pump delivers 5 mL of dry deoxygenated THF to the predrying tube. It has been shown that the solids adsorb approximately 5 mL of THF during this process, so wetting the solids with clean THF prevents loss of volume. Next, the primary pump transfers the organic layer from the deprotection tube into the predrying tube. The solution is passed over the solid mixture by repeated aspiration/injection (rate=15 mL/min) via the primary pump. In total, the solution is agitated in this manner 20 times. At this point the bulk water has been removed from the solution of boronic acid.

Drying of the ethereal boronic acid solution is required to remove the remaining residual water. In one embodiment, the drying tube is a 12-g Luknova cartridge containing a layer of Celite® (300 mg) topped with activated molecular sieves (4 Å, −325 mesh, 3.6 g). A 5-mL polypropylene syringe plunger is placed on top of these solids. The bottom layer of Celite® prevents clogging of the tube frit by the fine molecular sieves. The syringe plunger prevents movement of solids as described above. To begin the drying step, the primary pump delivers 5 mL of dry deoxygenated THF to the predrying tube. As described above, this prevents loss of volume. Next, the primary pump transfers the predried solution of boronic acid from the predrying tube to the drying tube. Similar to the agitation method described above, the solution is passed over the solids by repeated aspiration/injection (rate=5 mL/min) via the primary pump. In total, the solution is agitated in this manner 12 times. The rate of aspiration during the drying step achieves appropriate aspiration and thereby thorough agitation. Specifically, a slow aspiration rate of about 5 mL/min efficiently aspirates the boronic acid solution through the layer of molecular sieves. Faster rates result in the build-up of vacuum that is dissipated by solvent evaporation rather than solution aspiration; boronic acid solution is not efficiently passed over the molecular sieves and remains wet. At this point the boronic acid solution has been thoroughly dried.

Deoxygenating the boronic acid solution is required in preparation of the cross-coupling reaction. Specifically, the solution needs to be deoxygenated for the coupling to proceed productively. Additionally, concentration of the solution is useful to remove any diethyl ether that is still present from the deprotection workup, as well as to maintain a workable volume for the cross-coupling reaction. Workable relative volumes for the coupling reactions have been determined to be 9 mL of boronic acid solution for all couplings, regardless of reaction scale. As an exception, the final reaction in a sequence requires a boronic acid solution of 2 mL. In one embodiment, the concentration tube is an empty 12-g Luknova cartridge. To begin the deoxygenating/concentration step, the primary pump transfers the dry boronic acid solution to the concentration tube. Then, dry argon is bubbled through the solution to simultaneously deoxygenate and concentrate. The argon flow begins with short 0.5 second pulses and these pulses become progressively longer over the course of 3 minutes, at which point the argon flow remains on continuously. This concentration process has been shown to reduce volume at an approximate rate of 0.1 mL/min. Before concentration, the volume is 18 mL and, therefore, approximately 90 minutes of argon flow reduces the volume to 9 mL. The resulting dry, deoxygenated, concentrated solution of boronic acid is suitable for addition to an anhydrous cross-coupling reaction.

The aqueous deprotection module represents a robust and predictable method for the automation of chiral, non-racemic PIDA boronate deprotection reactions. These types of aqueous conditions are known to work for many sensitive boronic acids in the context of non-automated synthesis, and, as such, this automated deprotection is expected to work reliably for a wide range of sensitive substrates. This aqueous deprotection module, however, differs from previously reported methods of chiral, non-racemic PIDA boronate deprotection in several ways. The changes employed in the automated process relative to the procedure utilized in published solution-phase reactions include argon flow agitation and argon sparging deoxygenation/concentration, a three-step drying strategy, the minimization and use of specific solvent volumes, and controlled slow-rate aspiration for liquid handling.

In a non-automated chiral, non-racemic PIDA boronate deprotection, agitation of the biphasic reaction is achieved with conventional stirring (magnetic stir bar and stirring plate). The aqueous deprotection module of the invention utilizes argon gas flow to agitate the deprotection reaction. As argon is passed through the frit of the deprotection tube, the resulting bubbles provide highly efficient agitation of the biphasic system. The agitation is sufficient to achieve full conversion at room temperature in 10 min (similar to non-automated conditions) without the use of a stir plate. Furthermore, the aqueous deprotection module uses argon flow to sparge and concentrate the boronic acid solution. In non-automated syntheses with stable boronic acids, the acid is typically isolated as a solid and submitted to a cross-coupling in the presence of deoxygenated solvent. In the case of unstable boronic acids, the acid is typically not isolated, but concentrated to some small volume by iterative concentrations from deoxygenated solvent. Use of argon sparging and gas flow concentration simultaneously in the automated system deoxygenates the boronic acid solution and concentrates it. This provides a coupling-ready boronic acid solution without the need to isolate a potentially unstable boronic acid.

Drying of the boronic acid solution for a non-automated synthesis typically involves drying over an anhydrous drying reagent, filtration through Celite®, and subsequent washing of the drying reagent. The use of excess drying reagent can insure complete drying, and the use of copious solvent volumes can insure quantitative recovery. This increased solvent volume presents a challenge in the context of automation. That is, all the excess volume accumulated in the automated process would need to be concentrated downstream. In order to minimize the accumulation of solvent, which is closely connected to the drying process, the automated system utilizes a cooperative three-step drying strategy and specific solvent volumes. The first of the three steps is a 50% saturated sodium chloride extraction of the organic phase of the deprotection reaction. This removes some bulk water from the organic phase and, as described above, does so with reproducible specific volumes. The second of the three steps is the predrying of the boronic acid solution over anhydrous magnesium sulfate, which removes more bulk water from the solution. The final step is the drying over molecular sieves, which removes the remaining residual water. As described above, each step uses specific predetermined solvent volumes to maintain minimized, yet reproducible solvent accumulation. This process, coupled with the use of predetermined, minimized quantities of drying agents, maximizes drying and substrate recovery while minimizing solvent accumulation.

Another key difference between previously reported methods for non-automated syntheses and the automated system of the invention is the use of controlled slow-rate aspiration for liquid handling. The decreased aspiration rate during the drying step, as described above, has enabled efficient handling of liquids. Specifically, aspiration rates above 2 mL/min during the drying step cause a build-up of vacuum in the primary syringe pump. The vacuum is then relieved by the evaporation of solvent. As a result, the boronic acid solution is not fully aspirated and is not efficiently dried over the molecular sieves. Using a decreased aspiration rate minimizes the build-up of vacuum and allows for full aspiration of the boronic acid solution. This slow-rate aspiration approach has also been applied to the aspiration of crude cross-coupling reaction mixtures.

Specific volumes and amounts disclosed above can, of course, be scaled up or down to suit larger or smaller overall scale automated machines, respectively, provided that the scaled volumes and scaled amounts remain proportional to one another.

An exemplary automated coupling cycle. An example of one complete cycle of automated coupling proceeds as follows.

Step 1. In the deprotection module, catch and selective release-based hydrolysis of a chiral, non-racemic PIDA boronate yields a freshly-prepared boronic acid as a solution in THF.

In this example, the deprotection of PIDA-protected organoboronic acids via solid-supported ammonium hydroxide reagent proceeds without the use of added bulk water, thereby avoiding the need to remove bulk water prior to a subsequent anhydrous reactions (such as a cross-coupling). A range of aqueous deprotection conditions in the context of the automated synthesis were tried but the following problems were found:

The amount of solvent required to extract the boronic acid product depended on the identity of the boronic acid. Polar boronic acids required much more solvent. Some boronic acids were too polar to be effectively extracted.

The amount of solvent used in the extraction step would require an additional evaporation step to obtain a reasonable concentration.

Removing the large amount of water in the organic phase required very large amounts of drying reagents that became impractical.

Completely removing the water introduced in the deprotection step from the machine was very difficult from an engineering standpoint. Residual water persisted in the tubing and syringes.

Running the deprotection reaction with solid KOH and anhydrous THF did not proceed. Running the deprotection reaction with solid KOH and 1% water in THF was not a general solution because the two products of the deprotection reaction, N-pinine iminodiacetic acid bis potassium salt and the boronate salt (the boronic acid reacts with KOH to produce the anionic boronate species), were both insoluble in THF and aggregated to cause the water and the THF to separate and the KOH to be sequestered, thus stalling the reaction. The use of Amberlyst A26(OH) resin solved all of these problems. The resin is not anhydrous since it is prepared in water and is shipped damp; one can control the amount of water that is present based on the volumes of organic solvent that are used to wash the resin. Accordingly, it is possible to produce a free-flowing resin that contains only enough water to allow the deprotection reaction to proceed, and not so much water that the resulting reaction solutions can not be easily dried with a small amount of molecular sieves. Further, residual water does not contaminate the equipment since bulk water is never added to the reactions. The problem of aggregation is solved because the N-methyliminodiacetic acid bis potassium salt produced in the deprotection reaction becomes trapped within the pores of the resin and does not aggregate with unreacted KOH or water. Often the boronate salt produced in the deprotection reaction also becomes trapped within the pores of the resin. Boronate salts trapped in the resin do not aggregate and do not stall the reaction. Further, this protocol is the only deprotection condition for PIDA boronates that does not require stirring. The reaction with Amberlyst A26(OH) proceeds to full conversion within 60 minutes with periodic air bubbling to mix the mixture, thus allowing a large number of deprotection reactions to be performed in parallel with simple equipment. The mixture (resin and THF) is then treated with dilute acetic acid to convert the boronate salt to the boronic acid. The very fine, very polar N-pinene iminodiacetic acid produced in this process remains trapped in the Amberlyst resin which greatly facilitates filtration of the mixture. (Without the Amberlyst resin sequestering the N-pinene iminodiacetic acid, the subsequent filtration step was found to be unreliable.)

Step 2. This boronic acid solution is then transferred to the cross-coupling module where it is added slowly to a stirred reaction mixture containing the next halogen-bearing building block, a palladium catalyst, and a solid inorganic base. Conversion of each halide building block is maximized via: (a) using excess boronic acid (~3 equiv.) relative to halide (1 equiv.); (b) employing slow-addition or slow-release of the boronic acid to help avoid its decomposition in situ during the cross-coupling reaction; and (c) using Buchwald's highly effective and air-stable SPhosPd catalyst to maximize the generality, efficiency, and mild nature of the cross-coupling condition (D. M. Knapp, E. P. Gillis *J. Am. Chem. Soc.* 2009, 131, 6961-6963; and R. Martin S. L. Buchwald *Acc. Chem. Res.* 2008, 41, 1461-1473).

Step 3. The soluble components of the resulting crude reaction mixture are transferred to the purification module where the chiral, non-racemic PIDA boronate product is purified via tandem precipitation and catch-and-release processes, as described above.

In the automated system the THF:hexane solution, $Et_2O$ with 1.5% MeOH (v/v) solution and $Et_2O$ solution are withdrawn from the top of the $SiO_2$ column and through the bottom under vacuum. This approach is different from standard chromatography in which the solution is pushed through the top of the column under pressure. Again, the unique elution properties of the chiral, non-racemic PIDA boronate hold up under this modification, and this modification greatly simplifies the engineering of the purification step. In the automated system the THF is injected into the bottom of the column and flows out through the top under positive pressure. In this way the PIDA boronate, which is immobilized near the top of the column, has the least distance to be carried in the THF (has the smallest column volume) and thus the amount of THF used to elute the chiral, non-racemic PIDA boronate can be minimized. It is believed that flowing solvents in opposite directions at separate times on the same column is not a standard chromatography practice.

This three-step cycle of deprotection, cross-coupling, and purification is iterated until the final building block coupling step is reached. To maximize efficiency, the final coupling reaction in each sequence is performed via in situ hydrolysis of the final chiral, non-racemic PIDA boronate under aqueous basic conditions. "Slow-release" cross-coupling in this context can help maximize the yield of this final coupling reaction. Similar to the approach used in peptide, oligonucleotide, and oligosaccharide coupling, if the individual building blocks contain other types of protective groups, these are collectively removed using manually executed deprotection reactions prior to an automated chromatographic purification of the final product.

The development of a fully automated ICC platform for small molecule synthesis represents an important step towards increasing the efficiency and flexibility with which small molecules can be prepared in the laboratory. While certain types of small molecules (for example, those possessing many $Csp^2$-$Csp^2$ linkages) are at present more amenable to this approach than others, the rapidly expanding scope of the Suzuki-Miyaura reaction, which increasingly includes $Csp^3$ coupling partners (M. R. Netherton, G. C. Fu, *Adv. Synth. Catal.* 2004, 346, 1525-1532) suggest that the potential generality of this approach is substantial. This synthesis apparatus stands to extend the power of small molecule synthesis to the non-chemist and ultimately will help shift the rate-limiting step in small molecule science from achieving syntheses to understanding function. Given that the functional capacity for small molecules likely extends far beyond that which is currently understood or utilized, the developments described herein stand to have widespread impacts in both science and medicine.

EXEMPLIFICATION

The invention now being generally described, it will be more readily understood by reference to the following, which is included merely for purposes of illustration of certain aspects and embodiments of the present invention, and is not intended to limit the invention.

General Methods

Materials. Commercial reagents were purchased from Sigma-Aldrich, Fisher Scientific, Alfa Aesar, TCI America, or Frontier Scientific, and were used without further purification unless otherwise noted. Solvents were purified via passage through packed columns as described by Pangborn and coworkers (THF, $Et_2O$, $CH_3CN$, $CH_2Cl_2$: dry neutral alumina; hexane, benzene, and toluene, dry neutral alumina and Q5 reactant; DMSO, DMF: activated molecular sieves). Pangborn et al. (1996) *Organometallics* 15:1518-20. All water was deionized prior to use. Triethylamine, diisopropylamine, diethylamine, pyridine, 2,6-lutidine, and ethanol were freshly distilled under an atmosphere of nitrogen from $CaH_2$.

General Experimental Procedures. Unless noted, all reactions were performed in flame-dried round-bottom or modified Schlenk flasks fitted with rubber septa under a positive pressure of argon. Organic solutions were concentrated via rotary evaporation under reduced pressure with a bath temperature of 23° C. unless otherwise noted. Reactions were monitored by analytical thin layer chromatography (TLC) performed using the indicated solvent on E. Merck silica gel 60 F254 plates (0.25 mm) Compounds were visualized by exposure to a UV lamp ($\lambda$=254 nm), and/or a solution of $KMnO_4$, followed by brief heating using a Varitemp heat gun. Column chromatography was performed using Merck silica gel grade 9385 60 Å (230-400 mesh).

Structural analysis. $^1H$ NMR and $^{13}C$ NMR spectra were recorded at 20° C. on a Varian Unity 500 instrument. Chemical shifts ($\delta$) are reported in parts per million (ppm) downfield from tetramethylsilane and referenced to residual protium in the NMR solvent ($CHCl_3$, $\delta$=7.26; acetone, $\delta$=2.05, center line; 1,1,2,2-tetrachloroethane, 5.95) or to added tetramethylsilane ($\delta$=0.00). Data are reported as follows: chemical shift, multiplicity (s=singlet, d=doublet, t=triplet, q=quartet, quint=quintet, sept=septet, m=multiplet, b=broad, app=apparent), coupling constant (J) in Hertz (Hz), and integration. Chemical shifts ($\delta$) for $^{13}C$ NMR are reported in ppm downfield from tetramethylsilane and referenced to carbon resonances in the NMR solvent ($CDCl_3$, $\delta$=77.0, center line; acetone, $\delta$=39.5, center line). Carbons bearing boron substituents were not observed (quadrupolar relaxation). $^{11}B$ NMR were recorded using a Unity Inova 400 instrument and referenced to an external standard of ($BF_3.Et_2O$).

Example 1

Pinene-Derived Iminodiacetic Acid (PIDA) is a Powerful Ligand for Stereoselective Synthesis of $Csp^3$ Boronate Building Blocks The remarkable stability of the MIDA boronate motif to a wide range of common reaction conditions enables the transformation of simple boron-containing starting materials into many types of complex boronate building blocks. Crystal structures of many MIDA boronates have revealed that the N-methyl substituent is always closely positioned to the organic group appended to the boron atom, and variable temperature NMR studies have demonstrated that the iminodiacetic acid framework is conformationally rigid in solution.

We hypothesized that if the N-alkyl substituent of iminodiacetic acid were chiral, then highly effective transfer of stereochemical information might be achieved during functionalizations of the corresponding boronates due to enforced proximity (FIG. 1). Given the exceptional versatility of epoxides in the preparation of other chiral building blocks, we first questioned whether the epoxidation of alkenyl boronates could be rendered asymmetric via such modifications of the MIDA ligand.

A range of iminodiacetic acid ligands derived from different chiral amines were surveyed, leading to the discovery that ligand 1a (PIDA; see Table 1), which can be easily prepared from (+)-pinene (Brown et al. (1983) *J Am Chem Soc* 105: 2092-3; Rathke et al. (1988) *Coll Vol* 6:943), is exceptionally effective. Specifically, treatment of the corresponding styrenyl chiral, non-racemic PIDA boronate 2a with meta-chloroperbenzoic acid (mCPBA) under standard conditions yielded oxiranyl chiral, non-racemic PIDA boronate 3a with outstanding diastereoselectivity (Table 1, entry 1). Alternatively linking the pinene-derived appendage via a conformationally-flexible methylene spacer (1b) or employing some other less-sterically bulky chiral secondary amines (1c or 1d) also yielded some, albeit reduced, diastereoselectivity (Table 1, entries 2-4).

TABLE 1

Diastereoselective epoxidations of various iminodiacetic acid-based alkenyl boronates.

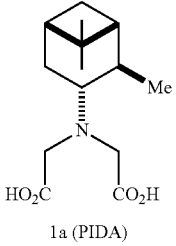

| entry | 1 | 3 | d.r.$^a$ |
|---|---|---|---|
| 1 | 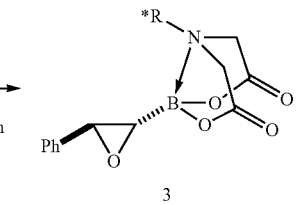 1a (PIDA) | 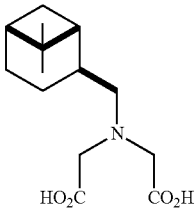 | >20:1 |
| 2 | 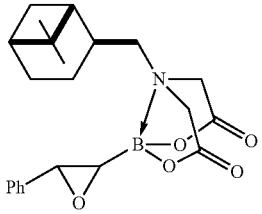 1b | 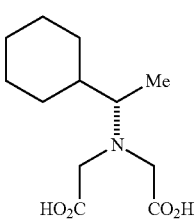 3b | 2.1:1 |
| 3 | 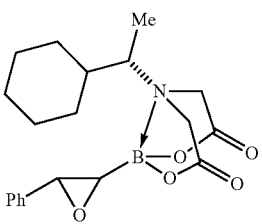 1c | 3c | 2.7:1 |

TABLE 1-continued

Diastereoselective epoxidations of various iminodiacetic acid-based alkenyl boronates.

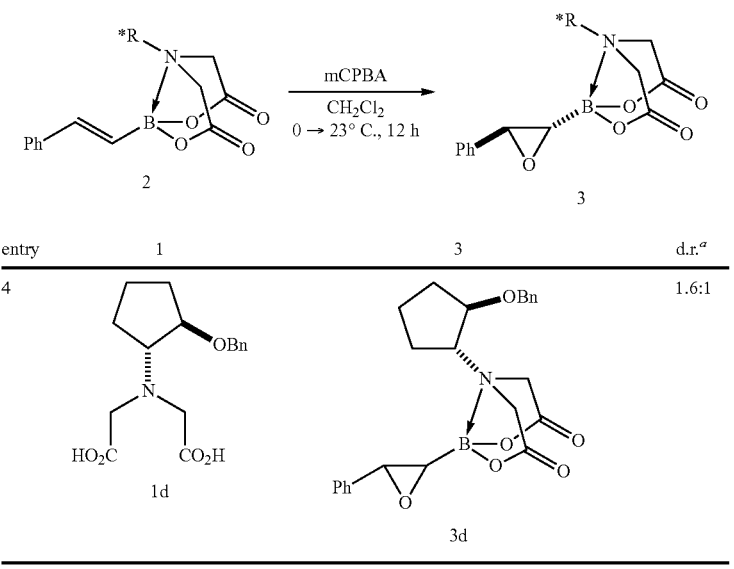

| entry | 1 | 3 | d.r.[a] |
|---|---|---|---|
| 4 | 1d | 3d | 1.6:1 |

[a] d.r. = diastereomeric ratio as determined via 500 MHz $^1$H NMR analysis of unpurified reaction mixture.

Single crystal X-ray analysis of 3a (Table 1, entry 1) revealed that, despite N-alkylation with a very sterically bulky substituent, the [3.3.0]-bicyclic structure of the iminodiacetic acid motif is preserved and the chiral alkyl group is positioned <2.4 Å from the newly formed epoxide. Moreover, variable-temperature NMR analysis confirmed that the iminodiacetic acid framework of the PIDA ligand is conformationally rigid for both the starting material 2a and product 3a. Collectively, these findings are consistent with the conclusion that highly effective transfer of stereochemical information in this system is attributable to enforced proximity between the chiral appendage and the site of reactivity during the transition state of the epoxidation reaction.

The capacity of PIDA to enable the diastereoselective epoxidation of a variety of alkenyl boronates was explored.

As shown in Table 2, the epoxidation of a series of 1,2-disubstituted olefins 2a-g were all efficiently epoxidized in good yields and with outstanding stereocontrol (entries 1-4). 2a can also be epoxidized on a 15 mmol scale and isolated via simple crystallization (entry 1). Strikingly, even the smallest olefin, vinyl boronate 2h, was epoxidized with outstanding diastereoselectivity (entry 5). All of these streochemically pure oxiranyl PIDA boronates 3 are crystalline free-flowing solids that are completely stable to silica gel chromatography and bench-top storage under air, making them highly desirable building blocks for many applications in complex molecule synthesis.

TABLE 2

Highly diastereoselective epoxidations with PIDA boronates.

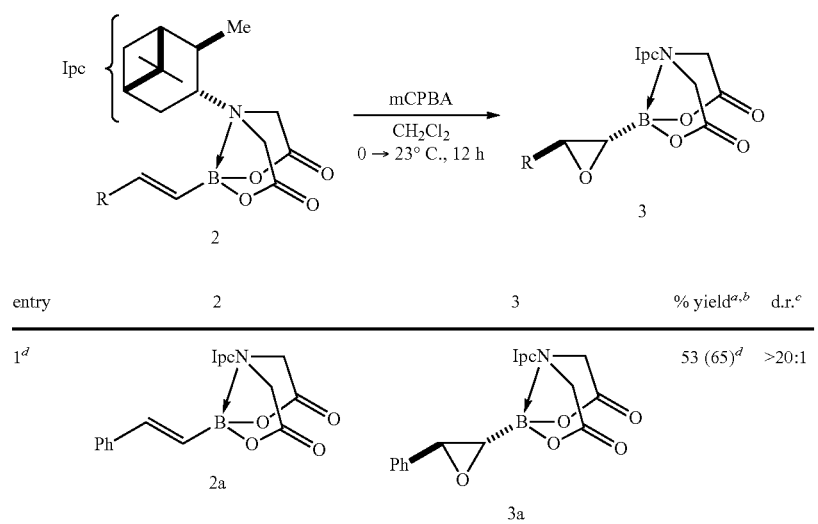

| entry | 2 | 3 | % yield[a,b] | d.r.[c] |
|---|---|---|---|---|
| 1[d] | 2a | 3a | 53 (65)[d] | >20:1 |

TABLE 2-continued

Highly diastereoselective epoxidations with PIDA boronates.

| entry | 2 | 3 | % yield[a,b] | d.r.[c] |
|---|---|---|---|---|
| 2 | 2e | 3e | 64 | >20:1 |
| 3 | 2f | 3f | 77 | >20:1 |
| 4 | 2g | 3g | 75 | >20:1 |
| 5 | 2h | 3h | 82 | >20:1 |

[a] Isolated yields after silica gel chromatography.
[b] The stereochemistry of epoxides 3a, 3e, and 3h were all determined unambiguously via single crystal X-ray analysis. Remaining product configurations were assigned by analogy.
[c] d.r. = diastereomeric ratio as determined via 500 MHz $^1$H NMR analysis of unpurified reaction mixtures.
[d] Conducted on a 15 mmol scale and isolated by crystallization.
Ipc = isopinocamphenyl.

Example 2

General Procedure for the Synthesis of Ligands 1a-d

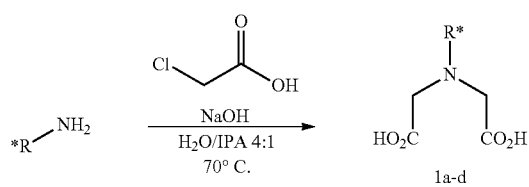

To a stirred solution of chloroacetic acid (69 mmol, 2.3 equiv) in H$_2$O (60 mL) at 0° C. was added dropwise 5 N NaOH solution (13.8 mL, 69 mmol, 2.3 equiv), keeping the temperature below 15° C. The amine (30 mmol, 1 equiv) in IPA (30 mL) was then added in one portion. The ice bath was then removed and the reaction heated at 70° C. (oil bath temperature). After stirring for 2.5 h, the reaction turned clear from an initial biphasic mixture. Another 8.1 mL (40.5 mmol, 1.35 equiv) of the 5 N NaOH solution was added, and the reaction stirred for a further 14 h at the same temperature. The third portion of the NaOH solution (8.1 mL, 40.5 mmol, 1.35 equiv) was then added and stirred for an additional 2 h at 70° C. The reaction was then heated up to 100° C. BaCl$_2$—H$_2$O (7.69 g, 31.5 mmol, 1.05 equiv) in H$_2$O (30 mL) was heated until the solid dissolved completely. This heated solution was then added dropwise via pipette into the reaction mixture. After the addition, the reaction was stirred for an additional 15 min, during which the reaction became a thick white suspension. After cooling to room temperature, the white solid was collected by filtration and dried in a vacuum oven set at 100° C. The mass of the Ba chelate was determined. The Ba chelate was then suspended in H₂O (60 mL) and heated in a 110° C. oil bath until boiling. 5M H₂SO₄ (1.95 equiv relative to the Ba chelate) was added dropwise, followed by rinsing with 5 mL H₂O. The resulting suspension was stirred for another 15 min in the oil bath, then cooled for 5 min and filtered through Celite, rinsing with 10 mL H₂O. The filtrate was concentrated to dryness. The solid obtained was then redissolved in Et₂O/CH₂Cl₂ (1:10, 100 mL) and filtered to remove insoluble solids. The CH₂Cl₂ solution was then concentrated in vacuo and the solid obtained was used without further purification.

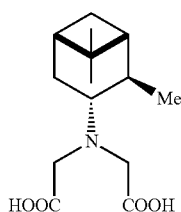

Ligand 1a. The general procedure was followed using (1R,2R,3R,5S)-(−)-Isopinocampheylamine (4.59 g, 30 mmol), chloroacetic acid (6.52 g, 69 mmol) and NaOH (30 mL, 150 mmol). 11.33 g of the Ba chelate (93%) was obtained. 5.4 mL of 5M H₂SO₄ was used for the hydrolysis, and the ligand 1a was obtained as an off-white solid (6.63 g, 82%).

$^1$H NMR (500 MHz, DMSO-$d_6$) δ 3.45 (s, 4H), 3.23-3.18 (m, 1H), 2.32-2.23 (m, 1H), 2.19-2.12 (m, 1H), 1.91-1.86 (m, 1H), 1.75-1.69 (m, 2H), 1.64-1.60 (m, 1H), 1.15 (s, 3H), 1.03 (d, J=6.5, 3H), 0.92 (s, 3H), 0.79 (d, J=10 Hz, 1H); $^{13}$C NMR (125 MHz, DMSO-$d_6$) δ173.5, 62.0, 53.8, 47.3, 40.9, 40.3, 38.7, 33.4, 29.6, 27.9, 23.0, 20.9; HRMS (ESI+) Calculated for $C_{14}H_{24}NO_4$: 270.1705, Found: 270.1703.

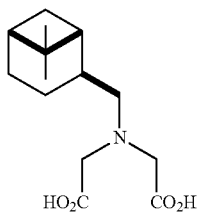

Ligand 1b. The general procedure was followed using (−)-cis-myrtanylamine (4.59 g, 30 mmol), chloroacetic acid (6.52 g, 69 mmol) and NaOH (30 mL, 150 mmol). 11.33 g of the Ba chelate (93%) was obtained. 5.4 mL of 5M H₂SO₄ was used for the hydrolysis, and the ligand 1b was obtained as an off-white solid in about 70-80% purity (1.62 g, 20%).

$^1$H NMR (500 MHz, DMSO-$d_6$) δ 3.38 (s, 4H), 2.56 (d, J=7.5 Hz, 2H), 2.51-2.42 (m, 1H), 2.30-2.26 (m, 1H), 22.1-2.06 (m, 1H), 1.94-1.72 (m, 5H, 1.53-1.45 (m, 1H), 1.12 (s, 3H), 0.91 (s, 3H); $^{13}$C NMR (125 MHz, DMSO-$d_6$) δ 172.5, 59.6, 55.4, 43.4, 40.9, 38.6, 38.2, 32.9, 27.8, 25.8, 22.9, 19.5; HRMS (ESI+) Calculated for $C_{14}H_{24}NO_4$: 270.1705, Found: 270.1700.

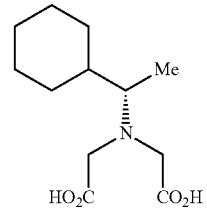

Ligand 1c. The general procedure was followed using (S)-(+)-1-cyclohexylethylamine (12.72 g, 100 mmol), chloroacetic acid (21.74 g, 230 mmol) and NaOH (100 mL, 500 mmol). 27.84 g of the Ba chelate (74%) was obtained. 14.4 mL of 5M H₂SO₄ was used for the hydrolysis, and the ligand 1c was obtained as an off-white solid (12.47 g, 51%). $^1$H NMR (500 MHz, DMSO-$d_6$) δ 3.37 (d, J=17.5 Hz, 2H), 3.29 (d, J=17.5 Hz, 2H), 2.39 (m, 1H), 1.91 (app d, J=7.5 Hz, 1H), 1.65-1.51 (m, 4H), 1.24-1.03 (m, 5H), 0.92 (d, J=6.5 Hz, 3H), 0.89-0.78 (m, 1H); $^{13}$C NMR (125 MHz, DMSO-$d_6$) δ 173.4, 62.6, 53.2, 40.8, 30.0, 29.4, 26.1, 25.8, 25.8, 12.6; HRMS (ESI+) Calculated for $C_{12}H_{22}NO_4$: 244.1550, Found: 244.1549.

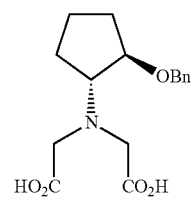

Ligand 1d. The general procedure was followed using (1S,2S)-(+)-2-benzyloxycyclopentylamine (5 g, 26.1 mmol), chloroacetic acid (5.68 g, 60.1 mmol) and NaOH (26.1 mL, 130.5 mmol). 5.87 g of the Ba chelate (67%) was obtained. 3.40 mL of 5M H₂SO₄ was used for the hydrolysis, and the ligand 1d was obtained as an off-white solid (3.36 g, 42%). $^1$H NMR (500 MHz, DMSO-$d_6$) δ 12.2 (br s, 2H), 7.32-7.24 (m, 5H), 4.42 (d, J=12 Hz, 1H), 4.36 (d, J=11.5 Hz, 1H), 3.76-3.74 (m, 1H), 3.48 (d, J=17.5 Hz, 2H), 3.43 (d, J=18 Hz, 2H), 3.24-3.20 (m, 1H), 1.88-1.82 (m, 1H), 1.82-1.76 (m, 1H), 1.59-1.48 (m, 3H), 1.38-1.30 (m, 1H); $^{13}$C NMR (125 MHz, DMSO-$d_6$) δ 173.0, 138.6, 128.1, 127.6, 127.3, 83.0, 70.4, 68.1, 53.6, 29.8, 28.4, 20.9; HRMS (ESI+) Calculated for $C_{16}H_{22}NO_5$: 308.1498, Found: 308.1493.

Example 3

General Procedure for the Complexation of Chiral Ligands 1a-d to Trans-2-Phenylvinylboronic Acid

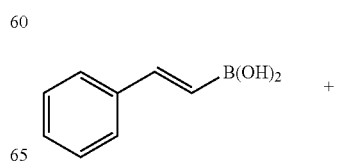

-continued

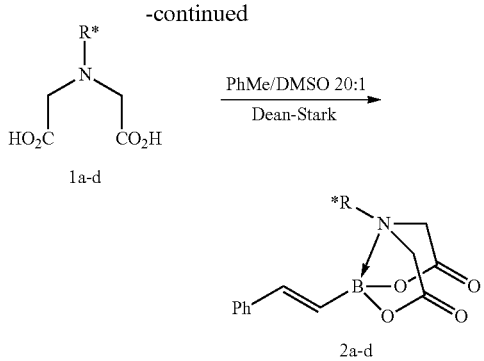

1a-d

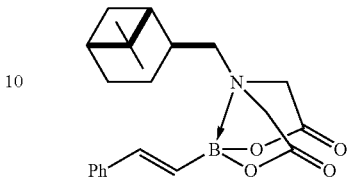

2a-d

To a solution of trans-2-phenylvinylboronic acid (1.5 equiv) in toluene (30 mL) and DMSO (1.5 mL) was added the ligand 1 (typically 1-5 mmol, 1 equiv). The flask was fitted with a Dean-Stark trap. The Dean-Stark trap was fitted with an air-cooled condenser vented to ambient atmosphere. The stirred solution was refluxed with azeotropic removal of water for 2 h. The toluene was removed in vacuo, and the residue was taken up in 2:1 EtOAc/acetone (60 mL) and washed twice with 1:1 brine/$H_2O$ (30 mL). The aqueous layer was extracted with 2:1 EtOAc/acetone (30 mL) and the combined organic phase washed with brine, dried over $MgSO_4$, filtered and concentrated in vacuo. The crude product was then purified by silica gel chromatography, eluting first with $Et_2O$ to remove impurities, then with 1:4 (acetone/$Et_2O$).

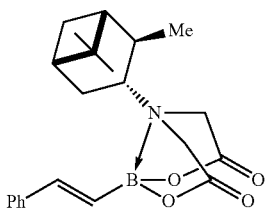

2a

Boronate ester 2a. The reaction was carried out on a 20 mmol scale with some modifications from the general procedure and purified without the use of silica gel chromatography: To a suspension of trans-2-phenylvinylboronic acid (2.96 g, 20 mmol) in toluene (200 mL) was added the ligand 1a (9.68 g, 36 mmol). The flask was fitted with a 50 mL Dean-Stark trap and an air-cooled condenser vented to ambient atmosphere. The stirred solution was refluxed with azeotropic removal of water for 2 h. After cooling to room temperature, the crude solid product was collected via vacuum filtration. The filtrate was then concentrated to dryness and $Et_2O$ (50 mL) was added. The resulting white precipitate was collected via vacuum filtration and the combined solids were then washed with additional $Et_2O$ (50 mL). This solid was then taken up in acetone (150 mL) and passed slowly through a pad of silica gel in a 100 mL sintered funnel, eluting with additional acetone (50 mL). The filtrate thus obtained was concentrated and dried in vacuo, giving the product (6.74 g, 88%).

Results: TLC (Hexanes:acetone 3:2) $R_f$=0.27, visualized by short wave UV; $^1$H NMR (500 MHz, acetone-$d_6$) δ 7.54-7.53 (m, 2H), 7.37-7.33 (m, 2H), 7.29-7.25 (m, 1H), 7.03, (d, J=18 Hz, 1H), 6.52 (d, J=18 Hz, 1H), 4.35 (d, J=16 Hz, 1H), 4.29 (d, J=17.5 Hz, 1H), 4.18 (d, J=15.5 Hz, 1H), 4.05 (d, J=18 Hz, 1H), 4.05-4.00 (m, 1H), 2.65-2.58 (m, 1H), 2.52-2.48 (m, 1H), 2.46-2.41 (m, 1H), 2.01-1.99 (m, 1H), 1.91 (dt, J=6, 2.5 Hz, 1H), 1.71 (ddd, J=15, 6.5, 2.5 Hz, 1H), 1.35 (d, J=6.5 Hz, 3H), 1.23 (s, 3H), 1.08 (d, J=10.5 Hz, 1H), 0.92 (s, 3H); $^{13}$C NMR (125 MHz, acetone-$d_6$) δ 170.8, 167.9, 143.5, 139.3, 129.4, 128.8, 127.4, 68.6, 61.1, 55.3, 50.2, 41.6, 39.6, 39.2, 32.4, 31.1, 27.4, 23.6, 23.5; $^{11}$B-NMR (100 MHz, acetone-$d_6$) δ 11.9; HRMS (ESI+) Calculated for $C_{22}H_{29}BNO_4$: 382.2190, Found: 382.2187.

2b

Boronate ester 2b. The general procedure was followed using trans-2-phenylvinylboronic acid (0.22 g, 1.5 mmol), ligand 1b (0.606 g, 2.25 mmol) in 20 mL toluene and 1 mL DMSO. A white solid was obtained (0.387 g, 68%). TLC (Hexanes:EtOAc:$Et_2O$ 2:2:1) $R_f$=0.20, visualized by short wave UV; $^1$H NMR (500 MHz, acetone-$d_6$) δ 7.50 (app d, J=7 Hz, 2H), 7.34 (app t, J=7.5 Hz, 2H), 7.28-7.25 (m, 1H), 6.93, (d, J=18 Hz, 1H), 6.33 (d, J=18 Hz, 1H), 4.17-4.08 (m, 4H), 3.45 (dd, J=13.5, 6.5 Hz, 1H), 3.34 (dd, J=13.5, 3 Hz, 1H), 2.74-2.68 (m, 1H), 2.38-2.26 (m, 2H), 2.16-2.11 (m, 1H), 2.01-1.94 (m, 1H), 1.92-1.76 (m, 3H), 1.15 (s, 3H), 1.08 (d, J=10 Hz, 1H), 0.92 (s, 3H); $^{13}$C NMR (125 MHz, CDCl$_3$) δ 167.8, 167.4, 144.2, 137.6, 128.6, 128.4, 126.7, 66.8, 58.5, 58.4, 47.3, 40.4, 38.1, 37.4, 31.9, 27.3, 25.6, 23.3 (2C); $^{11}$B-NMR (100 MHz, acetone-$d_6$) δ 11.9; HRMS (ESI+) Calculated for $C_{22}H_{29}BNO_4$: 382.2190, Found: 382.2187.

2c

Boronate ester 2c. The general procedure was followed using trans-2-phenylvinylboronic acid (0.74 g, 5 mmol), ligand 1c (1.82 g, 7.5 mmol) in 50 mL toluene and 2.5 mL DMSO. A white solid was obtained (0.311 g, 74%). TLC (Hexanes:acetone 3:2) $R_f$=0.38; $^1$H NMR (500 MHz, acetone-$d_6$) δ 7.52 (d, J=8 Hz, 2H), 7.35 (t, J=7.5 Hz, 2H), 7.27 (t, J=7.5 Hz, 1H), 6.96, (d, J=18 Hz, 1H), 6.46 (d, J=18 Hz, 1H), 4.27 (d, J=17 Hz, 1H), 4.19 (d, J=17 Hz, 1H), 4.05 (d, J=14.5 Hz, 1H), 4.02 (d, J=17 Hz, 1H), 3.42-3.38 (m, 1H), 2.05 (m, 1H), 1.86-1.83 (m, 1H), 1.78-1.74 (m, 1H), 1.69-1.62 (m, 2H), 1.50-1.44 (m, 1H), 1.36-1.27 (m, 6H), 1.18-1.08 (m, 2H); $^{13}$C NMR (125 MHz, CDCl$_3$) δ 168.5, 167.7, 144.3, 128.6, 128.4, 126.7, 67.6, 56.8, 39.2, 32.1, 27.7, 26.4, 25.7, 25.7, 10.5; $^{11}$B-NMR (100 MHz, acetone-$d_6$) δ 11.9; HRMS (ESI+) Calculated for $C_{20}H_{27}BNO_5$: 356.2033, Found: 356.2029.

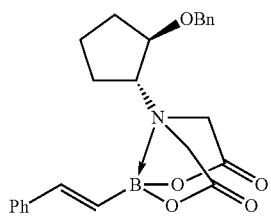

2d

Boronate ester 2d. The general procedure was followed using trans-2-phenylvinylboronic acid (0.148 g, 1 mmol), ligand 1d (0.461 g, 1.5 mmol) in 15 mL toluene and 0.5 mL DMSO. An off-white solid was obtained (0.311 g, 74%). TLC (Hexanes:acetone 3:2) $R_f$=0.38; $^1$H NMR (500 MHz, acetone-$d_6$) δ 7.50 (d, J=8 Hz, 2H), 7.38-7.29 (m, 6H), 7.26-7.22 (m, 1H), 7.18-7.13, (m, 1H), 6.96 (d, J=18 Hz, 1H), 6.46 (d, J=18.5 Hz, 1H), 4.62 (d, J=11.5 Hz, 1H), 4.55 (d, J=1 Hz, 1H), 4.41-4.38 (m, 1H), 4.29 (d, J=16.5 Hz, 1H), 4.19 (d, J=17.5 Hz, 1H), 4.14 (d, J=16.5 Hz, 1H), 4.05 (d, J=17 Hz, 1H), 3.70 (q, J=9 Hz, 1H), 2.30-2.25 (m, 1H), 2.20-2.15 (m, 1H), 1.82-1.6 (m, 4H); $^{13}$C NMR (125 MHz, CDCl$_3$) δ 168.8, 167.5, 144.3, 137.5, 136.4, 128.8, 128.6, 128.5, 128.4, 128.3, 126.8, 79.3, 73.4, 72.0, 60.0, 55.4, 29.6, 26.2, 21.1; $^{11}$B-NMR (100 MHz, acetone-$d_6$) δ 11.8; HRMS (ESI+) Calculated for C$_{24}$H$_{27}$BNO$_5$: 420.1978, Found: 420.1982.

Example 4

Synthesis of Boronate Ester 2e

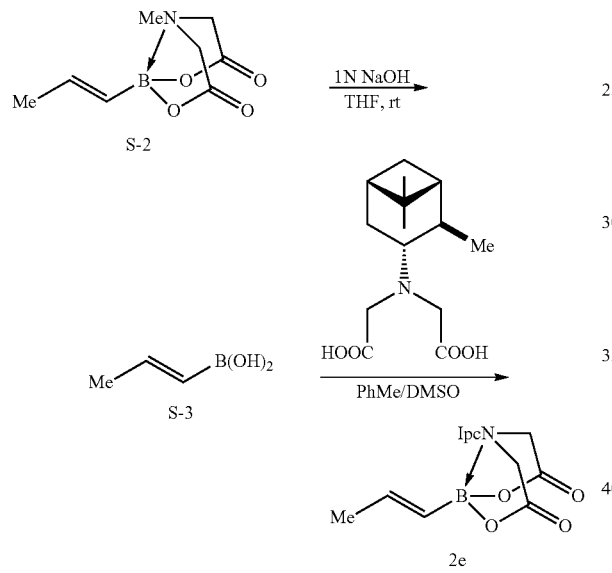

To a solution of S-2 (197 mg, 1 mmol) in THF (10 mL) was added 1N NaOH (3 mL, 3 mmol) under ambient atmosphere and temperature and stirred vigorously for 15 min. The reaction was quenched with the addition of sat. NH$_4$Cl solution (10 mL). The mixture was stirred for 3 min, then transferred to a separatory funnel, rinsing with Et$_2$O (10 mL). After phase separation, the organic phase was washed with another portion of sat. NH$_4$Cl solution (10 mL) and the combined aqueous phase extracted with 1:1 THF/Et$_2$O (15 mL). The organic phase was dried over MgSO$_4$, filtered and concentrated in vacuo to give the boronic acid as a white solid. The solid was taken up in toluene (15 mL) and DMSO (0.75 mL) and 1a (404 mg, 1.5 mmol) was added. The reaction was heated to reflux with a Dean-Stark trap for 1.5 h. After cooling to room temperature, toluene was removed in vacuo. The residue was taken up in 2:1 EtOAc/acetone (15 mL) and washed twice with 1:1 H$_2$O/brine (10 mL). The aqueous layers were extracted with 2:1 EtOAc/acetone (15 mL). The combined organic phase was dried over MgSO$_4$, filtered and concentrated. The crude product was purified by silica gel chromatography, eluting first with Et$_2$O then with 1:4 acetone/Et$_2$O to give a white solid as the pure product (166 mg, 52% over 2 steps).

Results. TLC (Hexanes:acetone 3:2) $R_f$=0.41, stained by KMnO$_4$; $^1$H NMR (500 MHz, acetone-$d_6$) δ 6.13 (dq, J=8.5 Hz, 1H), 5.66 (dd, J=17.5, 1.5 Hz, 1H), 4.19 (d, J=18 Hz, 1H), 4.18 (d, J=16 Hz, 1H), 4.09 (d, J=15.5 Hz, 1H), 3.94 (d, J=18 Hz, 1H), 3.87 (dt, J=10, 3 Hz, 1H), 2.57-2.51 (m, 1H), 2.49-2.42 (m, 2H), 2.00 (sept, J=3 Hz, 1H), 1.91 (dt, J=6, 2 Hz, 1H), 1.79 (dd, J=6.5, 1.5 Hz, 3H), 1.61 (ddd, J=15, 6.5, 1.5 Hz, 1H), 1.33 (d, J=7 Hz, 3H), 1.25 (s, 3H), 1.04 (d, J=10.5 Hz, 1H), 0.98 (s, 3H); $^{13}$C NMR (125 MHz, acetone-$d_6$) δ 170.2, 167.2, 140.8, 67.9, 60.3, 54.5, 49.6, 41.0, 39.0, 38.5, 31.8, 30.3, 26.9, 23.0, 22.9, 20.8; $^{11}$B-NMR (100 MHz, acetone-$d_6$) δ 11.5; HRMS (ESI+) Calculated for C$_{17}$H$_{27}$BNO$_4$: 320.2033, Found: 320.2035.

Example 5

Synthesis of Boronate Ester 2g

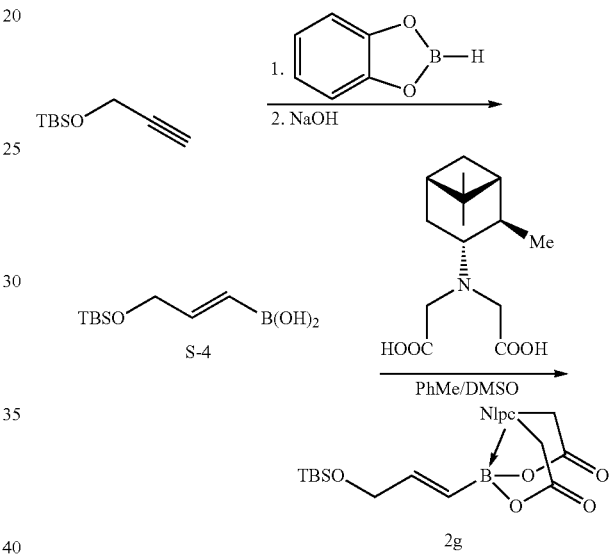

In an unoptimized procedure, TBS-protected propargyl alcohol (5.17 g, 30.4 mmol) was weighed into a dry 20 mL Ichem vial and the vial was sealed with a septum cap. The vial was flushed with N$_2$ for 20 min, then catecholborane (3.4 mL, 31.9 mmol) was added neat in one portion. The reaction was stirred at 60° C. in a heating block for 15 h. After cooling to room temperature, 4.36 g (approx. 15 mmol) of this crude product was diluted in THF (150 mL) and 1 N NaOH (45 mL, 45 mmol) was added. After vigorous stirring for 10 min, the mixture was transferred to a separatory funnel and the phases separated. The organic layer was washed with 1 N NaOH (60 mL), then H$_2$O (60 mL) and 1:1 H$_2$O/brine (60 mL). The organic phase was then dried over MgSO$_4$, filtered and concentrated to give a yellow oil as the boronic acid (1.48 g, 6.85 mmol). The boronic acid was then dissolved in toluene (60 mL) and DMSO (3 mL). Ligand 1a was then added, and the mixture was heated to reflux with a Dean-Stark trap for 2 h. The reaction was then cooled to room temperature. Toluene was then removed in vacuo. Et$_2$O was added to the residue and the precipitate, which is the crude product, was obtained by vacuum filtration. Purification by silica gel chromatography (30-100% EtOAc/hexane) gave a white solid (405 mg, ~30% from boronic acid).

Results. TLC (Hexanes:acetone 3:2) $R_f$=0.51 visualized by KMnO$_4$; $^1$H NMR (500 MHz, CDCl$_3$) δ 6.22 (dt, J=17.5, 4 Hz, 1H), 5.94 (dt, J=17.5, 2 Hz, 1H), 4.26-4.25 (m, 2H), 4.23 (d, J=18 Hz, 1H), 4.18 (d, J=15.5 Hz, 1H), 4.12 (d, J=15 Hz, 1H), 3.98 (d, J=18 Hz, 1H), 3.86 (dt, J=10.5, 6 Hz, 1H), 2.59-2.53 (m, 1H), 2.49-2.41 (m, 2H), 1.99 (sept, J=3 Hz, 1H), 1.92 (dt, J=6, 2 Hz, 1H), 1.66 (ddd, J=15, 6.5, 6 Hz, 1H), 1.34 (d, J=7 Hz, 3H), 1.25 (s, 3H), 1.07 (d, J=10.5 Hz, 1H), 0.99 (s, 3H), 0.9 (s, 9H), 0.1 (s, 6H); $^{13}$C NMR (125 MHz, CDCl$_3$) δ 169.7, 167.0, 146.2, 68.4, 64.3, 60.3, 54.2, 49.0, 40.6, 38.9, 38.8, 32.0, 30.8, 30.2, 27.0, 25.9, 23.5 (2C), 15.2, −5.4; $^{11}$B-NMR (100 MHz, acetone-d$_6$) δ 11.8; HRMS (ESI+) Calculated for C$_{23}$H$_{41}$BNO$_5$Si: 450.2847, Found: 450.2845.

Example 6

Synthesis of Boronate Ester 2f

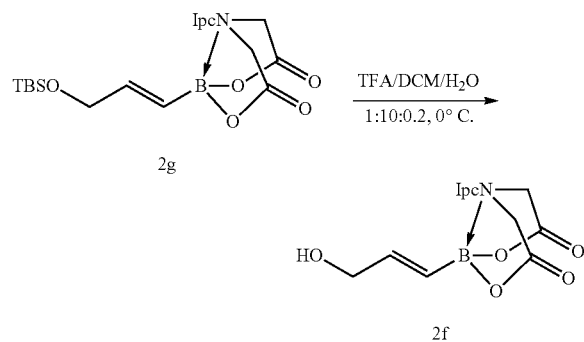

The boronate ester 2g (1.52 g, 3.38 mmol) was dissolved in CH$_2$Cl$_2$ (68 mL) and cooled to 0° C. H$_2$O (0.34 mL) followed by TFA (6.80 mL) was then added. The reaction was stirred at 0° C. for 30 min. The reaction was washed briefly with H$_2$O (30 mL), then twice with sat. aqueous NaHCO$_3$ (30 mL). The combined aqueous layer was washed with CH$_2$Cl$_2$ (30 mL). The organic phase was then dried over MgSO$_4$, filtered and concentrated. Following purification by silica gel chromatography (40→80% EtOAc/hexane), a white solid was obtained (737 mg, 65%).

Results. TLC (Hexanes:acetone 3:2) R$_f$=0.20, visualized by KMnO$_4$; $^1$H NMR (500 MHz, acetone-d$_6$) δ 6.26 (dt, J=18, 4 Hz, 1H), 5.89 (app d, J=17.5 Hz, 1H), 4.12 (d, J=15 Hz, 1H), 4.12 (m, 2H), 3.89 (dt, J=10, 6.5 Hz, 1H), 2.56 (m, 1H), 2.48-2.2 (m, 2H), 1.99 (sept, J=3 Hz, 1H), 1.91 (dt, J=6, 2.5 Hz, 1H), 1.63 (ddd, J=15, 6.5, 5 Hz, 1H), 1.35 (d, J=7 Hz, 3H), 1.25 (s, 3H), 1.06 (d, J=10.5 Hz, 1H), 0.97 (s, 3H); $^{13}$C NMR (125 MHz, acetone-d$_6$) δ 170.8, 167.9, 146.5, 68.5, 64.5, 60.9, 55.2, 50.2, 41.6, 39.6, 39.1, 32.3, 30.9, 27.5, 23.6, 23.6; $^{11}$B-NMR (100 MHz, acetone-d$_6$) δ 11.8; HRMS (ESI+) Calculated for C$_{17}$H$_{27}$BNO$_5$: 336.1982, Found: 336.1979.

Example 7

Synthesis of Boronate Ester 2h

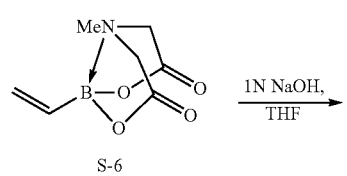

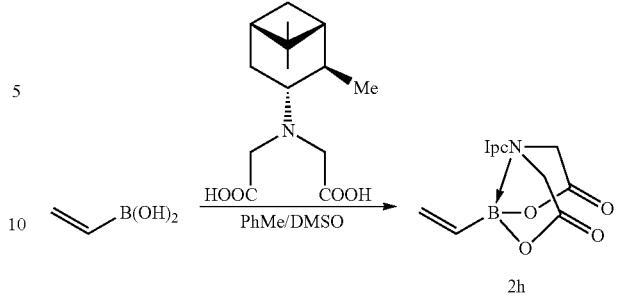

To a solution of S-6 (183 mg, 1 mmol) (Sigma-Aldrich product no. 704415) in THF (10 mL) was added 1 N NaOH (3 mL, 3 mmol) under ambient atmosphere and temperature and stirred vigorously for 15 min. The reaction was quenched with the addition of sat. NH$_4$Cl solution (10 mL). The mixture was stirred for 3 min, then transferred to a separatory funnel, rinsing with Et$_2$O (10 mL). After phase separation, the organic phase was washed with another portion of sat. NH$_4$Cl solution (10 mL) and the combined aqueous phase extracted with 1:1 THF/Et$_2$O (15 mL). The organic phase was dried over MgSO$_4$, filtered and concentrated in vacuo to give the boronic acid as a white solid. The solid was taken up in toluene (15 mL) and DMSO (0.75 mL) and 1a (404 mg, 1.5 mmol) was added. The reaction was heated to reflux with a Dean-Stark trap for 1.5 h. After cooling to room temperature, toluene was removed in vacuo. The residue was taken up in 2:1 EtOAc/acetone (15 mL) and washed twice with 1:1 H$_2$O/brine (10 mL). The aqueous layers were extracted with 2:1 EtOAc/acetone (15 mL). The combined organic phase was dried over MgSO$_4$, filtered and concentrated. The crude product was purified by silica gel chromatography, eluting first with Et$_2$O then with 1:4 acetone/Et$_2$O to give a white solid as the pure product (153 mg, 55% over 2 steps).

Results. TLC (Hexanes:acetone 3:2) R$_f$=0.39, visualized by KMnO$_4$; $^1$H NMR (500 MHz, acetone-d$_6$) δ 6.15 (dd, J=19, 13.5 Hz, 1H), 5.78 (app d, J=12.5 Hz, 1H), 5.73 (dd, J=19, 3.5 Hz, 1H), 4.24 (d, J=18 Hz, 1H), 4.23 (d, J=15.5 Hz, 1H), 4.14 (d, J=15.5 Hz, 1H), 4.00 (d, J=18 Hz, 1H), 3.90 (dt, J=10, 6.5 Hz, 1H), 2.58-2.52 (m, 1H), 2.50-2.41 (m, 2H), 2.00 (sept, J=3.5 Hz, 1H), 1.92 (ddd, J=6, 6, 2 Hz, 1H), 1.63 (ddd, J=15, 6, 2.5 Hz, 1H), 1.35 (d, J=7 Hz, 3H), 1.25 (s, 3H), 1.06 (d, J=10 Hz, 1H), 0.98 (s, 1H); $^{13}$C NMR (125 MHz, acetone-d$_6$) δ 170.2, 167.8, 130.1, 68.6, 61.0, 55.2, 50.2, 41.6, 39.6, 39.2, 32.3, 31.0, 27.4, 23.6; $^{11}$B-NMR (100 MHz, acetone-d$_6$) δ 11.3; HRMS (ESI+) Calculated for C$_{16}$H$_{25}$BNO$_4$: 306.1877, Found: 306.1872.

Example 8

General Procedure for the Epoxidation of Boronate Esters 2a-d (Table 1)

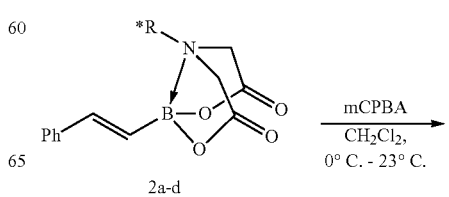

-continued

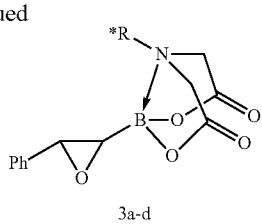

3a-d

To a solution of the boronate ester 2 (0.1 mmol) in CH$_2$Cl$_2$ at 0° C. was added meta-chloroperbenzoic acid (mCPBA) (max 77%, 43 mg, 0.19 mmol) portionwise over 3 min under ambient atmosphere. The reaction was stirred for 12 h, gradually raising the temperature to 23° C. The reaction was then concentrated in vacuo at 20° C., and $^1$H NMR analysis was carried out. Conversions for all 4 substrates (2a-d) was >95%. The peaks from the protons on the epoxide were used to determine the d.r. See Table 1 (Example 1) for more details.

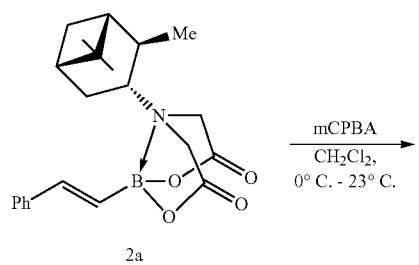

2a

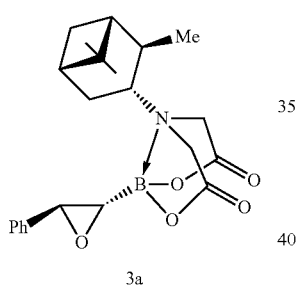

3a

Epoxide 3a. The general procedure was followed using boronate ester 2a (38 mg, 0.1 mmol) and mCPBA (43 mg, 0.19 mmol). d.r.>20:1.

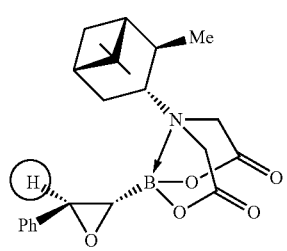

3a

Results. TLC (Hexanes:acetone 3:2) R$_f$=0.46, visualized by KMnO$_4$; $^1$H NMR (500 MHz, CDCl$_3$) δ 7.40-7.35 (m, 4H), 7.33-7.30 (m, 1H), 4.40 (dt, J=10.5, 3.5 Hz, 1H), 4.36 (d, J=18 Hz, 1H), 4.22 (d, J=15 Hz, 1H), 4.14 (d, J=17.5 Hz, 1H), 4.12 (d, J=17.5 Hz, 1H), 3.83 (d, J=2.5 Hz, 1H), 2.92-2.86 (m, 1H), 2.62-2.57 (m, 1H), 2.57 (d, J=2.5 Hz, 1H), 2.53-2.47 (m, 1H), 2.11-2.08 (m, 1H), 2.00 (dt, J=5.5, 2 Hz, 1H), 1.85 (ddd, J=14.5, 4, 2.5 Hz, 1H), 1.45 (d, J=6.5 Hz, 3H), 1.31 (s, 3H), 1.14 (d, J=11 Hz, 1H), 1.10 (s, 3H); $^{13}$C NMR (125 MHz, CDCl$_3$) δ 169.1, 166.4, 137.9, 128.5, 128.1, 125.5, 68.1, 61.8, 56.7, 54.7, 49.0, 40.6, 39.2, 39.0, 32.1, 30.6, 27.1, 23.5, 23.5; $^{11}$B-NMR (128 MHz, CDCl$_3$) δ 10.5; HRMS (ESI+) Calculated for C$_{22}$H$_{29}$BNO$_5$: 398.2139, Found: 398.2135.

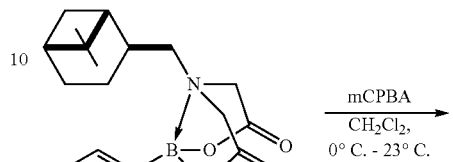

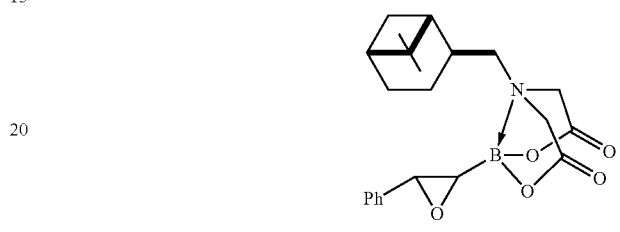

3b

Epoxide 3b. The general procedure was followed using boronate ester 2b (38 mg, 0.1 mmol) and mCPBA (43 mg, 0.19 mmol). d.r.=1.86:1.

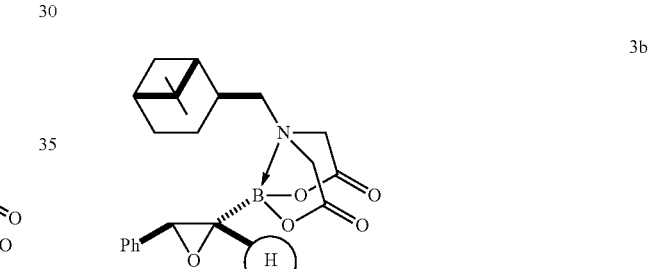

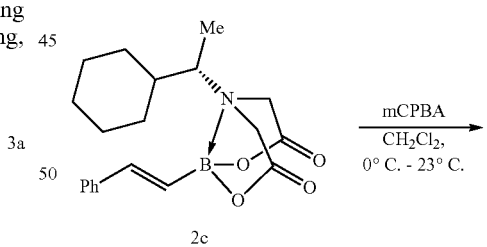

2c

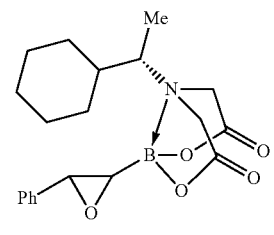

3c

Epoxide 3c. The general procedure was followed using boronate ester 2c (36 mg, 0.1 mmol) and mCPBA (43 mg, 0.19 mmol). d.r.=2.7:1.

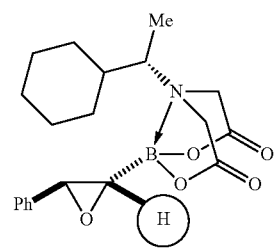

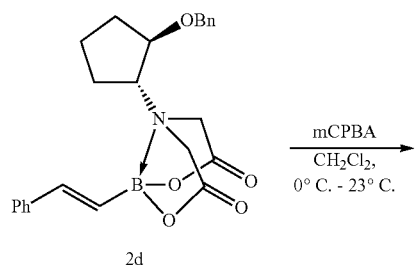

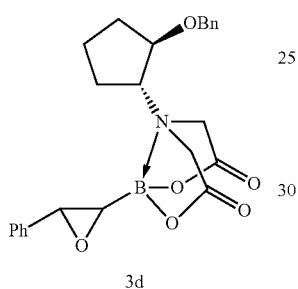

Epoxide 3d. The general procedure was followed using boronate ester 2d (42 mg, 0.1 mmol) and mCPBA (43 mg, 0.19 mmol). d.r.=1.56:1

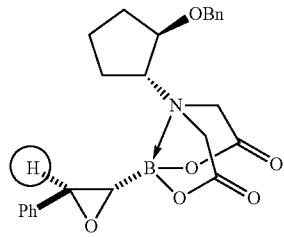

Example 9

General Procedure for the Epoxidation of Boronate Esters 2a, 2e-h (Table 2)

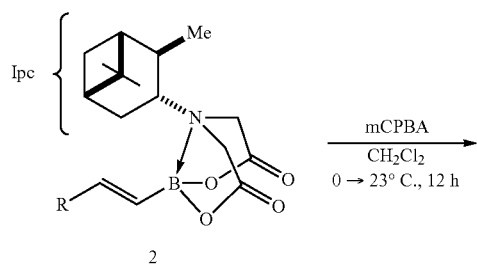

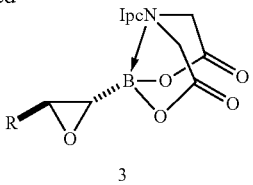

To a solution of the boronate ester 2 (0.25 mmol) in CH$_2$Cl$_2$ at 0° C. was added mCPBA (max 77%, 106 mg, 0.475 mmol) portionwise over 3 min under ambient atmosphere. The reaction was stirred for 12 h, gradually raising the temperature to rt in the ice/water bath. The reaction was then concentrated in vacuo at 20° C., and $^1$H NMR analysis of the crude reaction mixture was performed to determine the d.r. The crude product was then taken up in a minimum amount of CH$_2$Cl$_2$ and loaded onto a silica gel column equilibrated with 30% Et$_2$O/hexane. The non-polar impurities were eluted with 30% Et$_2$O/hexane. The product was then eluted with 2:2:6 (acetone/Et$_2$O/hexane). After concentration at room temperature, the solid was washed with Et$_2$O (10-20 mL) to remove residual mCPBA and vacuum filtered. The epoxide was then dried in vacuo.

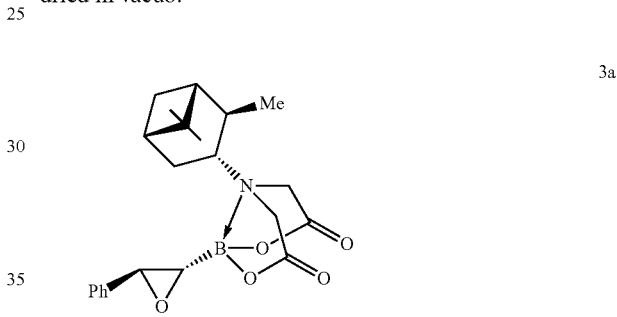

Epoxide 3a. The general procedure was followed using boronate ester 2a (95 mg, 0.25 mmol) and mCPBA (106 mg, 0.475 mmol), giving the product as a white solid (53 mg, 53%). d.r.>20:1. X-ray quality crystals were obtained by making a saturated solution of 3a in 1 mL of 1,2-dichloroethane and layering it with about 2 mL of hexane. The layers were allowed to slowly mix at room temperature, giving the desired crystals.

The epoxidation of 2a was also carried out on a 15 mmol scale as follows: A solution of boronate ester 2a (5.72 g, 15 mmol) in CH$_2$Cl$_2$ (300 mL) was cooled to 0° C. mCPBA (max 77%, 4.47 g, 20 mmol) was added portionwise under ambient atmosphere over 10 min. The reaction was stirred for 8 h, maintaining the bath temperature at 0-10° C. The reaction was then concentrated to approximately 50 mL of CH$_2$Cl$_2$, and Et$_2$O was added (150 mL). The solution was stirred vigorously for 5 min, and the white solid (crude product) formed was obtained by vacuum filtration. The filtrate was concentrated to approximately 20 mL of CH$_2$Cl$_2$ and Et$_2$O (100 mL) and hexane (50 mL) was added. The white solid formed was collected by vacuum filtration. The filtrate, containing mostly mCPBA, m-chlorobenzoic acid and other non-polar impurities, was discarded. The combined white solid was dissolved in a minimum amount of CH$_2$Cl$_2$ in a 250 mL Erlenmeyer flask and layered with hexane (CH$_2$Cl$_2$:hexane 1:2). The flask was then cooled to −20° C. in a freezer. This recrystallized product was then collected by vacuum filtration and washed with CH$_2$Cl$_2$/hexane 1:10. The white solid was then dried in vacuo (3.87 g, 65%). Spectral data are identical to that obtained in the reaction in Table 1.

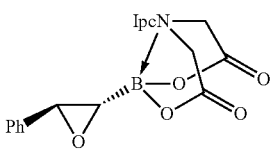

Epoxide 3e. The general procedure was followed using boronate ester 2e (80 mg, 0.25 mmol) and mCPBA (106 mg, 0.475 mmol), giving the product as a white solid (51 mg, 64%). d.r.>20:1. X-ray quality crystals were obtained by making a saturated solution of 3e in 1 mL of 1,2-dichloroethane and layering it with about 2 mL of hexane. The layers were allowed to slowly mix at room temperature, giving the desired crystals. TLC (Hexanes:acetone 3:2) $R_f$=0.46, visualized by KMnO$_4$; $^1$H NMR (500 MHz, CD$_3$CN) δ 4.29 (dt, J=10.5, 6.5 Hz, 1H), 4.20 (d, J=17 Hz, 1H), 3.98 (d, J=15 Hz, 1H), 3.65 (d, J=15 Hz, 1H), 3.42 (d, J=17 Hz, 1H), 3.07 (m, 1H), 2.72-2.66 (m, 1H), 2.51-2.45 (m, 1H), 2.17-2.14 (m, 1H), 2.12 (d, J=3 Hz, 1H), 2.05 (sept, J=3 Hz, 1H), 1.94 (dt, J=6, 2.5 Hz, 1H), 1.81 (ddd, J=15, 6. 2.5 Hz, 1H), 1.37 (d, J=5 Hz, 3H), 1.27 (s, 3H), 1.04 (s, 3H), 0.92 (d, J=10 Hz, 1H); $^{13}$C NMR (125 MHz, CDCl$_3$) δ 169.2, 166.3, 109.7, 67.9, 61.7, 54.6, 53.2, 49.0, 40.6, 39.2, 38.9, 32.1, 30.5, 27.0, 23.6, 23.5; $^{11}$B-NMR (128 MHz, CDCl$_3$) δ 10.7; HRMS (ESI+) Calculated for C$_{17}$H$_{27}$BNO$_5$: 336.1982, Found: 336.1977.

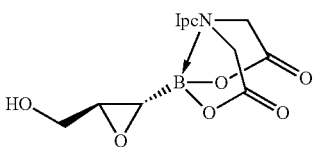

Epoxide 3f. The general procedure was followed using boronate ester 2f (84 mg, 0.25 mmol) and mCPBA (106 mg, 0.475 mmol), giving the product as a white solid (68 mg, 77%). d.r.>20:1. TLC (Hexanes:acetone 3:2) $R_f$=0.22, visualized by KMnO$_4$; $^1$H NMR (500 MHz, acetone-d$_6$) δ 4.29 (d, J=18 Hz, 1H), 4.30-4.26 (m, 1H), 4.13 (d, J=15.5 Hz, 1H), 4.06 (d, J=18.5 Hz, 1H), 3.98 (d, J=15.5 Hz, 1H), 3.02 (dt, J=6, 3 Hz, 1H), 2.80-2.74 (m, 1H), 2.57-2.51 (m, 1H), 2.50-2.44 (m, 1H), 1.97 (dt, J=6, 2.5 Hz, 1H), 1.79 (ddd, J=15, 6. 2.5 Hz, 1H), 1.39 (d, J=7.5 Hz, 3H), 1.28 (s, 3H), 1.10 (d, J=10.5 Hz, 1H), 1.05 (s, 3H); $^{13}$C NMR (125 MHz, acetone-d$_6$) δ 170.7, 167.2, 68.8, 64.1, 61.9, 57.8, 55.4, 50.2, 41.6, 39.7, 39.1, 32.3, 31.2, 27.4, 23.9, 23.7; $^{11}$B-NMR (128 MHz, acetone-d$_6$) δ 10.8; HRMS (ESI+) Calculated for C$_{17}$H$_{27}$BNO$_6$: 352.1931, Found: 352.1925.

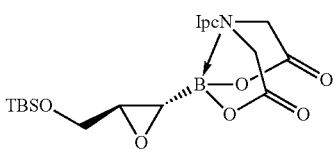

Epoxide 3g. The general procedure was followed using boronate ester 2g (45 mg, 0.1 mmol) and mCPBA (106 mg, 0.475 mmol), giving the product as a white solid (35 mg, 75%). d.r.>20:1. TLC (Hexanes:acetone 3:2) $R_f$=0.51, visualized by KMnO$_4$; $^1$H NMR (500 MHz, CDCl$_3$) δ 4.31 (dt, J=10.5, 6 Hz, 1H), 4.21 (d, J=18 Hz, 1H), 4.01 (dd, J=12.5, 2.5 Hz, 1H), 3.99 (d, J=15.5 Hz, 1H), 3.64 (d, J=15 Hz, 1H), 3.63 (dd, J=12.5, 4.5 Hz, 1H), 3.42 (d, J=17 Hz, 1H), 3.17 (quint, J=3 Hz, 1H), 2.70-2.65 (m, 1H), 2.50-2.46 (m, 1H), 2.39 (d, J=3 Hz, 1H), 2.16-2.15 (m, 1H), 2.05 (sept, J=3 Hz, 1H), 1.95 (dt, J=6.5, 2.5 Hz, 1H), 1.81 (ddd, J=15, 6, 3 Hz, 1H), 1.33 (d, J=6.5 Hz, 3H), 1.27 (s, 3H), 1.02 (s, 3H), 0.89 (s, 9H), 0.07 (s, 3H), 0.07 (s, 3H); $^{13}$C NMR (125 MHz, CDCl$_3$) δ 169.2, 166.3, 67.9, 63.2, 61.7, 57.2, 54.6, 49.0, 40.6, 39.2, 38.9, 32.0, 30.5, 27.0, 25.9, 23.5, 23.5, 18.3, −5.3, −5.4; $^{11}$B-NMR (128 MHz, CDCl$_3$) δ 11.3; HRMS (ESI+) Calculated for C$_{23}$H$_{41}$BNO$_6$Si: 466.2796, Found: 466.2798.

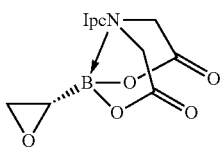

Epoxide 3h. The general procedure was followed using boronate ester 2h (76 mg, 0.25 mmol) and mCPBA (106 mg, 0.475 mmol), giving the product as a white solid (66 mg, 82%). d.r.>20:1. X-ray quality crystals were obtained by making a saturated solution of 3 h in 1 mL of 1,2-dichloroethane and layering it with about 2 mL of hexane. The layers were allowed to slowly mix at room temperature, giving the desired crystals. TLC (Hexanes:acetone 3:2) $R_f$=0.43, visualized by KMnO$_4$; $^1$H NMR (500 MHz, CDCl$_3$) δ 4.29 (dt, J=10.5, 6.5 Hz, 1H), 4.22 (d, J=17.5 Hz, 1H), 3.98 (d, J=15 Hz, 1H), 3.68 (d, J=15 Hz, 1H), 3.48 (d, J=17 Hz, 1H), 2.87 (dd, J=6, 5 Hz, 1H), 2.78 (dd, J=6, 3.5 Hz, 1H), 2.72-2.66 (m, 1H), 2.51-2.45 (m, 1H), 2.39 (dd, J=5, 3.5 Hz, 1H), 2.18-2.17 (m, 1H), 2.06 (sept, J=3 Hz, 1H), 1.95 (dt, J=6, 2 Hz, 1H), 1.83 (ddd, J=15, 6. 2.5 Hz, 1H), 1.34 (d, J=7 Hz, 3H), 1.27 (s, 3H), 1.03 (s, 3H), 0.92 (d, J=11 Hz, 1H); $^{13}$C NMR (125 MHz, CDCl$_3$) δ 169.5, 166.6, 68.1, 61.6, 54.7, 49.0, 45.5, 40.6, 39.2, 38.9, 32.0, 30.5, 27.0, 23.5, 23.5; $^{11}$B-NMR (128 MHz, CDCl$_3$) δ 11.0; HRMS (ESI+) Calculated for C$_{16}$H$_{25}$BNO$_5$: 322.1826, Found: 322.1824.

Example 10

Pinacol-Type Rearrangement of Epoxide 3a

Figure 2:
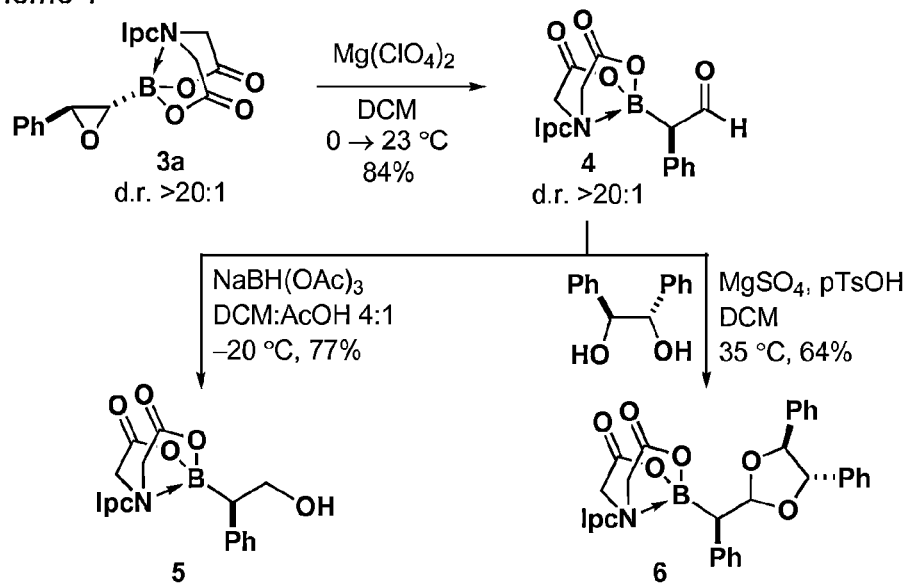
FIG. 2 represents chemical structure and reactions of stable α-boryl aldehyde 4. Ipc=isopinocamphenyl. d.r.=diastereomeric ratio.
Figure 3:
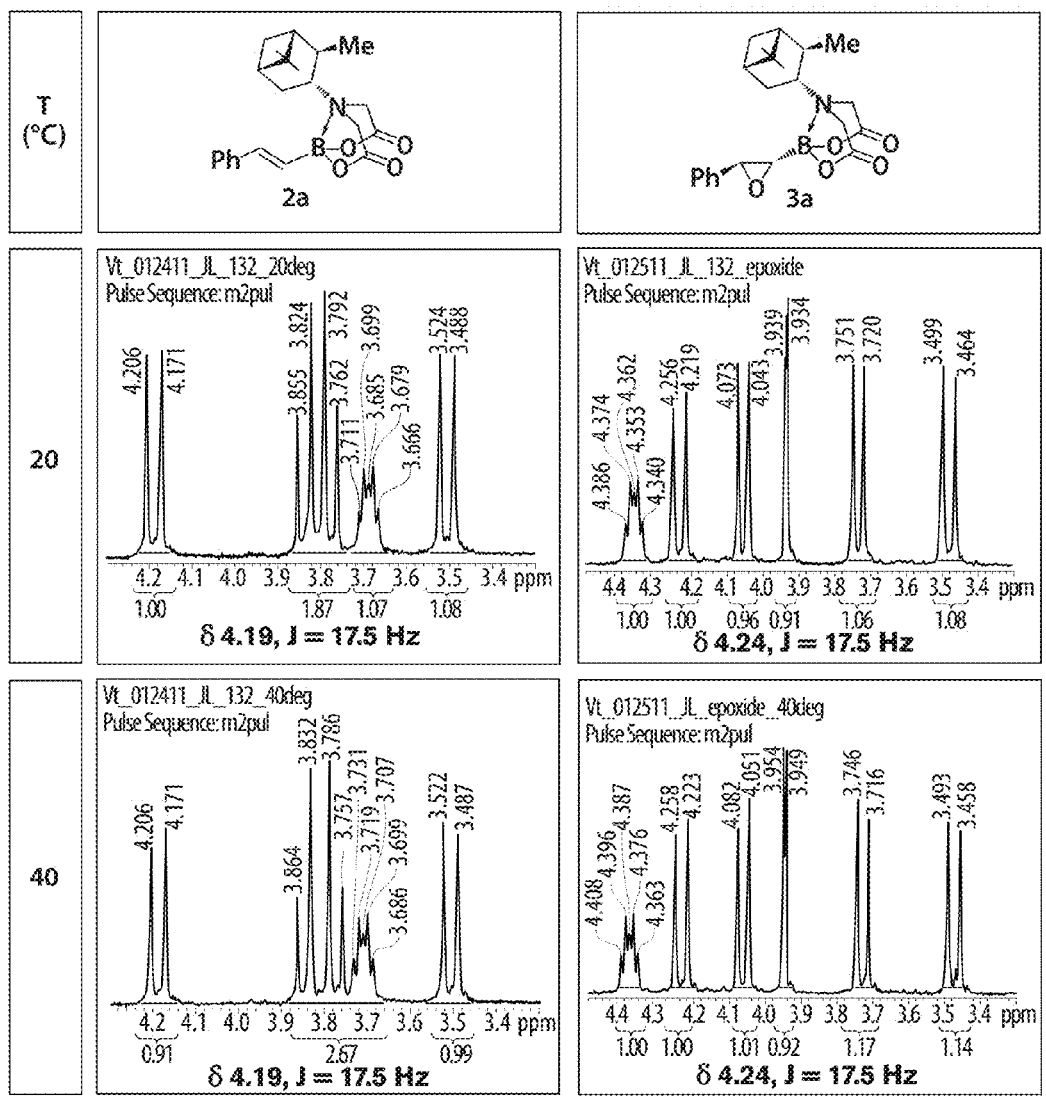
FIG. 3 is a series of variable-temperature NMR spectra of 2a and 3a. Spectra were collected in 1,1,2,2-tetrachloroethane at the indicated temperatures.
Figure 3:
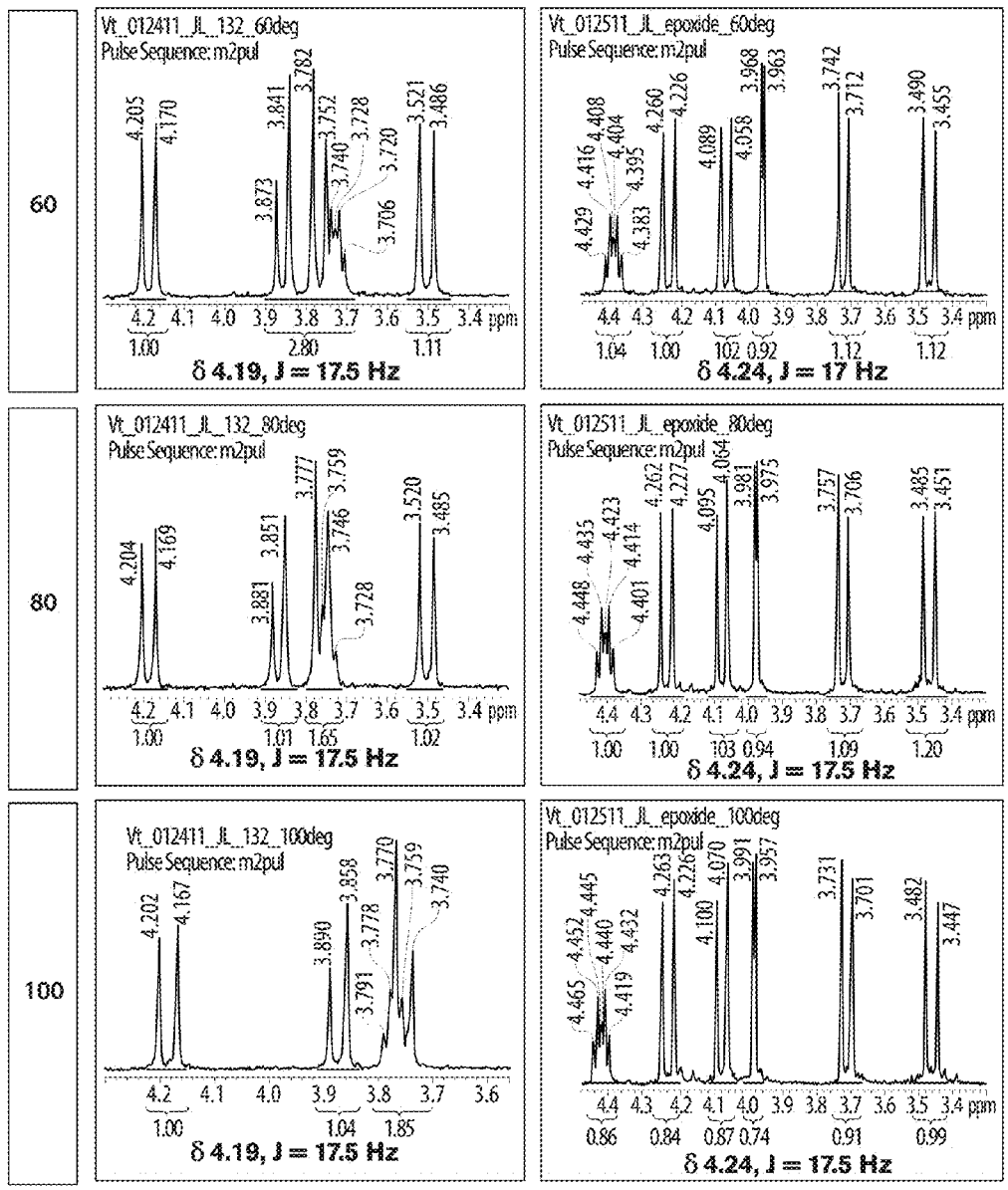

Preliminary studies have also revealed that oxiranyl PIDA boronates can be transformed into previously inaccessible Csp$^3$ boronate building blocks. For example, Mg(ClO$_4$)$_2$ promotes a very interesting pinacol-type rearrangement[12] (House et al. (1955) *J Am Chem Soc* 77:3070-5; Parker et al. (1959) *Chem Rev* 59:737; Rickborn in Comprehensive Organic Synthesis, Trost, Ed., Pergamon: Oxford, 1991, Vol. 3, Chapter 3.3, pp 733-75) of 3a to generate air stable α-boryl aldehyde 4 (Scheme 1 in FIG. 2). Stable α-boryl aldehydes do not appear to have been previously reported in the literature, and the stability of 4 is likely attributable to the unique properties of the iminodiacetic acid boronate motif. Importantly, this rearrangement also occurs with complete maintenance of stereochemical purity.

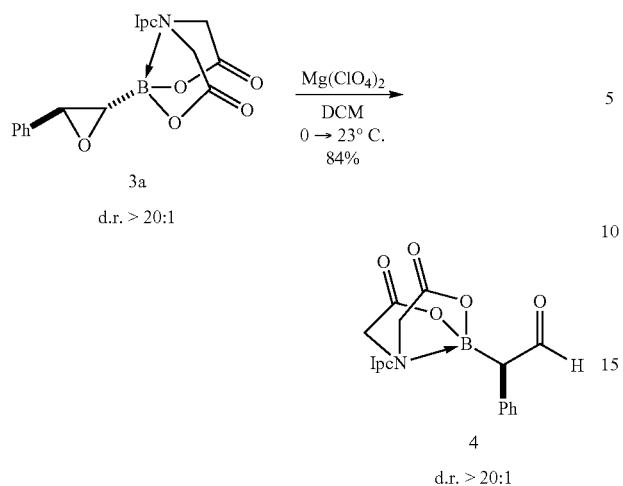

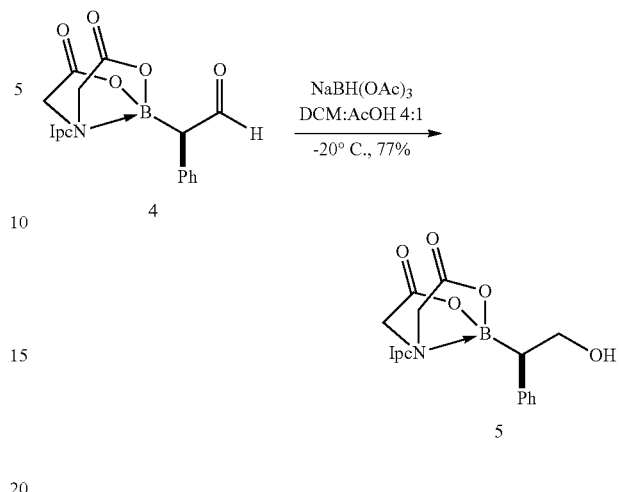

A dry Schlenk flask was charged with 3a (795 mg, 2 mmol) and dry CH$_2$Cl$_2$ (40 mL) under a nitrogen atmosphere. The flask was flushed with nitrogen and cooled to 0° C. Mg(ClO$_4$)$_2$ (2 mmol) was then added in one portion, and the reaction was stirred in the ice/water bath for 2 h. The reaction was then warmed up to room temperature and filtered through Celite, washing with additional CH$_2$Cl$_2$ (20 mL). (Any residual Mg(ClO$_4$)$_2$ may be removed by pushing the filtrate through a solvent-resistant syringe filter. PTFE filters from Sigma-Aldrich (product #54132-U) were used). The filtrate was then concentrated in vacuo at room temperature to afford an off-white solid (667 mg, 84%, d.r.>20:1 by 1H NMR based on aldehyde resonances). No purification of this product was necessary for subsequent reactions. Note: the stereogenic α-carbon of the aldehyde can epimerize on silica gel.

Results. $^1$H NMR (500 MHz, acetone-d$_6$) δ 9.88 (d, J=2.5 Hz, 1H), 7.45 (dd, J=7, 1.5 Hz, 2H), 7.39 (t, J=7.5 Hz, 2H), 7.32 (tt, J=7.5, 1.5 Hz, 1H), 4.29 (d, J=18 Hz, 1H), 4.07 (d, J=18 Hz, 1H), 4.04 (d, J=15.5 Hz, 1H), 3.93 (br s, 1H), 3.66 (d, J=10.5, 6 Hz, 1H), 2.98-2.92 (m, 1H), 2.86 (d, J=15.5 Hz, 1H), 2.45 (ddt, J=11, 6, 2 Hz, 1H), 2.38 (ddt, J=13, 6.5, 2 Hz, 1H), 2.11 (sept, J=3 Hz, 1H), 1.88-1.86 (m, 1H), 1.85-1.83 (m, 1H), 1.26 (s, 3H), 1.08 (d, J=11 Hz, 1H), 0.99 (s, 3H), 0.93 (d, J=7 Hz, 3H); $^{13}$C NMR (125 MHz, CDCl$_3$) δ 199.9, 168.5, 166.1, 134.4, 129.4, 128.7, 127.4, 67.0, 61.6, 55.3, 48.8, 40.6, 38.8, 38.6, 31.6, 30.3, 27.0, 23.1, 23.0; HRMS (ESI+) Calculated for C$_{22}$H$_{29}$BNO$_5$: 398.2139, Found: 398.2140.

Example 11

Reduction of Stable α-Boryl Aldehyde 4 to Alcohol 5

Stable α-boryl aldehydes such as 4 represent a new type of nucleophilic/electrophilic bifunctional reagent. The substantial potential of this motif for further structural modification has begun to be explored. For example, 4 can be readily reduced to alcohol 5 (this Example) or ketalized to generate complex Csp$^3$ boronate 6 (see Example 12).

A dry 20 mL Schlenk flask was charged with aldehyde 4 (397 mg, 1 mmol) under an atmosphere of nitrogen. CH$_2$Cl$_2$ (20 mL) was added and the solution was cooled to −20° C. NaBH(OAc)$_3$ (318 mg, 2 mmol) was added portionwise to the solution over 5 min. Following the addition, AcOH (4 mL) was added, and the reaction was allowed to stir at −20° C. for 3 h. After warming to 0° C., the reaction was quenched by the addition of sat. aqueous NaHCO$_3$ solution (10 mL). The mixture was stirred for 10 min, then transferred to a separatory funnel After phase separation, the organic layer was washed twice with sat. aqueous NaHCO$_3$ solution (10 mL), then with H$_2$O (10 mL) and dried over MgSO$_4$, filtered and concentrated. The solid residue was washed with Et$_2$O, then filtered and dried in vacuo. A white solid was obtained (287 mg, 72%).

Results. TLC (Hexanes:acetone) R$_f$=0.32, visualized by KMnO$_4$; $^1$H NMR (500 MHz, acetone-d$_6$) δ 7.39 (app d, J=7.5 Hz, 2H), 7.33 (app t, J=7.5 Hz, 2H), 7.24 (app t, J=7 Hz, 1H), 4.29 (d, J=18 Hz, 1H), 4.07 (d, J=18 Hz, 1H), 4.04 (d, J=15.5 Hz, 1H), 3.66 (d, J=10.5, 6 Hz, 1H), 2.82 (d, J=15 Hz, 1H), 2.82-2.77 (m, 1H), 2.61 (dd, J=6, 4 Hz, 1H), 2.44 (ddt, J=11, 6, 2 Hz, 1H), 2.33 (ddt, J=13, 6.5, 2 Hz, 1H), 2.08 (m, 2H), 1.86 (dt, J=5.5, 2 Hz, 1H), 1.76 (ddd, J=14.5, 6, 2.2 Hz, 1H), 1.27 (s, 3H), 1.05 (d, J=11 Hz, 1H), 1.01 (s, 3H), 0.93 (d, J=7 Hz, 3H); HRMS (ESI+) Calculated for C$_{22}$H$_{31}$BNO$_5$: 400.2295, Found: 400.2297.

Example 12

Ketalization of Stable α-Boryl Aldehyde 4 to Acetal 6

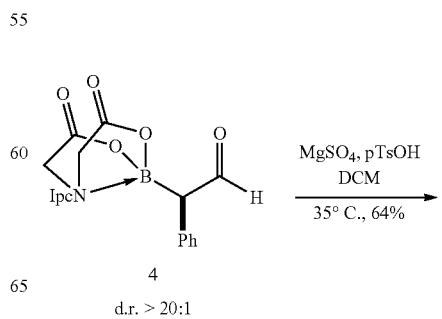

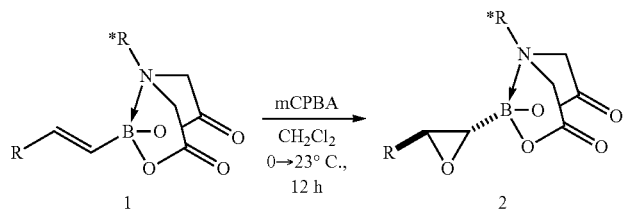

A 40 mL Ichem vial equipped with a stir bar was charged with aldehyde 4 (397 mg, 1 mmol), (S,S)-hydrobenzoin (643 mg, 3 mmol) and MgSO$_4$ (1 g). CH$_2$Cl$_2$ (20 mL) was added, followed by pTsOH.H$_2$O (3.8 mg, 0.02 mmol). The vial was flushed briefly with nitrogen and placed in a heat block. The reaction was stirred at 35° C. for 3 h. After cooling to room temperature, the suspension was filtered through Celite® and the filtrate was concentrated in vacuo. The crude product was purified by silica gel chromatography (acetone/Et$_2$O/hexane 1:4:15→1:2:7→1:1:3) to afford 6 (394 mg, 66%) as a white solid. X-ray quality crystals were obtained by layering a solution of 6 in 1 mL of 1,2-dichloroethane and layering it with about 2 mL of hexane. The layers were allowed to slowly mix at room temperature, giving the desired crystals.

Results. TLC (Hexanes:EtOAc:Et$_2$O 2:2:1) R$_f$=0.69, visualized by short wave UV; $^1$H NMR (500 MHz, CDCl$_3$) δ 7.61, (app d, J=6.5 Hz, 2H), 7.38 (app t, J=7.5 Hz, 2H), 7.32-7.25 (m, 7H), 7.19-7.17 (m, 2H), 7.15-7.13 (m, 2H), 6.04 (d, J=2.5 Hz, 1H), 4.75 (d, J=8 Hz, 1H), 4.31 (d, J=8 Hz, 1H), 4.17 (d, J=17.5 Hz, 1H), 3.79 (dt, J=10, 6 Hz, 1H), 3.44 (d, J=15 Hz, 1H), 3.42 (d, J=17 Hz, 1H), 3.00 (d J=2.5 Hz, 1H), 2.92 (d, J=15 Hz, 1H), 2.77-2.72 (m, 1H), 2.44-2.42 (m, 1H), 2.07 (m, 1H), 1.96 (m, 1H), 1.85-1.81 (m, 2H), 1.26 (s, 3H), 0.96 (s, 3H), 0.91-0.89 (m, 4H); $^{13}$C NMR (125 MHz, CDCl$_3$) δ 168.9, 166.5, 138.7, 137.7, 136.5, 130.8, 128.6, 128.4, 128.3, 128.2, 127.9, 127.2, 126.9, 126.4, 106.1, 87.4, 84.9, 66.4, 61.6, 55.3, 48.8, 40.6, 38.9, 38.8, 31.7, 30.9, 30.3, 27.0, 23.2, 23.1; HRMS (ESI+) Calculated for C$_{36}$H$_{41}$BNO$_6$: 594.3027, Found: 594.3028.

Example 13

1,2-Boryl Migration

Single crystal X-ray analysis of 6 enabled the full stereochemical assignment of 4, which is consistent with exclusive migration of the boronate group during the rearrangement of 3a. This type of 1,2-boryl migration appears never to have been previously reported in the literature. This finding further suggests that the potential of this platform to access a unique array of novel Csp$^3$ boronate building blocks is substantial.

Example 14

Epoxidation of Alkenyl Boronates

Table 3 summarizes the general scheme and results of a number of reactions for epoxidation of alkenyl boronates that have been performed using stereoisomerically enriched or substantially pure chiral organoboronic acids of the invention.

TABLE 3

Epoxidation of alkenyl boronates.

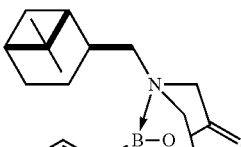

| Entry | 1 | 2 | d.r.$^a$ |
|---|---|---|---|
| 1 | 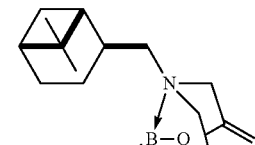 | 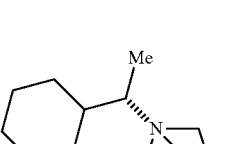 | 2.1:1 |
| 2 | 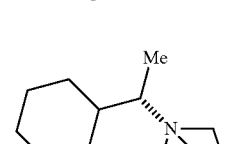 | 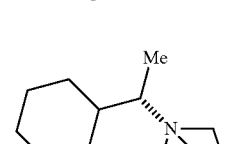 | 2.7:1 |

TABLE 3-continued

Epoxidation of alkenyl boronates.

| Entry | 1 | 2 | d.r.[a] |
|---|---|---|---|
| 3 | | | 4:1 |
| 4 | | | 1.6:1 |
| 5 | | | >20:1 |
| 6 | | | >20:1 |
| 7 | | | 12:1 |
| 8 | | | ~10:1 |

TABLE 3-continued
Epoxidation of alkenyl boronates.
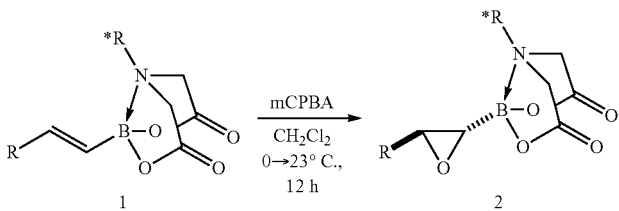
| Entry | 1 | 2 | d.r.[a] |
|---|---|---|---|
| 9 | | | >20:1 |
| 10 | | | >20:1 |
| 11 | | | >20:1 |
| 12 | | | >20:1 |
| 13 | | | 5:1 |
[a]d.r. = diastereomeric ratio as determined via 500 MHz $^1$H NMR anlaysis of unpurified reaction mixtures.

Example 15

General Apparatus Design Principles

Figure 5A:
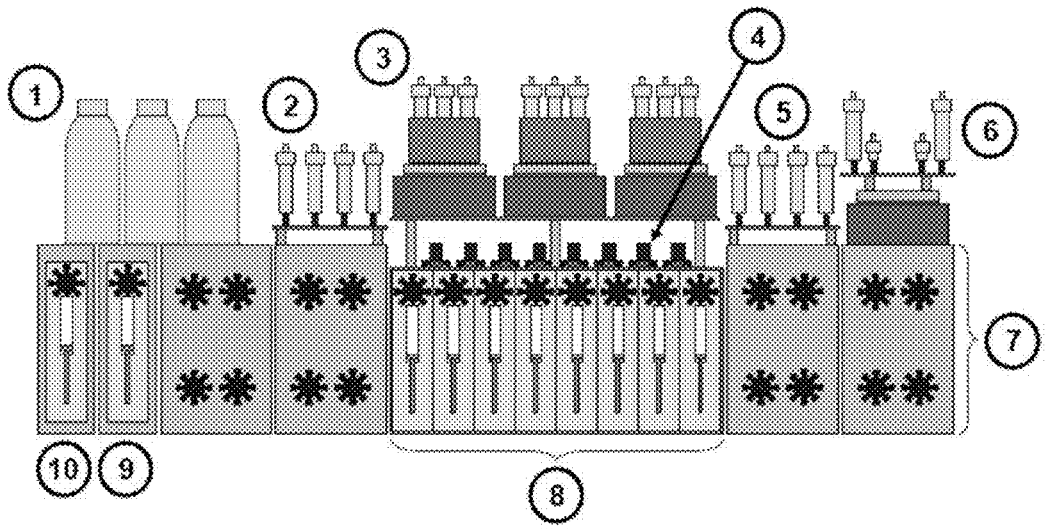
FIG. 5A depicts a design schematic of one embodiment of an automated small molecule synthesizer, wherein (1) denotes solvent reservoirs; (2) denotes a drying and degassing table; (3) denotes a heating block and stir-plate; (4) denotes solenoid valves and gas manifolds; (5) denotes a deprotection table; (6) denotes a purification table; (7) denotes a valve module (with one example of a valve map shown in FIG. 5); (8) denotes main syringe pumps; (9) denotes a syringe pump for purification; and (10) denotes a syringe pump for aqueous reactions.

One example of an automated small molecule synthesizer is shown in FIG. 4 and FIG. 5A. This custom-designed apparatus can execute the fully automated synthesis of eight small molecules simultaneously. Each synthesis consists of between one and three iterative coupling sequences, where each coupling sequence can include a deprotection step, a cross-coupling step and a purification step. The organization of the apparatus is centered on eight main syringe pumps. Each main syringe pump is dedicated to only one synthesis. These eight main syringe pumps operate independently to execute iterative coupling sequences in parallel. Resources for each synthesis are compartmentalized such that each main syringe pump does not access the resources of another main syringe pump, with the following exceptions: all solvents and all product output ports are shared by all of the main syringe pumps. Additionally, an auxiliary syringe pump is used as a shared resource for the purification steps. Another auxiliary syringe pump is used as a shared resource to handle all aqueous solutions. The custom designed software that operates the machine governs how the shared resources are distributed.

Figure 5B:
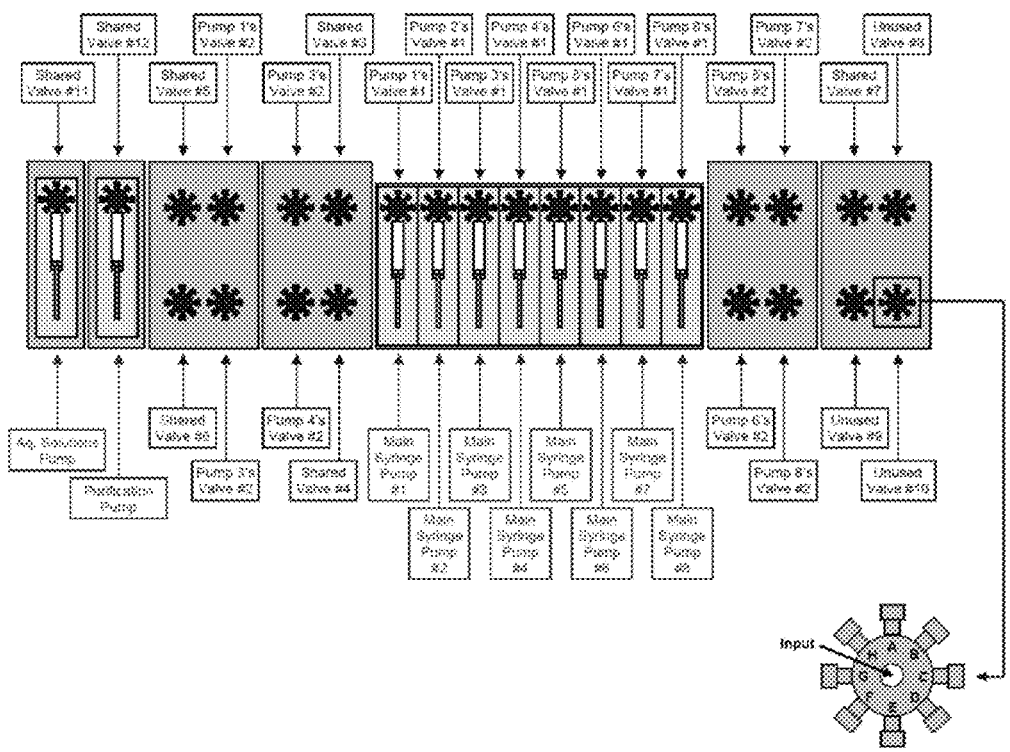
FIG. 5B depicts an example of the connectivity of the various pumps, valves, ports and tubes.

Standard Valve. The valve modules were purchased from J-KEM Scientific (part #Syr-054) and are connected to the controlling computer via a RS485 to USB connection. Each valve module is equipped with four eight-port stream-selecting valves (J-KEM, part #SPDV-058). Each valve connects the input stream, which enters through the center of the valve, to one of eight possible output streams (ports A thru H). The location of the standard valves is shown in FIG. 5B.

Syringe Pump Valve. Each syringe pump is fitted with an eight-port stream selecting valve (J-KEM, part #SPDV8) where the input stream enters from the syringe connected immediately in front of port "E". Port "E" is partially blocked by the syringe and requires a flush-net fitting (IDEX Health and Science, part #F-358) to connect the output stream. The location of the syringe pump valves is shown in FIG. 5B.

Syringe Pumps. Syringe pumps were purchased from J-KEM Scientific (part #SYR1400-8 for P1-P8, part #SYR-1400PC for P9 and P10) and are connected to the controlling computer via a RS485 to USB connection. Each syringe pump is fitted with an eight-port stream-selecting valve (J-KEM, part #SPDV8) and a 10 mL glass syringe equipped with a Teflon plunger (J-KEM, part #SPGS-10000). The syringe pump withdraws and injects at rates from 0.0 mL/min to 70.0 mL/min with a step of 0.0029 mL. The location of the syringe pumps is shown in FIG. 5B.

Figure 6A:
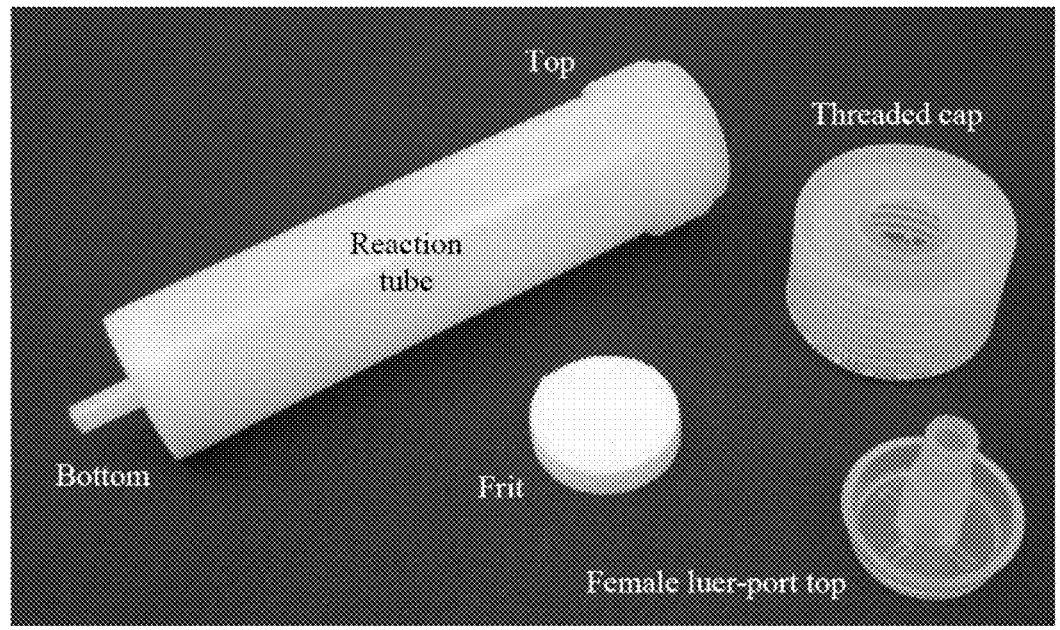
FIG. 6A is a photograph depicting exemplary reaction tubes and fittings.

Reaction Tubes. To minimize cross-contamination and allow the rapid setup of a synthesis, all chemical manipulations are performed in disposable polypropylene tubes purchased from Luknova, item #FC003012. The dimensions of the tube are 21 mm×120 mm (ID×length). The bottom of the tube is fitted with a 21 mm diameter×5 mm tall frit. The bottom of the tube is accessed through a male Luer tip, while the top of the tube is sealed with an air-tight, threaded cap containing a female Luer port. The tube holds a solvent volume of up to 25 mL. Examples of reaction tubes are shown in FIG. 6A and FIG. 8A.

Figure 6B:
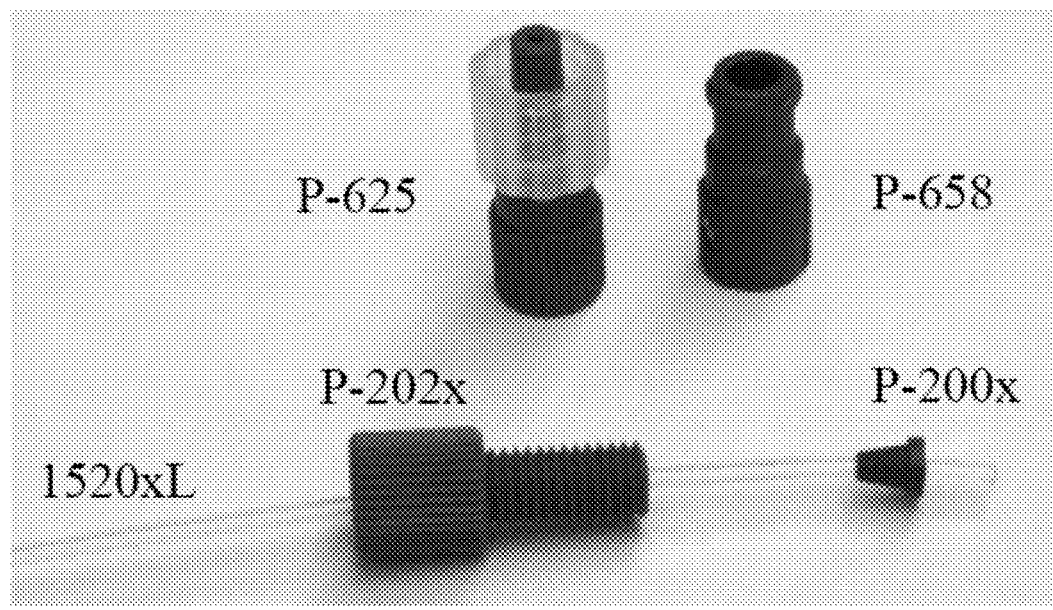
FIG. 6B is a photograph depicting exemplary tubing and fittings.
Figure 7:
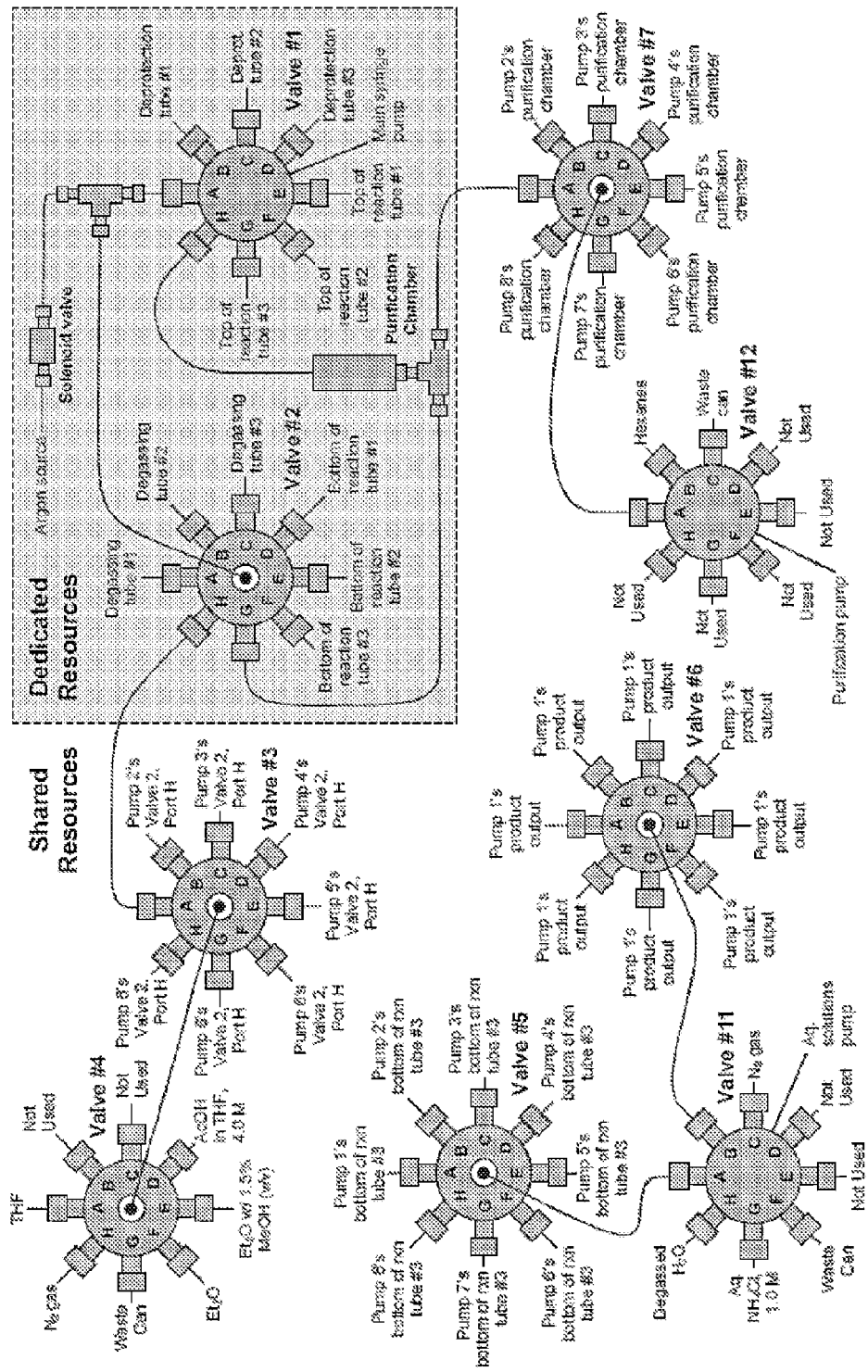
FIG. 7 depicts an example of a valve map.

Tubing and Fittings. All tubing and fittings were purchased from IDEX Health and Science. The tubing used in the machine is 0.030 inch (ID)×1/16 inch (OD) Teflon FEP tubing (part #1520xL). All tubing connections were made with 1/16 inch ETFE flangeless ferrules (part #P-200x) and 1/4-28 acetal fittings (part #P-202x). Male Luer fittings (part #P-625) and female Luer fittings (part #P-658) are ETFE and PEEK, respectively. Examples of tubes and fittings are shown in FIG. 6A and FIG. 6B.

Example 16

Computer Control of Apparatus

General Programming Design Principals. All apparatus equipment is controlled by a custom program written in VB.NET using Microsoft Visual Basic 2008 Express Edition.

The apparatus is controlled by a single computer running Windows Vista. The apparatus is designed to run an experiment independently on each of the eight main syringe pumps. Each main pump can be started and stopped at will without affecting the other pumps. Further, the scripts of simultaneously executing experiments do not need to be the same nor do they need to be synchronized in order for the experiments to perform successfully. The program is designed to manage distribution of shared resources such as common valve equipment and auxiliary syringe pumps as well as bandwidth on the COM ports.

Setting up and modifying the script used to execute an experiment is designed to be straightforward and *facile*. Towards this end, a simple custom scripting language was developed. The scripting language contains a small collection of commands used to send instructions to a virtual machine, manage the timing of these operations, and lock/unlock access to shared resources. The program serves as an interpreter for this custom scripting language and maps the virtual machine instructions to the required apparatus hardware. In this way the same script can be used on any of the main syringe pumps without modification.

Communication to the Apparatus Equipment. Commands are sent to the apparatus equipment using the computer's serial ports. The RS485 serial ports of the apparatus equipment are connected to a serial-to-USB converter which is connected to the computer. Each COM port can address up to 16 pieces of equipment, where a piece of equipment is defined as a valve or a syringe pump. The syringe pump may or may not additionally control a solenoid valve. As configured, communication to the apparatus is distributed across four COM ports. Commands can be sent to the equipment no faster than every 20 milliseconds. To enforce this delay, the program maintains a queue of commands to be sent to the equipment. Commands recognized by the equipment are: move the valve to a specific port, report the current position of the valve, move the syringe plunger to a specific position at a specific rate, turn the solenoid valve on/off, and report if the equipment has finished executing the previous command Program Architecture. Each valve and each syringe pump is represented programmatically as an "equipment object". Each of these equipment objects is given an identifier that can be used to map the commands of the scripting language to the actual hardware represented by the equipment object. Each main pump is assigned a "pump object" that is a container for all of the equipment objects that represent resources that are available to the main pump. No single pump object contains every equipment object, but every equipment object is contained in at least one pump object. When an experiment is executed on the main pump, the list of scripted commands is passed as a text file to the corresponding pump object. The pump object is responsible for proof-reading, interpreting and executing the scripted commands and updating the graphic user interface (GUI) as appropriate.

Script Execution. When the pump object is passed a text file of command lines, the pump object interprets each command line into a "command object". The command object contains all of the information that is necessary to execute the command. Once a command object is created it is entered into a queue managed by the pump object. Through this process the script is proof-read to identify any syntax errors that would prevent the code from executing properly. The script is then executing by retrieving an item from the queue, sending the appropriate commands to the equipment via the COM port, periodically checking the status of the machine equipment until the command is complete, and then repeating the process for the next command in the queue.

Scripting Language. The scripting language contains the following commands with indications on their usage:

'(apostrophe) Indicates everything following the apostrophe is comment and should not be interpreted.

[text](brackets) The brackets represent a placeholder value recognized by the identifier text that will be replaced at runtime with the define command.

define text=value At runtime replaces all brackets (placeholders) containing text with the value of value. This is a useful strategy for writing flexible scripts.

pause n Halts execution of the script for n seconds.

valve nL Moves valve n to port position L (A-H).

valve xon valve xon opens the solenoid valve associated with the main syringe pump.

valve xoff valve xoff closes this solenoid valve.

pump n in=L out=M ratein=x rateout=y Fills the syringe with n mL drawn from port position L (A-H) at a rate of x mL/min. and inject n mL out through port position M (A-H) at y mL/min. The port position refers to the valve that is directly connected to the syringe. Omitting the in= portion instructs the pump to only dispense n mL as per above. Omitting the out= portion instructs the pump to only fill n mL as per above. Use rafe=x to set both the rate of withdrawal and the rate of injection to x mL/min.

pump out=M rate=x Injects the entire contents of the syringe out through port position M (A-H) at a rate of x mL/min.

log "comment text" Writes a time-stamped entry to the log book containing the user-defined text (comment text).

lock n Claims valve n for the exclusive use by the main pump. If valve n is busy or has been locked by a different pump, execution of the script is halted until the valve becomes available. Auxiliary pumps can also be locked using this command.

unlock n Releases valve n from the exclusive use by the main pump. All lock commands should be eventually followed by an unlock command. Auxiliary pumps can also be released using this command.

sub sub_name end sub The sub and end sub commands mark the beginning and end, respectively, of command lines that will be interpreted as a sub routine with the identifier sub_name.

run sub_name Runs the sub routine identified as sub_name. This sub routine should have been previously defined using the sub and end sub commands. The command following the run command is not executed until all of the commands in the sub routine have completed (as opposed to the background command.)

background sub_name Runs the sub routine identified as sub_name. This command is similar to the run command except that as soon as the sub routine begins to execute, the command following the background command executes as well. Therefore, the sub routine is handled as a background process allowing multiple actions to be performed at once.

wait sub_name Halts execution of the script until the sub routine identified as sub_name (which was previously executed using the background command) finishes its execution. This command allows background processes to be synchronized with the main script.

Example 17

Chemical Synthesis

The following example, while not specific to a PIDA-based system, describes procedures that, when used with a PIDA-based system, are reasonably expected to achieve similarly effective results.

General Procedure. All chemical manipulations were performed in polypropylene tubes purchased from Luknova, item #FC003012. The dimensions of the tube are 21 mm×120 mm (ID×length). The bottom of the tube is fitted with a 21 mm diameter×5 mm tall frit. The bottom of the tube is accessed through a male Luer tip, while the top of the tube is sealed with an air-tight, threaded cap containing a female Luer port. The tube holds a solvent volume of up to 25 mL.

Deprotection Tubes. To enable automation, a novel MIDA boronate deprotection method was developed using Amberlyst A26(OH) resin. Amberlyst A26(OH) was purchased from Sigma-Aldrich and was stored under $N_2$ atm. at 4° C. Amberlyst A26(OH) (suspension volume of 20 mL) was twice washed with MeCN (50 mL) with vigorous agitation for 60 seconds in each wash. The residual solvent was evaporated under a fast stream of air for 5 minutes until the resin was light beige in color and was free-flowing. To each polypropylene tube was added the Amberlyst resin (2.0 g resin for every 1.0 mmol of MIDA boronate to be deprotected) and, optionally, the MIDA boronate starting material. The tube was capped and then placed on the machine where the bottom Luer tip connected to the deprotection table and the top Luer port is covered with aluminum foil.

Drying and Degassing Tubes. A polypropylene tube was charged with Celite®, activated molecular sieves (4 Å, 8-12 mesh) and $K_2CO_3$. The amounts of these reagents are proportional to the amount of Amberlyst A26 resin used in the deprotection step prior to drying/degassing, as indicated below. Onto the bed of solids was placed a plastic plunger, cut from the plunger of a 5 mL polypropylene syringe (Fisher #14-817-28, Norm-Ject).

The plunger prevents the solids from lifting during the degassing step. The tube was capped and then placed on the machine where the bottom Luer tip connects to the degassing table and the top Luer port is connected to the gas manifold.

| Amberlyst A26 (previous step) | Celite ® | Mol. sieves | $K_2CO_3$ |
|---|---|---|---|
| 2.0 g | 200 mg | 2.0 g | 2.0 g |
| 1.0 g | 100 mg | 1.0 g | 1.0 g |
| 0.5 g | 50 mg | 0.5 g | 0.5 g |

Reaction Tubes. To assist in the transfer of small amounts of $Pd(OAc)_2$ and S-Phos, these reagents were adsorbed onto $Cs_2CO_3$ as follows. To a 40 mL glass vial was added $Pd(OAc)_2$ (22 mg) and $Cs_2CO_3$ (2.723 g). To the vial was added THF (10 mL), and the suspension was concentrated in vacuo to afford a pale amber powder, the Pd-mixture. To a 40 mL glass vial was added S-Phos (76 mg) and $Cs_2CO_3$ (2.667 g). To the vial was added THF (10 mL), and the suspension was concentrated in vacuo to afford a white powder, the SPhos-mixture.

To a polypropylene tube was added a stir bar (Big Science Inc., SBM-1508-REH), the halide (0.333 mmol), the Pd-mixture (488 mg, 5% Pd) and the SPhos-mixture (488 mg, 10% S-Phos). For aqueous couplings, to the tube was added a KOH pellet (75 mg, 1.7 mmol). The tube was capped with a modified cap (see detail) and was placed in a heating block. The bottom of the tube is connected the reaction table, the top of the tube is vented to the gas manifold, and the second top input is connected to the reaction table for addition of the boronic acid. Building on the previously published reports of "slow-release" cross-coupling, the boronic acid was added slowly via syringe pump to minimize in situ decomposition and thereby maximize yields.

Automation. Each cross-coupling in the automated sequence was performed according to the following, fully automated script:

Deprotection a) Add THF (5 mL) to deprotection tube.
b) Agitate the mixture via gas bubbling for 60 minutes.
c) Add AcOH in THF (4.0 M, 5.0 mmol per 1.0 g of Amberlyst resin).
d) Agitate the mixture via gas bubbling for 15 minutes.
e) Transfer the solution to the drying tube, washing the resin with THF (5×1.0 mL).
f) Sparge the mixture with Ar gas for 15 minutes.
g) While sparging the reaction tube with Ar gas for 15 min., agitate the THF mixture via gas bubbling every 2 minutes.

Cross-Coupling h) Add THF (3 mL) to the reaction tube and allow the mixture to stir for 10 min.
i) Transfer the boronic acid solution from the drying tube to the reaction tube over 120 min., washing the solids with THF (3×1.0 mL).
j) Stir the reaction mixture at 150 rpm for 22 hours.

Purification k) Add hexanes (12 mL) to the ppt. chamber, then add a portion of the reaction solution (3 mL) to the ppt. chamber.
l) Withdraw the solution in the ppt. chamber through the SiO$_2$ plug and send to waste.
m) Repeat steps (k) and (l) until all of the reaction solution has been transferred.
n) Add Et$_2$O w/ MeOH (1.5% v/v) (7.5 mL) to the ppt. chamber, withdraw the solution through the SiO$_2$ plug, and send to waste. Repeat an additional four times.
o) Add Et$_2$O (7.5 mL) to the ppt. chamber, withdraw the solution through the SiO$_2$ plug, and send to waste. Repeat an additional two times.
p) Flow Ar gas through the SiO$_2$ plug for three minutes to evaporate residual solvent.
q) Add THF (6.8 mL) to the ppt. chamber.
r) Withdraw the THF solution through the SiO$_2$ plug and then inject the solution back into the ppt. chamber. Repeat an additional two times.
s) Withdraw the THF solution through the SiO$_2$ plug and inject the solution into the deprotection tube used in the next reaction. The next reaction begins at step a.

Direct Release/Aqueous Coupling Modification (Typically Performed as the Last Step of an Automated Synthesis).

This sequence begins after step (s) from the general automation script (above).
t) Sparge the THF solution derived from the purification of the previous cross-coupling with Ar gas for 15 minutes.
u) Transfer the THF solution to the reaction tube in one portion.
v) Stir the mixture for 5 minutes.
w) Add degassed H$_2$O (2 mL) to the reaction tube.
x) Stir the reaction mixture at room temperature for 12 hours.
y) Add aq. NH$_4$Cl (2.5 mL), mix for 5 minutes, then withdraw the entirety of the mixture and transfer it to the product test tube.

β-Parinaric Acid.

All steps were performed according to the general procedure.

The machine was equipped with reagent tubes as follows.

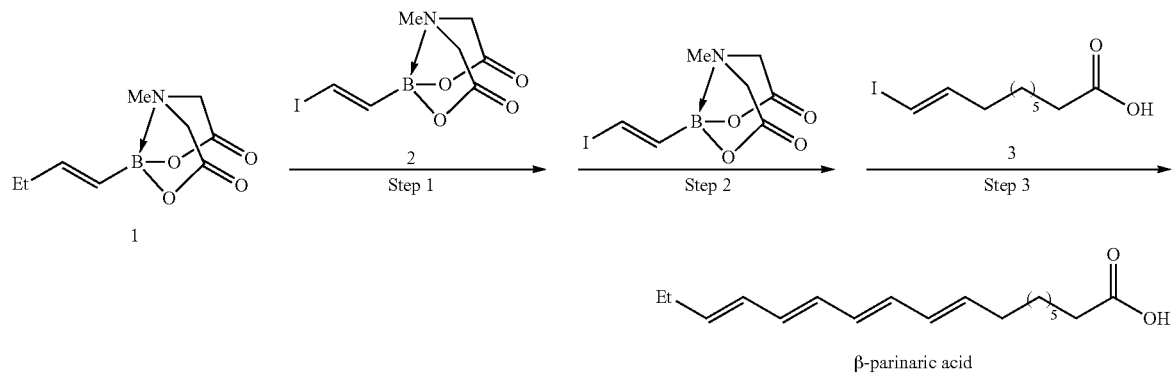

β-parinaric acid

Step 1. The machine was equipped with a deprotection tube charged with Amberlyst resin (2.0 g) and MIDA boronate 1 (211 mg, 1.0 mmol); a drying tube charged with molecular sieves (2.0 g), K$_2$CO$_3$ (2.0 g) and Celite® (0.2 g); and a reaction tube charged with the Pd-mixture (488 mg), the SPhos-mixture (488 mg) and boronate 2 (103 mg, 0.333 mmol).

Step 2. The machine was equipped with a deprotection tube charged with Amberlyst resin (1.0 g); a drying tube charged with molecular sieves (1.0 g), K$_2$CO$_3$ (1.0 g) and Celite® (0.1 g); and a reaction tube charged with the Pd-mixture (244 mg), the SPhos-mixture (244 mg), and boronate 2 (34 mg, 0.11 mmol).

Step 3. The machine was equipped with a deprotection tube (empty, but used for sparging the MIDA boronate solution) and a reaction tube charged with the Pd-mixture (60 mg), the SPhos-mixture (60 mg), KOH (75 mg, 1.7 mmol) and halide 3 (11 mg, 0.037 mmol).

Automation. The synthesis was performed in a fully automated fashion with no operator intervention. Step 1 and step 2 were performed following the standard script, and step 3 was performed following the direct release/aqueous coupling modification of the standard script. The aqueous mixture that was outputted from the machine was manually purified as follows: The mixture was transferred to a 60 mL separatory funnel and was diluted with sat. aq. NH₄Cl (10 mL). The mixture was extracted twice with Et₂O (20 mL) and the combined organics were washed with brine (20 mL); dried over MgSO₄; filtered, then concentrated in vacuo. The yellow residue was purified via SiO₂ chromatography to afford P-parinaric acid as a white solid (yield not yet determined). The ¹H NMR (CDCl₃) spectrum of the synthesized product 10.0 Hz, 1H), 6.11 (ddt, J=15.5, 10.5, 1.5 Hz, 1H), 5.82 (dt, J=15.0, 6.5 Hz, 1H), 5.64 (d, J=17.5 Hz, 1H), 4.21 (d, J=17.0 Hz, 2H), 4.03 (d, J=17.0 Hz, 2H), 2.99 (s, 3H), 2.12 (quint, J=7.5 Hz, 2H), 0.99 (t, J=7.5 Hz, 3H); ¹³C NMR (125 MHz, acetone-d₆): δ 169.0, 143.5, 138.3, 134.8, 133.5, 130.3, 62.2, 47.3, 26.4, 13.8.

all-trans-retinal. All steps were performed according to the general procedure. The machine was equipped with reagent tubes as follows.

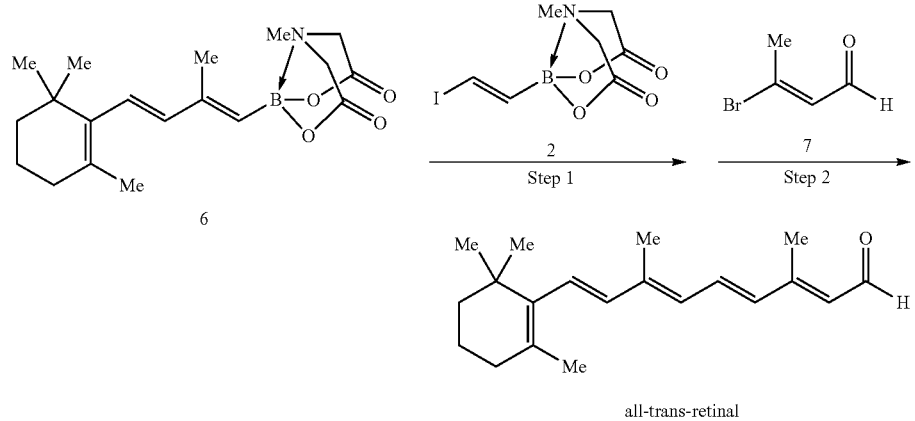

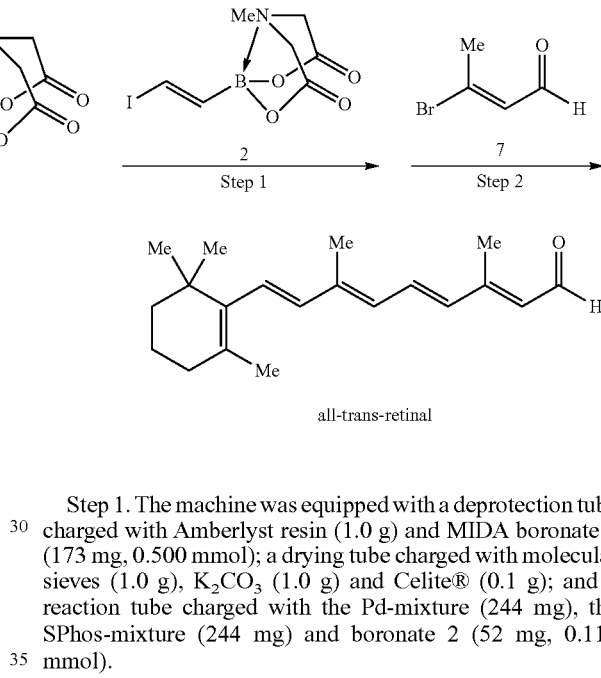

all-trans-retinal was fully consistent with the literature data (Lee, S. J.; Gray, K. C.; Paek, J. S.; Burke, M. D. *J. Am. Chem. Soc.*, 2008, 130, 466-468).

To characterize the efficiency of each step and characterize all intermediates, Step 1 was repeated and the MIDA boronate solution generated in line 19 of the standard script was diverted into a test tube and then concentrated to afford pure intermediate 4 as a colorless solid (40 mg, 52%).

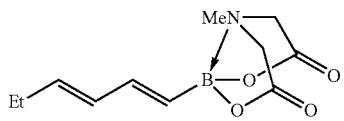

¹H NMR (500 MHz, acetone-d₆): δ 6.53 (dd, J=17.0, 10 Hz, 1H), 6.11 (dd, J=15.5, 10.0 Hz, 1H), 5.82 (dt, J=15.5, 6.5 Hz, 1H), 5.54 (d, J=17.5 Hz, 1H), 4.20 (d, J=17.5 Hz, 2H), 4.01 (d, J=17.0 Hz, 2H), 2.98 (s, 3H), 2.10 (quint, J=7.5 Hz, 2H), 0.99 (t, J=7.5 Hz, 3H); ¹³C NMR (125 MHz, acetone-d₆): δ 196.1, 143.7, 137.8, 132.6, 62.2, 47.2, 26.1, 13.7.

Step 1 and step 2 were repeated and the MIDA boronate solution generated during the second coupling (line 19 of the standard script) was diverted into a test tube and then concentrated to afford pure intermediate 5 as a colorless solid (22 mg, 76%).

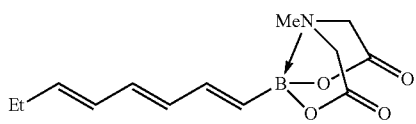

¹H NMR (500 MHz, acetone-d₆): δ 6.58 (dd, J=18.0, 10.5 Hz, 1H), 6.28 (dd, J=15.0, 10.0 Hz, 1H), 6.20 (dd, J=15.0, Step 1. The machine was equipped with a deprotection tube charged with Amberlyst resin (1.0 g) and MIDA boronate 6 (173 mg, 0.500 mmol); a drying tube charged with molecular sieves (1.0 g), K₂CO₃ (1.0 g) and Celite® (0.1 g); and a reaction tube charged with the Pd-mixture (244 mg), the SPhos-mixture (244 mg) and boronate 2 (52 mg, 0.111 mmol).

Step 2. The machine was equipped with a deprotection tube charged with Amberlyst resin (0.5 g); a drying tube charged with molecular sieves (0.5 g), K₂CO₃ (0.5 g) and Celite® (50 mg); and a reaction tube charged with the Pd-mixture (82 mg), the SPhos-mixture (82 mg). A separate polypropylene tube was charged with a solution of halide 7 (0.056 mmol) in degassed THF (3 mL).

Automation. The synthesis was performed in a fully automated fashion with no operator intervention. Step 1 was performed following the standard script. Step 2 was performed following the standard direct release/aqueous coupling modification script with the additional modification that the THF used in line 8 of the standard script was the entirety of the solution containing halide 7. Further, the script for step 2 was stopped after line 10 and the reaction solution was outputted to a test tube. The product was manually purified as follows: The reaction solution was concentrated in vacuo and the solid yellow residue was purified by SiO₂ chromatography using an Isco-Teledyne CombiFlash system to afford all-trans-retinal as a yellow solid (3.3 mg, 20%). The ¹H NMR (CDCl₃) spectrum of the product was fully consistent with the literature data (Lee, S. J.; Gray, K. C.; Paek, J. S.; Burke, M. D. *J. Am. Chem. Soc.*, 2008, 130, 466-468).

Example 18

Generality of Purification Platform

The following example, while not specific to a PIDA-based system, describes procedures that, when used with a PIDA-based system, are reasonably expected to achieve similarly effective results.

To establish the generality of the novel purification platform, its capacity to purify a series of MIDA boronates representing a diverse range of structures, including aryl, heteroaryl, alkynyl, alkenyl, and alkyl derivatives, was tested. Briefly, mock crude reaction mixtures were prepared by mixing each MIDA boronate (1 equiv.) (Table 4) with tolylboronic acid (1 equiv.) and a palladium catalyst (0.1 equiv) in THF. Each of these mixtures was then subjected to fully-automated purification via the hybrid precipitation/catch-and-release platform described in detail herein. At the end of this process, all of these MIDA boronates were obtained in >90% purity as judged by $^1$H NMR, and the yields of recovered MIDA boronates were good to outstanding (Table 4).

TABLE 4

Purification from mock crude reaction mixtures.

R—BMIDA + 4-Me-C6H4-B(OH)2 → R—BMIDA
(Pd(OAc)2 (2.5 mol %), SPhos (5 mol %), THF (0.0075M))

| Boronate | % Recovery |
|---|---|
| 2-MeO-C6H4-BMIDA | 69 |
| 2-thienyl-BMIDA | 76 |
| 2-naphthyl-BMIDA | 53 |
| Me(CH2)3-BMIDA | 86 |
| α-styryl-BMIDA | 92 |
| cyclopentyl-BMIDA | 87 |
| (E)-styryl-BMIDA | 92 |
| cyclopropyl-BMIDA | 90 |
| 2-OMe-pyridin-3-yl-BMIDA | 92 |
| ethynyl-BMIDA | 68 |
| 2-CN-C6H4-BMIDA | 83 |
| isopropenyl-BMIDA | 94 |
| N-SO2Ph-indol-2-yl-BMIDA | 81 |
| 3-BnO-C6H4-BMIDA | 86 |
| benzofuran-2-yl-BMIDA | 78 |
| 3-MeO2C-C6H4-BMIDA | 65 |

Details of the procedure are as follows.

Pre-activation of the Catalyst Solution: Palladium(II) acetate (0.001875 mmol, 2.5 mol %) and SPhos (0.00375 mmol, 5 mol %) per purification to be run were combined in an 8 mL scintillation vial equipped with a PTFE-coated magnetic stir bar and placed under an argon atmosphere. THF was added to generate a 0.01 M catalyst stock solution (with respect to palladium(II) acetate), and it was stirred vigorously for 30 min at room temperature to generate an orange, yellow, or clear solution. After this activation process, 1 mL catalyst stock solution was added to the solution in the polypropylene cartridge containing the simulated reaction mixture.

Preparation and Installation of Simulated Reaction Chamber: A new fitted 12 g Luknova polypropylene cartridge was charged with MIDA boronate (0.075 mmol, 1 eq), 4-methylbenzene boronic acid (0.075 mmol, 1 eq), and THF (10 mL). After addition of the pre-activated catalyst solution, the cartridge was installed into the Luer fittings in the reaction block of the automated synthesizer. Once all cartridges were in place, the automated purification routine was run using the computer interface. The samples were collected as THF solutions into tared 40 mL scintillation vials.

Concentration, Azeotropic Drying, and Analysis of Recovered Materials from Purifications: The THF solutions were concentrated under reduced pressure on a rotary evaporator, then the residue was azeotroped with dichloromethane (3×5 mL) to remove residual solvents. These residues were then placed under vacuum for 12-36 hours, after which yield and purity were determined by comparison of $^1$H NMR in acetone-d6 with a standard sample of the desired MIDA boronate and with a sample taken of a simulated reaction mixture.

Automated Purification Detailed Protocol

A) In the background, auxiliary pump aspirates 6 mL hexanes and delivers it to the bottom of the precipitation chamber, through the silica gel column. This process is repeated once for a total of 12 mL hexanes.

B) Primary pump aspirates 9 mL of reaction mixture from reaction chamber bottom and returns 6 mL, through bottom, to ensure no more than 3 mL will be delivered to the precipitation chamber.

C) Primary pump delivers 3 mL of reaction mixture to top of precipitation chamber containing 12 mL hexanes. This induces chiral, non-racemic PIDA boronate precipitation from the THF solution. Primary pump then delivers two 10-mL plugs of dry nitrogen to bottom of precipitation chamber (bypassing the silica gel column) to dislodge stir bar.

D) Suspension in precipitation chamber is aspirated from bottom and through silica gel column by auxiliary pump. Eluent is sent to waste.

E) Steps (A)-(D) repeat three additional times to send all of reaction mixture to precipitation chamber.

F) Primary pump aspirates 1.5 mL THF and delivers it to the top of reaction chamber as a rinse. Steps (A)-(C) are repeated.

G) Primary pump aspirates 1.5 mL THF and delivers it to top of reaction chamber as a rinse. Steps (B)-(C) are repeated.

H) Step (D) is repeated.

I) Steps (A)-(D) are repeated.

J) Step (D) is repeated.

K) Primary pump aspirates 6.5 mL 1.5% (v/v) MeOH in Et$_2$O and delivers it to top of precipitation chamber. This process is repeated once for a total delivery of 13 mL solvent.

L) Primary pump delivers two 10-mL plugs of dry nitrogen to the bottom of the precipitation chamber (bypassing the silica gel column) to dislodge stir bar.

M) Step (D) is repeated.

N) Steps (K)-(M) are repeated. Step (D) is repeated again.

O) Steps (K)-(M) are repeated twice with Et$_2$O instead of 1.5% (v/v) MeOH in Et$_2$O. Step (D) is repeated twice more to dry out silica gel column.

P) Auxiliary pump is rinsed with 2×1 mL THF to wash away any residual MeOH. Wash THF is sent to waste.

Q) Auxiliary pump aspirates 6 mL THF and delivers slowly to bottom of precipitation chamber through silica gel column. This process is repeated once for a total of 12 mL THF.

R) Primary pump aspirates 5 mL dry nitrogen and delivers it to bottom of precipitation chamber (bypassing the silica gel column) to agitate the suspension, thus promoting mixing chiral, non-racemic PIDA boronate dissolution. This process is done 40 times.

S) THF solution of chiral, non-racemic PIDA boronate is aspirated by primary pump out of the bottom of the precipitation chamber (bypassing the silica gel column) Solution is delivered to the collection tube. This aspiration/delivery is repeated an additional 5 times to ensure full transfer.

T) Auxiliary pump pushes residual THF in silica gel column into bottom of precipitation chamber as a rinse.

U) Primary pump aspirates 5 mL dry nitrogen and delivers it to bottom of precipitation chamber (bypassing the silica gel column) to agitate the suspension, thus promoting mixing chiral, non-racemic PIDA boronate dissolution. This process is done 5 times.

V) THF rinse is aspirated by primary pump out of bottom of the precipitation chamber (bypassing the silica gel column) Solution is delivered to the collection tube.

The results from this study of a wide range of structurally diverse MIDA boronates demonstrates that the hybrid precipitation/catch-and-release purification strategy is remarkably general.

Example 19

Aqueous Deprotection Module

The following example, while not specific to a PIDA-based system, describes procedures that, when used with a PIDA-based system, are reasonably expected to achieve similarly effective results.

Automated aqueous deprotection of phenyl MIDA boronate, trienyl MIDA boronate, and butenyl MIDA boronate was performed using the aqueous deprotection strategy and module described above.

Figure 12A:
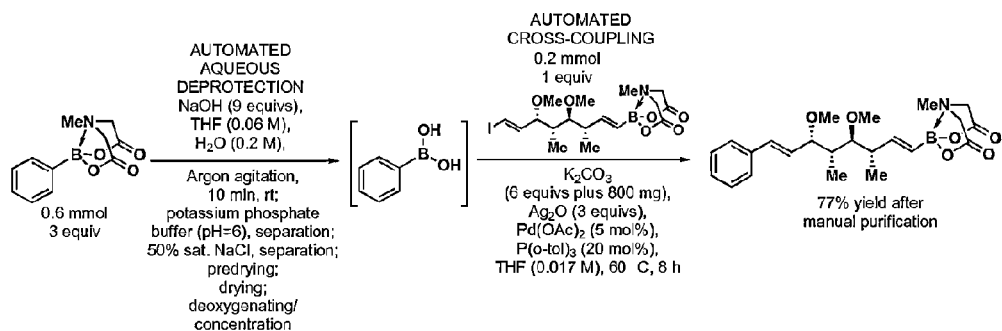
FIG. 12A depicts automated aqueous deprotection of phenyl MIDA boronate and subsequent automated cross-coupling of phenyl boronic acid with a vinyl iodide bifunctional building block.

Automated aqueous deprotection of phenyl MIDA boronate afforded phenyl boronic acid. Subsequent automated cross-coupling with the vinyl iodide bifunctional building block afforded the desired coupled product in 77% yield after manual purification. See FIG. 12A.

Figure 12B:
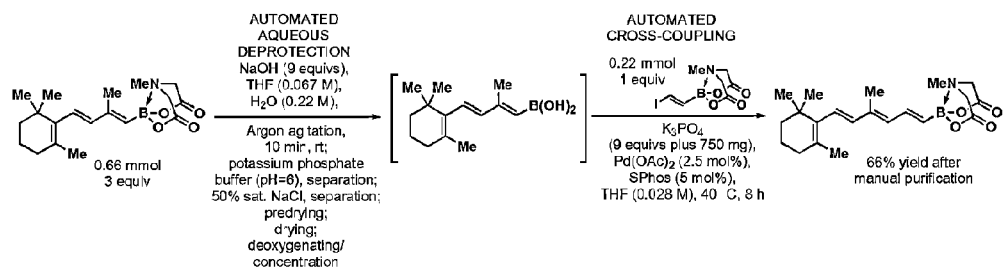
FIG. 12B depicts automated aqueous deprotection of trienyl MIDA boronate and subsequent automated cross-coupling of trienyl boronic acid with a vinyl iodide bifunctional building block.

Automated aqueous deprotection of the trienyl MIDA boronate afforded the trienyl boronic acid. Subsequent automated cross-coupling with the vinyl iodide bifunctional building block afforded the desired coupled product in 66% yield after manual purification. See FIG. 12B.

Figure 12C:
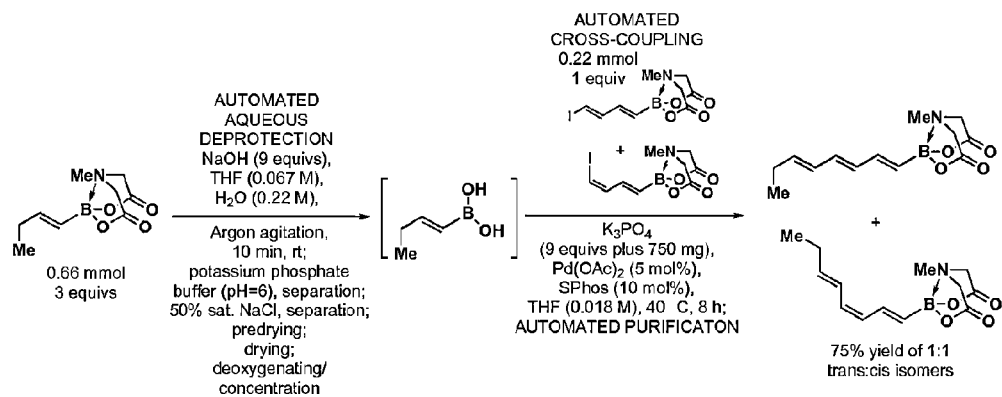
FIG. 12C depicts automated aqueous deprotection of butenyl MIDA boronate and subsequent automated cross-coupling of butenyl boronic acid with an isomeric mixture of dienyl vinyl iodide bifunctional building blocks.

Automated aqueous deprotection of the butenyl MIDA boronate afforded the butenyl boronic acid. Subsequent automated cross-coupling with an isomeric mixture of the dienyl vinyl iodide bifunctional building block afforded a 75% yield of the expected isomeric trienyl coupled products in a 75% yield after automated purification. See FIG. 12C.

Example 20

Fully Automated Synthesis of All-trans-Retinal Using Aqueous Deprotection Module The following example, while not specific to a PIDA-based system, describes procedures that, when used with a PIDA-based system, are reasonably expected to achieve similarly effective results.

The first deprotection tube was prepared as follows: To a new, fritted 12-g cartridge (Luknova, Mansfield, Mass. 02048, Part # FC003012) was added trienyl MIDA boronate (345.2 mg, 1 mmol, 9 equivs). To this was added sodium hydroxide (120.0 mg, 3 mmol, 27 equivs). The cartridge was capped with its female Luer-port screw cap. To this Luer port was attached a 5-mL polypropylene syringe barrel (Henke-Sass, Wolf GmbH, Tuttlingen, Germany, 78532, Part # A5) from which the plunger had been removed. This first deprotection tube was wrapped with aluminum foil.

The second deprotection tube was prepared as follows: To a new, fritted 12-g cartridge (Luknova, Mansfield, Mass. 02048, Part # FC003012) was added sodium hydroxide (40.0 mg, 1 mmol, 9 equivs). Sodium hydroxide pellets were shaved down to the correct mass with a clean razor blade and massed quickly to minimize adsorption of atmospheric moisture. The cartridge was capped with its female Luer-port screw cap. To this Luer port was attached a 5-mL polypropylene syringe barrel (Henke-Sass, Wolf GmbH, Tuttlingen, Germany, 78532, Part # A5) from which the plunger had been removed. This second deprotection tube was wrapped with aluminum foil.

The first and second predrying tubes were prepared as follows: To a new, fritted 12-g cartridge (Luknova, Mansfield, Mass. 02048, Part # FC003012) was added Celite® 545 filter aid (800 mg, not acid-washed, Acros Organics, Product #349670025, Lot # A0287832). To this was added anhydrous magnesium sulfate (2.1 g, ReagentPlus®, ≥99.5%, Sigma-Aldrich, Product # M7506, Lot #080M0246V). These two solids were mixed with a spatula until visibly homogenous. On top of the solid mixture was placed a 5-mL polypropylene syringe plunger (Henke-Sass, Wolf GmbH, Tuttlingen, Germany, 78532, Part # A5), manually cut to approximately 6.5 cm in length. The cartridge was capped with its female Luer-port screw cap. The Luer port was covered tightly with a small square (approximately 1 cm×1 cm) of aluminum foil. Each predrying tube was wrapped with aluminum foil.

The first and second drying tubes were prepared as follows: To a new, fitted 12-g cartridge (Luknova, Mansfield, Mass. 02048, Part # FC003012) was added Celite® 545 filter aid (300 mg, not acid-washed, Acros Organics, Product #349670025, Lot # A0287832). To this was added activated molecular sieves (3.6 g, 4 Å, −325 mesh, Sigma-Aldrich, Product #688363, Lot # MKBF4010V). Molecular sieves were activated at 300° C., ambient pressure, 24 h, and cooled/stored in a vacuum desiccator under dry argon over Drierite. These two solids were not mixed. On top of the layered solids was placed a 5-mL polypropylene syringe plunger (Henke-Sass, Wolf GmbH, Tuttlingen, Germany, 78532, Part # A5), manually cut to approximately 5.5 cm in length. The cartridge was capped with its female Luer-port screw cap. Each drying tube was wrapped with aluminum foil.

The first and second deoxygenating/concentrating tubes were prepared as follows: A new, fritted 12-g cartridge (Luknova, Mansfield, Mass. 02048, Part # FC003012) was capped with its female Luer-port screw cap. Each deoxygenating/concentrating tube was wrapped with aluminum foil.

The first reaction tube was prepared as follows: To a new, fritted 12-g cartridge (Luknova, Mansfield, Mass. 02048, Part # FC003012) was added a 4-g frit (Luknova, Mansfield, Mass. 02048, Part # FC003004). This frit was secured, concentrically, to the 12-g cartridge frit with 26 G Chromel A wire, pierced through the 12-g frit. To this reaction tube was added, in order, anhydrous potassium phosphate (1.39 g, 3 mmol+750 mg, 27 equivs+750 mg, 97%, Alfa Aesar, Product # L15168, Lot # L02U015), palladium (II) acetate (1.9 mg, 0.0083 mmol, 2.5 mol %, ≥99.9%, Sigma-Aldrich, Product #520764, Lot #1000824996), 2-dicyclohexylphosphino-2', 6'-dimethoxy-1,1'-biphenyl (Sphos, 6.8 mg, 0.017 mmol, 5 mol %, 98%, Strem Chemicals, Product #15-1143, Lot #18526300), vinyl iodide MIDA boronate (103.0 mg, 0.33 mmol, 3 equivs), and a PTFE-coated rare earth magnetic stir bar. Potassium phosphate was freshly ground in a 100° C. mortar and pestle. The cartridge was capped with its customized female Luer-port screw cap. The customized cap consists of a standard female Luer-port cap with a bent (by approximately 45°), 1.5 inch, 18 G, disposable needle installed through the cap and a small ball of Kimwipe inserted into the Luer port. It is important remove the cored-out polypropylene plug from the inside of the needle after installation. The cap was topped with a fritted 4-g cartridge (Luknova, Mansfield, Mass. 02048, Part # FC003004).

The precipitation tube was prepared as follows: To a new, fritted 12-g cartridge (Luknova, Mansfield, Mass. 02048, Part # FC003012) equipped with a PTFE-coated magnetic stir bar was added Celite® 545 filter aid (150 mg, not acid-washed, Acros Organics, Product #349670025, Lot # A0287832) and 3-aminopropyl functionalized silica gel (250 mg, 40-63 μm, approximately 1 mmol/g $NH_2$, Sigma-Aldrich, Product #364258, Lot #79096HM). The cartridge was capped with its female Luer-port screw cap. To the cartridge was added hexanes (5 mL, reagent grade) and the resulting suspension was swirled vigorously to mix the solids. The mixed suspension was allowed to settle for approximately 5 seconds and then the solvent was drained by forcing a plug of ambient air through the top of the cartridge by syringe. This process firmly embeds the stir bar in the solids to prevent stirring before the precipitation tube is utilized. This precipitation tube was wrapped with aluminum foil.

The silica gel chromatography column was prepared as follows: A silica gel chromatography column was freshly prepared from custom PTFE fittings using unfunctionalized silica gel. The cartridge was modeled after a 4-g cartridge (Luknova, Mansfield, Mass. 02048, Part # FC003004), but was made of PTFE instead of polypropylene. To a clean, fritted column was added silica gel. This was done by vacuum aspiration through the bottom male Luer tip fitting. This process ensured tight, even packing of the silica gel plug. Excess silica gel was removed manually with a spatula and a 4-g frit (Luknova, Mansfield, Mass. 02048, Part # FC003004) was placed on top of the silica plug. This doubly-fritted cartridge was capped with its female Luer-port screw cap, using PTFE tape to ensure a tight seal.

The second reaction vessel was prepared as follows: To a non-flame-dried 7-mL glass vial equipped with a PTFE-coated magnetic stir bar was added palladium (II) acetate (1.2 mg, 0.0056 mmol, 5 mol %, ≥99.9%, Sigma-Aldrich, Product #520764, Lot #1000824996), 2-dicyclohexylphosphino-2', 6'-dimethoxy-1,1'-biphenyl (Sphos, 4.6 mg, 0.011 mmol, 10 mol %, 98%, Strem Chemicals, Product #15-1143, Lot #18526300), and anhydrous potassium phosphate (212 mg, 1 mmol, 9 equivs, 97%, Alfa Aesar, Product # L15168, Lot # L02U015). Potassium phosphate was freshly ground in a 100° C. mortar and pestle. This vial was sealed with a PTFE-lined septum screw cap. Through the septum was added a 1.5 inch, 20 G, disposable needle connected to a dry argon gas line. Then, through the septum was added a 1.5 inch, 20 G, disposable needle to act as a vent. The reaction vial was then flushed with dry argon for approximately 7 min. The vent needle and then the argon needle were removed from the septum.

Figure 13:
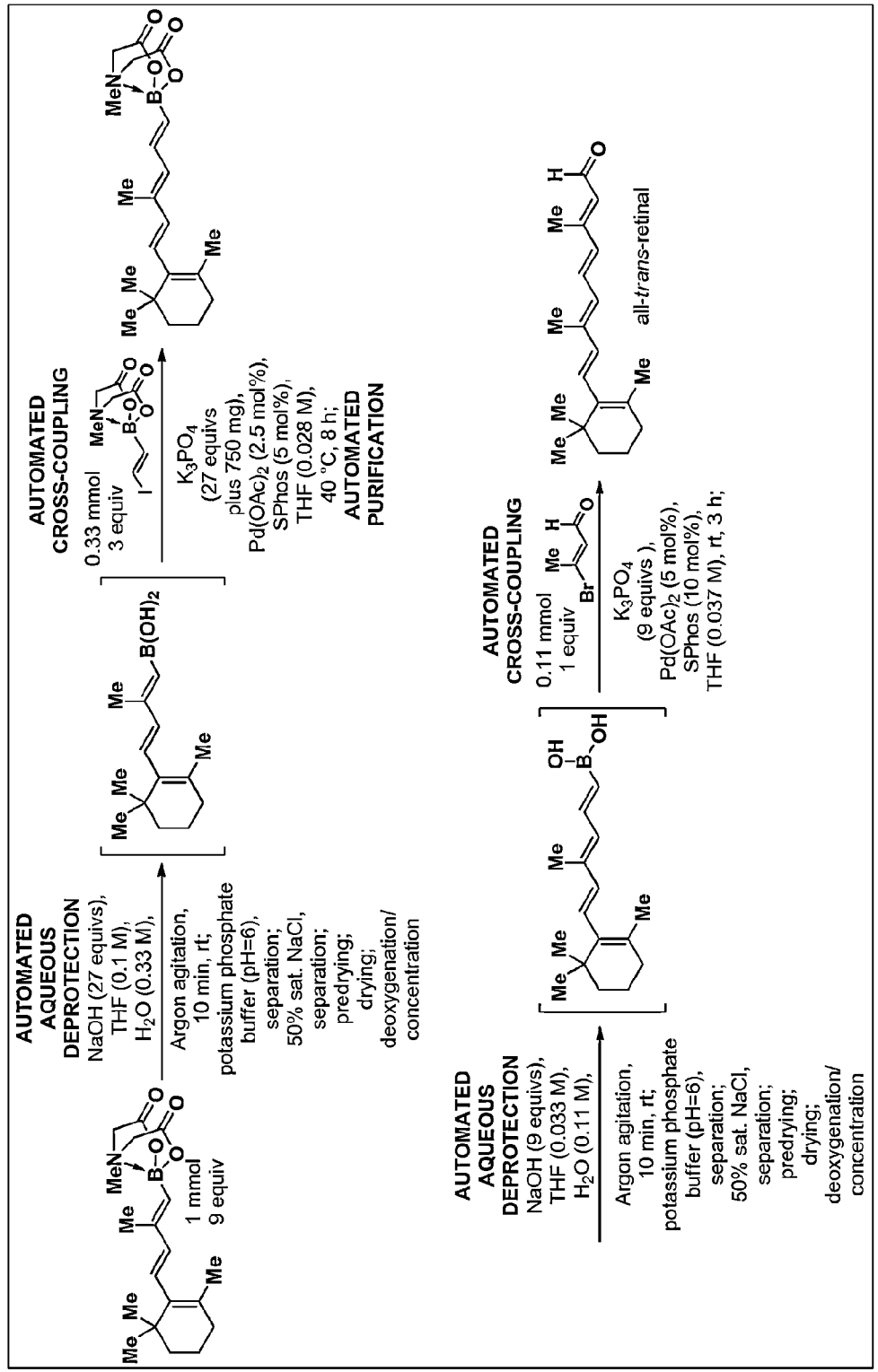
FIG. 13 depicts fully automated synthesis of all-trans-retinal using an aqueous deprotection module.

The tubes, vessels and columns described above were used as follows: See FIG. 13 for reaction scheme. Both deprotection tubes (wrapped with aluminum foil) were securely installed on the machine. Tubes were installed by placing the tube's male Luer tip into the machine's appropriate female Luer port and were secured with a firm downward force and slight (less that one quarter turn) clockwise rotation. Both predrying tubes (wrapped and topped with aluminum foil) were securely installed on the machine. Both drying tubes (wrapped in aluminum foil) were securely installed on the machine. Each drying tube was connected to the inert gas manifold by attaching a patch line to the machine's gas manifold and the tube's top Luer port. Patch lines are approximately 12-inch lengths of tubing with male Luer-tip fittings on both ends. Both deoxygenating/concentrating tubes (wrapped in aluminum foil) were securely installed on the machine. Each deoxygenating/concentrating tube was connected to the inert gas manifold by attaching a vented patch line to the machine's gas manifold and the tube's top Luer port. Vented patch lines are approximately 12-inch lengths of tubing with a male Luer-tip fitting on the machine-end and a Y-connector (one port connected to the line, one port connected to a male Luer-tip fitting, and one port left open) on the tube-end. The first reaction tube was securely installed on the machine (in a heating block preheated to 40° C.) and connected to the inert gas manifold by attaching the reaction vent line to the tube's top Luer port. The reaction tube was then covered with aluminum foil and set to stirring at 600 rpm. The silica gel column was securely installed on the machine and connected to the purification module by attaching the eluent line to the column's top Luer port. The precipitation tube (wrapped in aluminum foil) was securely installed on the machine and connected to the purification module by placing the eluent line (fixed with a 1.5 inch, 18 G, disposable needle) through the tube's top Luer port).

The experiment's pre-assembled code was then loaded and executed to begin the automated sequence. The first aqueous MIDA boronate deprotection commenced immediately. After running the first deprotection (rt, 10 min), the machine quenched and worked up the resulting boronic acid solution and then dried, deoxygenated, and concentrated it. The machine then ran the first, slow addition, cross-coupling reaction (40° C., 8 h total) and purified the resulting coupled product. The machine then ran the second aqueous MIDA boronate deprotection (rt, 10 min) and subsequently quenched, worked up, dried, deoxygenated, and concentrated the resulting boronic acid solution.

Approximately 5 minutes before the second cross-coupling began, the second reaction vessel was placed in an aluminum block (at room temperature) on a stir plate. An inert gas vent line (fixed with a 1.5 inch, 20 G, disposable needle) was connected, through the septum. The reaction tube was then covered with aluminum foil and set to stirring at 600 rpm. Separately, into a non-flame-dried 1.5-mL glass vial was added the aldehyde (16.6 mg, 0.11 mmol, 1 equiv). The vial was sealed with a septum screw cap and to this was added 100 µL deoxygenated dry THF from a 100 µL, gas tight, fixed needle, glass syringe. The vial was manually gently agitated to dissolve the aldehyde and then was added to the reaction vial with the same syringe. The remaining residual aldehyde was quantitatively transferred to the reaction vial with 2×50 µL of deoxygenated dry THF using the same syringe. As the machine automatically deoxygenated the reaction addition line (fixed with a 1.5 inch, 22 G, disposable needle), it was connected to the reaction vessel, through the septum. The machine then ran the second, fast addition, cross-coupling reaction (rt, 3 h).

At the end of 3 hours, the reaction vial was removed from the machine and the crude reaction mixture was filtered through a 1-cm pad of Celite® packed in a pipette. The reaction vial was washed with 3×2 mL dry THF and these washings were filtered through the Celite® pad. The pad was then washed with 3×2 mL dry THF. The resulting clear dark yellow filtrate was concentrated in vacuo (rt, 80 Torr), azeotroped with 3×5 mL dichloromethane (rt, 80 Torr), and residual solvent was removed on high vacuum (30 min, 200 mTorr) to afford a dark yellow/orange sticky solid. This crude product was manually purified by silica gel flash chromatography to afford a mixture of all-trans-retinal:13-cis-retinal in a ratio of 1:0.55 in a combined total 30% yield.

Example 21

Automated Purification of a Simulated Reaction Mixture Containing a PIDA Boronate Pre-activation of the Catalyst Solution: Palladium(II) acetate (4.4 mg, 0.01959 mmol, 5 mol %) and SPhos (7.7 mg, 0.01875 mmol, 5 mol %) were combined in an 8 mL scintillation vial equipped with a PTFE-coated magnetic stir bar and placed under a nitrogen atmosphere. THF (5 mL) was added to generate a catalyst stock solution (with respect to palladium(II) acetate), and it was stirred vigorously for 30 min at room temperature to generate an orange, yellow, or clear solution. After this activation process, 1 mL of the catalyst stock solution was added to the solution in the polypropylene cartridge containing the simulated reaction mixture.

Preparation and installation of Simulated Reaction Chamber: A new fitted 12 g Luknova polypropylene cartridge was charged with styrenyl PIDA boronate (28.6 mg, 0.075 mmol, 1 eq), 4-methylbenzene boronic acid (10.2 mg, 0.075 mmol, 1 eq), and THF (10 mL). After addition of the pre-activated catalyst solution, the cartridge was installed into the Luer fittings in the reaction block of the automated synthesizer. Once all cartridges were in place, the automated purification routine was run using the computer interface. The samples were collected as THF solutions into tared 40 mL scintillation vials.

Figure 14A:
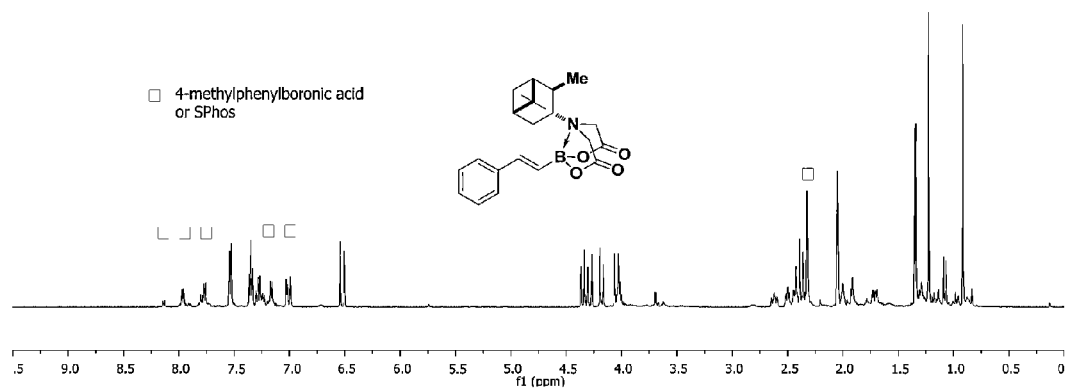
FIG. 14A is a ¹H NMR spectrum corresponding to a mock reaction mixture comprising a PIDA boronate.
Figure 14B:
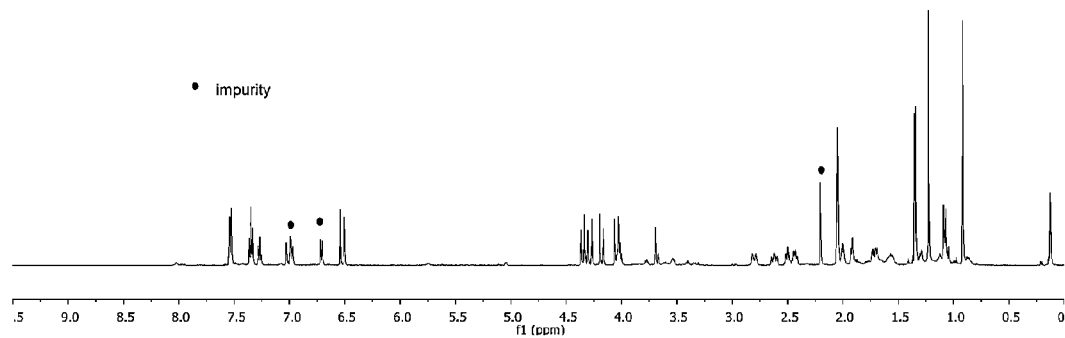
FIG. 14B is a ¹H NMR spectrum corresponding to the PIDA boronate after purification from the mixture.

Concentration, Azeotropic Drying, and Analysis of Recovered Material from Purification: The THF solution was concentrated under reduced pressure on a rotary evaporator, then the residue was azeotroped with dichloromethane (3×5 mL) to remove residual solvents. The residue was then dried in vacuo. The percentage recovery was determined to approximately 35%. SPhos and the boronic acid were purified away from the PIDA boronate; however an unknown side product was formed during the purification procedure as indicated in the NMR of the purified product (FIG. 14B). The $^1$H NMR of the purified product in acetone-d6 was compared with a sample of the stimulated reaction mixture before purification.

Example 22

Automated Hydrolysis of a PIDA Boronate with Aq. NaOH Procedure

A Luknova cartridge (12 g) was charged with styrenyl PIDA boronate (0.2 mmol, 1 equiv) and solid sodium hydroxide (0.6 mmol, 3 equiv). Automated aqueous deprotection, drying and concentration of the resulting boronic acid solution was then started using the computer interface. The boronic acid solution was then further concentrated under reduced pressure with a rotary evaporator. $^1$H NMR analysis of the residue showed a mixture of styrenyl boronic acid, the corresponding boroxine, and some PIDA ligand. No PIDA boronate starting material was found in the analysis.

INCORPORATION BY REFERENCE

All publications and patents mentioned herein are hereby incorporated by reference in their entirety as if each individual publication or patent was specifically and individually indicated to be incorporated by reference. In case of conflict, the present application, including any definitions herein, will control.

EQUIVALENTS

While specific embodiments of the subject invention have been discussed, the above specification is illustrative and not restrictive. Many variations of the invention will become apparent to those skilled in the art upon review of the specification. The appended claims are not intended to claim all such embodiments and variations.

We claim:

1. A compound of formula (II):

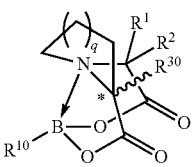

(II)

wherein:

B is a boron atom having sp³ hybridization;
the carbon atom marked "*" is a chiral carbon atom of at least 90% enantiomeric excess;
$R^{10}$ is selected from the group consisting of

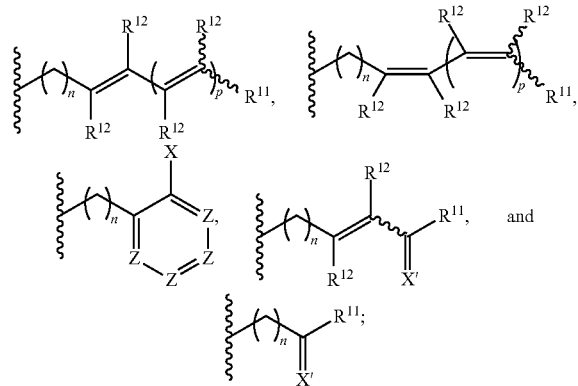

$R^{11}$ and each instance of $R^{12}$ are independently selected from the group consisting of hydrogen, halogen, hydroxyl, (C1-C10)alkyl, cycloalkyl, aryl, aralkyl, heteroaralkyl, alkoxyl, acyl, acyloxy, aryloxy, amino, and trialkylsilyloxy; or $R^{11}$ and any one instance of $R^{12}$, or any two instances of $R^{12}$, taken together, form a 3-10-membered ring;
X is halogen;
each instance of Z is independently selected from the group consisting of CH and N, provided that no more than two instances of Z are N;
X' is selected from the group consisting of $CR^5R^6$, O, S, and $NR^7$;
$R^1$ and $R^2$ are both hydrogen or identically selected (C1-C3)alkyl;
$R^5$ and $R^6$ are independently selected from the group consisting of hydrogen, halogen, hydroxyl, (C1-C10)alkyl, cycloalkyl, aryl, aralkyl, heteroaralkyl, alkoxyl, acyl, acyloxy, aryloxy, amino, and trialkylsilyloxy;
$R^7$ and $R^{30}$ are independently selected from the group consisting of hydrogen and (C1-C3)alkyl;
n is 0, 1, or 2;
p is 0, 1, or 2; and
q is 1 or 2.

2. The compound of claim 1, wherein the compound of formula (II) is

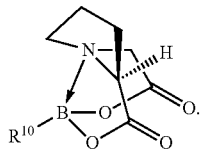

3. The compound of claim 1, wherein n is 0.

4. The compound of claim 2, wherein p is 0.

5. The compound of claim 1, wherein $R^{10}$ is

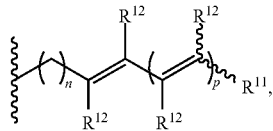

n is 0, p is 0, each instance of $R^{12}$ is hydrogen, and $R^{11}$ is selected from the group consisting of aryl and methyl.

6. The compound of claim 1, wherein $R^{10}$ is

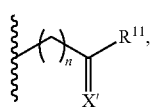

n is 0, X' is $CH_2$, and $R^{11}$ is methyl.

7. The compound claim 1, wherein $R^{10}$ is

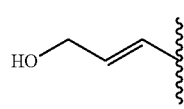

8. The compound of claim 1, wherein $R^{10}$ is

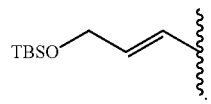 [SMILES: */C=C/CO[Si](C)(C)C(C)(C)C]

9. The compound of claim 1, wherein R* is a chiral group of at least 95% enantiomeric excess.

10. A method of forming a compound of formula (II)

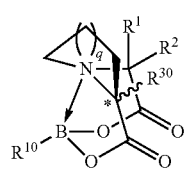

(II)

comprising reacting a compound represented by formula (IV)

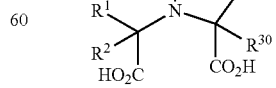

(IV)

with a compound of formula (V)

$R^{10}$—B(OH)$_2$ (V), wherein:
B in formula (II) is a boron atom having sp³ hybridization;
the carbon atom marked "*" is a chiral carbon atom of at least 90% enantiomeric excess;
$R^{10}$ is selected from the group consisting of

[structures]

$R^{11}$ and each instance of $R^{12}$ are independently selected from the group consisting of hydrogen, halogen, hydroxyl, (C1-C10)alkyl, cycloalkyl, aryl, aralkyl, heteroaralkyl, alkoxyl, acyl, acyloxy, aryloxy, amino, and trialkylsilyloxy; or $R^{11}$ and any one instance of $R^{12}$, or any two instances of $R^{12}$, taken together, form a 3-10-membered ring;

X is halogen;
each instance of Z is independently selected from the group consisting of CH and N, provided that no more than two instances of Z are N;
X' is selected from the group consisting of $CR^5R^6$, O, S, and $NR^7$;
$R^1$ and $R^2$ are both hydrogen or identically selected (C1-C3)alkyl;
$R^5$ and $R^6$ are independently selected from the group consisting of hydrogen, halogen, hydroxyl, (C1-C10)alkyl, cycloalkyl, aryl, aralkyl, heteroaralkyl, alkoxyl, acyl, acyloxy, aryloxy, amino, and trialkylsilyloxy;
$R^7$ and $R^{30}$ are independently selected from the group consisting of hydrogen and (C1-C3)alkyl;
n is 0, 1, or 2;
p is 0, 1, or 2; and
q is 1 or 2.

11. The method of claim 10, wherein the compound of formula (II) is

[structure]

12. A method of performing a stereoselective chemical reaction, comprising:
contacting a compound of formula (II) with a reagent

[structure] (II)

wherein:
$R^{10}$ is chemically transformed in a stereoselective manner;
the carbon atom marked "*" is a chiral carbon atom of at least 90% enantiomeric excess;
B is a boron atom having sp³ hybridization;
$R^{10}$ is selected from the group consisting of

[structures]

$R^{11}$ and each instance of $R^{12}$ are independently selected from the group consisting of hydrogen, halogen, hydroxyl, (C1-C10)alkyl, cycloalkyl, aryl, aralkyl, heteroaralkyl, alkoxyl, acyl, acyloxy, aryloxy, amino, and trialkylsilyloxy; or $R^{11}$ and any one instance of $R^{12}$, or any two instances of $R^{12}$, taken together, form a 3-10-membered ring;

X is halogen;
each instance of Z is independently selected from the group consisting of CH and N, provided that no more than two instances of Z are N;
X' is selected from the group consisting of $CR^5R^6$, O, S, and $NR^7$;
$R^1$ and $R^2$ are both hydrogen or identically selected (C1-C3)alkyl;
$R^5$ and $R^6$ are independently selected from the group consisting of hydrogen, halogen, hydroxyl, (C1-C10)alkyl, cycloalkyl, aryl, aralkyl, heteroaralkyl, alkoxyl, acyl, acyloxy, aryloxy, amino, and trialkylsilyloxy;
$R^7$ and $R^{30}$ are independently selected from the group consisting of hydrogen and (C1-C3)alkyl;
n is 0, 1, or 2;
p is 0, 1, or 2; and
q is 1 or 2.

13. The method of claim 12, wherein the compound of formula (II) is

[structure]

14. The method of claim 12, wherein $R^{10}$ is

[structure]

n is 0, p is 0, each instance of $R^{12}$ is hydrogen, and $R^{11}$ is selected from the group consisting of aryl and methyl.

15. The method of claim 12, wherein $R^{10}$ is

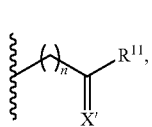

n is 0, X' is $CH_2$, and $R^{11}$ is methyl.

16. The method of claim 12, wherein $R^{10}$ is

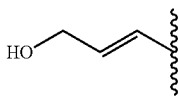

17. The method of claim 12, wherein $R^{10}$ is

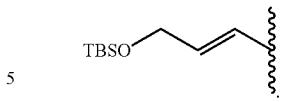

18. The method of claim 12, wherein the reagent is selected from the group consisting of oxidants, nucleophiles, bases, and electrophiles.

19. The method of claim 12, wherein the chemical reaction is selected from epoxidation, nucleophilic substitution, electrophilic substitution, oxidation, dihydroxylation, carbonylation, alkenation, cyclopropanation, cycloaddition, conjugate addition, Michael addition, Diels-Alder reaction, and transition metal-catalyzed cross-coupling reaction.

20. The method of claim 12, wherein the reagent is a chiral reagent.

* * * * *